USOO7947663B2

(12) United States Patent
Adams et al.

(10) Patent No.: US 7,947,663 B2
(45) Date of Patent: May 24, 2011

(54) INHIBITORS OF FATTY ACID AMIDE HYDROLASE

(75) Inventors: Julian Adams, Boston, MA (US); Mark L. Behnke, Somerville, MA (US); Alfredo C. Castro, Winchester, MA (US); Catherine A. Evans, Somerville, MA (US); Louis Grenier, Newton, MA (US); Michael J. Grogan, Winchester, MA (US); Tao Liu, Ashland, MA (US); Daniel A. Snyder, Somerville, MA (US); Thomas T. Tibbitts, Westford, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 329 days.

(21) Appl. No.: 11/870,130

(22) Filed: Oct. 10, 2007

(65) Prior Publication Data
US 2009/0099131 A1 Apr. 16, 2009

Related U.S. Application Data

(60) Provisional application No. 60/850,520, filed on Oct. 10, 2006.

(51) Int. Cl.
*A61K 31/69* (2006.01)
*C07K 1/113* (2006.01)
(52) U.S. Cl. .......................................... 514/64; 530/410
(58) Field of Classification Search ........................ None
See application file for complete search history.

(56) References Cited

U.S. PATENT DOCUMENTS

| | | | |
|---|---|---|---|
| 4,853,150 A | 8/1989 | Bezborodov et al. |
| 5,089,499 A | 2/1992 | Baker et al. |
| 5,340,898 A | 8/1994 | Cavezzan et al. |
| 5,550,236 A | 8/1996 | Schlosser et al. |
| 5,616,582 A | 4/1997 | Baker |
| 5,643,893 A | 7/1997 | Benson et al. |
| 5,693,688 A | 12/1997 | Priou |
| 5,847,149 A | 12/1998 | Fuss et al. |
| 5,892,131 A | 4/1999 | Barnes et al. |
| 5,998,673 A | 12/1999 | Barnes et al. |
| 6,075,014 A | 6/2000 | Weston et al. |
| 6,174,458 B1 | 1/2001 | Koga et al. |
| 6,218,445 B1 | 4/2001 | Priou et al. |
| 6,423,378 B1 | 7/2002 | Cotting et al. |
| 6,600,066 B1 | 7/2003 | Schottek et al. |
| 6,617,125 B2 | 9/2003 | Adler, Jr. |
| 6,753,046 B2 | 6/2004 | Manabe et al. |
| 6,911,235 B2 | 6/2005 | Frances |
| 6,924,269 B2 | 8/2005 | Miljkovic et al. |
| 7,037,938 B2 | 5/2006 | Hattori et al. |
| 7,049,304 B2 | 5/2006 | Holmes-Farley et al. |
| 7,074,836 B1 | 7/2006 | Kawada et al. |
| 7,101,915 B1 | 9/2006 | Kawada et al. |
| 7,148,219 B2 | 12/2006 | Lou et al. |
| 7,183,447 B2 | 2/2007 | Pauluth et al. |
| 7,220,783 B2 | 5/2007 | Kawada et al. |
| 7,351,452 B2 | 4/2008 | Goodby et al. |
| 7,411,100 B2 | 8/2008 | Pauluth et al. |
| 7,425,281 B2 | 9/2008 | Wand et al. |
| 7,432,375 B2 | 10/2008 | Graczyk et al. |
| 7,626,020 B2 | 12/2009 | Butlin et al. |
| 2004/0053889 A1* | 3/2004 | Ebdrup et al. .................. 514/64 |
| 2004/0115475 A1 | 6/2004 | Hashimoto |
| 2005/0182045 A1 | 8/2005 | Nagase et al. |
| 2005/0250825 A1 | 11/2005 | Brooks et al. |

(Continued)

FOREIGN PATENT DOCUMENTS

DE 19710614 9/1998

(Continued)

OTHER PUBLICATIONS

Vippagunta et al, "Crystalline Solids", Advanced Drug Delivery Reviews, vol. 48, pp. 3-26 (2001).*
Gavezzotti, "Are Crystal Structures Predictable?", Accounts of Chemical Research, vol. 27, pp. 309-314 (1994).*
Asano et al., Design, Synthesis, and Biological Evaluation of Aminoboronic Acids as Growth-Factor Receptor Inhibitors of EGFR and VEGFR-1 Tyrosine Kinases, ChemBioChem, (2004), 5, pp. 483-490.

(Continued)

*Primary Examiner* — Ardin Marschel
*Assistant Examiner* — Bong-Sook Baek
(74) *Attorney, Agent, or Firm* — Jones Day

(57) ABSTRACT

The present invention provide compounds, and pharmaceutical compositions thereof, encompassed by the formulae (I), (II) or (III).

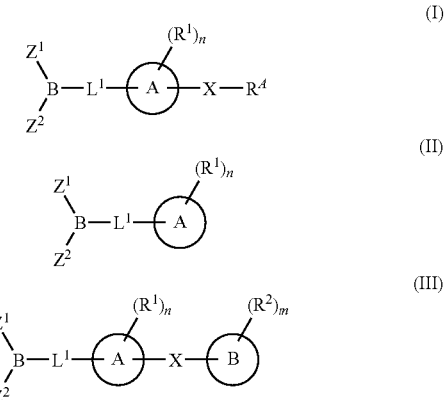

The present invention also provides methods for treating an FAAH mediated disease, disorder or condition by administering a therapeutically effective amount of a provided compound of the formulae (I), (II) or (III), or a pharmaceutical composition thereof, to a patient in need thereof. Additionally, the present invention provides methods for inhibiting FAAH in a patient by administering a therapeutically effective amount of a compound of the formulae (I), (II) or (III), or a pharmaceutical composition thereof, to a patient in need thereof.

12 Claims, No Drawings

U.S. PATENT DOCUMENTS

| | | |
|---|---|---|
| 2006/0135423 A1 | 6/2006 | Ambati |
| 2006/0211698 A1 | 9/2006 | Boryanski et al. |
| 2006/0234981 A1 | 10/2006 | Baker et al. |
| 2007/0082877 A1 | 4/2007 | Dunkel et al. |
| 2007/0129544 A1 | 6/2007 | Ackermann et al. |
| 2008/0132716 A1 | 6/2008 | Lietzau et al. |
| 2008/0171786 A1 | 7/2008 | Bruggemeier et al. |
| 2008/0188371 A1 | 8/2008 | Fischer et al. |
| 2008/0280992 A1 | 11/2008 | Kunz et al. |

FOREIGN PATENT DOCUMENTS

| | | |
|---|---|---|
| DE | 19710614 A1 | 9/1998 |
| DE | 19858594 | 6/2000 |
| DE | 19858594 A1 | 6/2000 |
| EP | 145441 B1 | 3/1992 |
| EP | 562897 | 9/1993 |
| EP | 562897 A1 | 9/1993 |
| EP | 614958 | 9/1994 |
| EP | 614958 A1 | 9/1994 |
| EP | 792883 B1 | 12/1997 |
| EP | 811593 | 12/1997 |
| EP | 811593 A1 | 12/1997 |
| EP | 811596 | 12/1997 |
| EP | 811596 A1 | 12/1997 |
| EP | 0987238 | 3/2000 |
| EP | 1236726 | 9/2002 |
| EP | 1444981 | 8/2004 |
| FR | 2727416 | 5/1996 |
| FR | 2727416 A1 | 5/1996 |
| FR | 2758329 | 1/1997 |
| GB | 2280181 | 1/1995 |
| GB | 2344817 A | 6/2000 |
| JP | 07165717 | 6/1995 |
| JP | 10059882 | 3/1998 |
| JP | 2000336045 | 12/2000 |
| JP | 2000336045 A | 12/2000 |
| JP | 2002284768 | 10/2002 |
| JP | 2002284768 A | 10/2002 |
| JP | 3555325 | 8/2004 |
| WO | WO 92/19707 | 11/1992 |
| WO | WO 95/12655 | 5/1995 |
| WO | WO-95/35300 | 12/1995 |
| WO | WO 96/20689 | 7/1996 |
| WO | WO 98/31688 | 7/1998 |
| WO | WO9828663 | 7/1998 |
| WO | WO 98/35924 | 8/1998 |
| WO | WO 00/04111 | 1/2000 |
| WO | WO-00/42213 | 7/2000 |
| WO | WO-02/057273 | 7/2002 |
| WO | WO-02/059155 | 8/2002 |
| WO | WO-02/085916 | 10/2002 |
| WO | WO-03/045228 | 6/2003 |
| WO | WO-03/105860 | 12/2003 |
| WO | WO-2004/081008 | 9/2004 |
| WO | WO2005/004799 A2 | 1/2005 |
| WO | WO-2005/013892 | 2/2005 |
| WO | WO2005037227 | 4/2005 |
| WO | WO-2006/007384 | 1/2006 |
| WO | WO-2006/050053 | 5/2006 |
| WO | WO-2006/050054 | 5/2006 |
| WO | WO-2006/050236 | 5/2006 |
| WO | WO-2006/053250 | 5/2006 |
| WO | WO-2006/089067 | 8/2006 |
| WO | WO-2006/099261 | 9/2006 |
| WO | WO 2006/133559 A1 | 12/2006 |
| WO | WO-2007/028104 | 3/2007 |
| WO | WO2007031512 | 3/2007 |
| WO | WO2007064809 | 6/2007 |
| WO | WO-2007/076875 | 7/2007 |
| WO | WO-2007/078340 | 7/2007 |
| WO | WO20050808403 | 7/2007 |
| WO | WO-2007/095638 | 8/2007 |
| WO | WO2007088148 | 8/2007 |
| WO | WO-2007/146965 | 12/2007 |
| WO | WO-2008/002674 | 1/2008 |
| WO | WO-2008/020920 | 2/2008 |
| WO | WO-2008/047229 | 4/2008 |
| WO | WO-2008/107480 | 9/2008 |
| WO | WO2009138176 | 11/2009 |
| WO | WO2009136646 | 12/2009 |
| WO | WO2009/126691 | 2/2010 |

OTHER PUBLICATIONS

Caujolle et al., Arylboronic Acid Metabolism in the Rat, Sciences Naturelles, (1970), 270(11), pp. 1529-1531, including English language abstract.

Carter et al., The Inhibition of Rat Liver Chromatin Potease by Congeners of the Phenyboronic Acids, Biochimica et Biophysica Acta, 484, (1977), pp. 103-108.

Ebdrup et al., Structure-Activity Relationship for Aryl and Heteroaryl Boronic Acid Inhibitors of Hormone-Sensitive Lipase, Bioorganic & Medicinal Chemistry, (2005), vol. 13, Issue 6, pp. 2305-2312.

Jauhiainen et al., Aromatic Boronic Acids as Probes of the Catalytic Site of Human Plasma Lecithin-Cholesterol Acyltransferase, Biochimica et Biophysica Acta 918, (1987), pp. 175-188.

Kong et al., Structure-Based Discovery of a Boronic Acid Bioisotere of Combrestastatin A-4, Chemistry & Biology, (2005), vol. 12, 1007-1014.

Martin et al., Inhibition of the RTEM-1 β-Lactamase by Boronic Acids, Bioorganic & Medicincal Chemistry Letters, (1994), pp. 1229-1234, vol. 4.

Morandi et al., Nanomolar Inhibitors of AmpC β-Lactamase, J. Am. Chem. Soc., (2003), pp. 685-695, 125.

Nakamura et al., Synthesis and Biological Evaluation of Boronic Acid Containing cis-Stilbenes as Apoptotic Tubulin Polymerization Inhibitors, ChemMedChem, (2006), pp. 729-740, 1.

Philipp et al., Inhibition of Serine Proteases by Arylboronic Acids, Proceedings of the National Academy of Sciences, (1971), pp. 478-480, vol. 68, No. 2.

Seufer-Wasserthal et al., Probing the Specificity of the $S_1$ Binding Site of Subtilisin Carlsberg with Boronic Acids, Bioorganic & Medicinal Chemistry, (1994), pp. 35-48, vol. 2, No. 1.

Simpelkamp et al., Borinic Acid Inhibitors as Probes of the Factors Involved in Binding at the Active Sites of Subtilisin Carlsberg and α-Chymotrypsin, Bioorganic & Medicinal Chemistry Letters, (1994) pp. 1391-1394, vol. 2, No. 11.

Smoum et al., Noncovalent Inhibition of the Serine Proteases, α-chymotrypsin and Trypsin by Trifluoro(organo)borates, Org. Biomol. Chem., (2005), pp. 941-944, 3.

Smoum et al., A Study of the Effect on Nucleophilic Hydrolytic Activity of Pancreatic Elastase, Trypsin, Chmotrypsin, and Leucine Aminopeptidase by Boronic Acids in the Presence of Arabinogalactan: A Subsequent Study on the Hydrolytic Activity of Chymotrypsin by Boronic Acids in the Presence of Mono-, Di-, and Trisaccharides, Bioorganic Chemistry, (2003), pp. 464-474, 31.

Frings et al., Salt Excretion by Nasal Gland of Laysan and Black-Footed Albatrosses, Science, (1958), pp. 1572-1574, vol. 128.

Tondi et al., Structure-based design and in-parallel synthesis of inhibitors of AmpC β-lactamase, Chemistry & Biology (2001) pp. 593-610, 8/6.

Yang et al., Boronic Acid Compounds as Potential Pharmaceutical Agents, Medicinal Research Reviews, (2003), pp. 346-368, vol. 23, No. 3.

Weston et al., Structure-Based Enhancement of Boronic Acid-Based Inhibitors of AmpC β-Lactamase, J.Med.Chem, (1998), pp. 4577-4586, 41.

Buzzoni et al., Aza-boronic Acids as Non- β-Lactam Inhibitors of AmpC- β-Lactamase, Bioorganice & Medicinal Chemistry Letters, (2004), pp. 3979-3983, 14.

Innocenti et al., Carbonic Anhydrase Inhibitors. Inhibition of Fungal β-Carbonic Anhydrases from *Candida albicans* and *Cryptococcus neoformans* with Boronic Acids, Bioorganic & Medicinal Chemistry Letters, (2009), pp. 1-4.

Lienhard et al., 2 Phenylethaneboronic Acid, A Possible Transition-State Analog for Chymotrypsin, Biochemistry, (1971), 10(13), 2477-2483.

Suzuki et al., Design, Synthesis, and Biological Activity of Boronic Acid-Based Histone Deacetylase Inhibitors, J. Med. Chem., (2009). 52(9), 2909-2922.

Labar et al., Fatty Acid Amide Hydrolase: From Characterization to Therapeutics, Chemistry & Biodiversity, (2007), 4, pp. 1882-1902.

Caujolle et al., "Etude comparee du pouvoir renforcateur des organoboriques a l'egard des hypnotiques//potentiation of hypnotics by organoboron derivatives" Agressologie, 1969, 51-54, 10(1).

Caujolle et al., "The effect of organoboron derivatives on cardiovascular and ventilatory manifestations of electroshock" Agressologie: Revue Internationale De Physio-Biologie et de Pharmacologie Appliquees aux Effets de l'Agression, 1967, 425-432, 8(5).

Miller et al., "The hypolipidemic and anti-inflammatory activity of boronated aromatic amino acids in CF1 male mice" Metal-Based Drugs, 1999, 337-344, 6(6), ISSN: 0793-0291.

Tanaka et al., "Suppression of arthritis by the inhibitors of dipeptidyl peptidase IV" International Journal of Immunopharmacology, 1997, 15-24, ISSN: 0192-0561.

CAS File Registry, Registry No. 874288-40-1, published Feb. 15, 2006.

CAS File Registry, Registry No. 874289-19-7, published Feb. 15, 2006.

CAS File Registry, Registry No. 874290-59-2, published Feb. 15, 2006.

CAS File Registry for [4-[2-(2,6-difluoro-4-propylphenyl)ethyl]-2,6-difluorophenyl]-boronic acid, published Mar. 3, 2003 in Japanese patent application No. JP10059882.

International Search Report for International Application No. PCT/US07/021626 published as WO2008/063300 on May 29, 2008.

Written Opinion for International Application No. PCT/US07/021626 published as WO2008/063300 on May 29, 2008.

Vandervoorde, "Overview of the Chemical Families of Fatty Acid Amide Hydrolase and Monoacylglycerol Lipase Inhibitors," Current Topics in Medicinal Chemistry 2008, 8, 247-267.

Minkkila et al., "Discovery of Boronic Acids as Novel and Potent Inhibitors of Fatty Acid Amide Hydrolase," J. Med. Chem. 2008, 51, 7057-7060.

Winum et al., "Carbonic anhydrase inhibitors. Synthesis and inhibition of cytosolic/tumor-associated carbonic anhydrase isozymes I, II, and IX with boron-containing sulfonamides, sulfamides, and sulfamates: Toward agents for boron neutron capture therapy of hypoxic tumors" Bioorganic & Medicinal Chemistry Letters 2005, 15(13), 3302-3306.

International Search Report for International Application No. PCT/US2009/039872 published as WO2009/126691 on Oct. 15, 2009.

European Office Action for EP 07870774.2 dated Sep. 11, 2009.

International Search Report for International Patent Application PCT/US2010/030276 mailed from the International Searching Authority on Jul. 7, 2010.

Written Opinion for International Patent Application PCT/US2010/030276 mailed from the International Searching Authority on Jul. 7, 2010.

McKinney, et al., "Structure and Function of Fatty Acid Amide Hydrolase," Ann. Rev. Biochem. 2005, vol. 74, p. 411-432.

* cited by examiner

INHIBITORS OF FATTY ACID AMIDE HYDROLASE

PRIORITY INFORMATION

This application claims priority under 35 U.S.C. §119(e) to United States provisional patent application, U.S. Ser. No. 60/850,520, filed Oct. 10, 2006, the entirety of which is incorporated herein by reference.

BACKGROUND OF THE INVENTION

Fatty acid amide hydrolase (FAAH), also referred to as oleamide hydrolase and anandamide amidohydrolase, is an integral membrane protein that degrades fatty acid primary amides and ethanolamides, including oleamide and anandamide. FAAH degrades neuromodulating fatty acid amides at their sites of action and is intimately involved in their regulation.

FAAH has been demonstrated to be involved in a number of biological processes and its inhibition has been shown to be effective in treating a variety of conditions. For example, inhibiting FAAH has been shown to be useful in treating chronic pain, acute pain, neuropathic pain, anxiety, depression, feeding behaviors, movement disorders, glaucoma, neuroprotection and cardiovascular disease.

However, current inhibitors of FAAH lack the target selectivity, biological activity and/or bioavailability needed for in vivo studies and therapeutic use. Thus, to date, the therapeutic potential of FAAH inhibitors remains essentially unexplored.

SUMMARY OF THE INVENTION

Compounds of the present invention, and pharmaceutical compositions thereof, are effective inhibitors of fatty acid amide hydrolase (FAAH). Such compounds provided herein are encompassed by any of the formulae (I), (II) or (III):

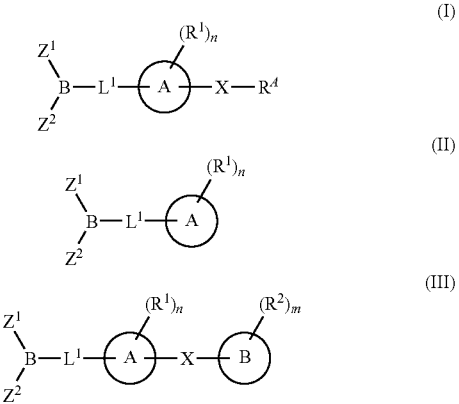

or a pharmaceutically acceptable form thereof, wherein $Z^1$, $Z^2$, $L^1$, X, Ring A, Ring B, $R^1$, $R^2$, n and m are as defined herein.

The present invention also provides methods for treating conditions associated with excessive FAAH activity by administering a therapeutically effective amount of a provided compound of the formulae (I), (II) or (III), or a pharmaceutical composition thereof, to a patient in need thereof.

Additionally, the present invention provides methods for inhibiting FAAH in a patient by administering a therapeutically effective amount of a compound of the formulae (I), (II) or (III), or a pharmaceutical composition thereof, to a patient in need thereof.

The details of additional or alternative embodiments of the invention are set forth in the accompanying Detailed Description of Certain Embodiments and Examples as described below. Other features, objects, and advantages of the invention will be apparent from this description and from the claims.

```
Sequence Identification Numbers
SEQ ID NO. 1: Homo sapiens FAAH amino acid
sequence
MVQYELWAALPGASGVALACCFVAAAVALRWSGRRTARGAVVRARQRQRA

GLENMDRAAQRFRLQNPDLDSEALLALPLPQLVQKLHSRELAPEAVLFTY

VGKAWEVNKGTNCVTSYLADCETQLSQAPRQGLLYGVPVSLKECFTYKGQ

DSTLGLSLNEGVPAECDSVVVHVLKLQGAVPFVHTNVPQSMFSYDCSNPL

FGQTVNPWKSSKSPGGSSGGEGALIGSGGSPLGLGTDIGGSIRFPSSFCG

ICGLKPTGNRLSKSGLKGCVYGQEAVRLSVGPMARDVESLALCLRALLCE

DMFRLDPTVPPLPFREEVYTSSQPLRVGYYETDNYTMPSPAMRRAVLETK

QSLEAAGHTLVPFLPSNIPHALETLSTGGLFSDGGHTFLQNFKGDFVDPC

LGDLVSILKLPQWLKGLLAFLVKPLLPRLSAFLSNMKSRSAGKLWELQHE

IEVYRKTVIAQWRALDLDVVLTPMLAPALDLNAPGRATGAVSYTMLYNCL

DFPAGVVPVTTVTAEDEAQMEHYRGYFGDIWDKMLQKGMKKSVGLPVAVQ

CVALPWQEELCLRFMREVERLMTPEKQSS
```

DETAILED DESCRIPTION OF CERTAIN EMBODIMENTS OF THE INVENTION

1. General Description of Compounds of the Invention

The present invention is based on the discovery that inhibitors of FAAH which contain at least one Lewis acidic boron head group, such as, for example, a boronic acid, boronic ester, borinic acid or borinic ester head group, are highly active antagonists of FAAH function.

Thus, in one aspect, the present invention provides compounds of formula (I):

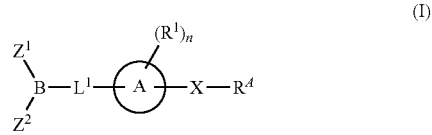

and pharmaceutically acceptable forms thereof;
wherein:
(i) $Z^1$ is —OR and $Z^2$ is —OR, an optionally substituted $C_{1-6}$ aliphatic, $C_{1-6}$ heteroaliphatic, $C_{6-12}$ aryl, or $C_{6-12}$ heteroaryl group (ii) $Z^1$ and $Z^2$ taken together form a 5- to 8-membered ring having at least one O atom directly attached to B, wherein the ring is comprised of carbon atoms and optionally one or more additional heteroatoms independently selected from the group consisting of N, S, and O; or (iii) $Z^1$ is —OR, and $Z^2$ and Ring A taken together form an optionally substituted 5- to 7-membered ring, wherein the ring is comprised of carbon atoms and optionally one or more additional heteroatoms independently selected from the group consisting of N, S, and O;

each R is hydrogen or an optionally substituted $C_{1-6}$ aliphatic, $C_{1-6}$ heteroaliphatic, $C_{6-12}$ aryl, or $C_{6-12}$ heteroaryl group;

$L^1$ is a covalent bond, or an optionally substituted straight or branched $C_{1-6}$ alkylene or $C_{2-6}$ alkenylene moiety;

Ring A is an optionally substituted saturated, partially unsaturated or aromatic $C_{5-8}$ monocyclic, $C_{6-10}$ bicyclic or $C_{10-16}$ tricyclic ring system optionally containing one or more heteroatoms independently selected from the group consisting of N, S and O;

X is a covalent bond or a bivalent $C_{1-6}$ hydrocarbon chain, wherein one, two or three methylene units of X are optionally and independently replaced with one or more —O—, —N=N—, —NR'—, —(C=NR')—, —S—, —C(=O)—, —S(=O)—, —S(=O)$_2$— or an optionally substituted phenylene moiety;

each R' is hydrogen, —C(O)R, a suitable amino protecting group, or an optionally substituted $C_{1-6}$ aliphatic, $C_{1-6}$ heteroaliphatic, $C_{6-12}$ aryl, or $C_{6-12}$ heteroaryl group;

$R^A$ is (i) hydrogen, halogen, —OR, —CF$_3$, —CN, —NO$_2$, —NC, —SO$_2$R, —SOR, —C(O)R, —CO$_2$R, —C(O)N(R')$_2$, —CHO, —N$_3$, —N$_2$R, or —N(R')$_2$; or (ii) Ring B having the formula:

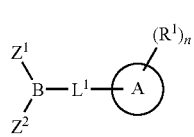

wherein Ring B is an optionally substituted saturated, partially unsaturated or aromatic $C_{5-8}$ monocyclic, $C_{6-10}$ bicyclic or $C_{10-16}$ tricyclic ring system optionally containing one or more heteroatoms independently selected from the group consisting of N, S and O;

each occurrence of $R^1$ is, independently, halogen, —OR, —CF$_3$, —CN, —NO$_2$, —NC, —SO$_2$R, —SOR, —C(O)R, —CO$_2$R, —C(O)N(R')$_2$, —CHO, —N$_3$, —N$_2$R, —N(R')$_2$, —B(OH$_2$), or an optionally substituted $C_{1-8}$ aliphatic group;

each instance of $R^2$ is, independently, halogen, —OR, —CF$_3$, —CN, —NO$_2$, —NC, —SO$_2$R, —SOR, —C(O)R, —CO$_2$R, —C(O)N(R')$_2$, —N$_3$, —N$_2$R, —N(R')$_2$, an optionally substituted $C_{1-8}$ aliphatic or $C_{6-12}$ aryl group; and each instance of n and m is, independently, an integer between 0 to 10, inclusive.

In certain embodiments, the present invention provides a compound of formula I wherein said compound excludes any compound of Table 1, infra.

In certain embodiments, wherein X is a covalent bond and $R^A$ is hydrogen, the present invention provides compounds of formula (II):

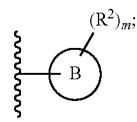

and pharmaceutically acceptable forms thereof; wherein $Z^1$, $Z^2$, $L^1$, Ring A, $R^1$ and n are as defined above and herein.

In certain embodiments, the present invention provides a compound of formula II wherein said compound excludes any compound of Table 1, infra.

Further, in other embodiments, wherein $R^A$ is Ring B, the present invention provides compounds of formula (III):

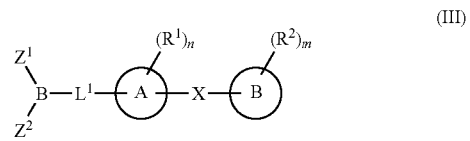

and pharmaceutically acceptable forms thereof; wherein $Z^1$, $Z^2$, $L^1$, X, Ring A, Ring B, $R^1$, $R^2$, n and m are as defined above and herein.

In certain embodiments, the present invention provides a compound of formula III wherein said compound excludes any compound of Table 1, infra.

For example, in certain embodiments, the present invention provides compounds of the formula (III-a):

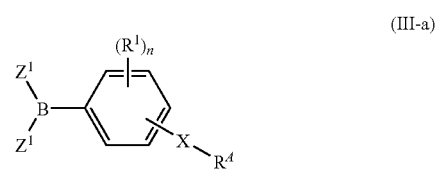

and pharmaceutically acceptable forms thereof; wherein $Z^1$, $Z^2$, $L^1$, X, and $R^A$ are as defined above and herein; and n is an integer between 0 to 4, inclusive.

In certain embodiments, the present invention provides a compound of formula III-a wherein said compound excludes any compound of Table 1, infra.

In certain embodiments, the present invention provides compounds of the formula (III-b):

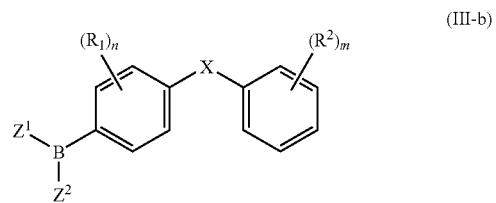

and pharmaceutically acceptable forms thereof; wherein $Z^1$, $Z^2$, $L^1$, X, $R^1$ and $R^2$ are as defined above and herein; n is an integer between 0 to 4, inclusive; and m is an integer between 0 to 5, inclusive.

In certain embodiments, the present invention provides a compound of formula III-b wherein said compound excludes any compound of Table 1, infra.

2. Compounds and Definitions

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Certain compounds of the present invention can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, Ind. 1972).

As used herein a "direct bond" or "covalent bond" refers to a single bond.

As used herein, the term "boronic acid" refers to any chemical compound comprising a —B(OH)$_2$ moiety. Arylboronic acid compounds readily form oligomeric anhydrides by dehydration of the boronic acid moiety (see, for example, Snyder et al., *J. Am. Chem. Soc.* (1958) 80: 3611). Thus, unless otherwise apparent from context, the term "boronic acid" is expressly intended to encompass free boronic acids, oligomeric anhydrides, including, but not limited to, dimers, trimers, and tetramers, and mixtures thereof. Furthermore, the term "boronic ester" refers to any chemical compound comprising a —B(OR)$_2$ moiety. The term "borinic acid" refers to any chemical compound comprising a —B(R)OH moiety. The term "borinic ester" refers to any chemical compound comprising a —B(R)OR moiety.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic or bicyclic ring systems, as described herein, having from 3 to 10 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring.

The term "alkyl," as used herein, refers to saturated, straight- or branched-chain hydrocarbon radicals derived from an aliphatic moiety containing between one and six carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiments, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. In certain embodiments, the alkynyl group employed in the invention contains 2-6 carbon atoms. In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

The term "aryl" used alone or as part of a larger moiety as in "aralkyl", "aralkoxy", or "aryloxyalkyl", refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenantriidinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)SiR^\circ_3$; $-(CH_2)_{0-4}OC$ (O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•_2$, —NO$_2$, —SiR$^•_3$, —OSiR$^•_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

An "suitable amino-protecting group," as used herein, is well known in the art and include those described in detail in *Protecting Groups in Organic Synthesis*, T. W. Greene and P. G. M. Wuts, 3 edition, John Wiley & Sons, 1999, the entirety of which is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "suitable hydroxyl protecting group" as used herein, is well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacecetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4- dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

As used herein, a "pharmaceutically acceptable form thereof" includes any pharmaceutically acceptable salts, prodrugs, tautomers, isomers, and/or polymorphs of a compound of the present invention, as defined below and herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\,alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "prodrug" refers to a derivative of a parent compound that requires transformation within the body in order to release the parent compound. In certain cases, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage. The compounds of the invention readily undergo dehydration to form oligomeric anhydrides by dehydration of the boronic acid moiety to form dimers, trimers, and tetramers, and mixtures thereof. These oligomeric species hydrolyze under physiological conditions to reform the boronic acid. As such, the oligomeric anhydrides are contemplated as a "prodrug" of the compounds of the present invention, and may be used in the treatment of disorder and/or conditions a wherein the inhibition of FAAH provides a therapeutic effect.

Prodrugs of boronic acids can be in the form of the "ate" form when the boron is in its tetrahedral form. Examples of this are trifluoroborates which will rapidly hydrolyze to the boronic acid. Salt forms (e.g., $Na^+$, $Li^+$, $Mg^{2+}$, $Ca^{2+}$, and the like) of the boronic acid could be considered to exist as an "ate" as well. Other 1,2 and 1,3 hydroxy sugars can be used to form "ate" prodrugs as depicted above, such as, for example, glycerol, erythritol, threitol, ribitol, arabinitol, xylitol, allitol, altritol, galactitol, sorbitol, mannitol, and iditol. Other sugars which useful in the formation of prodrugs include, but are not limited to, maltitol, lactitol, and isomalt; other monosaccharides which include hexoses (e.g., allose, altrose, glucose, mannose, gulose, idose, galactose, talose) and pentoses (e.g., ribose, arabinaose, xylose, lyxose); pentaerythritols and structural derivatives thereof, such as methylated, ethylated, acetate, ethoxylate, and propoxylate derivatives; and phenolic polyols such as 1,2,4 benzenetriol, 5-methyl benzene1, 2,3-triol, 2,3,4-trihydroxybenzaldehyde, and 3,4,5-trihydroxybenzamide. Prodrugs also include NMIDA-derivatives as provided in the Examples (such as the synthesis of compound (165), Example 113).

As used herein, the term "tautomer" includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, Ind. 1972).

As used herein, "polymorph" refers to a crystalline inventive compound existing in more than one crystalline form/structure. When polymorphism exists as a result of difference in crystal packing it is called packing polymorphism. Polymorphism can also result from the existence of different conformers of the same molecule in conformational polymorphism. In pseudopolymorphism the different crystal types are the result of hydration or solvation.

3. Description of Exemplary Compounds (i) $Z^1$ and $Z^2$

As defined generally above, $Z^1$ may be —OR, and $Z^2$ may be —OR, an optionally substituted $C_{1-6}$ aliphatic, $C_{1-6}$ heteroaliphatic, $C_{6-12}$ aryl, or $C_{6-12}$ heteroaryl group, wherein R is independently hydrogen or an optionally substituted $C_{1-6}$ aliphatic, $C_{1-6}$ heteroaliphatic, $C_{6-12}$ aryl, or $C_{6-12}$ heteroaryl group.

In certain embodiments, $Z^1$ is —OH and $Z^2$ is —OH.

In some embodiments, $Z^1$ is —OH and $Z^2$ is —OR.

In other embodiments, $Z^1$ is —OR and $Z^2$ is —OR.

In yet other embodiments, $Z^1$ is —OH or —OR, and $Z^2$ is an optionally substituted $C_{1-6}$ aliphatic.

In yet other embodiments, $Z^1$ is —OH or —OR, and $Z^2$ is an optionally substituted $C_{1-6}$ heteroaliphatic.

In yet other embodiments, $Z^1$ is —OH or —OR, and $Z^2$ is a $C_{6-12}$ aryl.

In yet other embodiments, $Z^1$ is —OH or —OR, and $Z^2$ is a $C_{6-12}$ heteroaryl.

Alternatively, as generally defined above, $Z^1$ and $Z^2$ may be taken together form a 5- to 8-membered ring having at least one O atom directly attached to B, wherein the ring is comprised of carbon atoms and optionally one or more additional heteroatoms independently selected from the group consisting of N, S, and O.

In some embodiments, $Z^1$ and $Z^2$ form a 5-membered ring. Exemplary 5-membered ring structures include, but are not limited to:

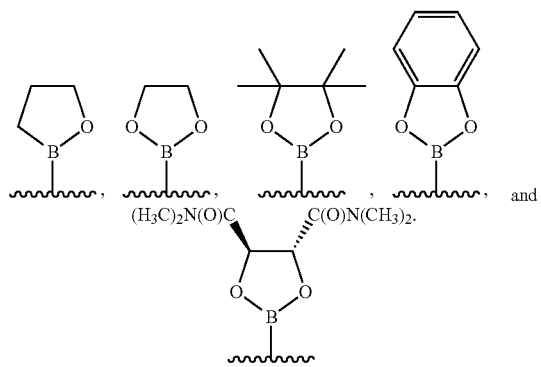

In other embodiments, $Z^1$ and $Z^2$ form a 6-membered ring. Exemplary 6-membered ring structures include, but are not limited to:

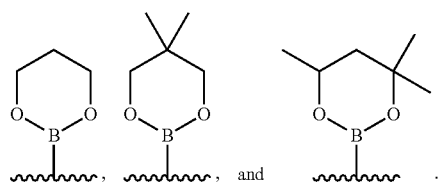

In yet other embodiments, $Z^1$ and $Z^2$ form an 8-membered ring. Exemplary 8-membered ring structures include, but are not limited to:

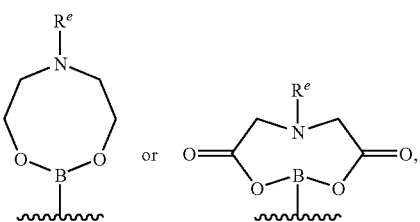

wherein $R^e$ is hydrogen, a suitable amino protecting group, or an optionally substituted $C_{1-6}$ aliphatic, $C_{1-6}$ heteroaliphatic, $C_{6-12}$ aryl, or $C_{6-12}$ heteroaryl group.

Furthermore, as generally defined above, $Z^1$ may be —OR, wherein R is hydrogen or a $C_{1-6}$ aliphatic, $C_{1-6}$ heteroaliphatic, $C_{6-12}$ aryl, or $C_{6-12}$ heteroaryl group, and $Z^2$ and Ring A taken together form an optionally substituted 5- to 7-membered ring, wherein the ring is comprised of carbon atoms and optionally one or more additional heteroatoms independently selected from the group consisting of N, S, and O.

For example, in certain embodiments, $Z^1$ is —OR, and $Z^2$ and Ring A taken together form an optionally substituted 6-membered ring. Exemplary ring structures include, but are not limited to:

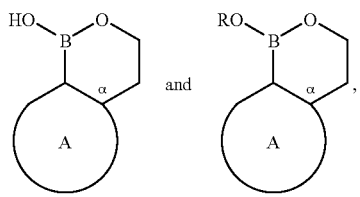

wherein Ring A is as defined above and herein.

(ii) $L^1$

As is also defined generally above, $L^1$ may be a covalent bond or an optionally substituted straight or branched $C_{1-6}$ alkylene or $C_{2-6}$ alkenylene moiety.

In certain embodiments $L^1$ is a covalent bond.

In some embodiments, $L^1$ is an optionally substituted $C_{1-6}$ alkylene moiety. In some embodiments, $L^1$ is an optionally substituted $C_{1-3}$ alkylene moiety. In other embodiments, $L^1$ is an optionally substituted $C_{1-2}$ alkylene moiety.

In yet other embodiments, $L^1$ is a —CH(R°)— group, wherein R° is as defined herein. In some embodiments, $L^1$ is a —CH$_2$— group.

In other embodiments, $L^1$ is a —CH$_2$CH(R°)— group, wherein R° is as defined herein. In yet other embodiments, $L^1$ is a —CH$_2$CH$_2$— group.

In some embodiments, $L^1$ is an optionally substituted $C_{2-6}$ alkenylene moiety. In other embodiments, $L^1$ is an optionally substituted $C_{2-4}$ alkenylene moiety. In yet other embodiments, $L^1$ is a —CH=CH— group.

(iii) Ring A

As is also defined generally above, Ring A is a optionally substituted saturated, partially unsaturated or aromatic $C_{5-8}$ monocyclic, $C_{6-10}$ bicyclic or $C_{10-16}$ tricyclic ring system optionally containing one or more heteroatoms independently selected from the group consisting of N, S and O.

In certain embodiments, Ring A is a substituted saturated, partially unsaturated or aromatic $C_{5-8}$ monocyclic, $C_{6-10}$ bicyclic or $C_{10-16}$ tricyclic ring system optionally containing one or more heteroatoms independently selected from the group consisting of N, S and O, wherein Ring A has at least one fluorine substituent (e.g., as defined by $R^1$). In certain embodiments, Ring A has at least two fluorine substituents. In certain embodiments, Ring A has at least three fluorine substituents.

In certain embodiments, Ring A is an aromatic ring system. In certain embodiments, both Ring A and Ring B are aromatic ring systems. However, in certain embodiments, Ring A is a saturated or partially unsaturated ring system.

(a) Monocyclic Ring A Groups

In certain embodiments, Ring A is a optionally substituted saturated, partially unsaturated or aromatic $C_{5-8}$ monocyclic ring system, optionally containing one or more heteroatoms independently selected from the group consisting of N, S and O.

In some embodiments, Ring A is a optionally substituted saturated, partially unsaturated or aromatic $C_{5-8}$ monocyclic carbocyclic ring system.

For example, in some embodiments, Ring A is an optionally substituted aromatic $C_6$ or $C_8$ monocyclic carbocyclic ring system. Such monocyclic carbocyclic ring systems include, but are not limited to:

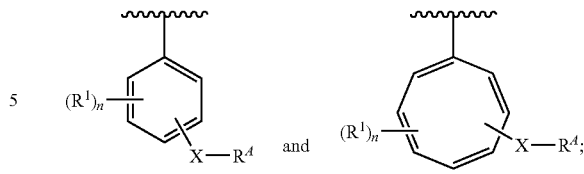

wherein X, $R^A$, $R^1$ and n are as defined above and herein.

In certain embodiments, Ring A is an optionally substituted phenyl ring system of the formula:

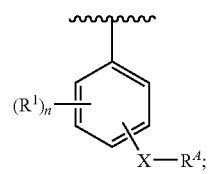

wherein X, $R^A$, $R^1$ are as defined above and herein; and n is an integer between 0 to 5, inclusive.

In certain embodiments, Ring A is phenyl. In certain embodiments, Ring A is phenyl and at least one $R^1$ group is fluoro in the ortho position relative to the boron atom.

In certain embodiments, Ring A is phenyl, $R^A$ is Ring B, and Ring B is also phenyl. In other embodiments, Ring A is phenyl, and the group:

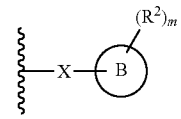

is attached to Ring A para to the boron (B) atom.

In certain embodiments, n is an integer between 0 to 3. In some embodiments, n is an integer between 0 to 2. In other embodiments, n is 1 or 2. In yet other embodiments, n is 1. In still yet other embodiments, n is 2. In still yet other embodiments, n is 0.

In certain embodiments, Ring A is an optionally substituted phenyl ring system of any one of the formulae:

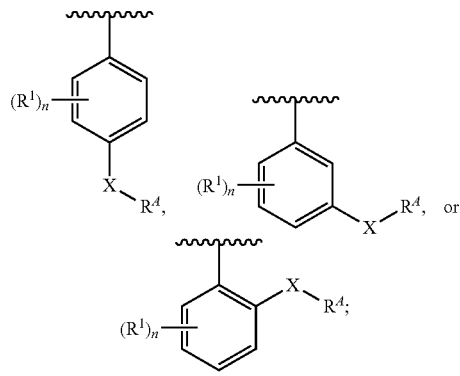

wherein X, $R^A$, $R^1$ and n are as defined above and herein.

In other embodiments, Ring A is an optionally substituted phenyl ring system having an —XR$^A$ group para to the boron atom of any one of the formulae:

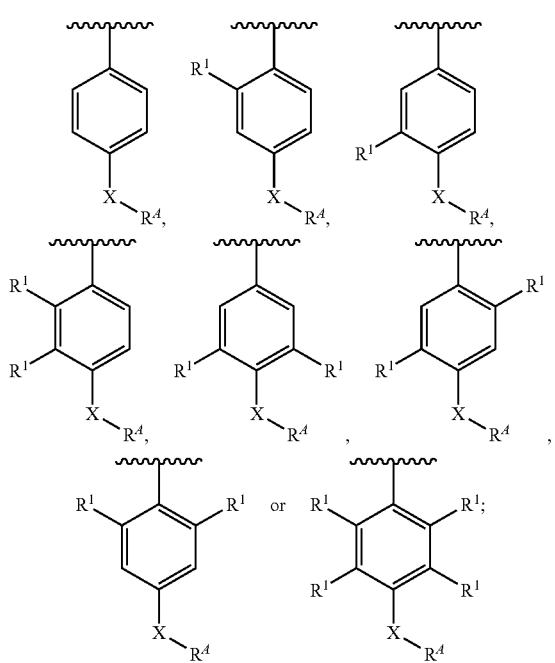

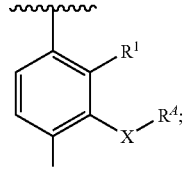

wherein X, $R^A$, $R^1$ and n are as defined above and herein.

In yet other embodiments, Ring A is an optionally substituted phenyl ring system having an —$XR^A$ group meta to the boron atom of any one of the formulae:

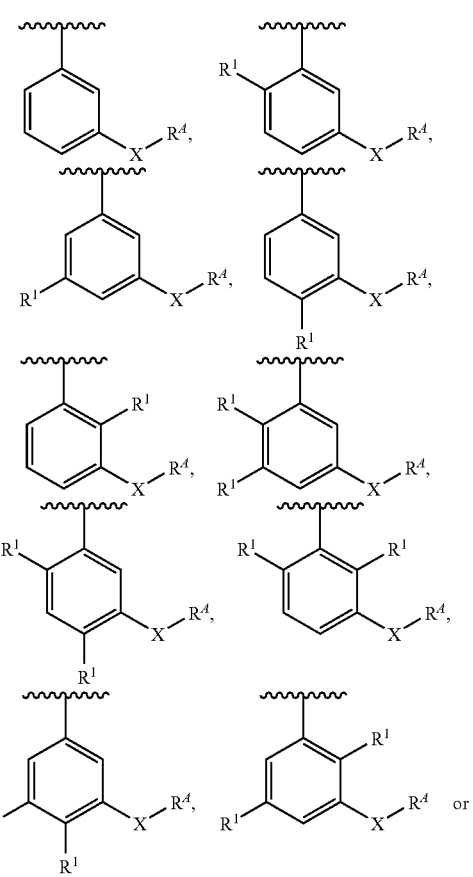

wherein X, $R^A$, $R^1$ and n are as defined above and herein.

In yet other embodiments, Ring A is an optionally substituted phenyl ring system having an —$XR^A$ group ortho to the boron atom of any one of the formulae:

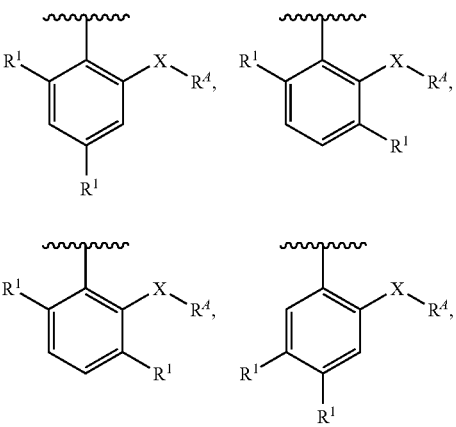

wherein X, $R^A$, $R^1$ and n are as defined above and herein.

However, also in certain embodiments, wherein X is a covalent bond and $R^A$ is hydrogen, Ring A is an optionally substituted phenyl ring system of the formula:

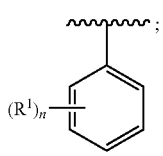

wherein $R^1$ and n is as defined above and herein.

For example, in certain embodiments wherein X is a covalent bond and $R^4$ is hydrogen, Ring A is an optionally substituted phenyl ring system of any one of the formulae:

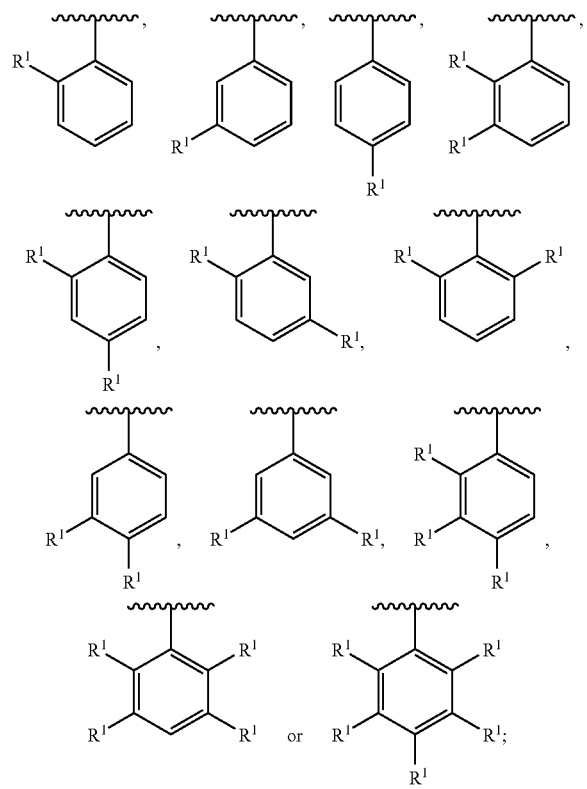

wherein $R^1$ and n are as defined above and herein.

In other embodiments, Ring A is an optionally substituted saturated or partially unsaturated $C_{5-8}$ monocyclic carbocyclic ring system. Such monocyclic carbocyclic ring systems include, but are not limited to:

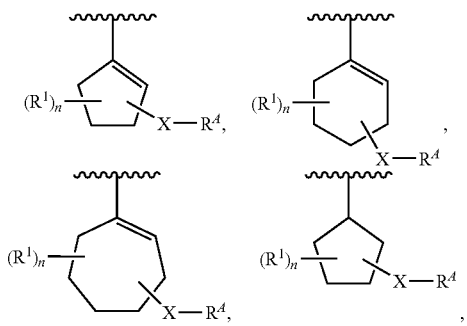

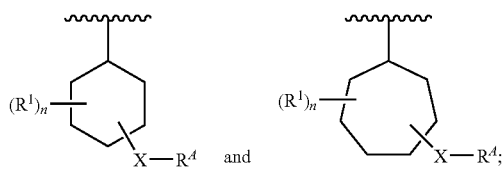

wherein X, $R^4$, $R^1$ and n are as defined above and herein.

In other embodiments, Ring A is a optionally substituted saturated, partially unsaturated or aromatic $C_{5-8}$ monocyclic ring system containing one or more heteroatoms independently selected from the group consisting of N, S and O.

For example, in certain embodiments, Ring A is a optionally substituted aromatic $C_{5-8}$ monocyclic ring system containing one or more heteroatoms independently selected from the group consisting of N, S and O. Such aromatic monocyclic ring systems include, but are not limited to:

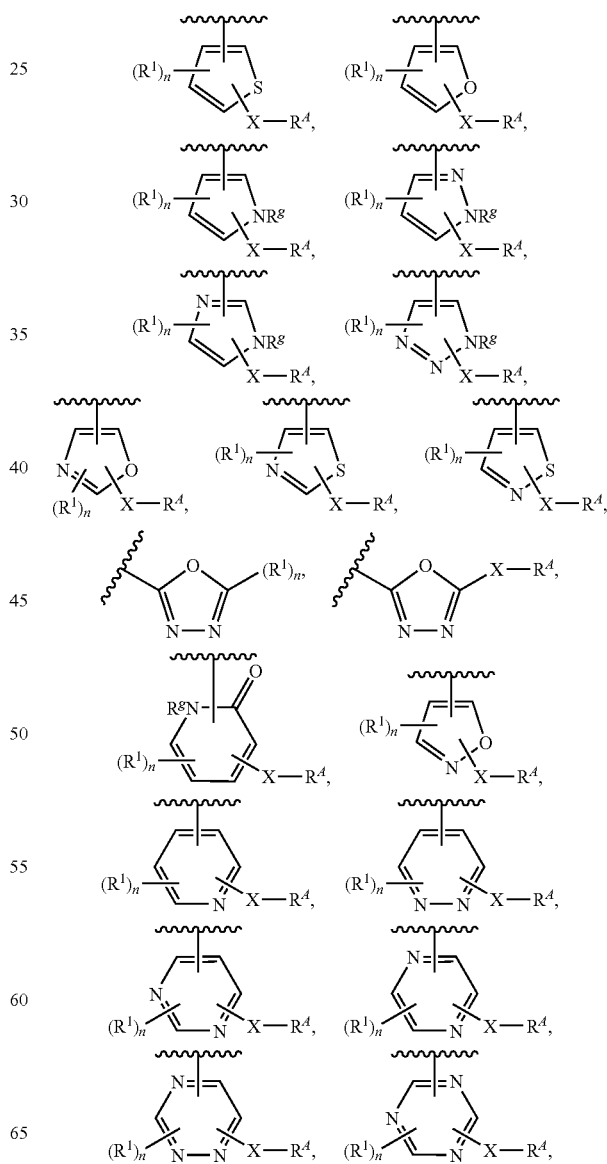

23

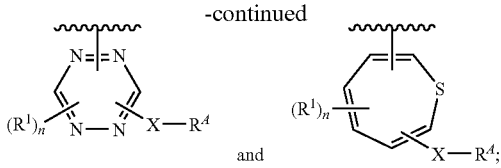
and wherein X, $R^A$, $R^1$ and n are as defined above and herein, and $R^g$ is hydrogen, a suitable amino protecting group, or an optionally substituted $C_{1-6}$ aliphatic, $C_{1-6}$ heteroaliphatic, $C_{6-12}$ aryl, or $C_{6-12}$ heteroaryl group.

In other embodiments, Ring A is a optionally substituted saturated or partially unsaturated $C_{5-8}$ monocyclic ring system containing one or more heteroatoms independently selected from the group consisting of N, S and O. Such saturated or partially unsaturated monocyclic ring systems include, but are not limited to:

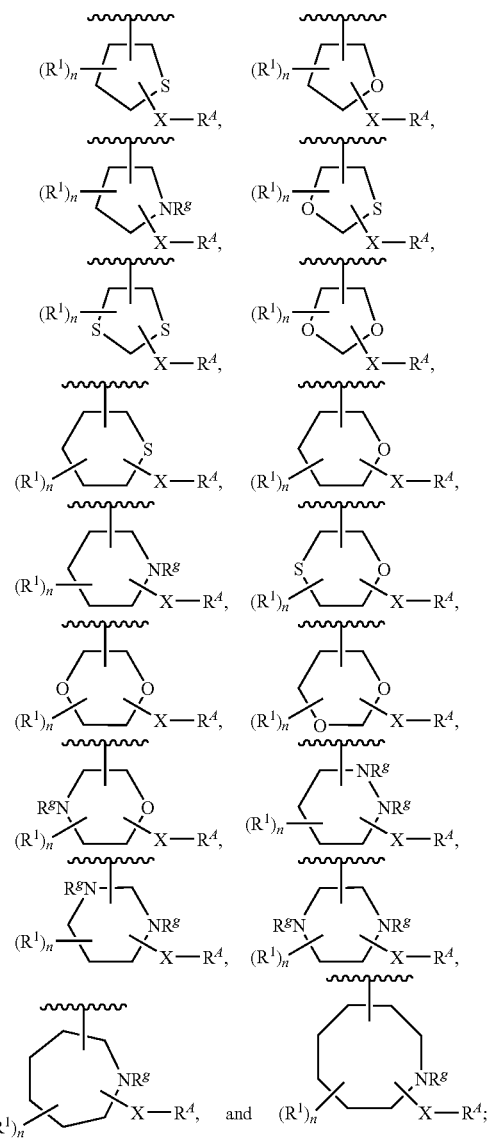

wherein X, $R^A$, $R^1$, $R^g$ and n are as defined above and herein.

(b) Bicyclic Ring A Groups

In certain embodiments, Ring A is a optionally substituted saturated, partially unsaturated or aromatic $C_{6-10}$ bicyclic ring system optionally containing one or more heteroatoms independently selected from the group consisting of N, S and O.

In certain embodiments, Ring A is a optionally substituted saturated, partially unsaturated or aromatic $C_{6-10}$ bicyclic carbocyclic ring system.

In certain embodiments, Ring A is a optionally substituted aromatic $C_{6-10}$ bicyclic carbocyclic ring system. Aromatic $C_{6-10}$ bicyclic ring systems of this type may be either fully aromatic (i.e., wherein both rings are aromatic) or partially aromatic (i.e., wherein one ring is aromatic and one ring is not aromatic).

For example, in certain embodiments, Ring A is a optionally substituted fully aromatic $C_{6-10}$ bicyclic carbocyclic ring system. Such bicyclic carbocyclic ring systems include, but are not limited to:

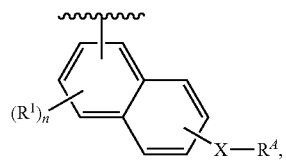

wherein X, $R^A$, $R^1$ and n are as defined above and herein.

In other embodiments, Ring A is a optionally substituted partially aromatic $C_{6-10}$ bicyclic carbocyclic ring system. Such bicyclic carbocyclic ring systems include, but are not limited to:

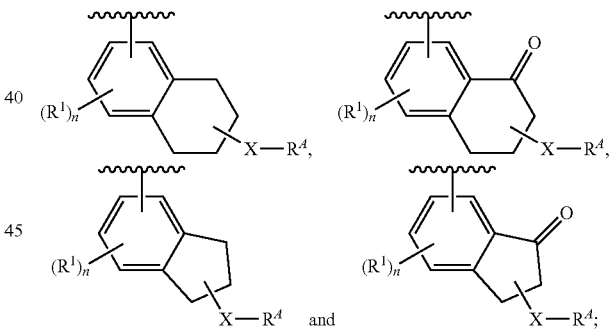

wherein X, $R^A$, $R^1$ and n are as defined above and herein.

In yet other embodiments, Ring A is a optionally substituted saturated or partially unsaturated $C_{6-10}$ bicyclic carbocyclic ring system.

In certain embodiments, Ring A is a optionally substituted aromatic $C_{6-10}$ bicyclic ring system containing one or more heteroatoms independently selected from the group consisting of N, S and O. Aromatic $C_{6-10}$ bicyclic ring systems of this type may be either fully aromatic (i.e., wherein both rings are aromatic) or partially aromatic (i.e., wherein one ring is aromatic and one ring is not aromatic).

For example, in certain embodiments, Ring A is a optionally substituted fully aromatic $C_{6-10}$ bicyclic ring system containing one or more heteroatoms independently selected from the group consisting of N, S and O. Such aromatic bicyclic ring systems include, but are not limited to:

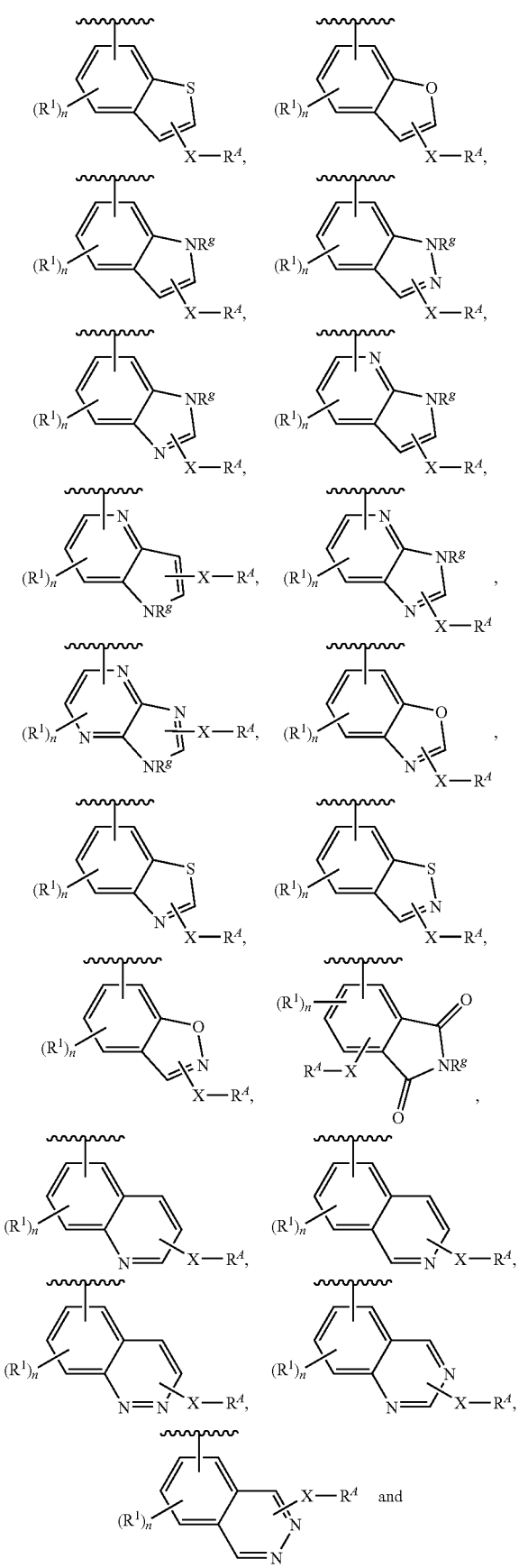

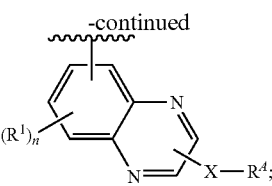

wherein X, $R^A$, $R^1$, $R^g$ and n are as defined above and herein.

In other embodiments, Ring A is a optionally substituted partially aromatic $C_{6-10}$ bicyclic ring system containing one or more heteroatoms independently selected from the group consisting of N, S and O. Such bicyclic ring systems include, but are not limited to:

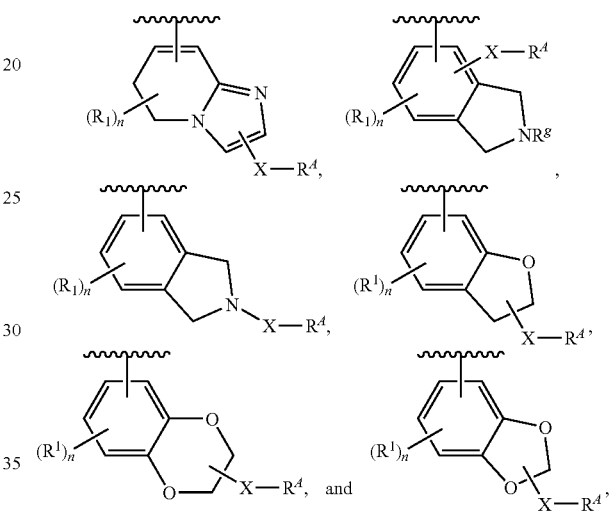

wherein X, $R^A$, $R^1$, $R^g$ and n are as defined above and herein.

In yet other embodiments, Ring A is a optionally substituted saturated or partially unsaturated $C_{6-10}$ bicyclic ring system containing one or more heteroatoms independently selected from the group consisting of N, S and O.

(c) Tricyclic Ring A Groups

In certain embodiments, Ring A is a optionally substituted saturated, partially unsaturated or aromatic $C_{10-16}$ tricyclic ring system optionally containing one or more heteroatoms independently selected from the group consisting of N, S and O.

In certain embodiments, Ring A is a optionally substituted saturated, partially unsaturated or aromatic $C_{10-16}$ tricyclic, carbocyclic ring system. Such tricyclic carbocyclic ring systems include, but are not limited to:

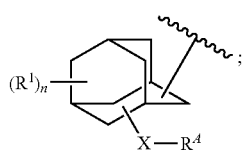

wherein X, $R^A$, $R^1$ and n are as defined above and herein.

In certain embodiments, Ring A is a optionally substituted aromatic $C_{10-16}$ tricyclic, carbocyclic ring system. Aromatic $C_{6-14}$ tricyclic ring systems of this type may be either fully aromatic (i.e., wherein all three rings are aromatic) or partially aromatic (i.e., wherein at least one ring is aromatic and at least one ring is not aromatic).

For example, in certain embodiments, Ring A is a optionally substituted fully aromatic $C_{10-16}$ tricyclic, carbocyclic ring system. Such tricyclic carbocyclic ring systems include, but are not limited to:

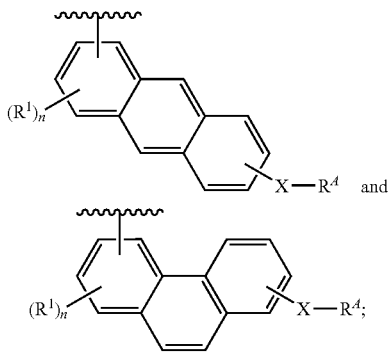

wherein X, $R^A$, $R^1$ and n are as defined above and herein.

In other embodiments, Ring A is a optionally substituted partially aromatic $C_{10-16}$ tricyclic, carbocyclic ring system. Such tricyclic carbocyclic ring systems include, but are not limited to:

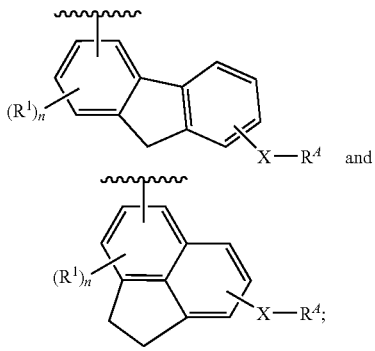

wherein X, $R^A$, $R^1$ and n are as defined above and herein.

In certain embodiments, Ring A is a optionally substituted saturated, partially unsaturated or aromatic $C_{10-16}$ tricyclic ring system containing one or more heteroatoms independently selected from the group consisting of N, S and O.

For example, in certain embodiments, Ring A is a optionally substituted aromatic $C_{10-16}$ tricyclic ring system containing one or more heteroatoms independently selected from the group consisting of N, S and O. Aromatic $C_{6-14}$ tricyclic ring systems of this type may be either fully aromatic (i.e., wherein all three rings are aromatic) or partially aromatic (i.e., wherein at least one ring is aromatic and at least one ring is not aromatic).

For example, in certain embodiments, Ring A is a optionally substituted fully aromatic $C_{10-16}$ tricyclic ring system containing one or more heteroatoms independently selected from the group consisting of N, S and O. Such tricyclic ring systems include, but are not limited to:

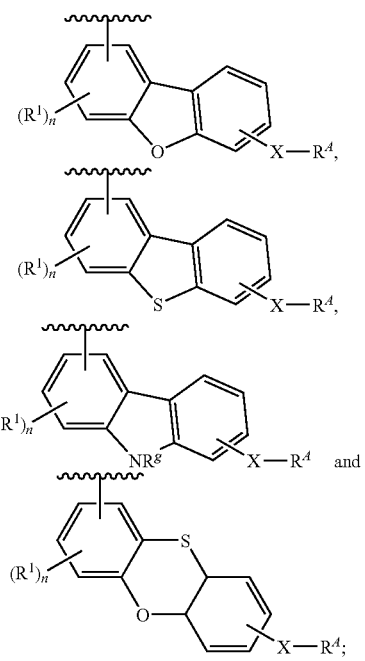

wherein X, $R^A$, $R^1$, $R^g$ and n are as defined above and herein.

In other embodiments, Ring A is a optionally substituted partially aromatic $C_{10-16}$ tricyclic ring system containing one or more heteroatoms independently selected from the group consisting of N, S and O.

In yet other embodiments, Ring A is a optionally substituted saturated or partially unsaturated $C_{10-16}$ tricyclic ring system containing one or more heteroatoms independently selected from the group consisting of N, S and O.

(iv) X

As is also defined generally above, X is a covalent bond or a bivalent $C_{1-6}$ hydrocarbon chain, wherein one, two or three methylene units of X are optionally and independently replaced with one or more —O—, —N=N—, —CH=CH—, —NR'—, —S—, —C(=O)—, —C(=NR')—, —S(=O)—, —S(=O)$_2$— or an optionally substituted phenylene moiety.

As is used herein, when one, two or three methylene units of X are optionally and independently replaced with one or more —O—, —N=N—, —CH=CH—, —NR'—, —S—, —C(=O)—, —C(=NR')—, —S(=O)—, —S(=O)$_2$— or an optionally substituted phenylene moiety, it is meant that one, two or three methylene units may be replaced with any of the groups —O—, —N=N—, —CH=CH—, —NR'—, —S—, —C(=O)—, —C(=NR')—, —S(=O)—, —S(=O)$_2$—, and/or any combination thereof (e.g., —C(=O)O—, —C(=O)S—, —C(=O)NR'—, —O-phenylene-, and the like).

In certain embodiments, X is a covalent bond.

In certain embodiments, X is a bivalent $C_{1-6}$ hydrocarbon chain. In other embodiments, X is a bivalent $C_{1-4}$ hydrocarbon chain. In yet other embodiments, X is a bivalent $C_{1-2}$ hydrocarbon chain. In yet other embodiments, X is —CH$_2$—.

In certain embodiments, X is a bivalent $C_{1-6}$ hydrocarbon chain, wherein one, two or three methylene units of X are optionally and independently replaced with one or more —O—, —N=N—, —CH=CH—, —NR'—, —S—, —C(=O)—, —C(=NR')—, —S(=O)—, —S(=O)$_2$— or an optionally substituted phenylene moiety.

In certain embodiments, X is a bivalent $C_{1-6}$ hydrocarbon chain, wherein one methylene unit of X are optionally and independently replaced with one or more —O—, —N=N—, —CH=CH—, —NR'—, —S—, —C(=O)—, —C(=NR')—, —S(=O)—, —S(=O)$_2$— or an optionally substituted phenylene moiety.

In certain embodiments, X is a bivalent $C_{1-6}$ hydrocarbon chain, wherein one methylene unit of X is replaced with —O—.

In certain embodiments, X is a bivalent $C_{1-6}$ hydrocarbon chain, wherein one methylene unit of X is replaced with —NR'—.

In certain embodiments, X is a bivalent $C_{1-6}$ hydrocarbon chain, wherein one methylene unit of X is replaced with an optionally substituted phenylene moiety.

Exemplary bivalent $C_{1-6}$ hydrocarbon chains of X include, but are not limited to:
—(CHR$^h$)$_r$O(CHR$^h$)$_q$—; —O(CHR$^h$)$_s$O(CHR$^h$)$_r$—; —(CHR$^h$)$_r$S(CHR$^h$)$_q$—; —(CHR$^h$)$_r$NR'(CHR$^h$)$_q$—; —(CHR$^h$)$_r$(C=O)(CHR$^h$)$_q$—; —(CHR$^h$)$_r$(C=O)O(CHR$^h$)$_q$—; —(C=O)(CHR$^h$)$_q$O—; —(CHR$^h$)$_r$(C=NR')(CHR$^e$)$_q$—; —(CHR$^h$)$_r$NR'(C=O)NR'(CHR$^h$); —O(CHR$^h$)$_r$(C=O)(CHR$^h$)$_r$NR'(CHR$^h$); —(CHR$^h$)$_r$(S=O)(CHR$^h$)$_q$—; —(CHR$^h$)$_r$SO$_2$(CHR$^h$)$_q$—; —(CHR$^h$)$_r$SO$_2$NR'(CHR$^h$)$_q$—; —(CHR$^h$)$_r$CH=CH(CHR$^h$)$_q$—; —(CHR$^h$)$_r$N=N(CHR$^h$)$_q$—; —(CHR$^h$)$_r$C(=O)NR'(CHR$^h$)$_q$—;

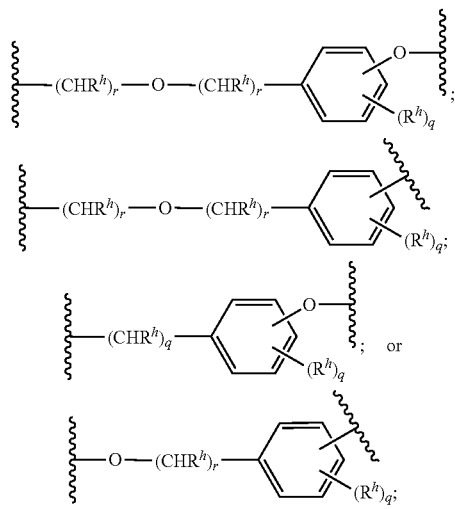

wherein R' is as defined above and herein;
$R^h$ is hydrogen, halogen, —OR$^i$, —NR$^k$$_2$, —C(=O)R$^m$, —C(=O)OR$^i$, —C(=O)N(R$^k$)$_2$, or an optionally substituted $C_{1-6}$ aliphatic, $C_{1-6}$ heteroaliphatic, $C_{6-12}$ aryl, or $C_{6-12}$ heteroaryl group; wherein R$^i$ is hydrogen, a suitable hydroxyl protecting group or an optionally substituted $C_{1-6}$ aliphatic, $C_{1-6}$ heteroaliphatic, $C_{6-12}$ aryl, or $C_{6-12}$ heteroaryl group, each instance of R$^k$ is, independently, hydrogen, a suitable amino protecting group, an optionally substituted $C_{1-6}$ aliphatic, $C_{1-6}$ heteroaliphatic, $C_{6-12}$ aryl, or $C_{6-12}$ heteroaryl group, or two R$^k$ are joined to form a 5- to 6-membered ring; and R$^m$ is hydrogen, or an optionally substituted $C_{1-6}$ aliphatic, $C_{1-6}$ heteroaliphatic, $C_{6-12}$ aryl, or $C_{6-12}$ heteroaryl group;
q is 0 to 4;
r is 0 to 1; and
s is 1 to 3.

In certain embodiments, when X is —(CHR$^h$)$_r$NR'(CHR$^h$)$_q$—, at least one fluorine substituent of Ring A is ortho to the boron (B) atom. In other embodiments, when X is —(CH$_2$)$_r$NR'(CH$_2$)$_q$—, at least one fluorine substituent of Ring A is ortho to the boron (B) atom. In yet other embodiments, when X is —NHCH$_2$—, at least one fluorine substituent of Ring A is ortho to the boron (B) atom. In still yet other embodiments, when X is —NHCH$_2$—, one fluorine substituent of Ring A is ortho to the boron (B) atom.

(v) R$^A$

As is defined generally above, R$^A$ is (i) hydrogen, halogen, —OH, —OR, —CF$_3$, —CN, —NO$_2$, —NC, —SO$_2$R, —SOR, —C(O)R, —CO$_2$R, —C(O)N(R')$_2$, —N$_3$, —N$_2$R, or —N(R')$_2$, wherein R and R' is as described herein; or (ii) Ring B having the formula:

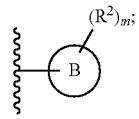

wherein Ring B is an optionally substituted saturated, partially unsaturated or aromatic $C_{5-8}$ monocyclic, $C_{6-10}$ bicyclic or $C_{10-16}$ tricyclic ring system optionally containing one or more heteroatoms independently selected from the group consisting of N, S and O.

In certain embodiments, R$^A$ is hydrogen, halogen, —OH, —OR, —CF$_3$, —CN, —NO$_2$, —NC, —SO$_2$R, —SOR, —C(O)R, —CO$_2$R, —C(O)N(R')$_2$, —N$_3$, —N$_2$R, or —N(R')$_2$, wherein R and R' are as defined above and herein.

In certain embodiments, X is a covalent bond and R$^A$ is hydrogen, halogen, —OH, —OR, —CF$_3$, —CN, —NO$_2$, —NC, —SO$_2$R, —SOR, —C(O)R, —CO$_2$R, —C(O)N(R')$_2$, —C(O)NH$_2$, —CHO, —N$_3$, —N$_2$R, or —N(R')$_2$, wherein R and R' are as defined above and herein.

(vi) Ring B

As is defined generally above, R$^A$ is, in certain embodiments, Ring B of the formula:

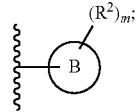

wherein Ring B is an optionally substituted saturated, partially unsaturated or aromatic $C_{5-8}$ monocyclic, $C_{6-10}$ bicyclic or $C_{10-16}$ tricyclic ring system optionally containing one or more heteroatoms independently selected from the group consisting of N, S and O.

In certain embodiments, Ring B is an aromatic ring system. In certain embodiments, both Ring B and Ring A are aromatic ring systems. However, in certain embodiments, Ring B is a saturated or partially unsaturated ring system.

(a) Monocyclic Ring Systems

In certain embodiments, Ring B is a optionally substituted saturated, partially unsaturated or aromatic $C_{5-8}$ monocyclic ring system, optionally containing one or more heteroatoms independently selected from the group consisting of N, S and O.

In some embodiments, Ring B is a optionally substituted saturated, partially unsaturated or aromatic $C_{5-8}$ monocyclic carbocyclic ring system.

For example, in some embodiments, Ring B is an optionally substituted aromatic $C_6$ or $C_8$ monocyclic carbocyclic ring system. Such monocyclic carbocyclic ring systems include, but are not limited to:

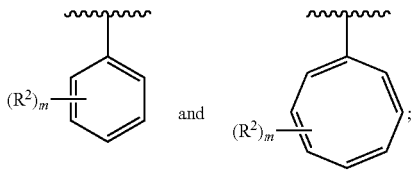

wherein $R^2$ and m are as defined above and herein.

In certain embodiments, Ring B is an optionally substituted phenyl ring system of the formula:

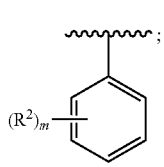

wherein $R^2$ and m are as defined above and herein; and m is an integer between 0 to 5, inclusive.

In certain embodiments, m is an integer between 0 to 3. In some embodiments, m is an integer between 0 to 2. In other embodiments, m is 1 or 2. In yet other embodiments, m is 1. In still yet other embodiments, m is 2. In still yet other embodiments, m is 0.

In certain embodiments, Ring B is an optionally substituted phenyl ring system of any one of the formulae:

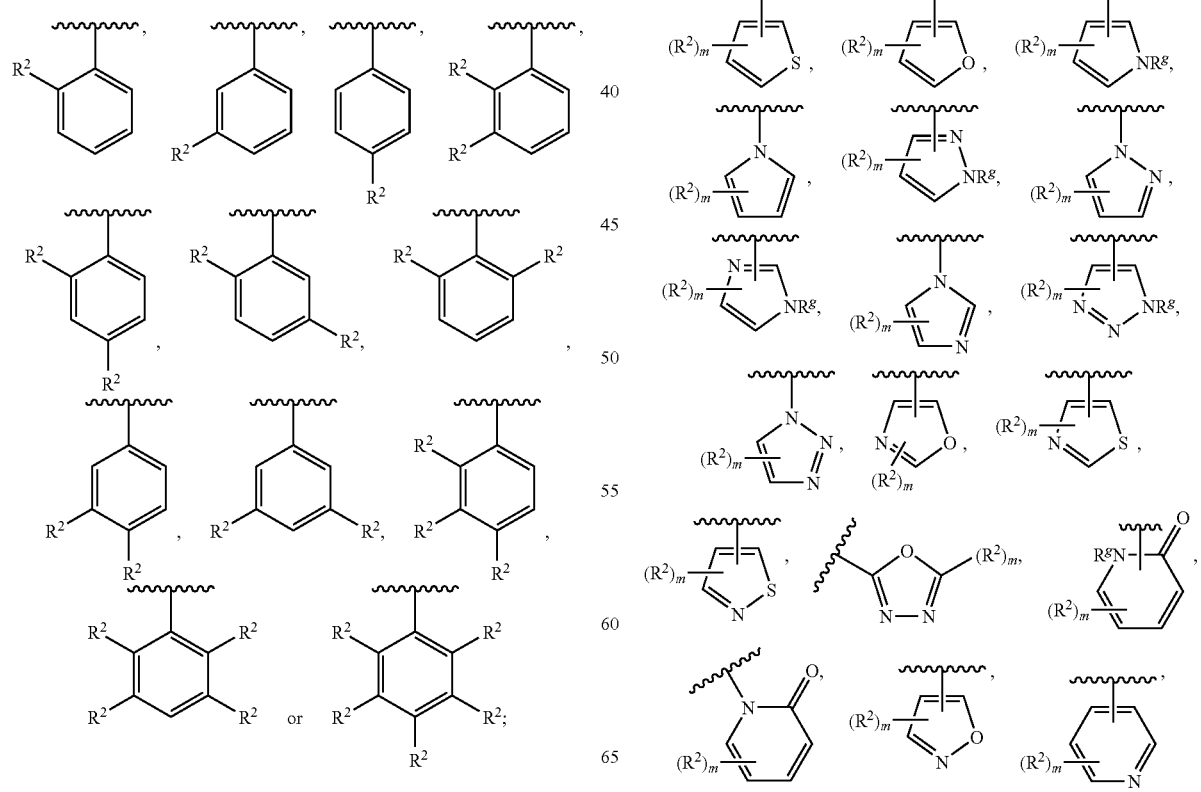

wherein $R^2$ is as defined above and herein.

In certain embodiments, Ring B is phenyl. In certain embodiments, both Ring B and Ring A are phenyl.

In other embodiments, Ring B is an optionally substituted saturated or partially unsaturated $C_{5-8}$ monocyclic carbocyclic ring system. Such monocyclic carbocyclic ring systems include, but are not limited to:

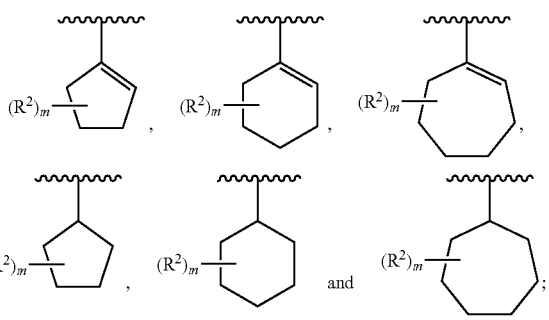

wherein $R^2$ and m are as defined above and herein.

In other embodiments, Ring B is a optionally substituted saturated, partially unsaturated or aromatic $C_{5-8}$ monocyclic ring system containing one or more heteroatoms independently selected from the group consisting of N, S and O.

For example, in certain embodiments, Ring B is a optionally substituted aromatic $C_{5-8}$ monocyclic ring system containing one or more heteroatoms independently selected from the group consisting of N, S and O. Such aromatic monocyclic ring systems include, but are not limited to:

-continued

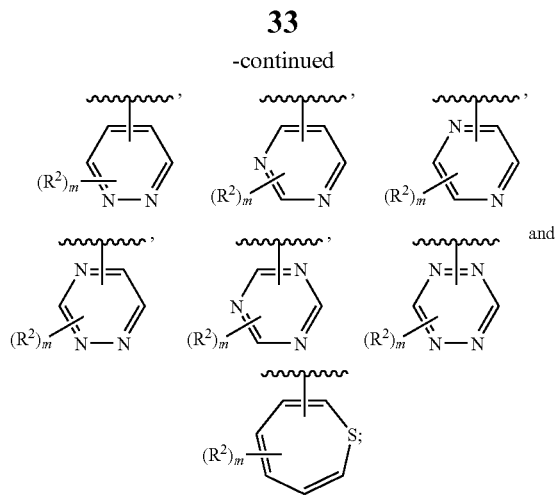

wherein $R^2$ and m are as defined above and herein, and $R^g$ is hydrogen, a suitable amino protecting group, or an optionally substituted $C_{1-6}$ aliphatic, $C_{1-6}$ heteroaliphatic, $C_{6-12}$ aryl, or $C_{6-12}$ heteroaryl group.

In other embodiments, Ring B is a optionally substituted saturated or partially unsaturated $C_{5-8}$ monocyclic ring system containing one or more heteroatoms independently selected from the group consisting of N, S and O. Such saturated or partially unsaturated monocyclic ring systems include, but are not limited to:

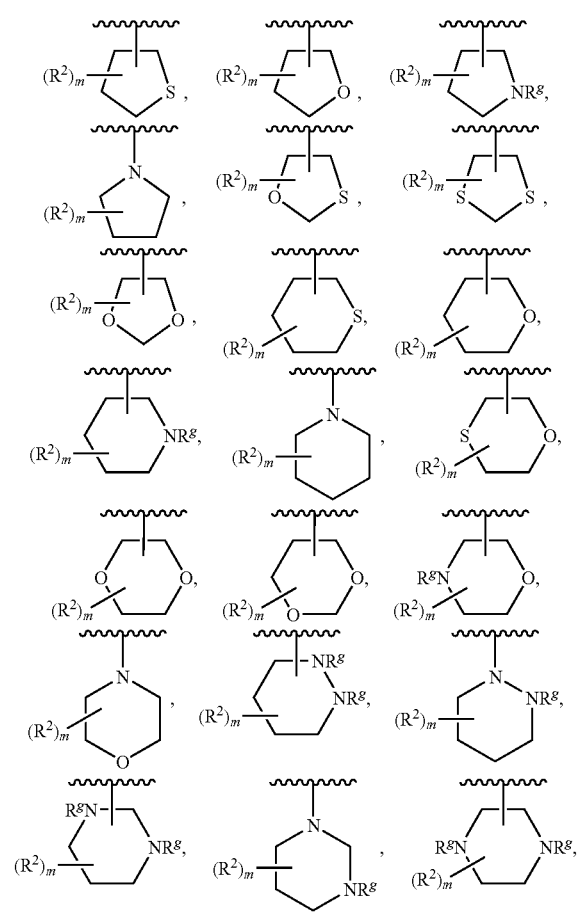

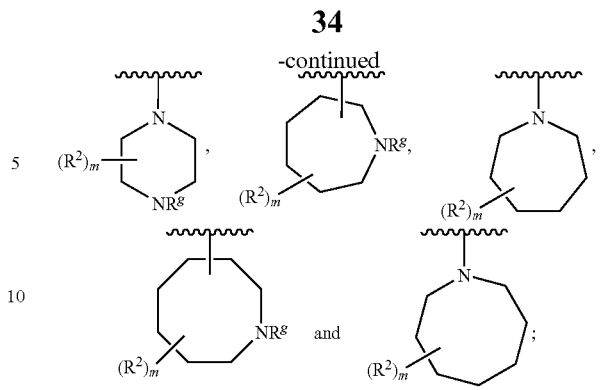

wherein $R^2$, $R^g$ and m are as defined above and herein.

(b) Bicyclic Ring B Groups

In certain embodiments, Ring B is a optionally substituted saturated, partially unsaturated or aromatic $C_{6-10}$ bicyclic ring system optionally containing one or more heteroatoms independently selected from the group consisting of N, S and O.

In certain embodiments, Ring B is a optionally substituted saturated, partially unsaturated or aromatic $C_{6-10}$ bicyclic carbocyclic ring system.

In certain embodiments, Ring B is a optionally substituted aromatic $C_{6-10}$ bicyclic carbocyclic ring system. Aromatic $C_{6-10}$ bicyclic ring systems of this type may be either fully aromatic (i.e., wherein both rings are aromatic) or partially aromatic (i.e., wherein one ring is aromatic and one ring is not aromatic).

For example, in certain embodiments, Ring B is a optionally substituted fully aromatic $C_{6-10}$ bicyclic carbocyclic ring system. Such bicyclic carbocyclic ring systems include, but are not limited to:

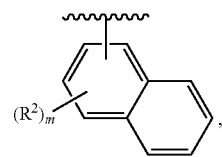

wherein $R^2$ and m are as defined above and herein.

In other embodiments, Ring A is a optionally substituted partially aromatic $C_{6-10}$ bicyclic carbocyclic ring system. Such bicyclic carbocyclic ring systems include, but are not limited to:

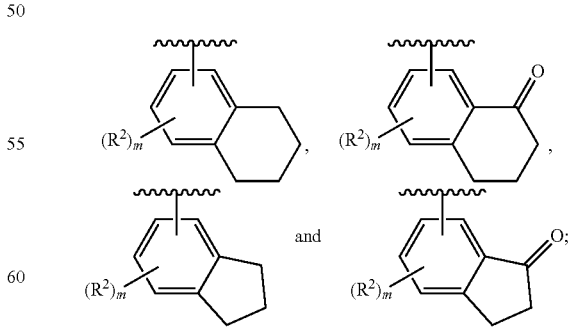

wherein $R^2$ and m are as defined above and herein.

In yet other embodiments, Ring B is a optionally substituted saturated or partially unsaturated $C_{6-10}$ bicyclic carbocyclic ring system.

In certain embodiments, Ring B is a optionally substituted aromatic $C_{6-10}$ bicyclic ring system containing one or more heteroatoms independently selected from the group consisting of N, S and O. Aromatic $C_{6-10}$ bicyclic ring systems of this type may be either fully aromatic (i.e., wherein both rings are aromatic) or partially aromatic (i.e., wherein one ring is aromatic and one ring is not aromatic).

For example, in certain embodiments, Ring B is a optionally substituted fully aromatic $C_{6-10}$ bicyclic ring system containing one or more heteroatoms independently selected from the group consisting of N, S and O. Such aromatic bicyclic ring systems include, but are not limited to:

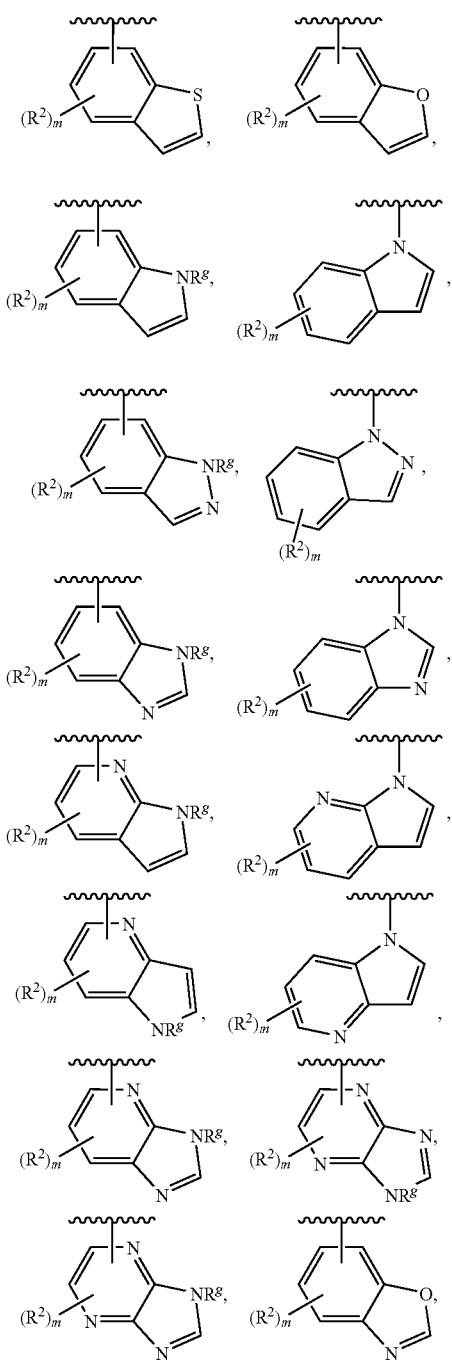

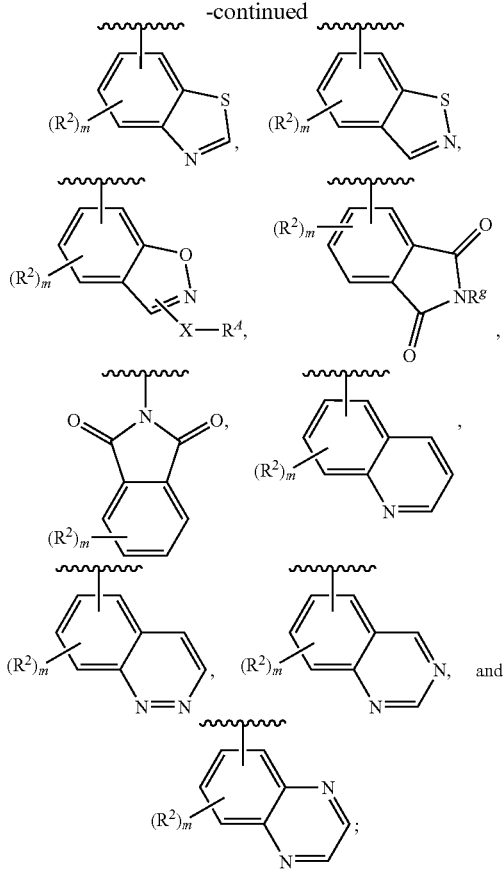

wherein $R^2$, $R^g$ and m are as defined above and herein.

In other embodiments, Ring B is a optionally substituted partially aromatic $C_{6-10}$ bicyclic ring system containing one or more heteroatoms independently selected from the group consisting of N, S and O. Such bicyclic ring systems include, but are not limited to:

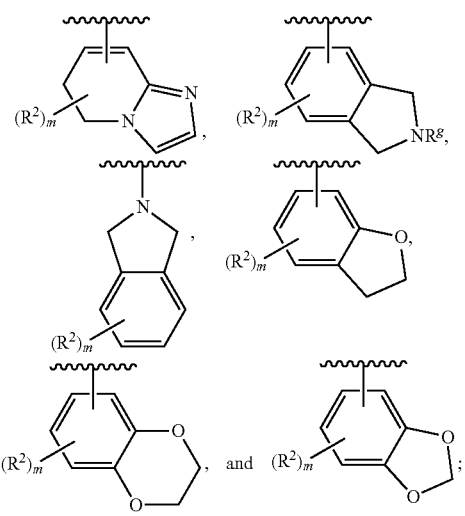

wherein $R^2$, $R^g$ and m are as defined above and herein.

In yet other embodiments, Ring B is a optionally substituted saturated or partially unsaturated $C_{6-10}$ bicyclic ring system containing one or more heteroatoms independently selected from the group consisting of N, S and O.

(c) Tricyclic Ring B Groups

In certain embodiments, Ring B is a optionally substituted saturated, partially unsaturated or aromatic $C_{10-16}$ tricyclic ring system optionally containing one or more heteroatoms independently selected from the group consisting of N, S and O.

In certain embodiments, Ring B is a optionally substituted saturated, partially unsaturated or aromatic $C_{10-16}$ tricyclic, carbocyclic ring system. Such tricyclic carbocyclic ring systems include, but are not limited to:

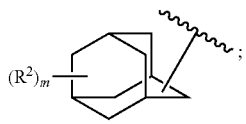

wherein $R^2$ and m are as defined above and herein.

In certain embodiments, Ring B is a optionally substituted aromatic $C_{10-16}$ tricyclic, carbocyclic ring system. Aromatic $C_{6-14}$ tricyclic ring systems of this type may be either fully aromatic (i.e., wherein all three rings are aromatic) or partially aromatic (i.e., wherein at least one ring is aromatic and at least one ring is not aromatic).

For example, in certain embodiments, Ring B is a optionally substituted fully aromatic $C_{10-16}$ tricyclic, carbocyclic ring system. Such tricyclic carbocyclic ring systems include, but are not limited to:

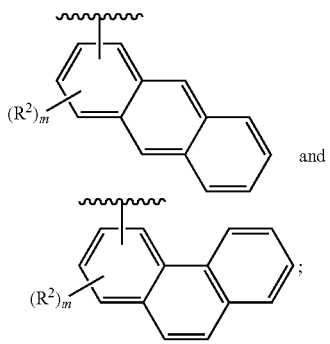

wherein $R^2$ and m are as defined above and herein.

In other embodiments, Ring B is a optionally substituted partially aromatic $C_{10-16}$ tricyclic, carbocyclic ring system. Such tricyclic carbocyclic ring systems include, but are not limited to:

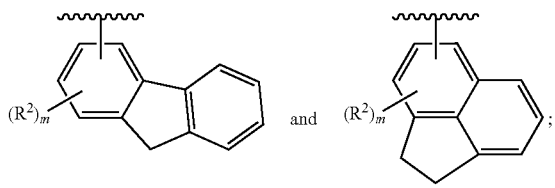

wherein $R^2$ and m are as defined above and herein.

In certain embodiments, Ring B is a optionally substituted saturated, partially unsaturated or aromatic $C_{10-16}$ tricyclic ring system containing one or more heteroatoms independently selected from the group consisting of N, S and O.

For example, in certain embodiments, Ring B is a optionally substituted aromatic $C_{10-16}$ tricyclic ring system containing one or more heteroatoms independently selected from the group consisting of N, S and O. Aromatic $C_{6-14}$ tricyclic ring systems of this type may be either fully aromatic (i.e., wherein all three rings are aromatic) or partially aromatic (i.e., wherein at least one ring is aromatic and at least one ring is not aromatic).

For example, in certain embodiments, Ring B is a optionally substituted fully aromatic $C_{10-16}$ tricyclic ring system containing one or more heteroatoms independently selected from the group consisting of N, S and O. Such tricyclic ring systems include, but are not limited to:

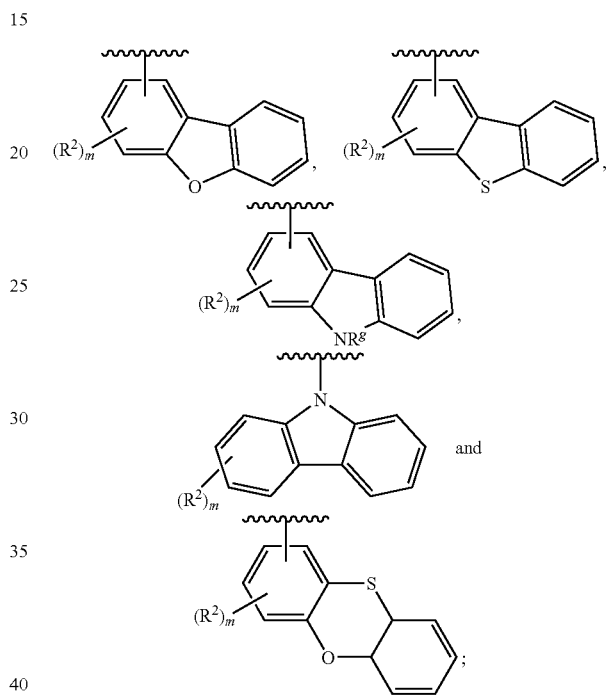

wherein $R^2$, $R^g$ and m are as defined above and herein.

In other embodiments, Ring B is a optionally substituted partially aromatic $C_{10-16}$ tricyclic ring system containing one or more heteroatoms independently selected from the group consisting of N, S and O.

In yet other embodiments, Ring B is a optionally substituted saturated or partially unsaturated $C_{10-16}$ tricyclic ring system containing one or more heteroatoms independently selected from the group consisting of N, S and O.

(vii) $R^1$

As is also defined generally above, each instance of $R^1$ is, independently, halogen, —OR, —CF$_3$, —CN, —NO$_2$, —NC, —SO$_2$R, —SOR, —C(O)R, —CO$_2$R, —C(O)N(R')$_2$, —N$_3$, —N$_2$R, —N(R')$_2$, —B(OH)$_2$, or an optionally substituted $C_{1-8}$ aliphatic group, wherein each instance of R and R' is as described herein; or two $R^1$ groups together form a 5- to 6-membered heterocyclic ring.

In certain embodiments, each instance of $R^1$ is, independently, halogen, —OR, —CF$_3$, —CN, —NO$_2$, —NC, —SO$_2$R, —SOR, —C(O)R, —CO$_2$R, —C(O)N(R')$_2$, —N$_3$, —N$_2$R, or —N(R')$_2$.

In certain embodiments, each instance of $R^1$ is, independently, halogen, or —OR. In some embodiments, $R^1$ is halogen. In other embodiments, $R^1$ is —F or —Cl. In yet other embodiments, $R^1$ is —F.

In certain embodiments, at least one $R^1$ is ortho to the boron atom. In other embodiments, at least one $R^1$ is meta to the boron atom. In yet other embodiments, at least one $R^1$ is para to the boron atom.

In yet other embodiments, n is 1 and $R^1$ is ortho to the boron atom. In other embodiments, n is 1 and $R^1$ is meta to the boron atom. In yet other embodiments, n is 1 and $R^1$ is para to the boron atom.

(viii) $R^2$

As is also defined generally above, each instance of $R^2$ is, independently, halogen, —OR, —$CF_3$, —CN, —$NO_2$, —NC, —$SO_2R$, —SOR, —C(O)R, —$CO_2R$, —C(O)N(R')$_2$, —$N_3$, —$N_2R$, —N(R')$_2$, or an optionally substituted $C_{1-8}$ aliphatic group, wherein each instance of R and R' is, as described herein.

In certain embodiments, each instance of $R^2$ is, independently, halogen, —OR, —$CF_3$, —CN, —$NO_2$, —NC, —$SO_2R$, —SOR, —C(O)R, —$CO_2R$, —C(O)N(R')$_2$, —$N_3$, —$N_2R$, —N(R')$_2$ or an optionally substituted $C_1$ aliphatic group.

In certain embodiments, each instance of $R^2$ is, independently, halogen or —OR. In some embodiments, $R^2$ is halogen. In other embodiments, $R^2$ is —F or —Cl. In yet other embodiments, $R^2$ is —F.

In certain embodiments, at least one $R^2$ is ortho to the linker group X. In other embodiments, at least one $R^2$ is meta to the linker group X. In other embodiments, at least one $R^2$ is para to the linker group X.

In yet other embodiments, m is 1 and $R^2$ is ortho to the linker group X. In other embodiments, m is 1 and $R^2$ is meta to the linker group X. In yet other embodiments, m is 1 and $R^2$ is para to the linker group X.

(ix) Exemplary Compounds

Exemplary compounds of the present invention are set forth in the Examples and in Tables 1 and 2, provided below. Compounds of the present invention were assayed as inhibitors of human or rat FAAH using the method described in detail in Example 172. Activity of exemplified compounds is provided in Tables 1 and 2, below, wherein activity designated as "A" refers to compounds having a $K_i$ of less than or equal to 0.01 microM, "B" refers to compounds having a $K_i$ of between 0.01 microM and 0.1 microM, "C" refers to compounds having a $K_i$ of between 0.01 microM and 1 microM, and "D" refers to compounds having a $K_i$ of greater than 1 microM.

TABLE 1

| Compound | Activity |
|---|---|
| 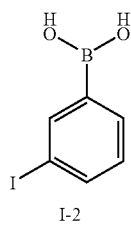 I-1 | C |
| 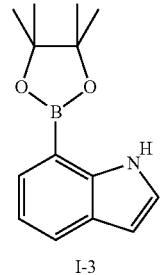 I-2 | B |
| 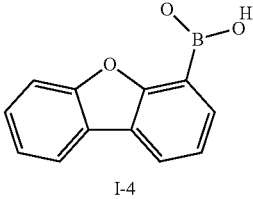 I-3 | D |
| 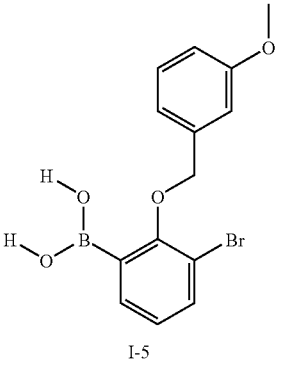 I-4 | C |
| 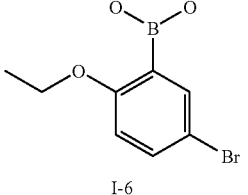 I-5 | D |
| 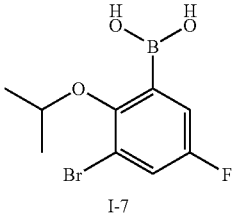 I-6 | D |
| 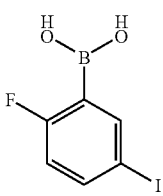 I-7 | D |

TABLE 1-continued
| Compound | Activity |
|---|---|
| 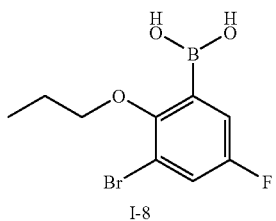<br>I-8 | D |
| 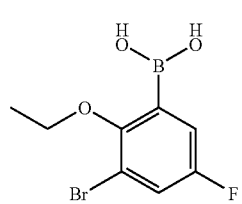<br>I-9 | C |
| 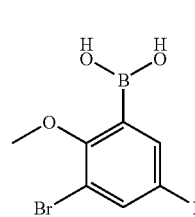<br>I-10 | B |
| 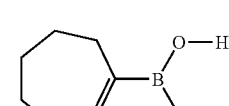<br>I-11 | D |
| 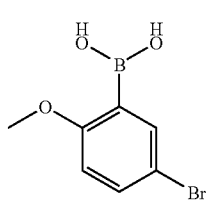<br>I-12 | D |
| 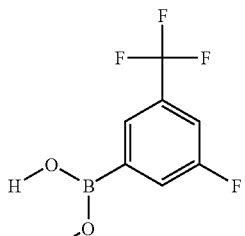<br>I-13 | B |
| 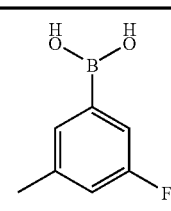<br>I-14 | C |
| 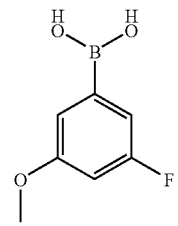<br>I-15 | C |
| 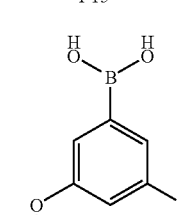<br>I-16 | C |
| 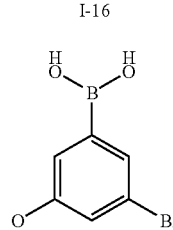<br>I-17 | D |
| 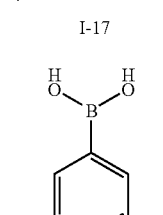<br>I-18 | B |
| 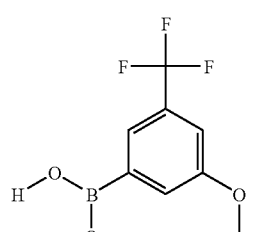<br>I-19 | D |

TABLE 1-continued
| Compound | Activity |
|---|---|
| 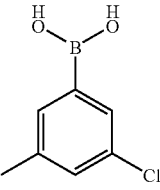<br>I-20 | C |
| 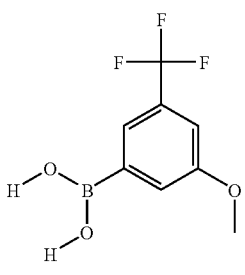<br>I-21 | D |
| 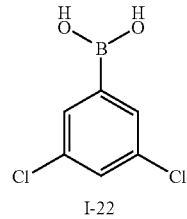<br>I-22 | C |
| 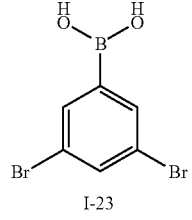<br>I-23 | C |
| 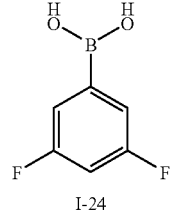<br>I-24 | C |
| 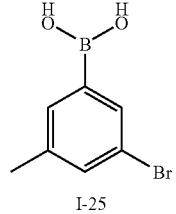<br>I-25 | C |
| 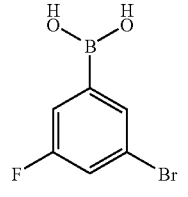<br>I-26 | B |
| 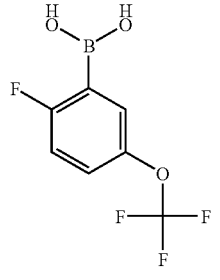<br>I-27 | B |
| 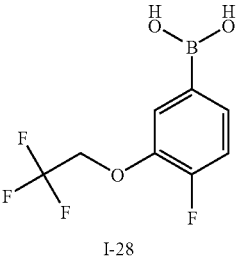<br>I-28 | C |
| 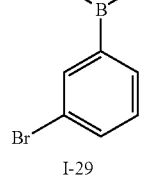<br>I-29 | B |
| 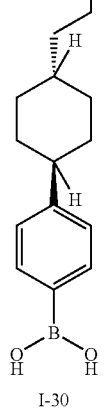<br>I-30 | A |

TABLE 1-continued
| Compound | Activity |
|---|---|
| 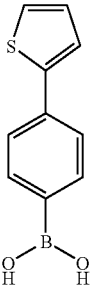 I-31 | B |
| 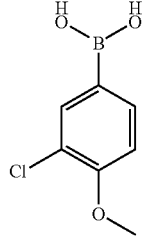 I-32 | C |
| 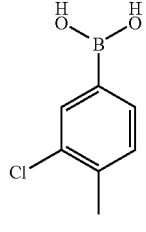 I-33 | C |
| 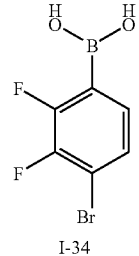 I-34 | B |
| 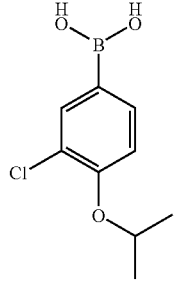 I-35 | B |
| 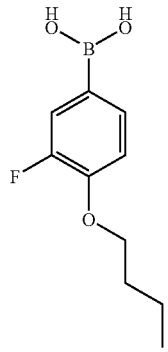 I-36 | A |
| 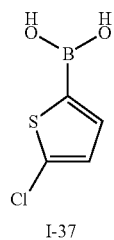 I-37 | C |
| 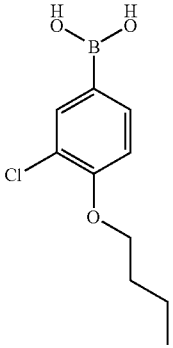 I-38 | A |
| 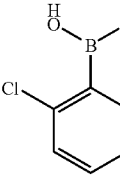 I-39 | C |
| 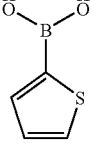 I-40 | D |

TABLE 1-continued

| Compound | Activity |
|---|---|
| I-41 (isoquinolin-5-yl boronic acid) | D |
| I-42 (3-acetylphenyl boronic acid) | C |
| I-43 (4-cyclopentylphenyl boronic acid) | A |
| I-44 (4-bromo-2,3,5,6-tetrafluorophenyl boronic acid) | D |
| I-45 (3-(trifluoromethoxy)phenyl boronic acid) | C |
| I-46 (4-cyanophenyl boronic acid) | C |
| I-47 (3-(methylsulfonyl)phenyl boronic acid) | D |
| I-48 (2-(2,2,2-trifluoroethyl)phenyl boronic acid) | C |
| I-49 (4-heptylphenyl boronic acid) | A |
| I-50 (3-(trifluoromethyl)phenyl boronic acid) | B |

TABLE 1-continued
| Compound | Activity |
|---|---|
| 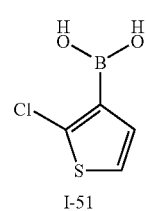 I-51 | C |
| 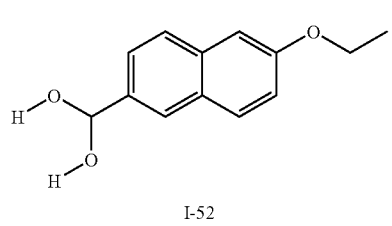 I-52 | A |
| 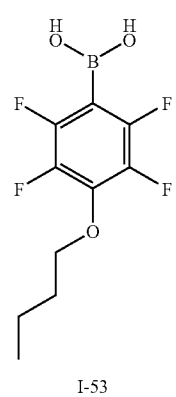 I-53 | D |
| 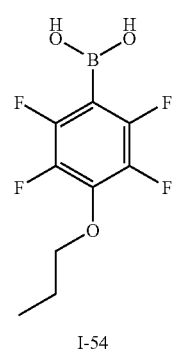 I-54 | D |
| 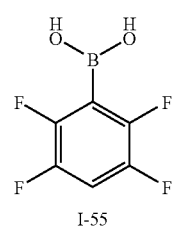 I-55 | D |
TABLE 1-continued
| Compound | Activity |
|---|---|
| 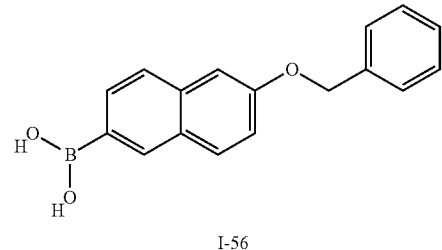 I-56 | A |
| 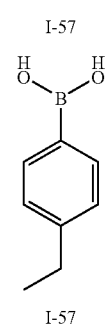 I-57 | C |
| 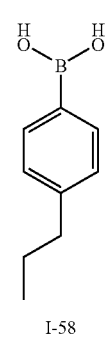 I-58 | B |
| 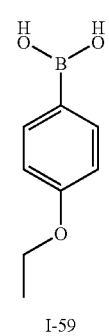 I-59 | C |
| 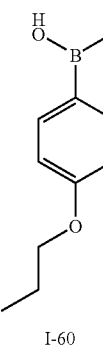 I-60 | B |

TABLE 1-continued
| Compound | Activity |
|---|---|
| 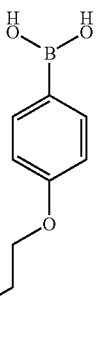 I-61 | B |
| 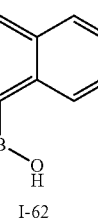 I-62 | D |
| 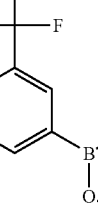 I-63 | D |
| 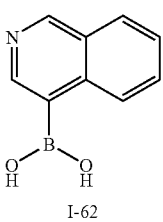 I-64 | D |
| 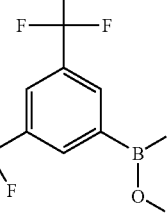 I-65 | D |
| 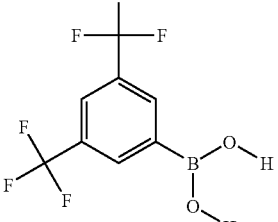 I-66 | D |
| 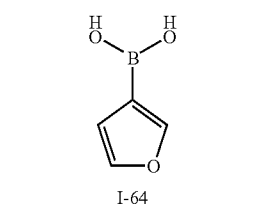 I-67 | C |
| 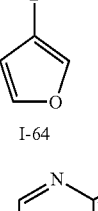 I-68 | D |
| 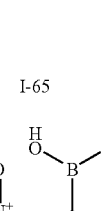 I-69 | C |
| 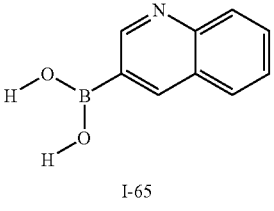 I-70 | B |
| 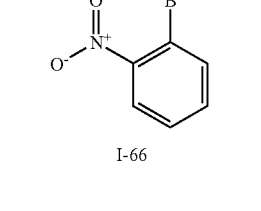 I-71 | D |
| 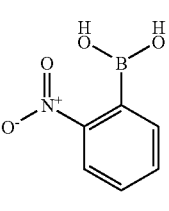 I-72 | D |

TABLE 1-continued
| Compound | Activity |
|---|---|
| 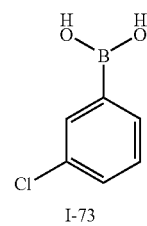<br>I-73 | C |
| 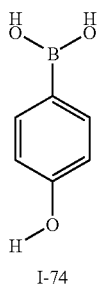<br>I-74 | D |
| 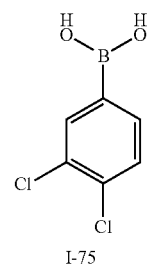<br>I-75 | B |
| 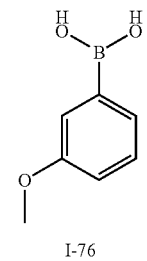<br>I-76 | D |
| 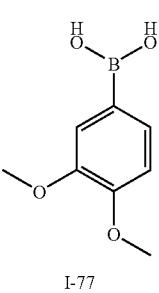<br>I-77 | D |
| 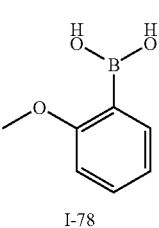<br>I-78 | D |
TABLE 1-continued
| Compound | Activity |
|---|---|
| 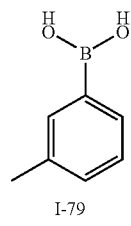<br>I-79 | D |
| 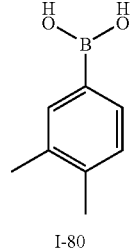<br>I-80 | C |
| 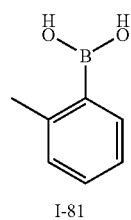<br>I-81 | D |
| 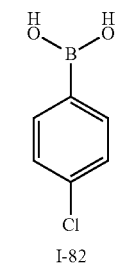<br>I-82 | C |
| 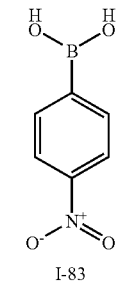<br>I-83 | C |
| 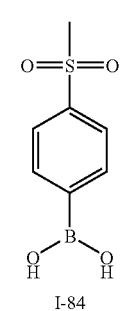<br>I-84 | C |

TABLE 1-continued
| Compound | Activity |
|---|---|
| 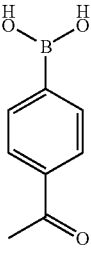 I-85 | C |
| 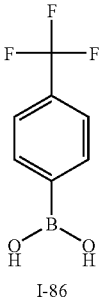 I-86 | B |
| 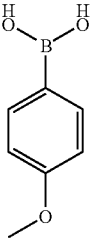 I-87 | D |
| 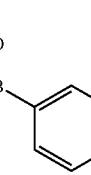 I-88 | D |
| 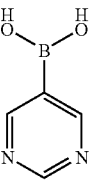 I-89 | D |
| 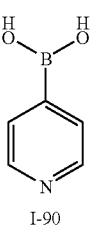 I-90 | D |
| 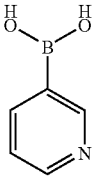 I-91 | D |
| 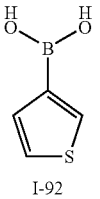 I-92 | D |
| 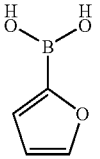 I-93 | D |
| 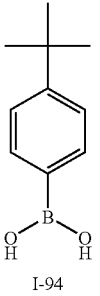 I-94 | B |
| 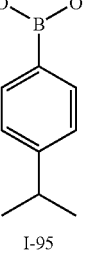 I-95 | B |
| 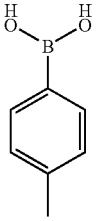 I-96 | D |

TABLE 1-continued
| Compound | Activity |
|---|---|
| 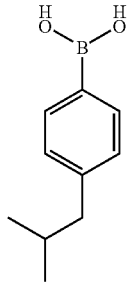 I-97 | B |
| 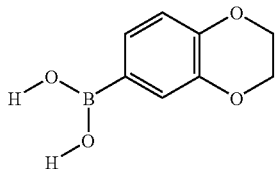 I-98 | C |
| 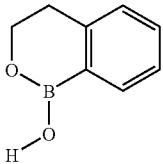 I-99 | D |
| 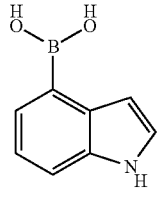 I-100 | D |
| 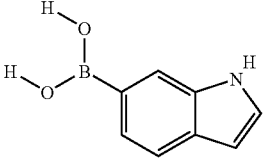 I-101 | D |
| 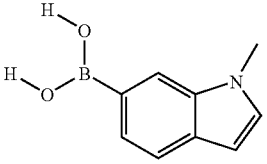 I-102 | D |
TABLE 1-continued
| Compound | Activity |
|---|---|
| 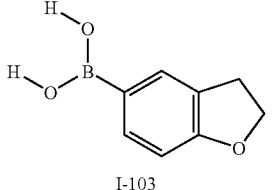 I-103 | D |
| 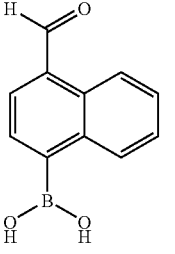 I-104 | C |
| 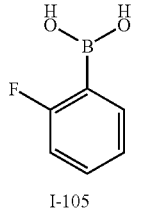 I-105 | C |
| 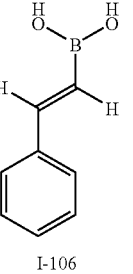 I-106 | D |
| 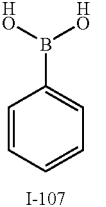 I-107 | D |
| 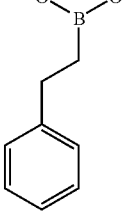 I-108 | D |

TABLE 1-continued
| Compound | Activity |
|---|---|
| 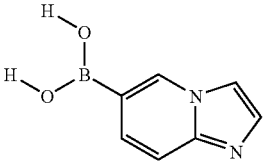 I-109 | D |
| 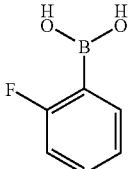 I-110 | C |
| 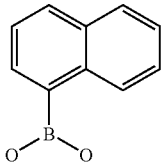 I-111 | C |
| 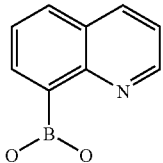 I-112 | D |
| 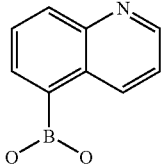 I-113 | C |
| 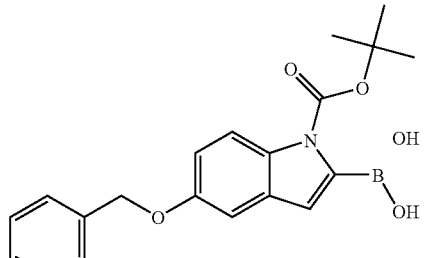 I-114 | D |
| 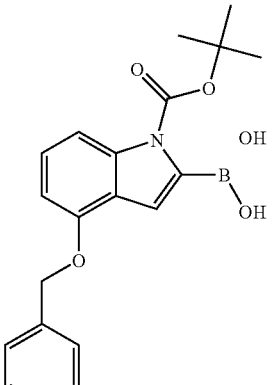 I-115 | D |
| 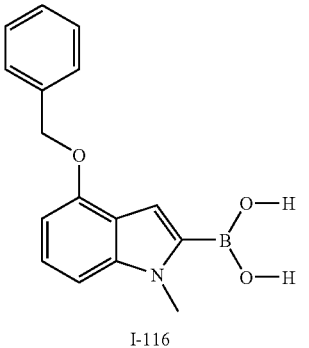 I-116 | D |
| 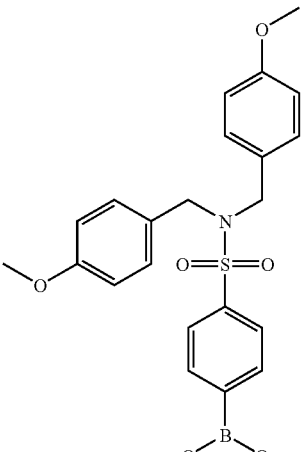 I-117 | D |

TABLE 1-continued
| Compound | Activity |
|---|---|
| 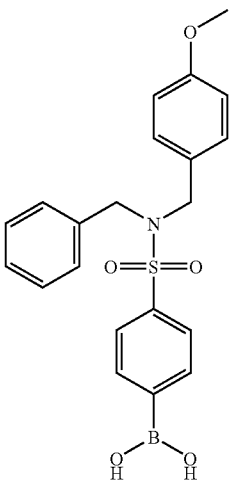 I-118 | C |
| 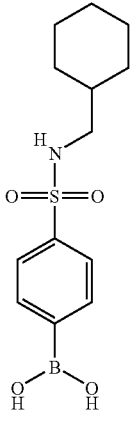 I-119 | C |
| 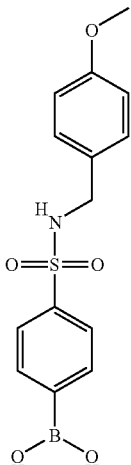 I-120 | B |
TABLE 1-continued
| Compound | Activity |
|---|---|
| 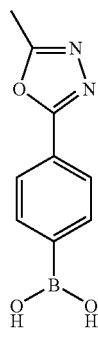 I-121 | B |
| 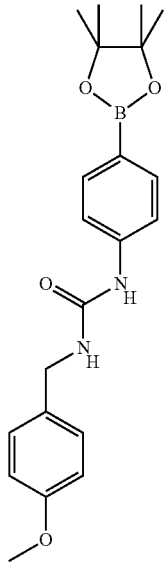 I-122 | C |
| 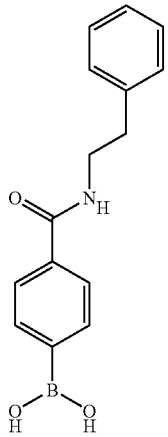 I-123 | A |

TABLE 1-continued

| Compound | Activity |
|---|---|
| I-124 | B |
| I-125 | D |
| I-126 | D |
| I-127 | C* |
| I-128 | D |
| I-129 | — |
| I-130 | C* |
| I-131 | D |
| I-130 | — |

TABLE 1-continued
| Compound | Activity |
|---|---|
| 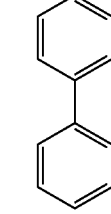 I-131 | D |
| I-132 | D |
| I-133 | D |
| I-134 | B |
| I-135 | C |
| I-136 | D |
| I-137 | — |
| I-138 | C |
| I-139 | C |

TABLE 1-continued

| Compound | Activity |
|---|---|
| I-140 | B |
| I-141 | B |
| I-142 | — |
| I-143 | D |
| I-144 | — |
| I-145 | — |
| I-146 | A |

TABLE 1-continued
| Compound | Activity |
|---|---|
| 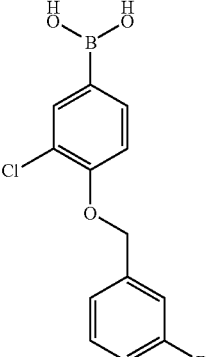 I-147 | A |
| 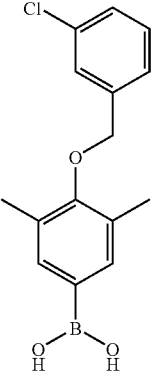 I-148 | A |
| 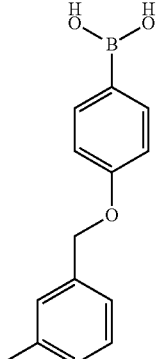 I-149 | — |
| 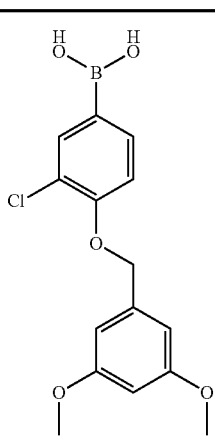 I-150 | — |
| 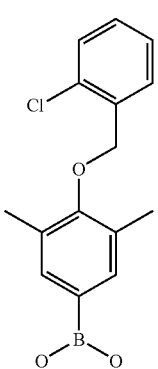 I-151 | — |
| 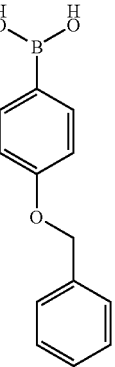 I-152 | A |

TABLE 1-continued
| Compound | Activity |
|---|---|
| 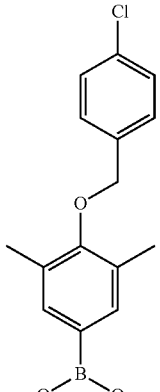 I-153 | — |
| 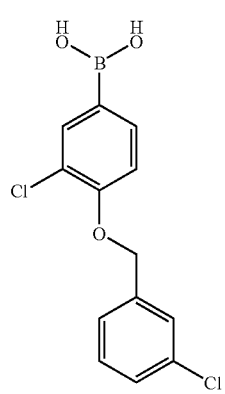 I-154 | A |
| 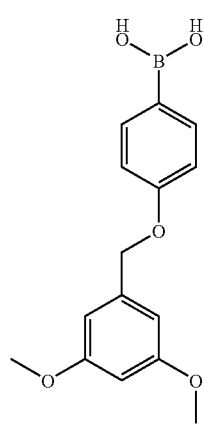 I-155 | — |
| 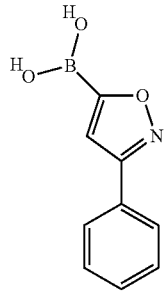 I-156 | — |
| 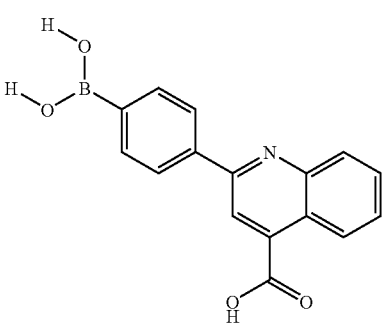 I-157 | — |
| 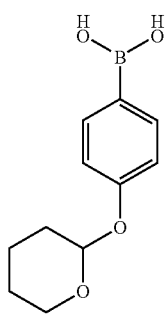 I-158 | B |
| 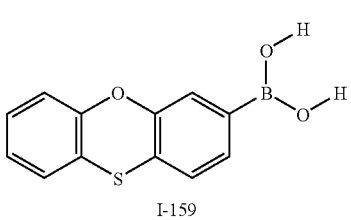 I-159 | D |
| 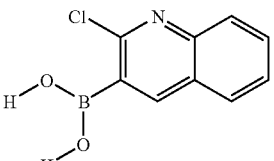 I-160 | D |

TABLE 1-continued
| Compound | Activity |
|---|---|
| 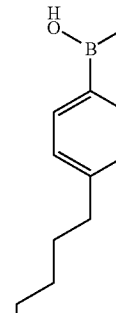 I-161 | A |
| 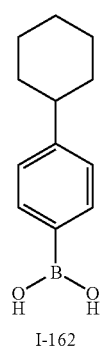 I-162 | A |
| 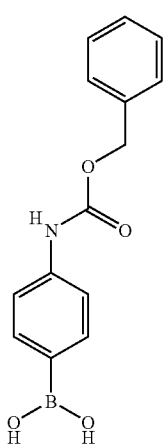 I-163 | B |
TABLE 1-continued
| Compound | Activity |
|---|---|
| 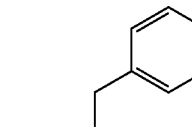 I-164 | A |
| I-165 | D |
| I-166 | — |

TABLE 1-continued
| Compound | Activity |
|---|---|
| 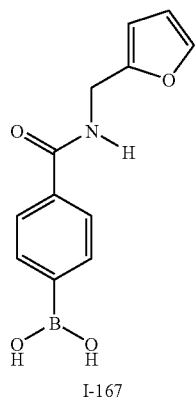<br>I-167 | B |
| 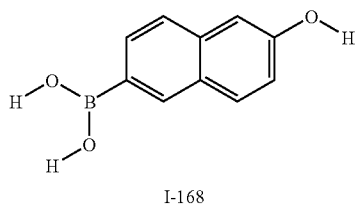<br>I-168 | B |
| 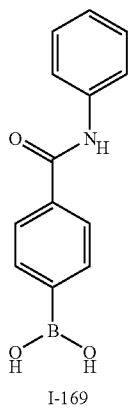<br>I-169 | B |
| 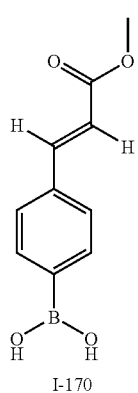<br>I-170 | — |
TABLE 1-continued
| Compound | Activity |
|---|---|
| 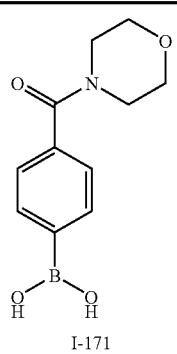<br>I-171 | C |
| 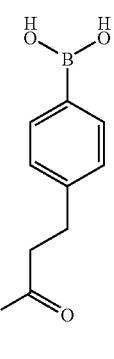<br>I-172 | — |
| 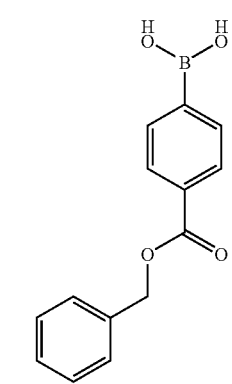<br>I-173 | A |
| 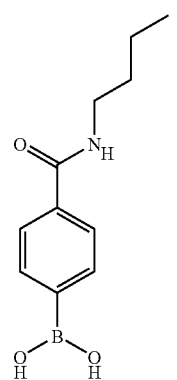<br>I-174 | — |

TABLE 1-continued
| Compound | Activity |
|---|---|
| 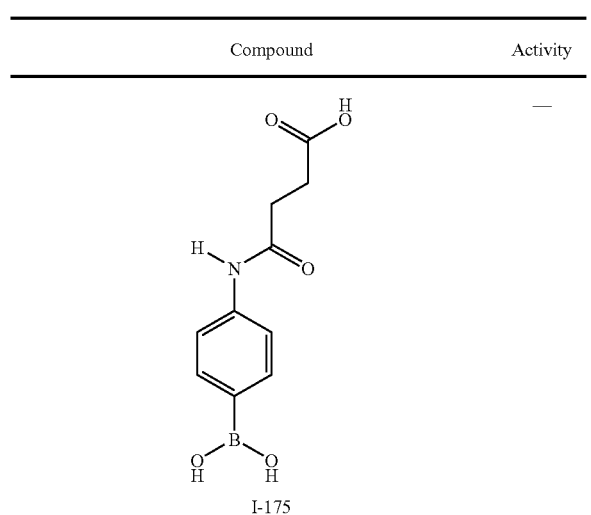  I-175 | — |
| I-176 | D |
| I-177 | — |
| I-178 | B |
| I-179 | — |
| I-180 | — |
| I-181 | C |
| I-182 | D |
| I-183 | D |
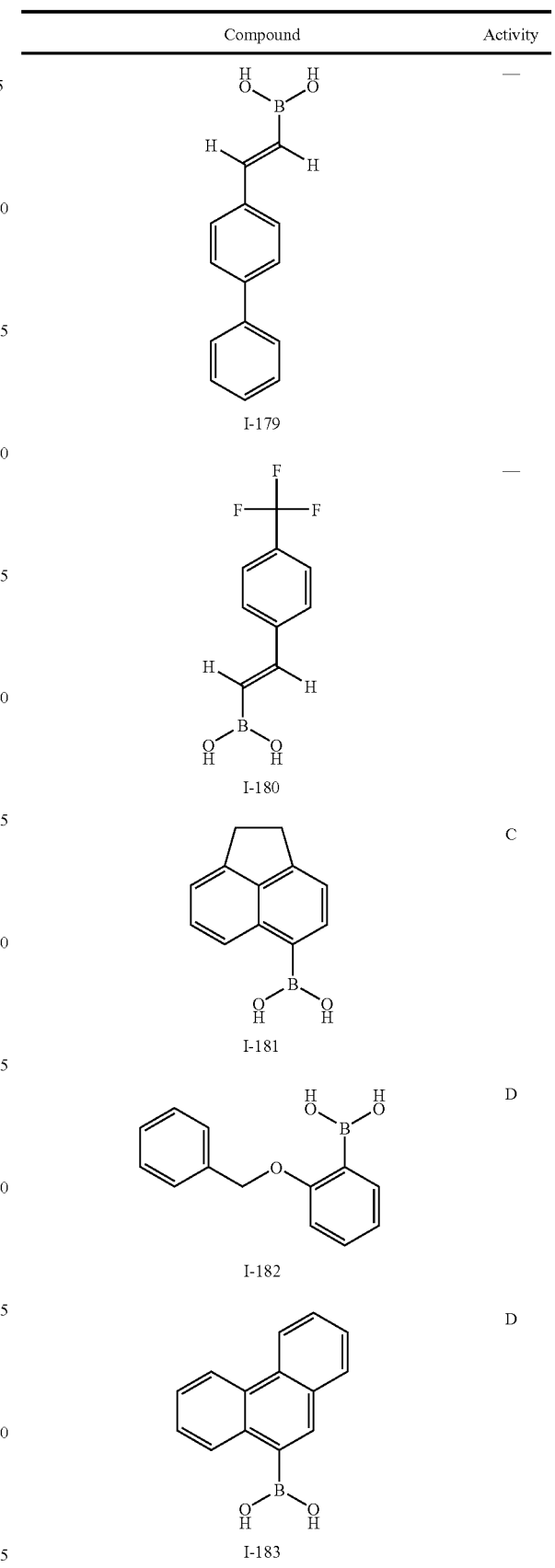

TABLE 1-continued
| Compound | Activity |
|---|---|
| 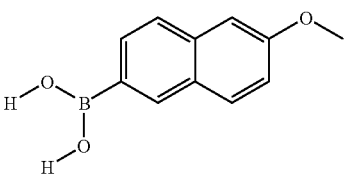 I-184 | B |
| 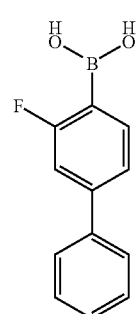 I-185 | A |
| 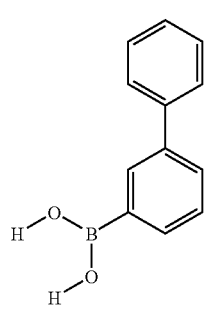 I-186 | C |
| 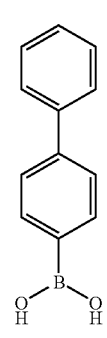 I-187 | B |
| 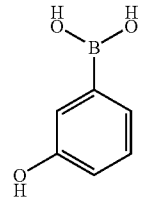 I-188 | — |
| 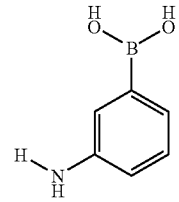 I-189 | — |
| 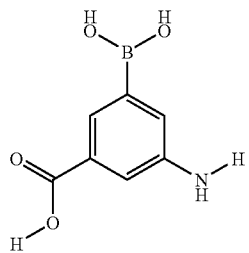 I-190 | — |
| 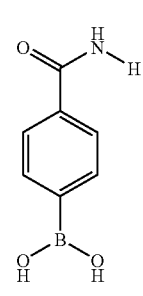 I-191 | — |
| 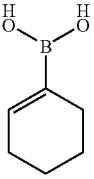 I-192 | — |
| 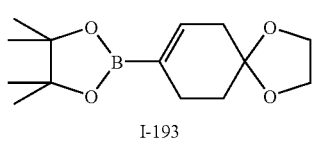 I-193 | — |
| 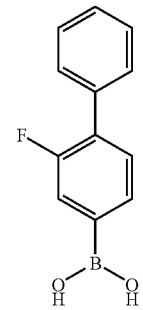 I-194 | A |

TABLE 1-continued
| Compound | Activity |
|---|---|
| 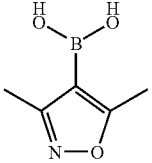 I-195 | — |
| 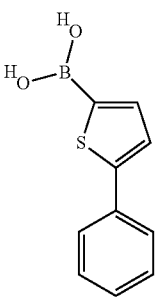 I-196 | B |
| 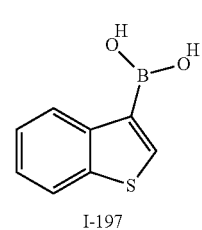 I-197 | B |
| 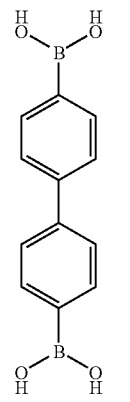 I-198 | B |
| 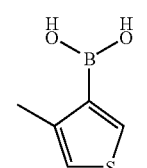 I-199 | — |
| 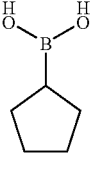 I-200 | — |
| 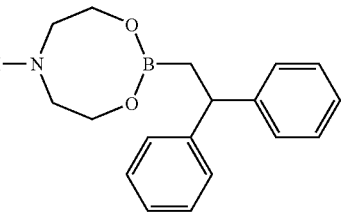 I-201 | — |
| 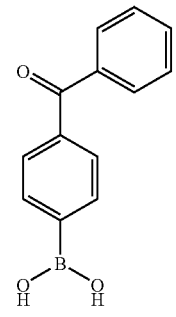 I-202 | A |
| 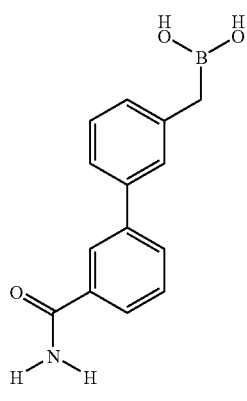 I-203 | — |
| 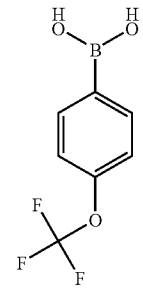 I-204 | B |
*rat FAAH activity

TABLE 2

| Compound | Activity |
|---|---|
| II-1 | B |
| II-2 | A |
| II-3 | A |
| II-4 | A |

TABLE 2-continued

| Compound | Activity |
|---|---|
| II-5 | A |
| II-6 | A |
| II-7 | A |

TABLE 2-continued
| Compound | Activity |
|---|---|
| 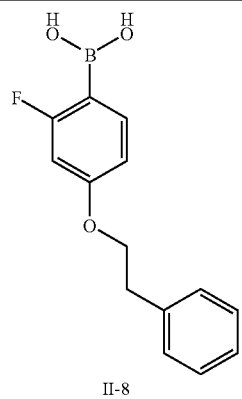<br>II-8 | A |
| 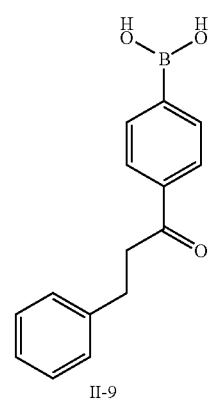<br>II-9 | A |
| 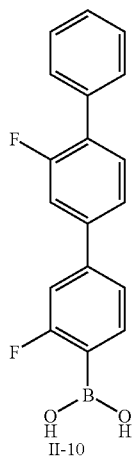<br>II-10 | A |
| 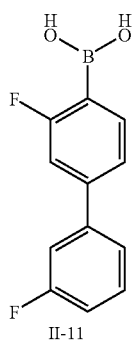<br>II-11 | A |
| 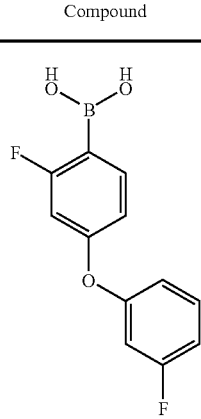<br>II-12 | A |
| 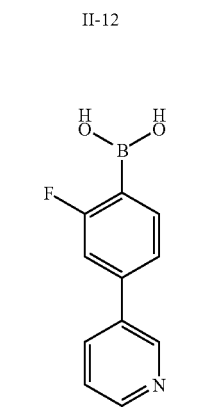<br>II-13 | B |
| 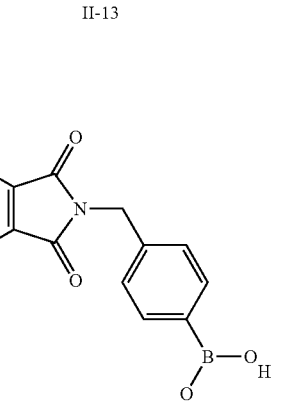<br>II-14 | B |
| 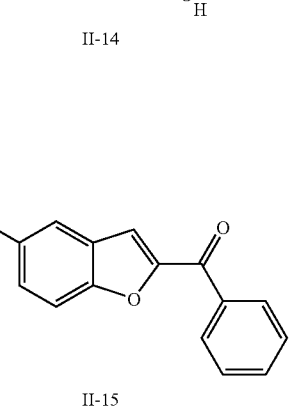<br>II-15 | B |

TABLE 2-continued
| Compound | Activity |
|---|---|
| II-16 | B |
| II-17 | A |
| II-18 | A |
| II-19 | A |
| II-20 | B |
| II-21 | A |
| II-22 | C |
| II-23 | B |
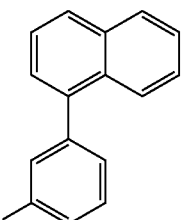

TABLE 2-continued
| Compound | Activity |
|---|---|
| 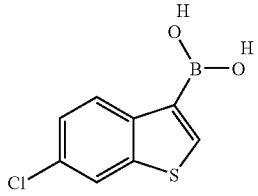<br>II-24 | B |
| 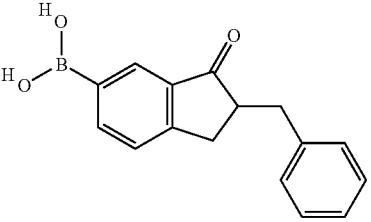<br>II-25 | A |
| 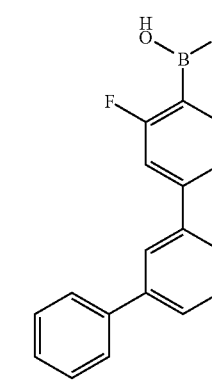<br>II-26 | A |
| 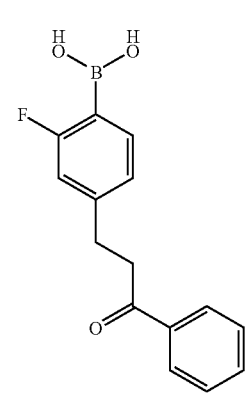<br>II-27 | A |
| 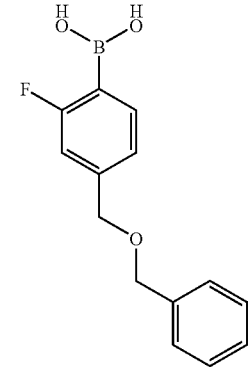<br>II-28 | A |
| 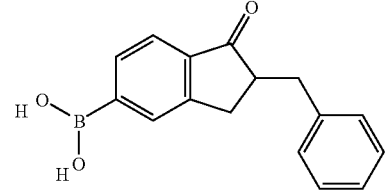<br>II-29 | A |
| 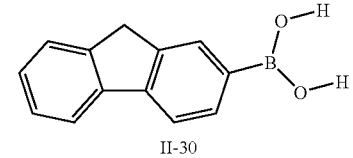<br>II-30 | B |
| 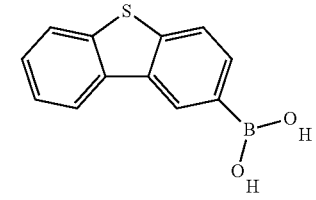<br>II-31 | C |
| 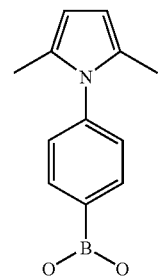<br>II-32 | D |

TABLE 2-continued

| Compound | Activity |
|---|---|
| II-33 | B |
| II-35 | A |
| II-36 | D |
| II-37 | A |
| II-38 | D |
| II-39 | B |
| II-40 | D |
| II-41 | D |
| II-42 | C |

TABLE 2-continued
| Compound | Activity |
|---|---|
| 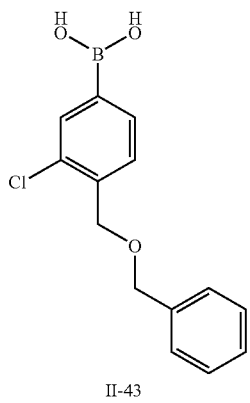 II-43 | A |
| 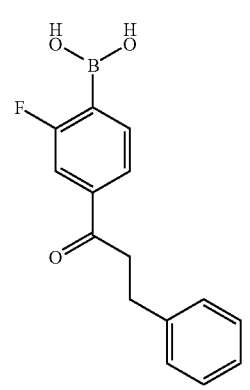 II-44 | A |
| 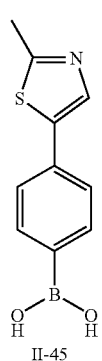 II-45 | D |
| 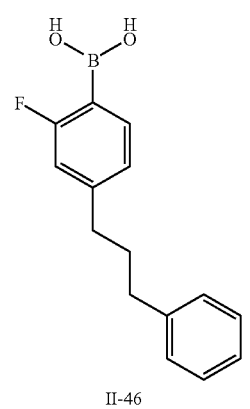 II-46 | A |
| 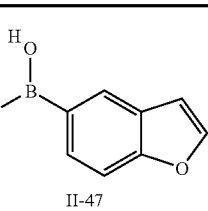 II-47 | C |
| 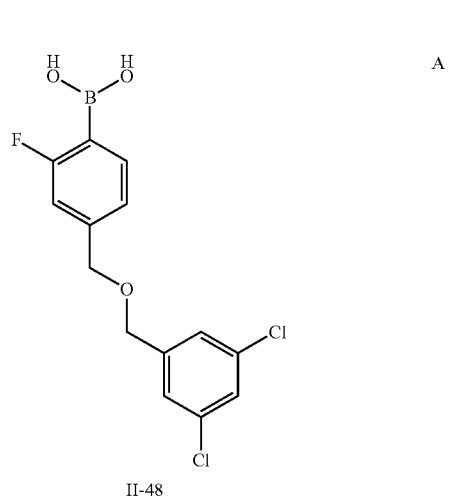 II-48 | A |
| 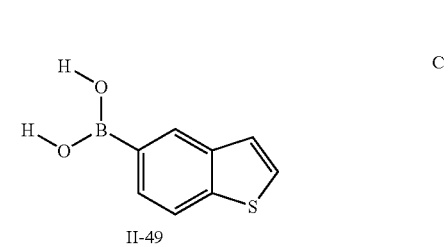 II-49 | C |
| 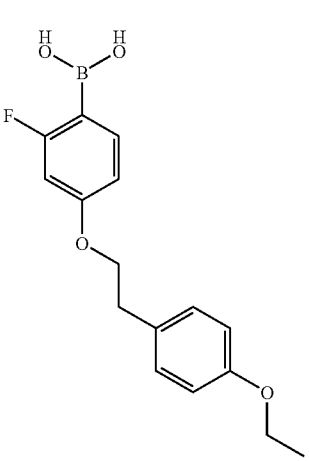 II-50 | A |

TABLE 2-continued
| Compound | Activity |
|---|---|
| 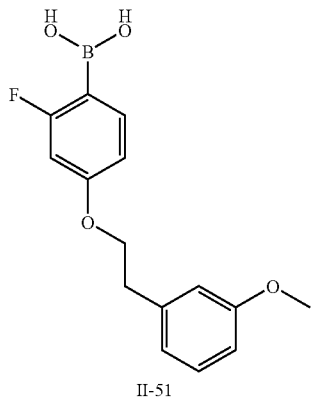 II-51 | A |
| 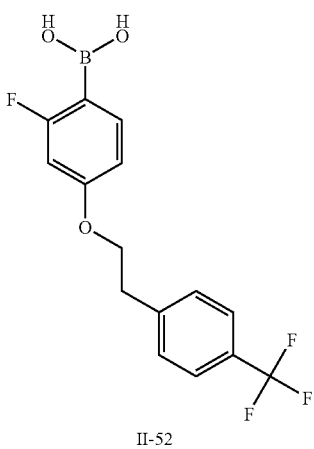 II-52 | A |
| 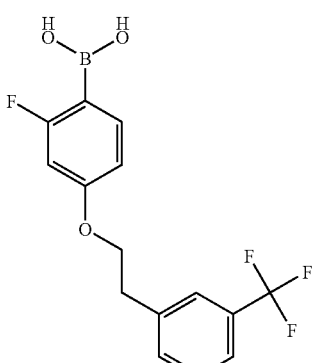 II-53 | A |
| 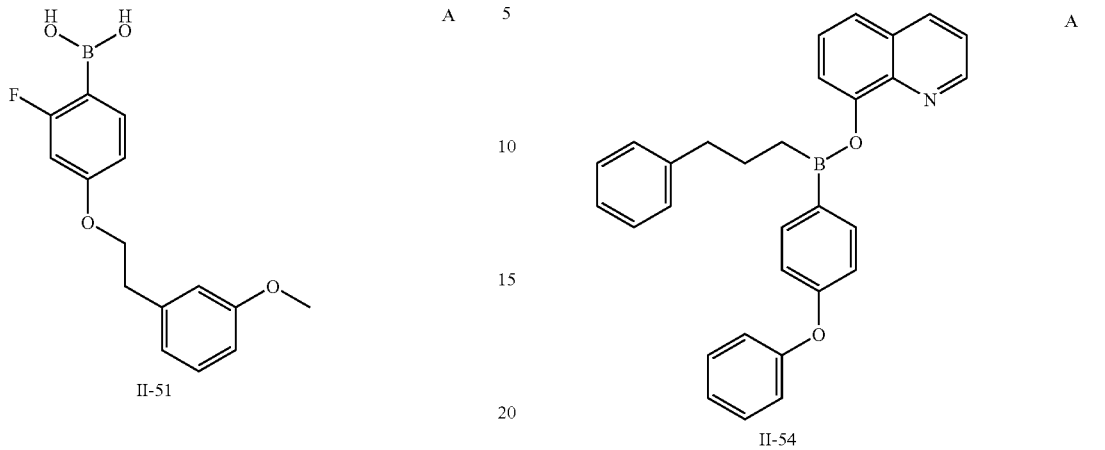 II-54 | A |
| 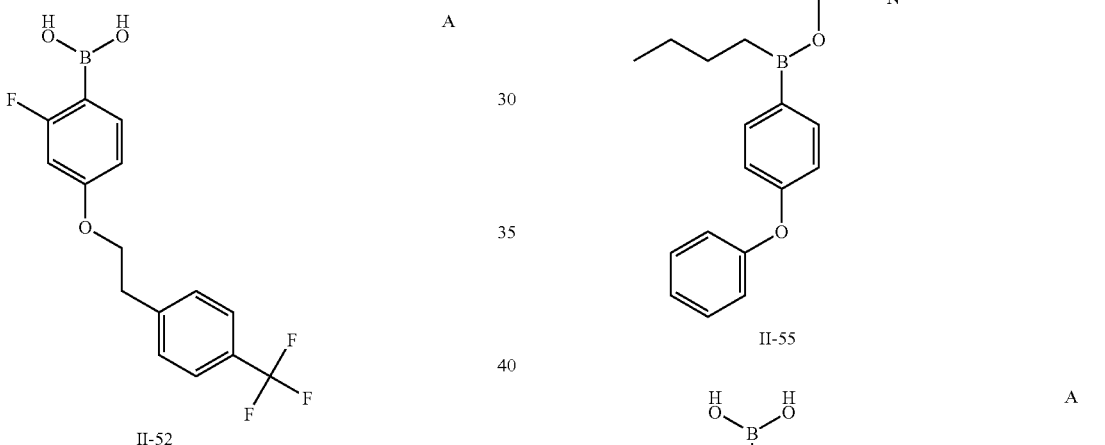 II-55 | A |
| 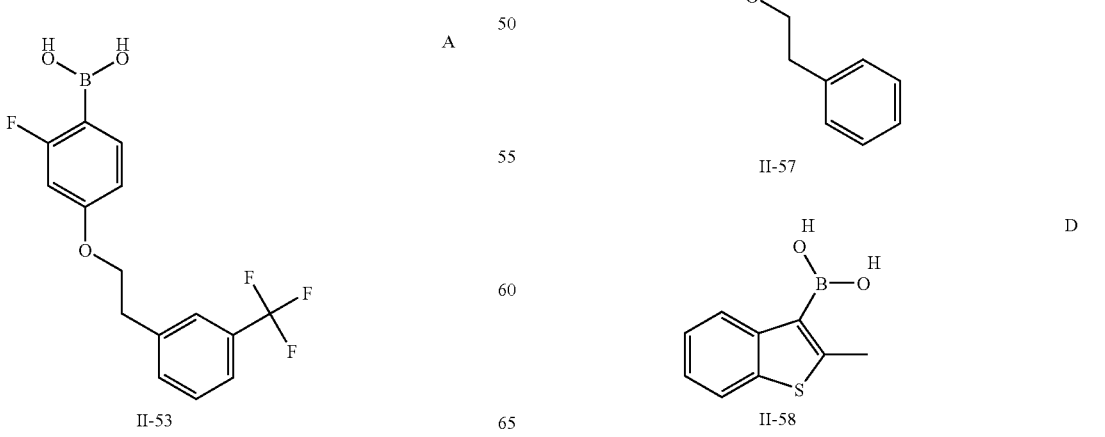 II-57 | A |
| 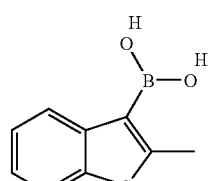 II-58 | D |

TABLE 2-continued

| Compound | Activity |
|---|---|
| II-59 | B |
| II-60 | D |
| II-61 | A |
| II-62 | A |
| II-63 | C |
| II-64 | D |
| II-65 | C |
| II-66 | B |
| II-67 | D |

TABLE 2-continued
| Compound | Activity |
|---|---|
| 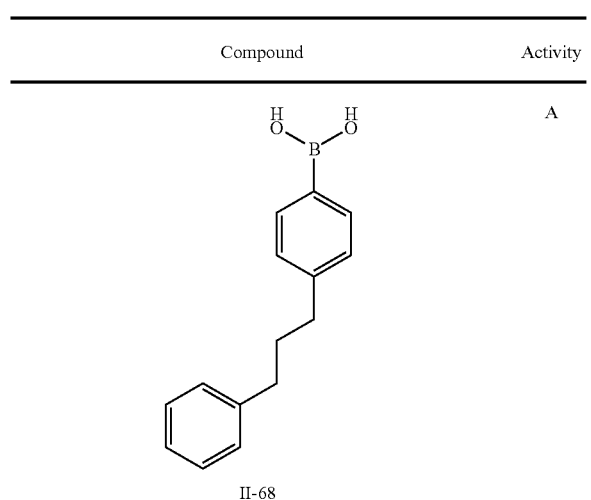 II-68 | A |
| 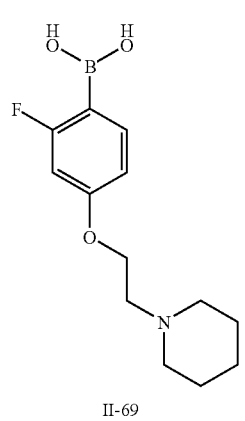 II-69 | C |
| 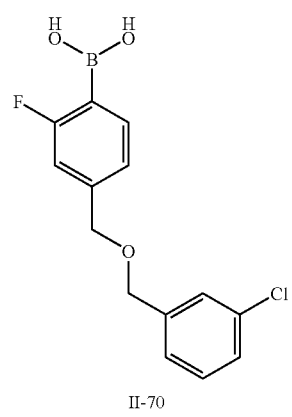 II-70 | A |
| 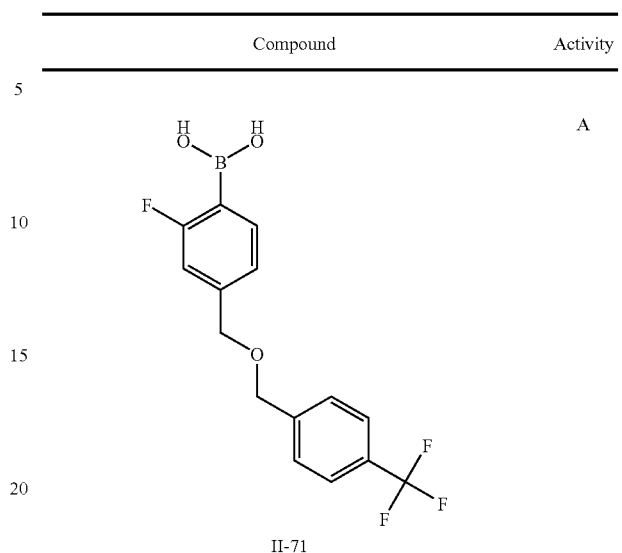 II-71 | A |
| 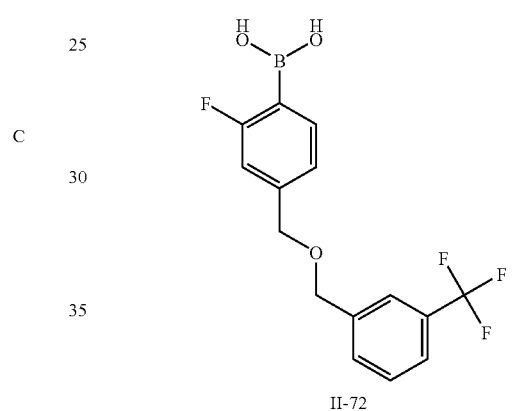 II-72 | A |
| 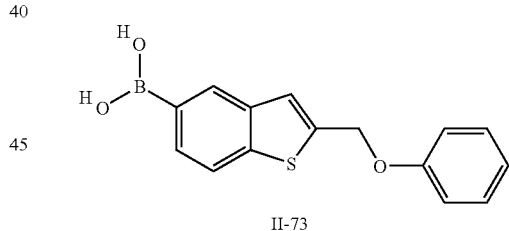 II-73 | A |
| 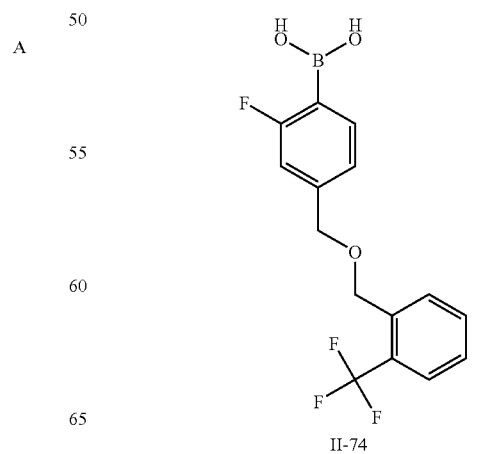 II-74 | A |

TABLE 2-continued
| Compound | Activity |
|---|---|
| 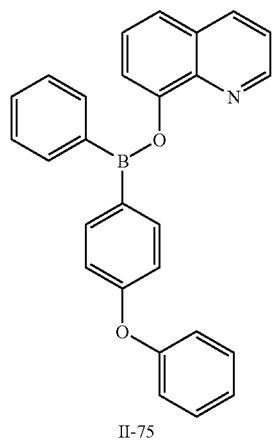 II-75 | A |
| 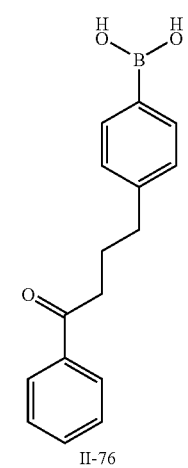 II-76 | A |
| 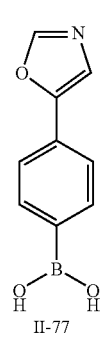 II-77 | B |
| 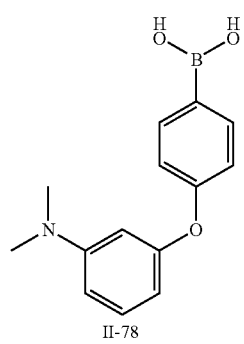 II-78 | A |
TABLE 2-continued
| Compound | Activity |
|---|---|
| II-79 | D |
| II-80 | D |
| II-81 | C |
| II-82 | A |

TABLE 2-continued
| Compound | Activity |
|---|---|
| 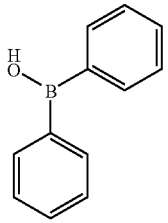 II-83 | D |
| 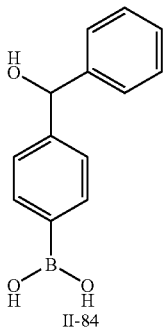 II-84 | B |
| 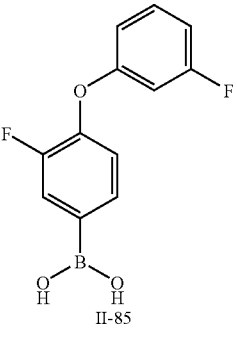 II-85 | A |
| 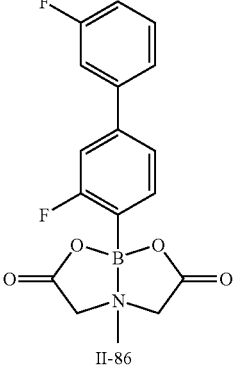 II-86 | A |
| 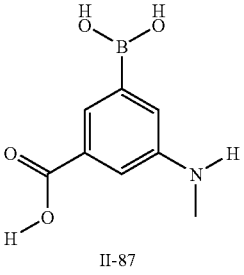 II-87 | D |
| 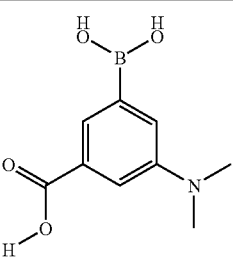 II-88 | D |
| 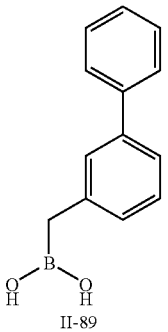 II-89 | — |
| 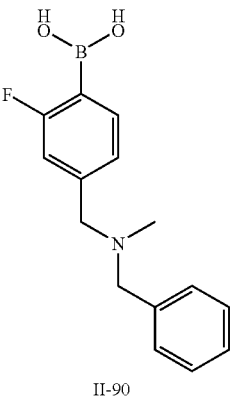 II-90 | B |
| 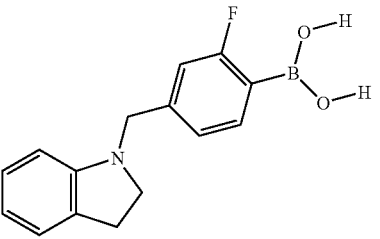 II-91 | A |

TABLE 2-continued
| Compound | Activity |
|---|---|
| 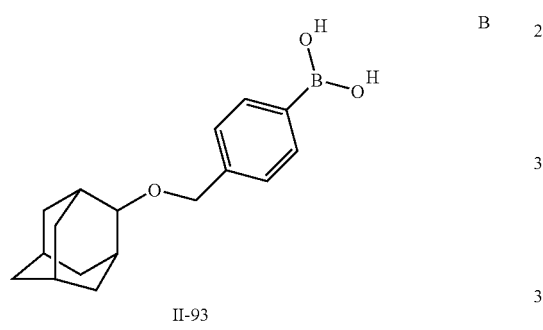 II-92 | A |
| 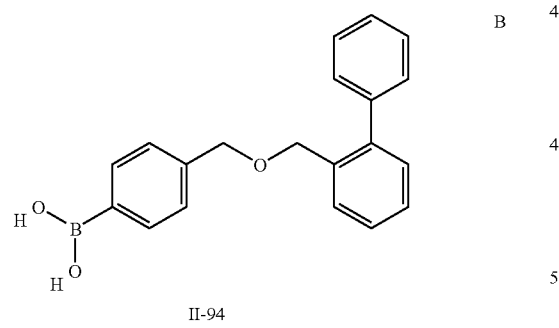 II-93 | B |
| 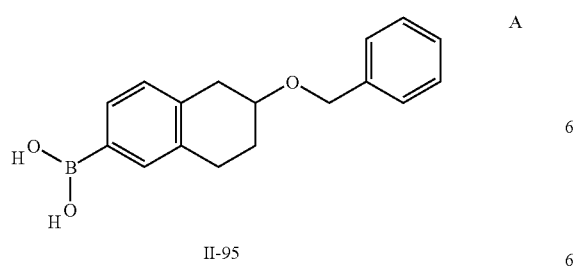 II-94 | B |
| II-95 | A |
| 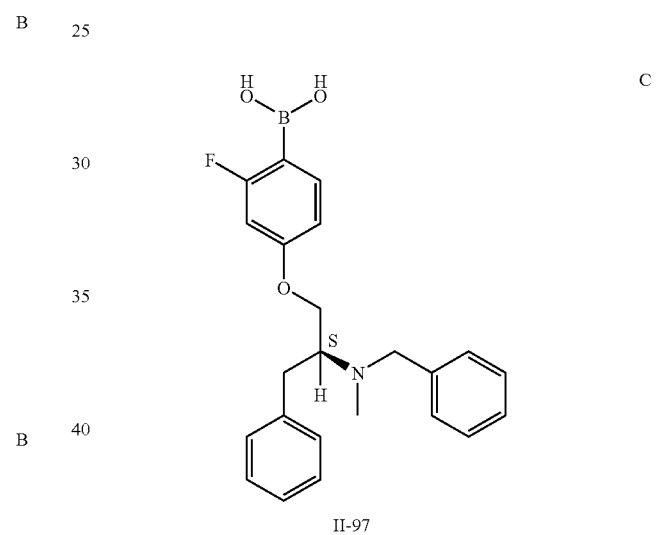 II-96 | B |
| II-97 | C |
| 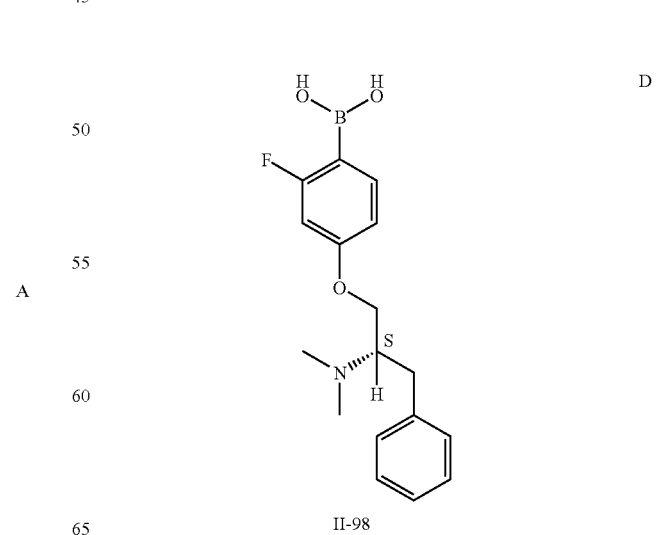 II-98 | D |

TABLE 2-continued
| Compound | Activity |
|---|---|
| 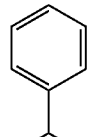 II-99 | D |
| 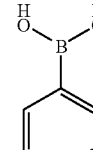 II-100 | B |
| 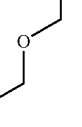 II-101 | B |
| 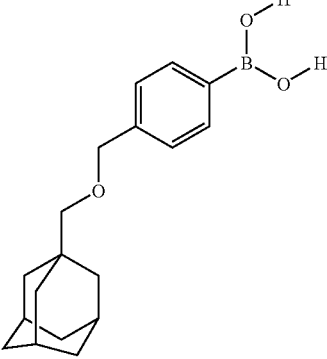 II-102 | B |
| 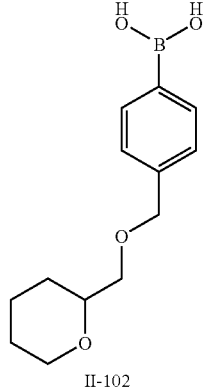 II-103 | D |
| 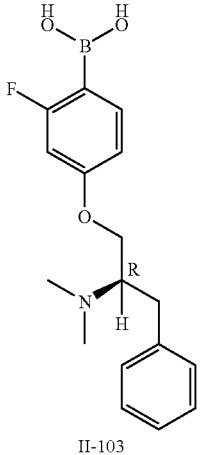 II-104 | A |
| 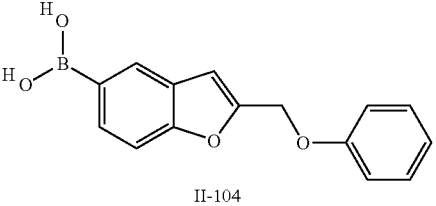 II-105 | C |
| 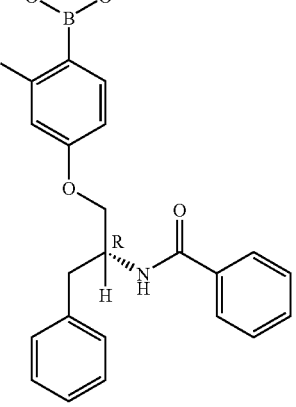 II-106 | C |

TABLE 2-continued
| Compound | Activity |
|---|---|
| II-107 | B |
| II-108 | B |
| II-109 | A |
| II-110 | A |
| II-111 | A |
| II-112 | D |
| II-113 | B |
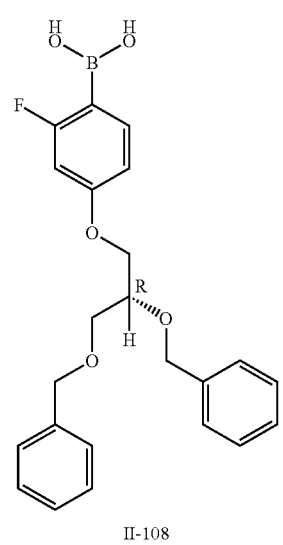

TABLE 2-continued
| Compound | Activity |
|---|---|
| 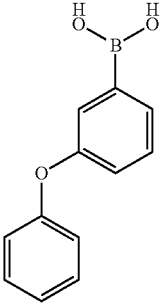 II-114 | A |
| 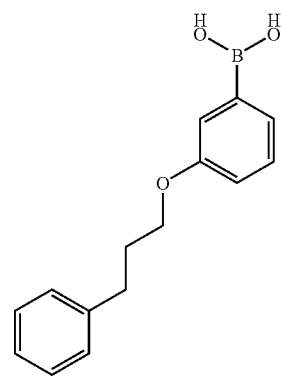 II-115 | B |
| 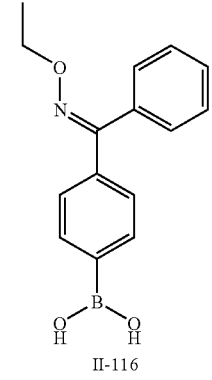 II-116 | B |
| 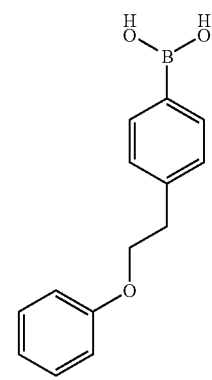 II-117 | B |
| 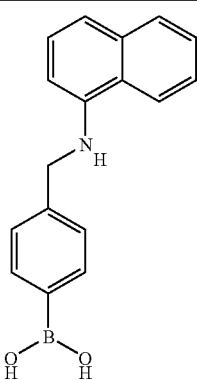 II-118 | D |
| 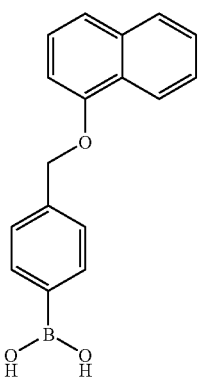 II-119 | A |
| 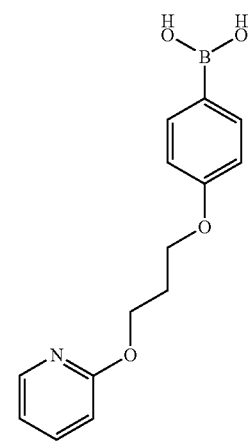 II-120 | B |

TABLE 2-continued
| Compound | Activity |
|---|---|
| 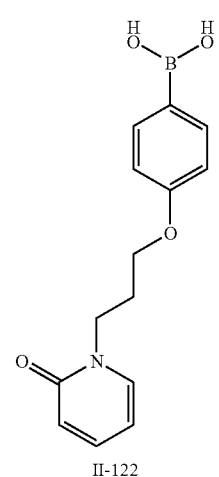 II-121 | B |
| II-122 | B |
| 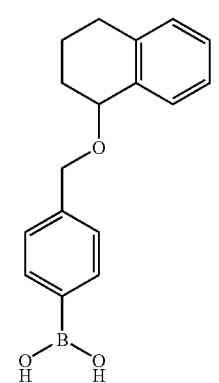 II-123 | B |
| II-124 | A |
| II-125 | D |
| II-126 | A |
| II-127 | A |

TABLE 2-continued
| Compound | Activity |
|---|---|
| 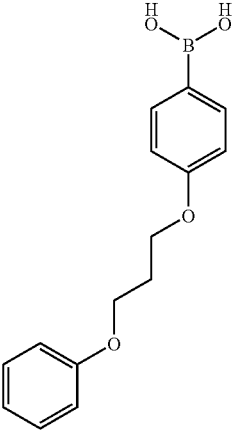<br>II-128 | A |
| 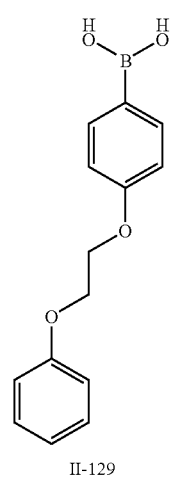<br>II-129 | A |
| 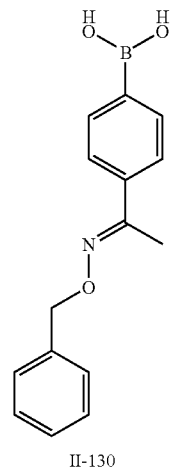<br>II-130 | A |
| 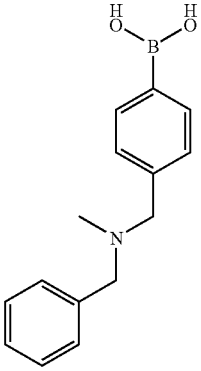<br>II-131 | A |
| 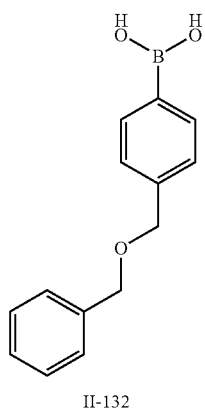<br>II-132 | A |
| 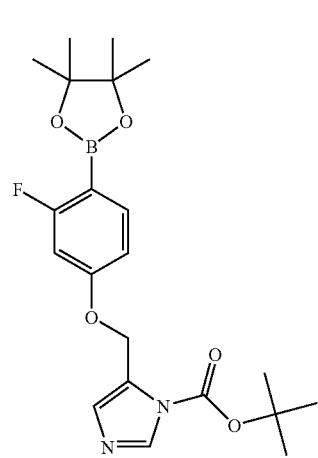<br>II-133 | A |

TABLE 2-continued
| Compound | Activity |
|---|---|
| 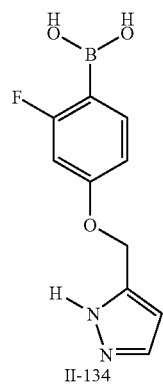 II-134 | B |
| 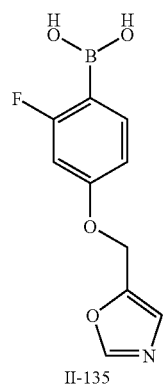 II-135 | B |
| 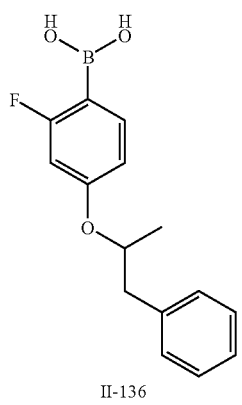 II-136 | A |
| 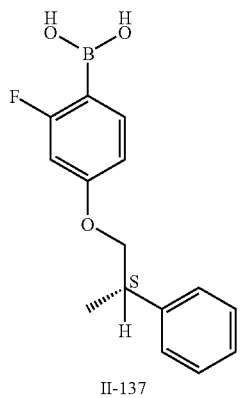 II-137 | A |
| 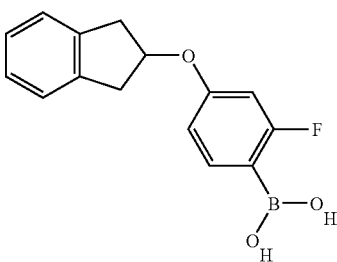 II-138 | A |
| 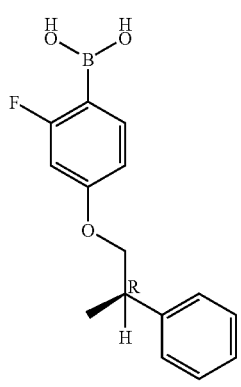 II-139 | A |
| 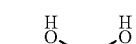 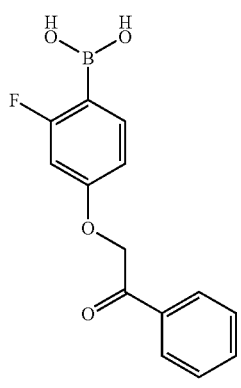 II-140 | A |
| II-141 | A |

TABLE 2-continued
| Compound | Activity |
|---|---|
| 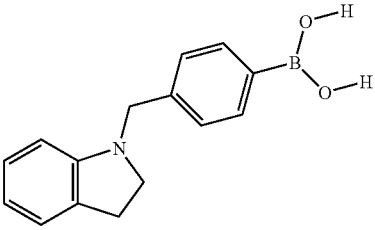<br>II-142 | A |
| 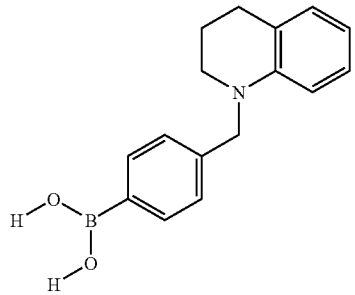<br>II-143 | A |
| 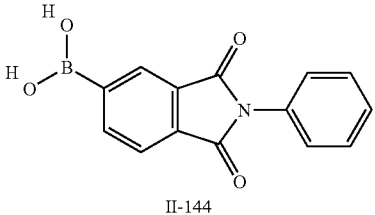<br>II-144 | B |
| 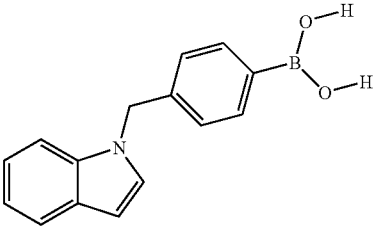<br>II-145 | A |
| 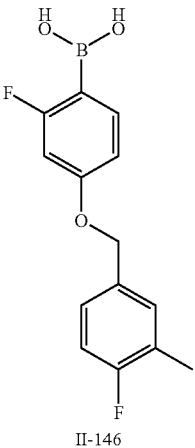<br>II-146 | A |
| 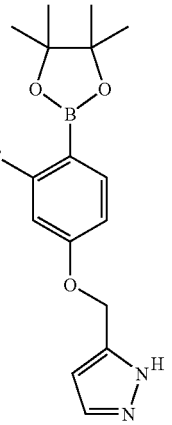<br>II-147 | B |
| 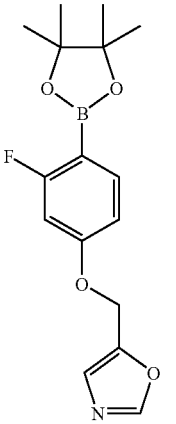<br>II-148 | B |
| 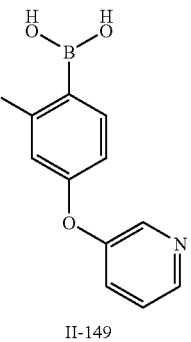<br>II-149 | A |

TABLE 2-continued
| Compound | Activity |
|---|---|
| 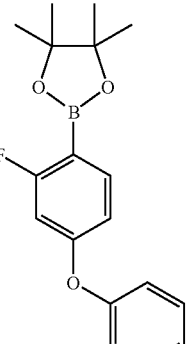 II-150 | A |
| 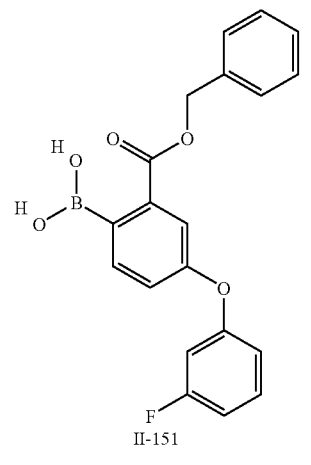 II-151 | C |
| 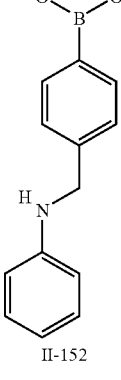 II-152 | A |
| 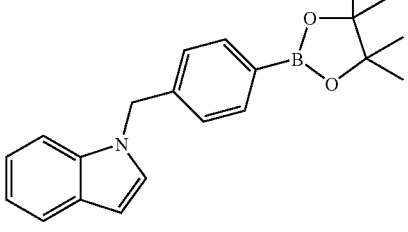 II-153 | A |
| 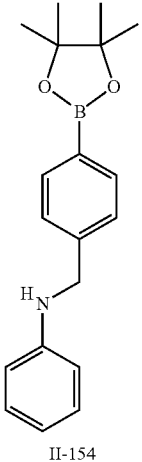 II-154 | A |
| 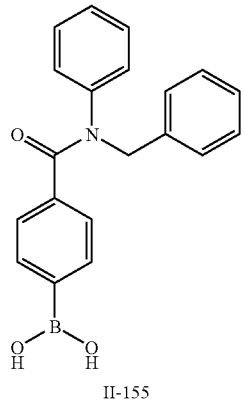 II-155 | B |
| 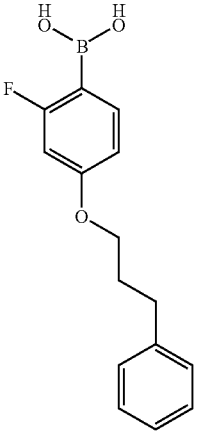 II-156 | A |

TABLE 2-continued
| Compound | Activity |
|---|---|
| 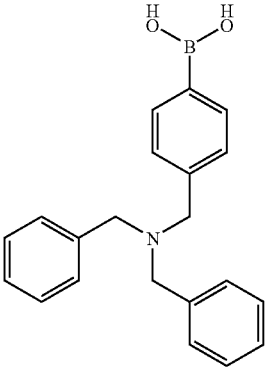 II-157 | C |
| 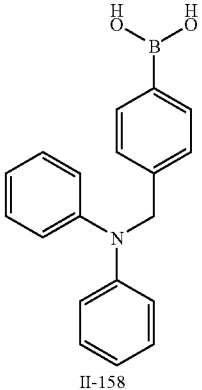 II-158 | D |
| 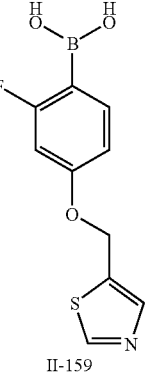 II-159 | B |
| 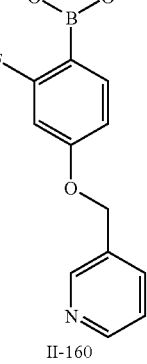 II-160 | B |
| 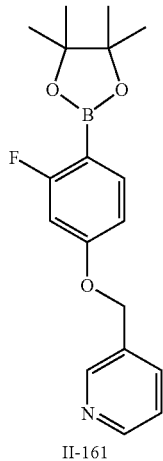 II-161 | B |
| 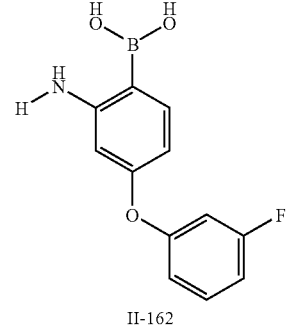 II-162 | D |
| 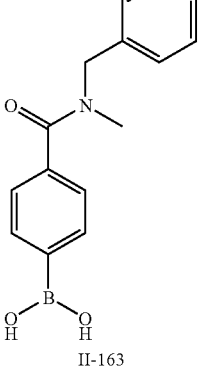 II-163 | B |
| 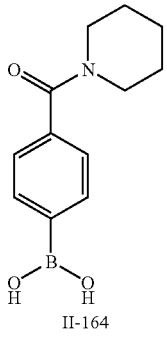 II-164 | B |

TABLE 2-continued
| Compound | Activity |
|---|---|
| 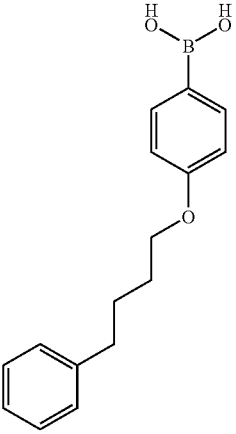 II-165 | B |
| II-166 | B |
| II-167 | A |
| II-168 | B |
| II-169 | A |
| II-170 | B |

TABLE 2-continued
| Compound | Activity |
|---|---|
| 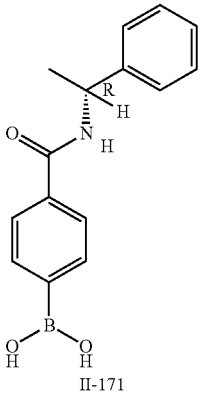 II-171 | B |
| 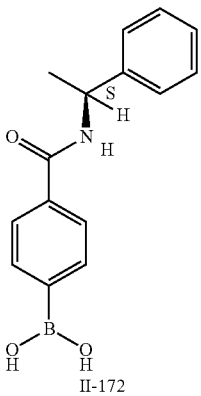 II-172 | B |
| 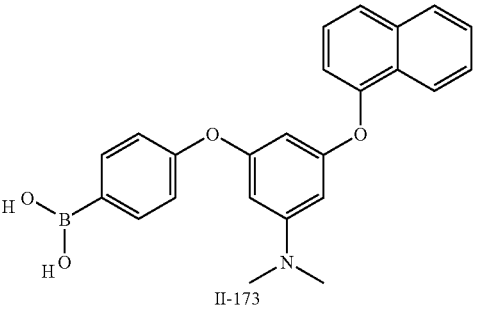 II-173 | D |
| 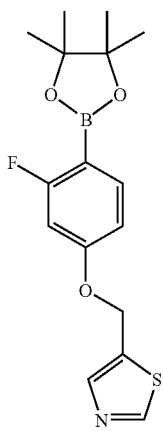 II-174 | A |
| 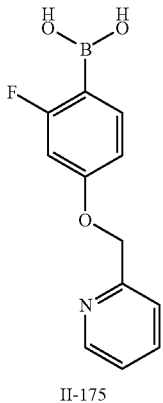 II-175 | D |
| 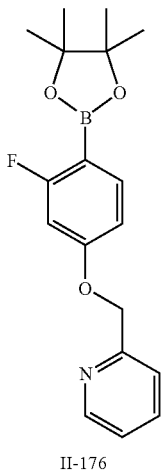 II-176 | A |
| 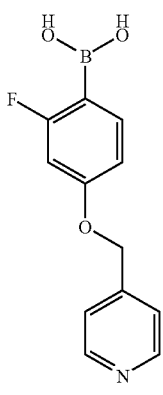 II-177 | B |

TABLE 2-continued

| Compound | Activity |
|---|---|
| II-178 | D |
| II-179 | B |
| II-180 | D |
| II-181 | C |
| II-182 | B |
| II-183 | B |

TABLE 2-continued
| Compound | Activity |
|---|---|
| 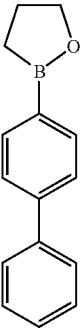<br>II-184 | B |
| 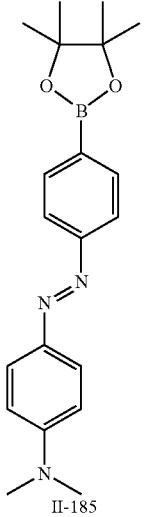<br>II-185 | C |
| 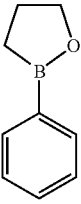<br>II-186 | D |
| 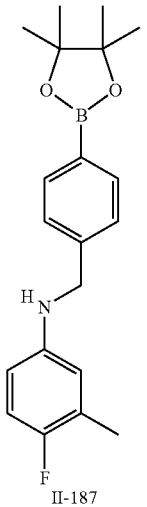<br>II-187 | B |
| 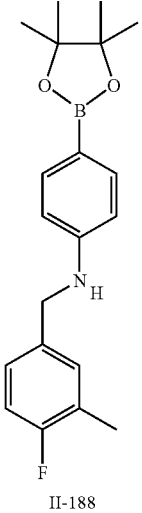<br>II-188 | D |
| 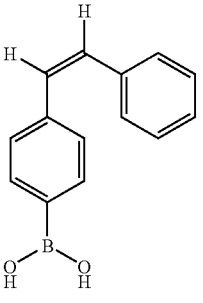<br>II-189 | D |
| 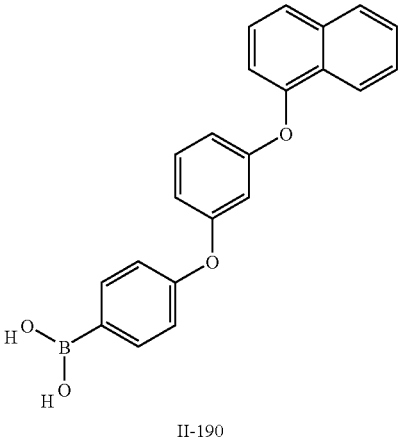<br>II-190 | B |

TABLE 2-continued
| Compound | Activity |
|---|---|
| 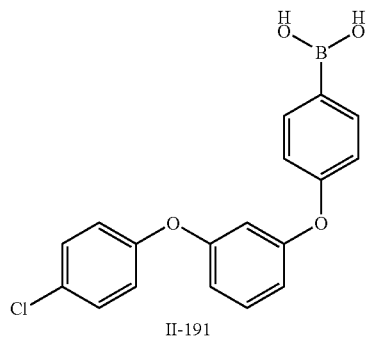 II-191 | A |
| 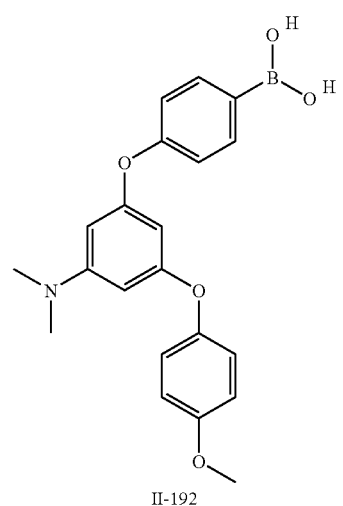 II-192 | B |
| 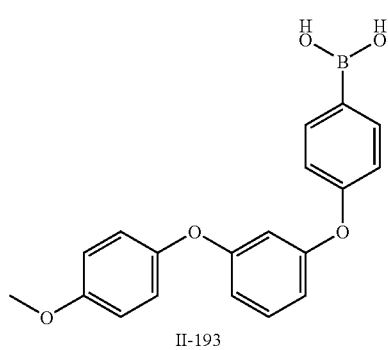 II-193 | A |
| 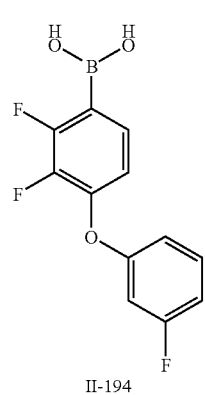 II-194 | A |
| 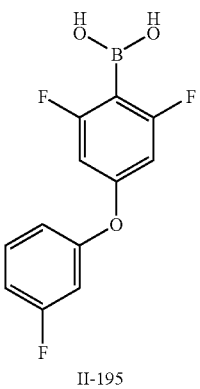 II-195 | A |
| 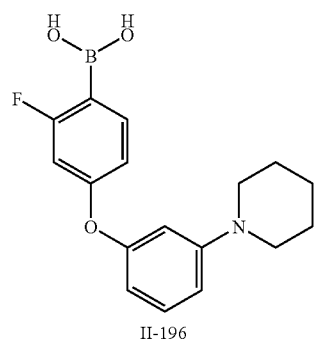 II-196 | D |
| 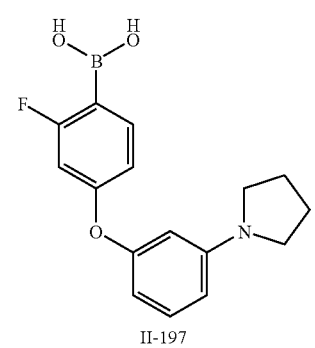 II-197 | B |
| 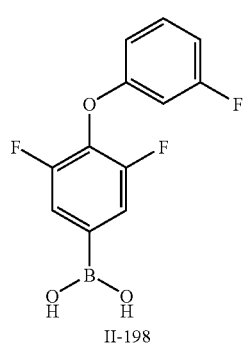 II-198 | A |

TABLE 2-continued
| Compound | Activity |
|---|---|
| 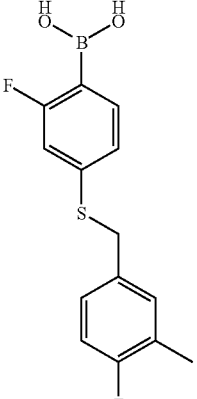 II-199 | A |
| 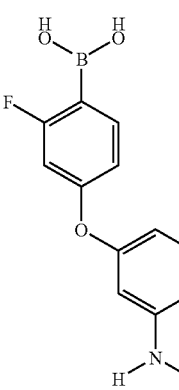 II-200 | A |
| 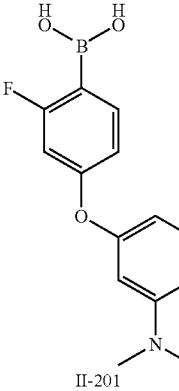 II-201 | B |
| 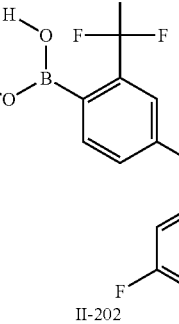 II-202 | B |
| 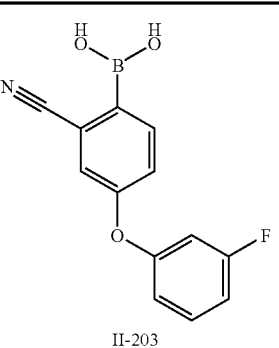 II-203 | A |
| 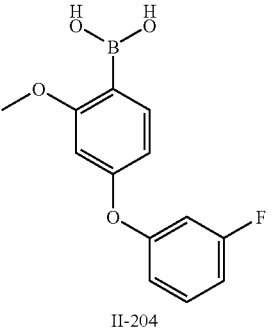 II-204 | A |
| 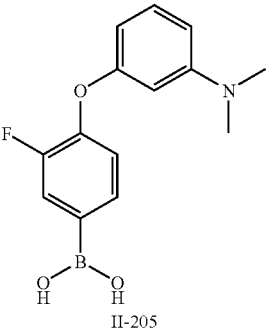 II-205 | A |
| 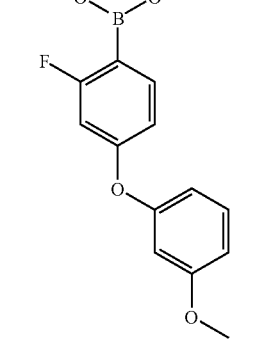 II-206 | A |

TABLE 2-continued
| Compound | Activity |
|---|---|
| 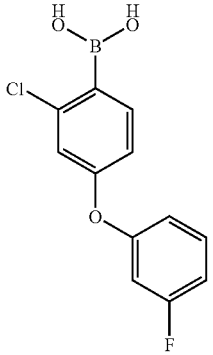 II-207 | A |
| 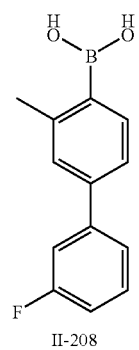 II-208 | B |
| 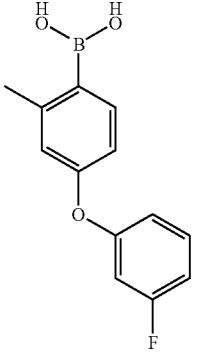 II-209 | B |
| 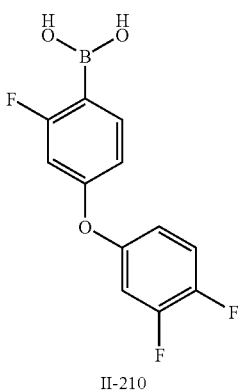 II-210 | A |
| 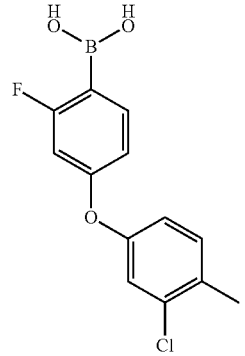 II-211 | A |
| 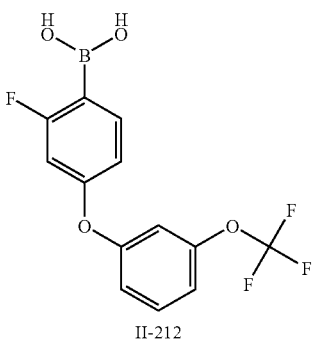 II-212 | A |
| 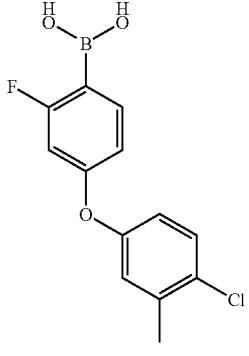 II-213 | A |
| 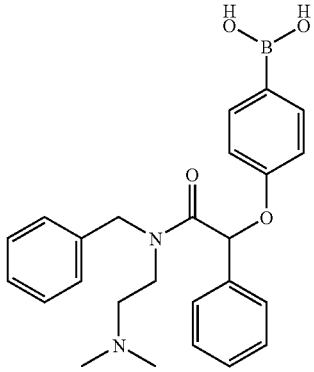 II-214 | D |

TABLE 2-continued

| Compound | Activity |
|---|---|
| II-215 | D |
| II-216 | C |
| II-217 | C |
| II-218 | C |
| II-219 | C |
| II-220 | A |
| II-221 | A |

TABLE 2-continued
| Compound | Activity |
|---|---|
| 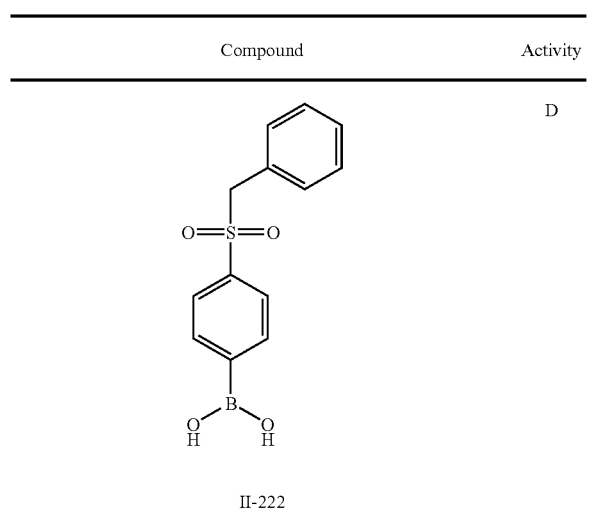 II-222 | D |
| 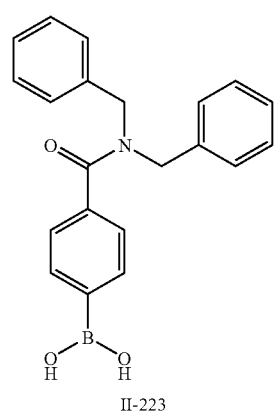 II-223 | C |
| 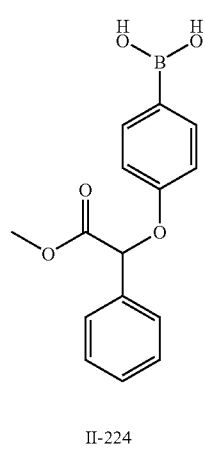 II-224 | B |
| 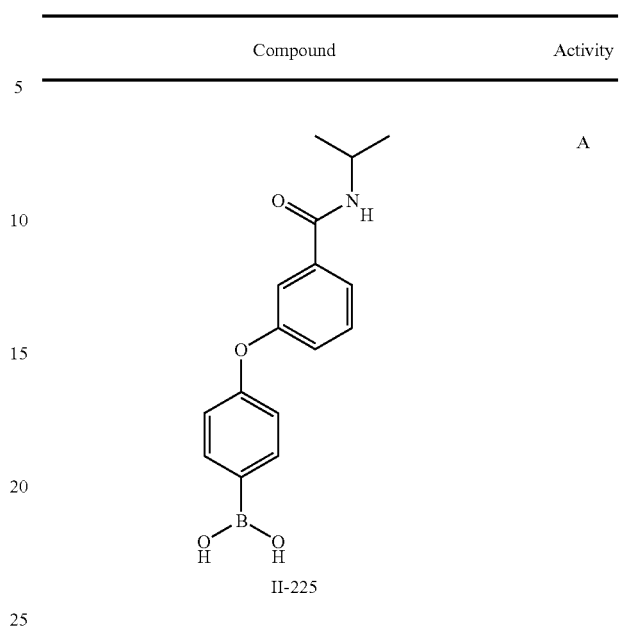 II-225 | A |
| 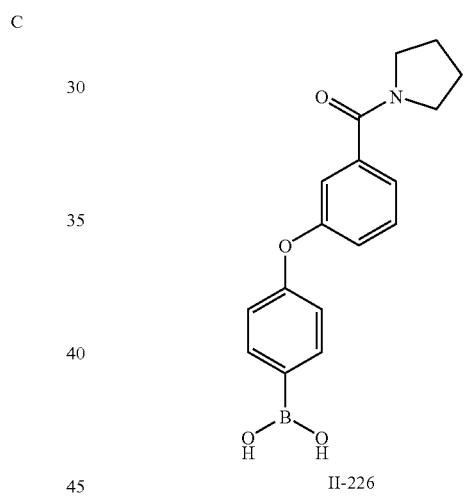 II-226 | B |
| 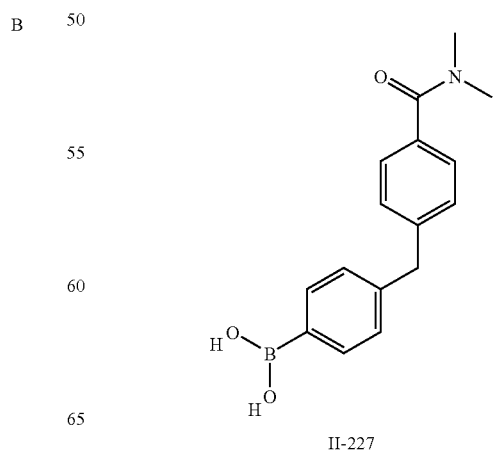 II-227 | B |

TABLE 2-continued

| Compound | Activity |
|---|---|
| II-228 | B |
| II-229 | A |
| II-230 | B |
| II-231 | A |
| II-232 | C |
| II-233 | B |
| II-234 | A |

TABLE 2-continued
| Compound | Activity |
|---|---|
| 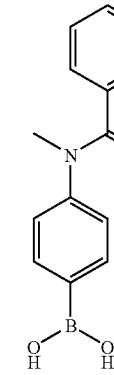<br>II-235 | C |
| 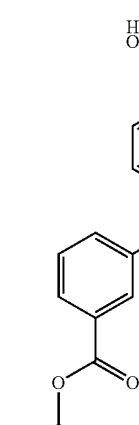<br>II-236 | A |
| II-237 | A |
| II-238 | B |
| II-239 | B |
| II-240 | B |
| II-241 | D |
| II-242 | A |

TABLE 2-continued
| Compound | Activity |
|---|---|
| 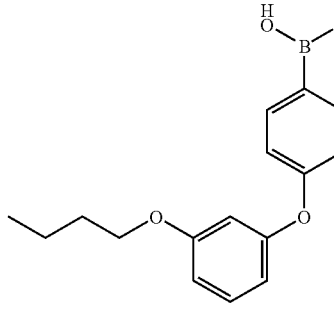 II-243 | A |
| 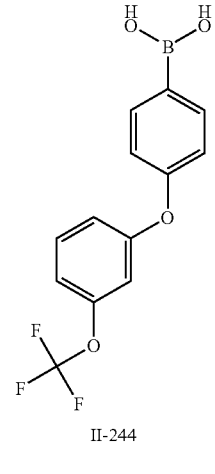 II-244 | A |
| II-245 | A |
| II-246 | A |
| 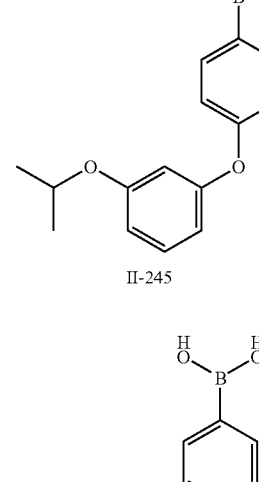 II-247 | B |
| II-248 | B |
| 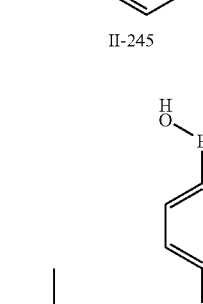 II-249 | C |

TABLE 2-continued
| Compound | Activity |
|---|---|
| 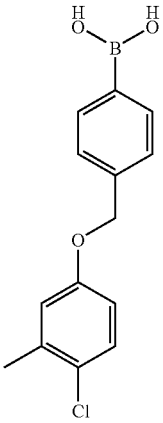 II-250 | A |
| 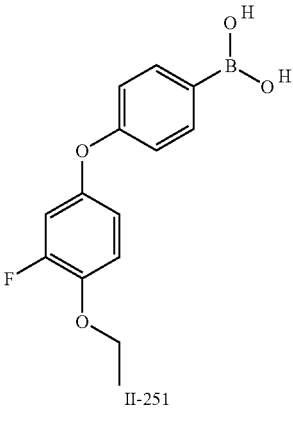 II-251 | A |
| 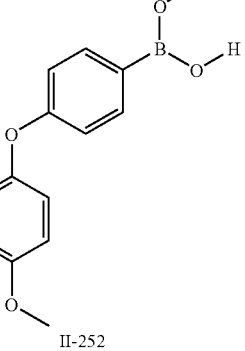 II-252 | A |
| 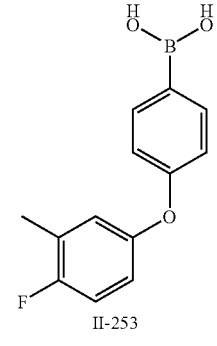 II-253 | A |
| 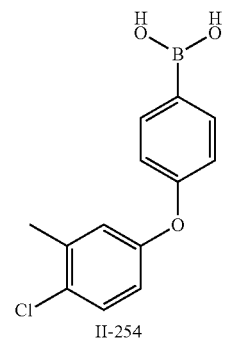 II-254 | A |
| 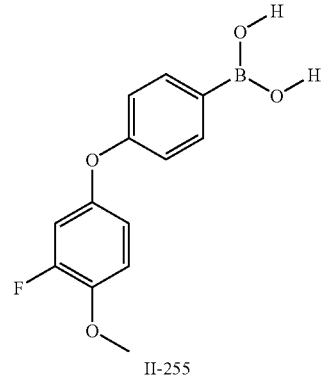 II-255 | A |
| 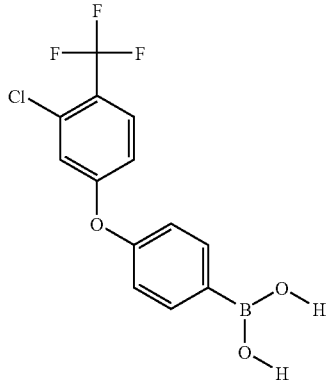 II-256 | A |
| 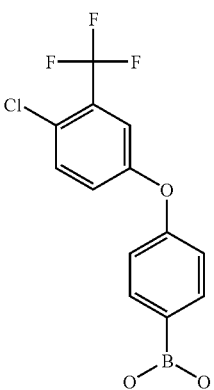 II-257 | A |

TABLE 2-continued
| Compound | Activity |
|---|---|
| 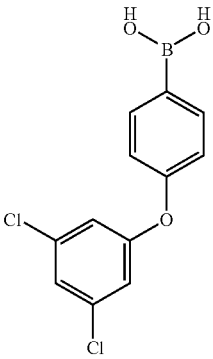<br>II-258 | B |
| 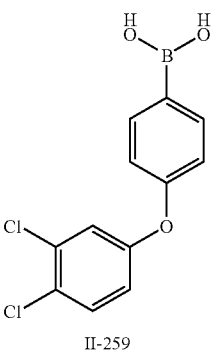<br>II-259 | A |
| 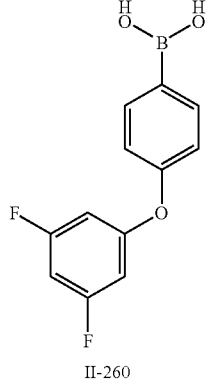<br>II-260 | A |
| 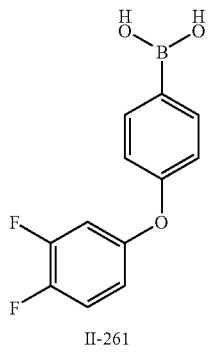<br>II-261 | A |
| 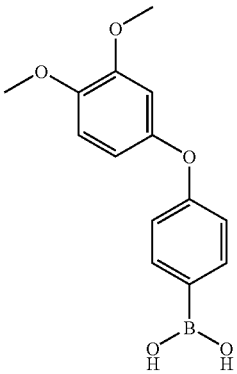<br>II-262 | A |
| 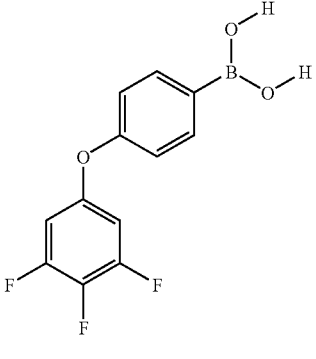<br>II-263 | A |
| 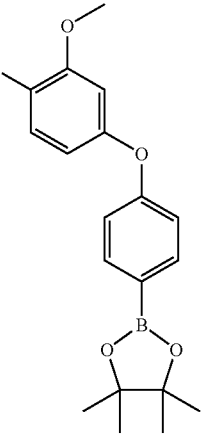<br>II-264 | A |

TABLE 2-continued
| Compound | Activity |
|---|---|
| 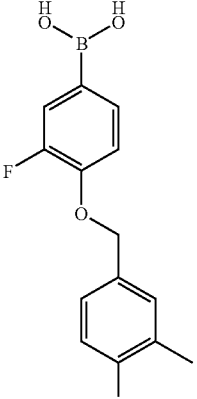　II-265 | A |
| 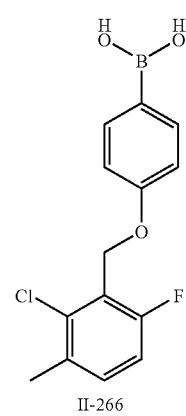　II-266 | B |
| II-267 | B |
TABLE 2-continued
| Compound | Activity |
|---|---|
| II-268 | B |
| II-269 | A |
| II-270 | B |

TABLE 2-continued
| Compound | Activity |
|---|---|
| 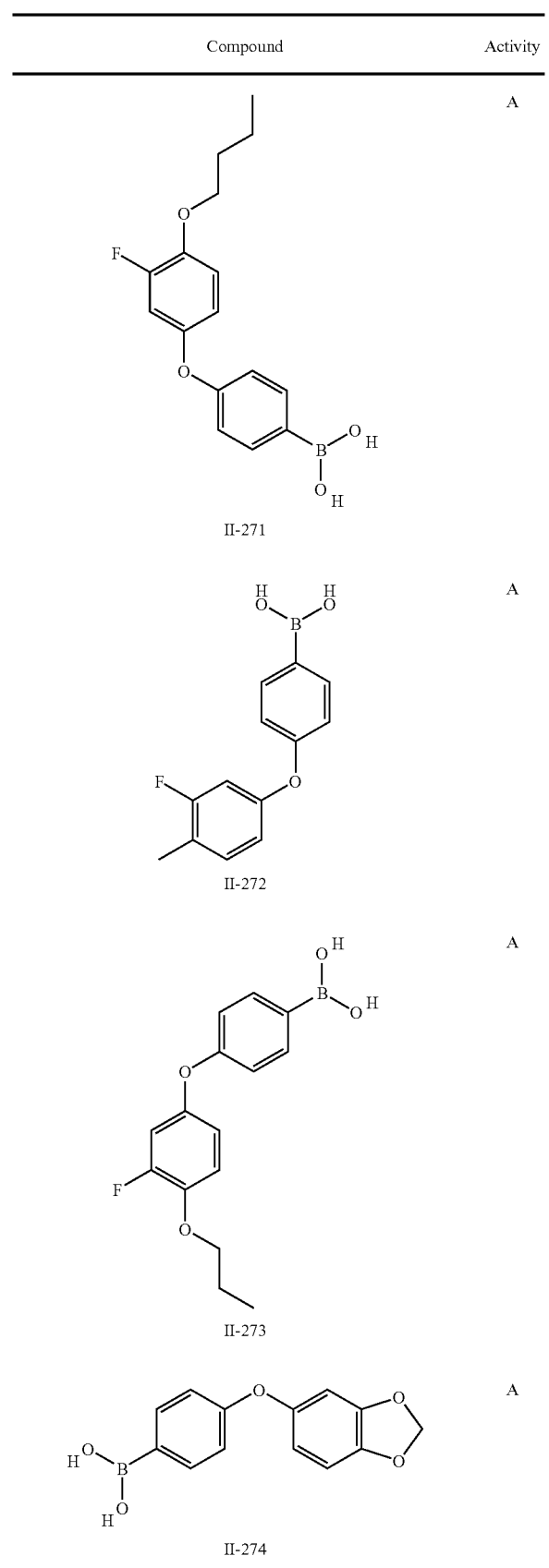 II-271 | A |
| II-272 | A |
| II-273 | A |
| II-274 | A |
| II-275 | A |
| 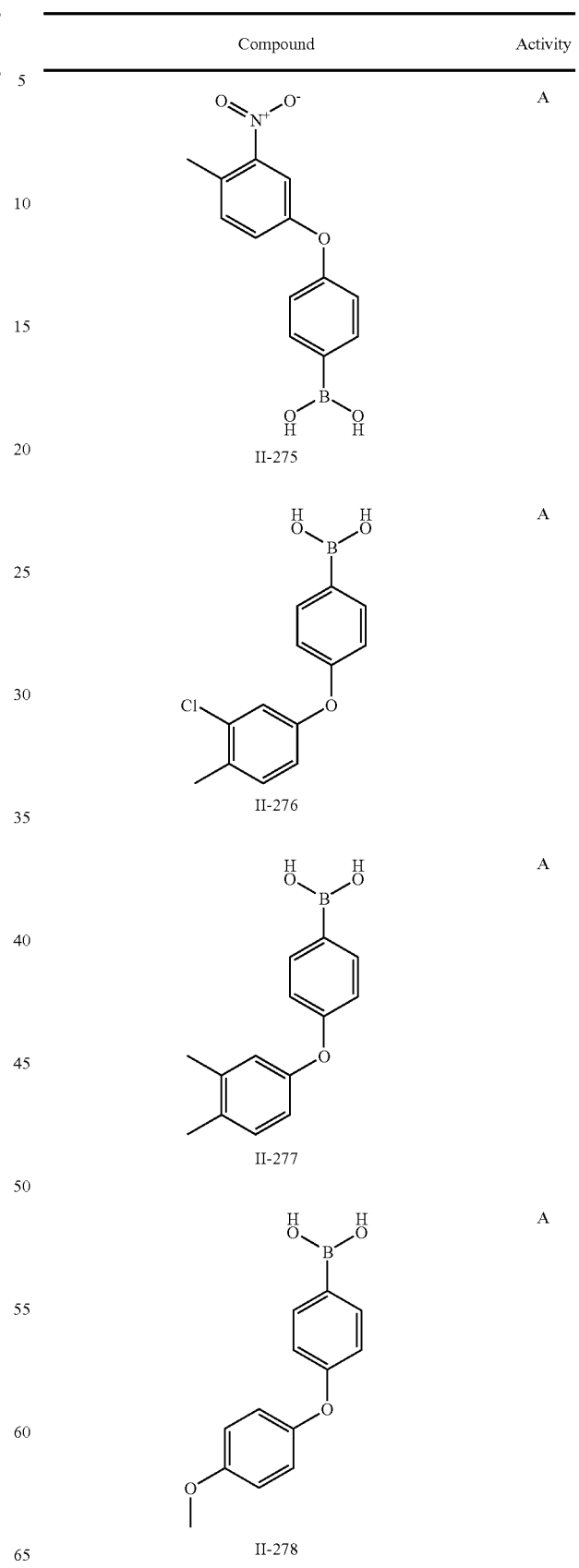 II-276 | A |
| II-277 | A |
| II-278 | A |

TABLE 2-continued
| Compound | Activity |
|---|---|
| 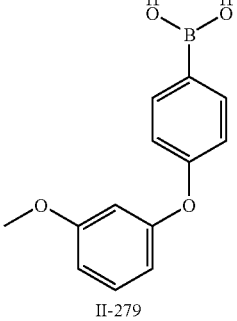 II-279 | A |
| 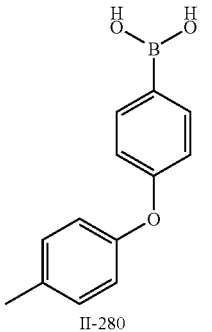 II-280 | A |
| 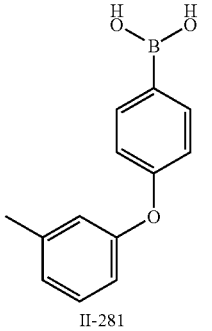 II-281 | A |
| 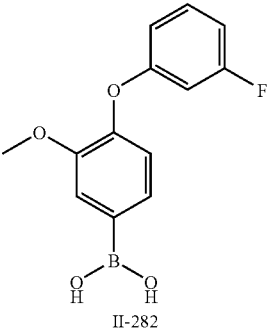 II-282 | A |
| 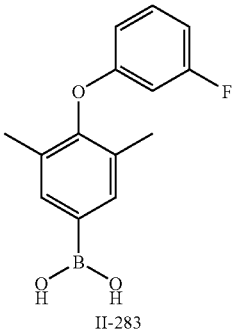 II-283 | B |
| 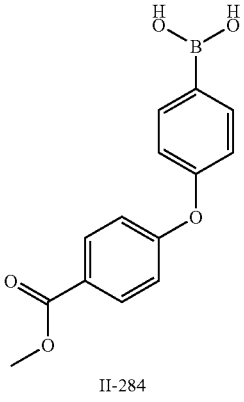 II-284 | A |
| 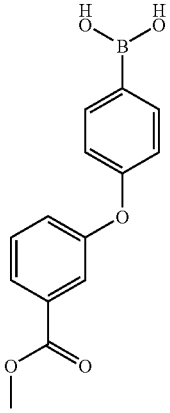 II-285 | A |
| 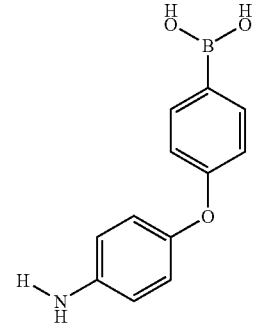 II-286 | B |

TABLE 2-continued
| Compound | Activity |
|---|---|
| 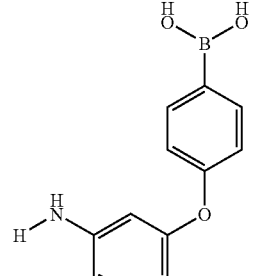 II-287 | B |
| 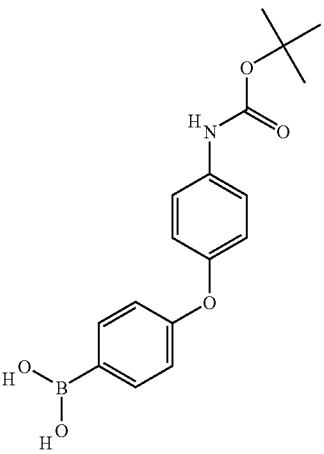 II-288 | B |
| 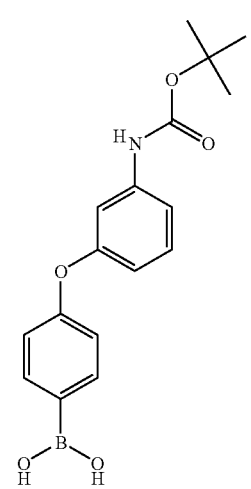 II-289 | B |
TABLE 2-continued
| Compound | Activity |
|---|---|
| 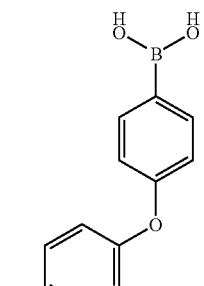 II-290 | A |
| 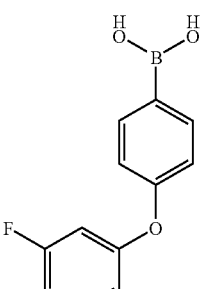 II-291 | A |
| 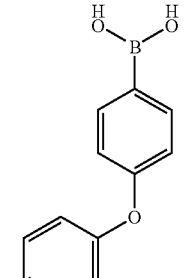 II-292 | C |
| 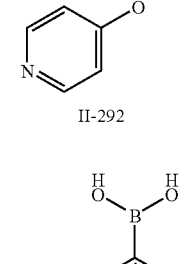 II-293 | A |

TABLE 2-continued
| Compound | Activity |
|---|---|
| 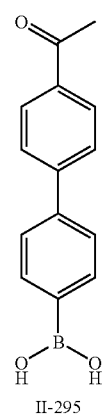<br>II-294 | — |
| II-295 | A |
| II-296 | C |
TABLE 2-continued
| Compound | Activity |
|---|---|
| II-297 | B |
| II-298 | B |
| 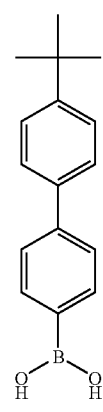<br>II-299 | B |

TABLE 2-continued

| Compound | Activity |
|---|---|
| II-300 | B |
| II-301 | — |
| II-302 | D |
| II-303 | D |
| II-304 | D |
| II-305 | A |
| II-306 | A |
| II-307 | — |

TABLE 2-continued
| Compound | Activity |
|---|---|
| 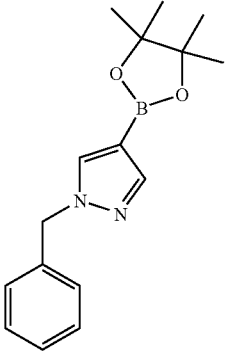 II-308 | — |
| 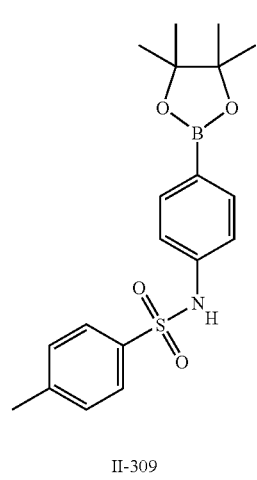 II-309 | — |
| 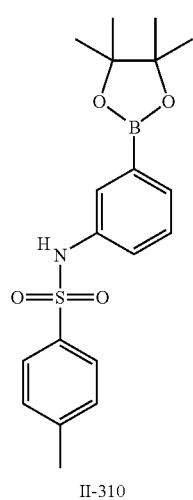 II-310 | — |
| II-311 | — |
| II-312 | — |
| II-313 | B |
| II-314 | B |

TABLE 2-continued

| Compound | Activity |
|---|---|
| 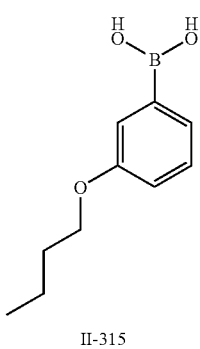<br>II-315 | C* |
| 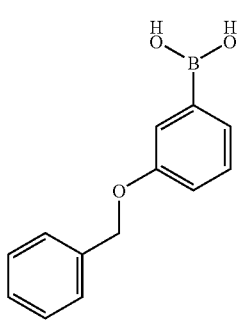<br>II-316 | B |
| 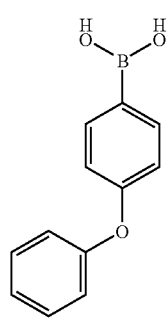<br>II-317 | A |
| 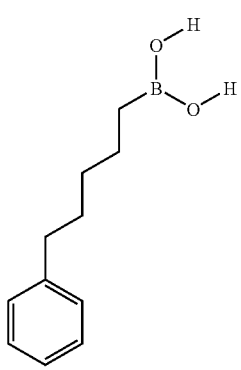<br>II-318 | — |

TABLE 2-continued

| Compound | Activity |
|---|---|
| 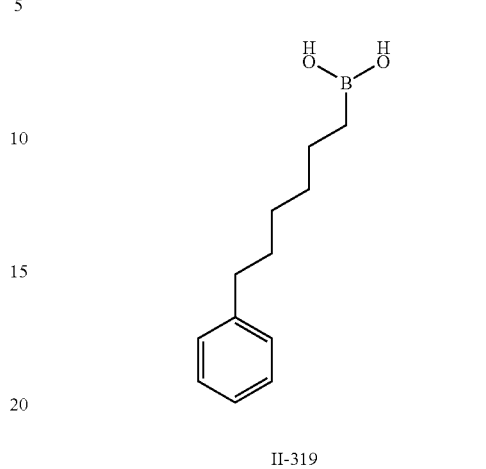<br>II-319 | — |

*rat FAAH activity

In certain embodiments, the present invention provides a compound of formulae (I), (II) or (III), or a pharmaceutically acceptable form thereof, as provided in Table 2. In some embodiments, the present invention provides a compound of formulae (I), (II) or (III), or a pharmaceutically acceptable form thereof, as provided in Table 2 having a $K_i$ of less than or equal to 0.01 microM or having a $K_i$ of between 0.01 microM and 0.1 microM (i.e., a compound with activity designated "A" or "B"). In some embodiments, the present invention provides a compound of formulae (I), (II) or (III), or a pharmaceutically acceptable form thereof, as provided in Table 2 having a $K_i$ of less than or equal to 0.01 microM (i.e., compounds with activities "A"). In certain embodiments, the present invention provides a compound of formulae (I), (II) or (III), or a pharmaceutically acceptable form thereof, selected from the any one of the following compounds set forth in Table 3:

TABLE 3

TABLE 3-continued
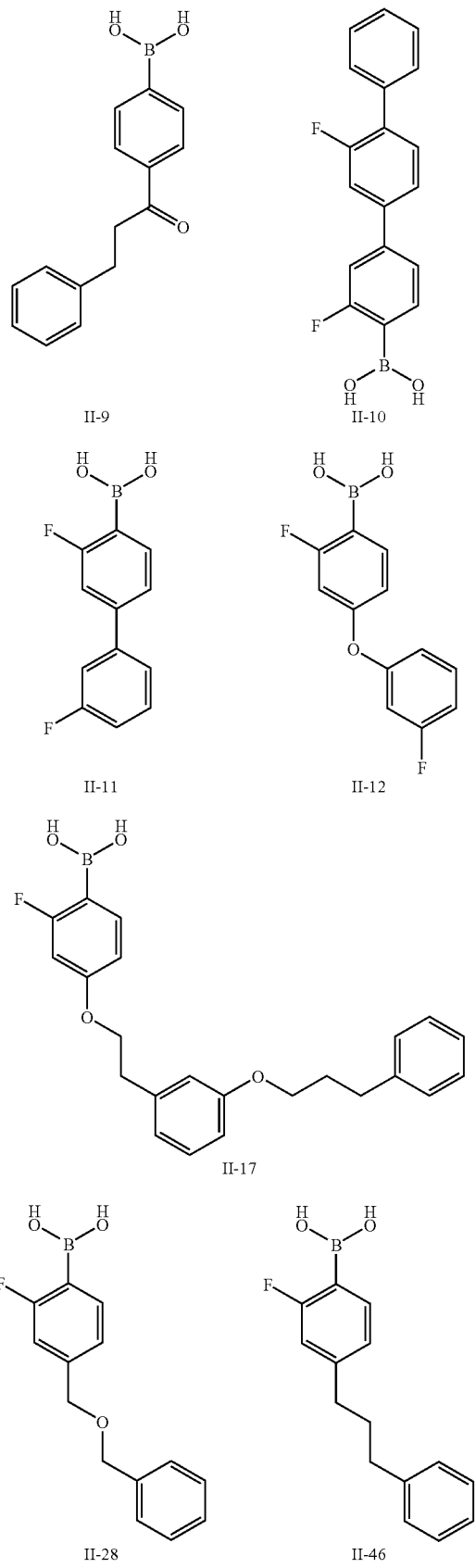
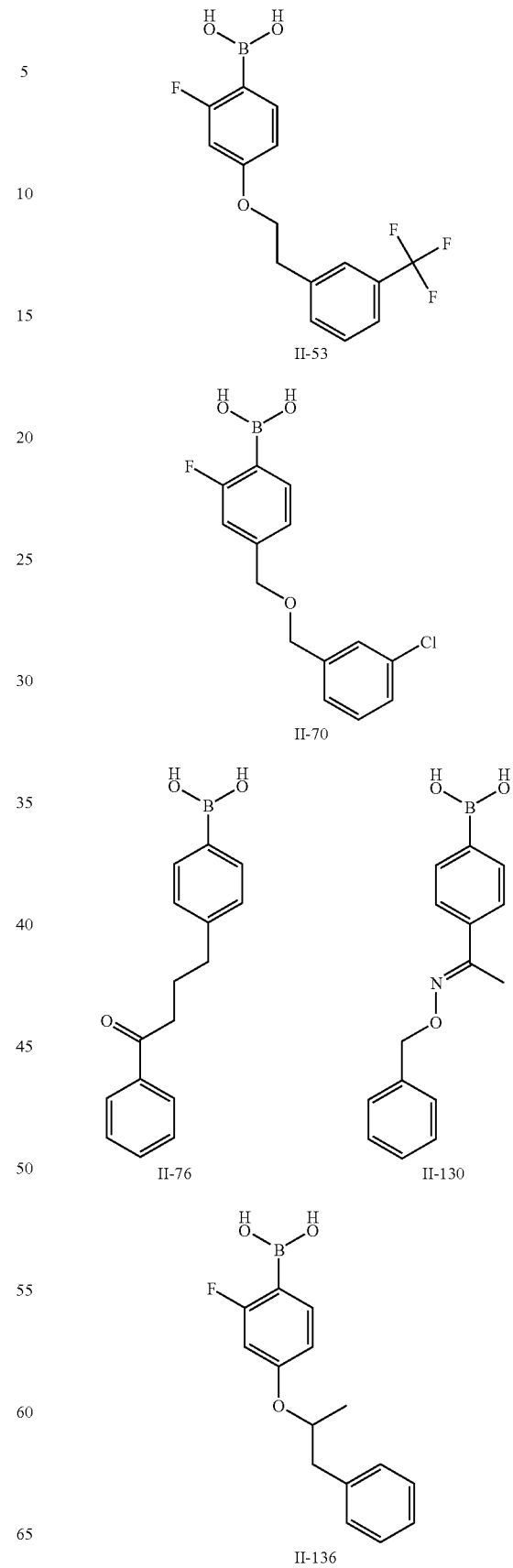

TABLE 3-continued
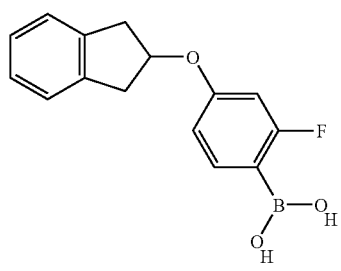
II-138
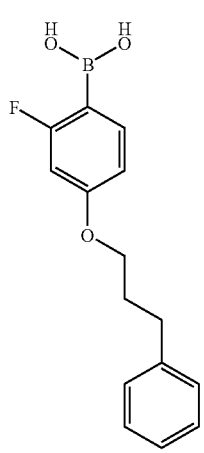
II-156
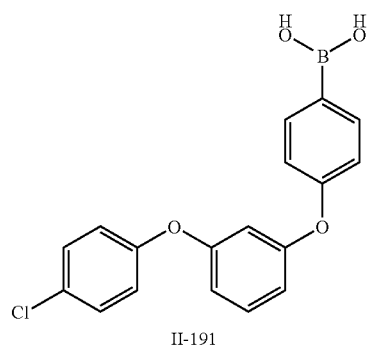
II-191
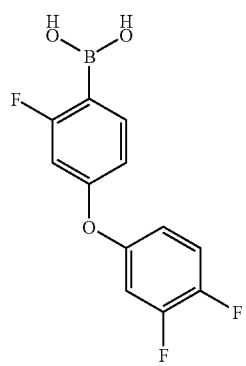
II-210
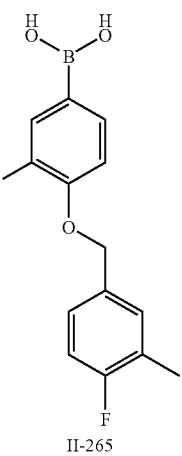
II-265
TABLE 3-continued
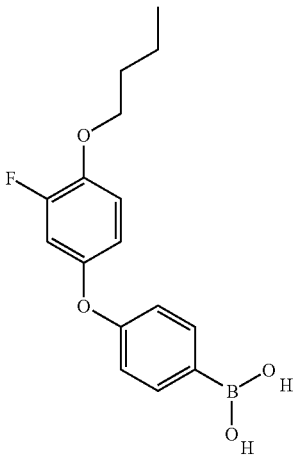
II-271
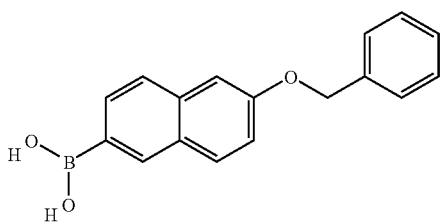
I-56
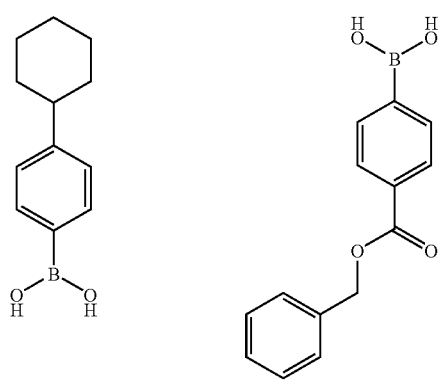
I-162        I-173
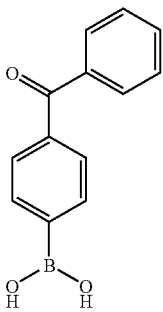
I-202

In certain embodiments, the present invention provides a compound of formula A:

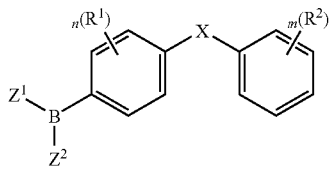

wherein $Z^1$ and $Z^2$ independently for each occurrence represent hydroxy, alkoxy, aryloxy, or aralkyloxy; or $Z_1$ and $Z_2$ taken together form a moiety derived from a dihydroxyl compound having at least two hydroxyl groups separated by at least two connecting carbon atoms in a chain or ring, said chain or ring comprising carbon atoms and optionally one or more heteroatoms independently selected from the group consisting of N, S, and O;

n is 0, 1, 2, 3, or 4;

m is 0, 1, 2, 3, 4, or 5;

X is a bond, O, S, $NR^3$, $CR^4R^5$, $OCR^4R^5$, $CR^4R^5O$, $SCR^4R^5$, $CR^4R^5S$, $NR^3CR^4R^5$, or $CR^4R^5NR^3$;

$R^1$ for each occurrence is independently halide, alkyl, perhaloalkyl, alkoxy, or trihaloalkoxy;

$R^2$ for each occurrence is independently halide, alkyl, perhaloalkyl nitro, alkoxy, trihaloalkoxy, aryloxy, carboxy, amido, ester, or —$NR^4CO_2R^5$; or two $R^2$ on adjacent carbons taken together form a 5-7 membered optionally substituted ring which contains 0-3 heteroatoms selected from the group consisting of N, O, and S; and each of $R^3$, $R^4$, and $R^5$ for each occurrence is independently H, alkyl, aralkyl, aryl, ester, or amido.

In certain embodiments, $Z^1$ and $Z^2$ groups of formula A are each hydroxyl. In other embodiments, the present invention provides a compound selected from the group consisting of:

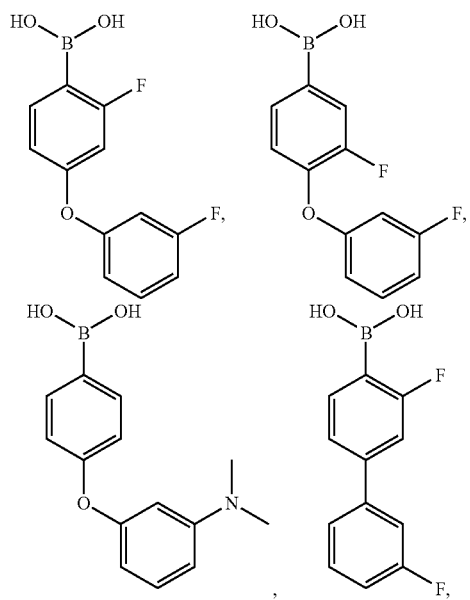

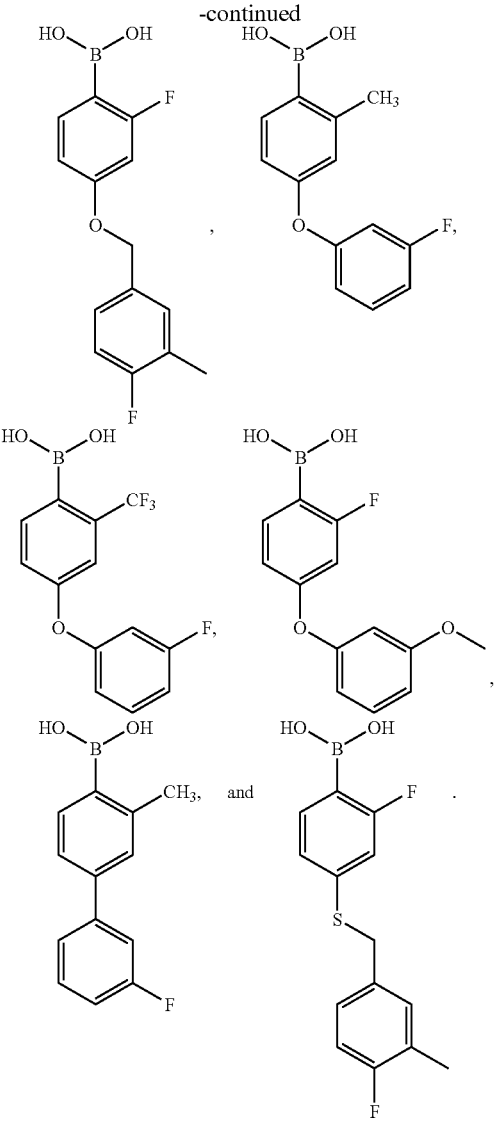

4. Pharmaceutically Acceptable Compositions and Formulations

In certain embodiments, the present invention provides a pharmaceutical composition comprising a compound of formulae (I), (II) or (III), or a pharmaceutically acceptable form thereof, and a pharmaceutically acceptable excipient.

In some embodiments, the present invention provides a pharmaceutical composition comprising a compound of formulae (I), (II) or (III), or a pharmaceutically acceptable form thereof, as provided in Tables 1, 2 or 3, and a pharmaceutically acceptable excipient. In other embodiments, the present invention provides a pharmaceutical composition comprising a compound of formulae (I), (II) or (III), or a pharmaceutically acceptable form thereof, as provided in Tables 1, 2 or 3 having a $K_i$ of less than or equal to 0.01 microM or having a $K_i$ of between 0.01 microM and 0.1 microM (i.e., compounds with activities designated "A" and "B"), and a pharmaceutically acceptable excipient. In yet other embodiments, the present invention provides a pharmaceutical composition comprising a compound of formulae (I), (II) or (III), or a pharmaceutically acceptable form thereof, as provided in Tables 1, 2 or 3 having a $K_i$ of less than or equal to 0.01 microM (i.e., compounds with activities designated "A") and a pharmaceutically acceptable excipient. In still yet other embodiments, the present invention provides a pharmaceutical composition comprising a compound of formulae (I), (II) or (III), or a pharmaceutically acceptable form thereof, and a pharmaceutically acceptable excipient, wherein said compound is selected from the any compound depicted in Table 3.

As described above, the pharmaceutically acceptable compositions of the present invention additionally comprise a pharmaceutically acceptable excipient, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The formulations of the pharmaceutical compositions described herein may be prepared by any method known or hereafter developed in the art of pharmacology. In general, such preparatory methods include the step of bringing the active ingredient into association with a carrier and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol, etc.); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* $21^{st}$ ed., Lippincott Williams & Wilkins, 2005.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Kits

Still further encompassed by the invention are kits comprising one or more inventive compounds (or pharmaceutically acceptable forms thereof), and/or an inventive pharmaceutical composition. Kits are typically provided in a suitable container (e.g., for example, a foil, plastic, or cardboard package). In certain embodiments, an inventive kit may include one or more pharmaceutical excipients, pharmaceutical additives, therapeutically active agents, and the like, as described herein. In certain embodiments, an inventive kit may include means for proper administration, such as, for example, graduated cups, syringes, needles, cleaning aids, and the like. In certain embodiments, an inventive kit may include instructions for proper administration and/or preparation for proper administration.

5. Methods of Treatment

The present invention also provides methods for treating an FAAH-mediated disease, disorder or condition by administering a therapeutically effective amount of a compound of the formulae (I), (II) or (III), or a pharmaceutical composition thereof, to a patient in need thereof.

Additionally, the present invention provides methods for inhibiting FAAH in a patient by administering a therapeutically effective amount of a compound of the formulae (I), (II) or (III), or a pharmaceutical composition thereof, to a patient in need thereof.

A patient to which administration is contemplated includes, but is not limited to, humans (e.g., male, female, infant, child, adolescent, adult, elderly, etc.) and/or other primates; mammals, including commercially relevant mammals such as cattle, pigs, horses, sheep, cats, and/or dogs; and/or birds, including commercially relevant birds such as chickens, ducks, geese, and/or turkeys. "Treating," as used herein, refers to partially or completely inhibiting or reducing the condition from which the patient is suffering. "Therapeutically effective amount," as used herein, refers to the minimal amount or concentration of an inventive compound or inventive pharmaceutical composition that, when administered, is sufficient in treating the patient. Treating may be via prophylactic or therapeutic therapy.

In other embodiments, the present invention provides a method for inhibiting FAAH in a biological sample comprising the step of contacting said sample with a compound of formula I, II, or III, or with a compound set forth in any of Tables 1, 2 or 3.

FAAH-mediated diseases, disorders or conditions include, but are not limited to, painful syndromes, diseases and/or disorders, inflammatory disorders, immune disorders, depression, anxiety, sleep disorders, feeding behaviors, movement disorders, glaucoma, neuroprotection and cardiovascular disease.

In certain embodiments, the FAAH-mediated disease, disorder or condition is a painful syndrome, disease and/or disorder. As used herein, "painful syndromes, diseases and/or disorders" include, but are not limited to, those characterized by neuropathic pain (e.g., peripheral neuropathic pain), central pain, deafferentiation pain, chronic pain (e.g., chronic nociceptive pain, and other forms of chronic pain such as post-operative pain), stimulus of nociceptive receptors, acute pain (e.g., phantom and transient acute pain), non-inflammatory pain, inflammatory pain, pain associated with cancer, preoperative pain, arthritic pain, lumbosacral pain, musculoskeletal pain, headache, migraine, muscle ache, lower back and neck pain, toothache and the like.

In certain embodiments, the FAAH-mediated disease, disorder or condition is neuropathic pain. The term "neuropathic pain" is meant pain resulting from injury to a nerve. Neuropathic pain is distinguished from nociceptive pain, which is the pain caused by acute tissue injury involving small cutaneous nerves or small nerves in muscle or connective tissue. Neuropathic pain typically is long-lasting or chronic and often develops days or months following an initial acute tissue injury. Neuropathic pain can involve persistent, spontaneous pain as well as allodynia, which is a painful response to a stimulus that normally is not painful. Neuropathic pain also can be characterized by hyperalgesia, in which there is an accentuated response to a painful stimulus that usually is trivial, such as a pin prick. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes include: diabetic neuropathy; sciatica; non-specific lower back pain; multiple sclerosis pain; fibromyalgia; HIV-related neuropathy; neuralgia, such as post-herpetic neuralgia and trigeminal neuralgia; and pain resulting from physical trauma, amputation, cancer, toxins or chronic inflammatory conditions. Neuropathic pain can result from a peripheral nerve disorder such as neuroma; nerve compression; nerve crush, nerve stretch or incomplete nerve transsection; mononeuropathy or polyneuropathy. Neuropathic pain can also result from a disorder such as dorsal root ganglion compression; inflammation of the spinal cord; contusion, tumor or hemisection of the spinal cord; tumors of the brainstem, thalamus or cortex; or trauma to the brainstem, thalamus or cortex.

The symptoms of neuropathic pain are heterogeneous and are often described as spontaneous shooting and lancinating pain, or ongoing, burning pain. In addition, there is pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

In certain embodiments, the FAAH-mediated disease, disorder or condition is non-inflammatory pain and/or inflammatory pain. The types of non-inflammatory pain include, without limitation, peripheral neuropathic pain (e.g., pain caused by a lesion or dysfunction in the peripheral nervous system), central pain (e.g., pain caused by a lesion or dysfunction of the central nervous system), deafferentation pain (e.g., pain due to loss of sensory impart into the central nervous system), chronic nociceptive pain (e.g., certain types of cancer pain), noxious stimulus of nociceptive receptors (e.g., pain felt in response to tissue damage or impending tissue damage), phantom pain (e.g., pain felt in a part of the body that no longer exists), pain felt by psychiatric patients (e.g., pain where no physical cause may exist), and wandering pain (e.g., wherein the pain repeatedly changes location in the body). In certain embodiments, non-inflammatory pain and/or inflammatory pain are associated with disorders such as inflammatory disorders (e.g., autoimmune disorders).

In certain embodiments, the FAAH-mediated disease, disorder or condition is an inflammatory disorder. The term "inflammatory disorders" refers to those diseases or conditions that are characterized by one or more of the signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and loss of function (functio laesa, which may be partial or complete, temporary or permanent). Inflammatory disorders include, without limitation, those affecting the blood vessels (polyarteritis, temporal arteritis); joints (arthritis: crystalline, osteo-, psoriatic, reactive, rheumatoid, Reiter's); gastrointestinal tract (chron's disease, ulcerative colitis); skin (dermatitis); or multiple organs and tissues (systemic lupus erythematosus). Inflammatory disorders include, but are not limited to, inflammation associated with vascular diseases, migraine headaches, tension headaches, periarteritis nodosa, thyroiditis, aplastic anemia, Hodgkin's disease, scierodoma, rheumatic fever, type I diabetes, myasthenia gravis, sarcoidosis, nephrotic syndrome, Behcet's syndrome, polymyositis, gingivitis, hypersensitivity, conjunctivitis, multiple sclerosis, and ischemia (e.g., myocardial ischemia), and the like. The compounds and compositions may be useful for treating neuroinflammation associated with brain disorders (e.g., Parkinson's disease and Alzheimer's disease) and chronic inflammation associated with cranial radiation injury. The compounds may be useful for treating acute inflammatory conditions (e.g., conditions resulting from infection) and chronic inflammatory conditions (e.g., conditions resulting from asthma, arthritis and inflammatory bowel disease). The compounds may also be useful in treating inflammation associated with trauma and non-inflammatory myalgia. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

In certain embodiments, the FAAH-mediated disease, disorder or condition is an immune disorder. Immune disorders, such as auto-immune disorders, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin inflammation disorders (e.g., psoriasis, eczema, burns, dermatitis), enuresis, eosinophilic disease, gastrointestinal disorders (e.g., inflammatory bowel disease (IBD), peptic ulcers, regional enteritis, diverticulitis, gastrointestinal bleeding, Crohn's disease, gastritis, diarrhoea, irritable bowel syndrome and ulcerative colitis), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP)).

In certain embodiments, the immune disorder is a gastrointestinal disorder. In some embodiments, the immune disorder is inflammatory bowel disease (IBD), peptic ulcers, regional enteritis, diverticulitis, gastrointestinal bleeding, Crohn's disease, gastritis, diarrhoea, irritable bowel syndrome and ulcerative colitis. In other embodiments, the immune disorder is inflammatory bowel disease (IBD).

In certain embodiments, the immune disorder is a skin inflammation disorder. In some embodiments, the immune disorder is psoriasis, eczema, burns or dermatitis. In yet other embodiments, the immune disorder is psoriasis.

In certain embodiments, the FAAH-mediated disease, disorder or condition is anxiety. "Anxiety," as used herein, includes, but is not limited to anxiety and anxiety disorders or conditions, such as, for example, clinical anxiety, panic disorder, agoraphobia, generalized anxiety disorder, specific phobia, social phobia, obsessive-compulsive disorder, acute stress disorder, and post-traumatic stress disorder; and adjustment disorders with anxious features, anxiety disorders due to general medical conditions, and substance-induced anxiety disorders. This treatment may also be to induce or promote sleep in a patient (e.g., for example, a patient with anxiety).

In certain embodiments, the FAAH-mediated disease, disorder or condition is a sleep disorder. "Sleep disorders" include, but are not limited to, insomia, sleep apnea, restless legs syndrome (RLS), delayed sleep phase syndrome (DSPS), periodic limb movement disorder (PLMD), hypopnea syndrome, rapid eye movement behavior disorder (RBD), shift work sleep disorder (SWSD), and sleep problems (e.g., parasomnias) such as nightmares, night terrors, sleep talking, head banging, snoring, and clenched jaw and/or grinding of teeth (bruxism).

In certain embodiments, the FAAH-mediated disease, disorder or condition is depression. "Depression," as used herein, includes, but is not limited to, depressive disorders or conditions, such as, for example, major depressive disorders (unipolar depression), dysthymic disorders (chronic, mild depression) and bipolar disorders (manic-depression). The depression may be clinical or subclinical depression.

In certain embodiments, the FAAH-mediated disease, disorder or condition is feeding behavior. "Feeding behavior," as used herein, includes but is not limited to, eating disorders (e.g., anorexias and cachexias of various natures, over-eating leading to obesity), weight loss associated with cancer and other wasting conditions. The compounds disclosed herein can also be used to reduce body fat and for treating or preventing obesity in a mammal. The compounds disclosed herein can also be used for preventing or treating the diseases associated with these health conditions.

In certain embodiments, the FAAH-mediated disease, disorder or condition is a movement disorder. In other embodiments, the FAAH-mediated disease, disorder or condition is glaucoma. In yet other embodiments, the FAAH-mediated disease, disorder or condition is neuroprotection. In still yet other embodiments, the FAAH-mediated disease, disorder or condition is cardiovascular disease.

In certain embodiments, the above methods provide administering a compound of formulae formulae (I), (II) or (III), or a pharmaceutically acceptable form thereof, to a patient in need thereof. In some embodiments, the above methods provide administering a compound of formulae (I), (II) or (III), or a pharmaceutically acceptable form thereof, as provided in Tables 1, 2 or 3. In other embodiments, the above methods provide administering a compound of formulae (I), (II) or (III), or a pharmaceutically acceptable form thereof, as provided in Tables 1, 2 or 3, having a $K_i$ of less than or equal to 0.01 microM or having a $K_i$ of between 0.01 microM and 0.1 microM (i.e., compounds with activities designated "A" or "B"). In yet other embodiments, the above methods provide administering a compound of formulae (I), (II) or (III), or a pharmaceutically acceptable form thereof, as provided in Tables 1, 2 or 3, having a $K_i$ of less than or equal to 0.01 microM (i.e., compounds with activities designated "A").

6. Administration

The inventive compounds may be administered using any amount and any route of administration effective for treatment. The exact amount required will vary from subject to subject, depending on the species, age, and general condition of the subject, the severity of the infection, the particular composition, its mode of administration, its mode of activity, and the like. The compounds of the present invention are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The inventive compounds and compositions of the present invention may be administered by any route. In some embodiments, the inventive compounds and compositions are administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc. At present the oral and/or nasal spray and/or aerosol route is most commonly used to deliver therapeutic agents directly to the lungs and/or respiratory system. However, the invention encompasses the delivery of the inventive pharmaceutical composition by any appropriate route taking into consideration likely advances in the sciences of drug delivery.

The exact amount of a compound required to achieve a therapeutically effective amount will vary from subject to subject, depending on species, age, and general condition of a subject, severity of the side effects or disorder, identity of the particular compound(s), mode of administration, and the like. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

In certain embodiments of the present invention, a therapeutically effective amount of an inventive compound for administration one or more times a day to a 70 kg adult human may comprise about 0.0001 mg to about 1000 mg of an inventive compound per unit dosage form. It will be appreciated that dose ranges as described herein provide guidance for the administration of inventive pharmaceutical compositions to an adult. The amount to be administered to, for example, a child or an adolescent can be determined by a medical practitioner or person skilled in the art and can be lower or the same as that administered to an adult.

It will be also appreciated that an inventive compound or composition, as described above and herein, can be administered in combination with one or more additional therapeutically active agents.

By "in combination with," it is not intended to imply that the agents must be administered at the same time and/or formulated for delivery together, although these methods of delivery are certainly within the scope of the invention. The compositions can be administered concurrently with, prior to, or subsequent to, one or more other additional therapeutically active agents. In general, each agent will be administered at a dose and/or on a time schedule determined for that agent. In will further be appreciated that the additional therapeutically active agent utilized in this combination may be administered together in a single composition or administered separately in different compositions. The particular combination to employ in a regimen will take into account compatibility of the inventive compound with the additional therapeutically active agent and/or the desired therapeutic effect to be achieved.

In general, it is expected that additional therapeutically active agents utilized in combination be utilized at levels that do not exceed the levels at which they are utilized individually. In some embodiments, the levels utilized in combination will be lower than those utilized individually.

By a "therapeutically active agent" or "active agent" refers to any substance that is useful for therapy, including prophylactic and therapeutic treatment.

The invention encompasses the delivery of the inventive pharmaceutical compositions in combination with agents that may improve their bioavailability, reduce and/or modify their metabolism, inhibit their excretion, and/or modify their distribution within the body. It will also be appreciated that the therapy employed may achieve a desired effect for the same disorder (for example, an inventive compound may be administered in combination with an anti-Page inflammatory, anti-anxiety and/or anti-depressive agent, etc.), and/or they may achieve different effects (e.g., control of any adverse side-effects).

Exemplary active agents include, but are not limited to, anti-cancer agents, antibiotics, anti-viral agents, anesthetics, anti-coagulants, inhibitors of an enzyme, steroidal agents, steroidal or non-steroidal anti-inflammatory agents, antihistamine, immunosuppressant agents, anti-neoplastic agents, antigens, vaccines, antibodies, decongestants, sedatives, opioids, pain-relieving agents, analgesics, anti-pyretics, hormones, prostaglandins, progestational agents, anti-glaucoma agents, ophthalmic agents, anti-cholinergics, anti-depressants, anti-psychotics, hypnotics, tranquilizers, anti-convulsants, muscle relaxants, anti-spasmodics, muscle contractants, channel blockers, miotic agents, anti-secretory agents, anti-thrombotic agents, anticoagulants, anti-cholinergics, β-adrenergic blocking agents, diuretics, cardiovascular active agents, vasoactive agents, vasodilating agents, anti-hypertensive agents, angiogenic agents, modulators of cell-extracellular matrix interactions (e.g. cell growth inhibitors and anti-adhesion molecules), or inhibitors/intercalators of DNA, RNA, protein-protein interactions, protein-receptor interactions, etc. Active agents include small organic molecules such as drug compounds (e.g., compounds approved by the Food and Drugs Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the additional therapeutically active agent is a pain-relieving agent. In other embodiments, the additional therapeutically active agent is an anti-inflammatory agent.

7. Methods of Determining Biological Activity

Methods of determining the activity of compounds of the present invention for various therapeutic uses are well known in the art. These include, but are not limited to, high throughput screening to find compounds that bind to and/or modulate the activity of isolated FAAH, as well as animal and cellular models of therapies.

The assays for compounds described herein are amenable to high throughput screening. Assays useful for screening the compounds of the present invention may detect the binding of the inhibitor to FAAH or the release of a reaction product (e.g., fatty acid amide or ethanolamine) produced by the hydrolysis of a substrate such as oleoylethanolamide or anandamide. The substrate may be labeled to facilitate detection of the released reaction products. U.S. Pat. No. 5,559,410 discloses high throughput screening methods for proteins, and U.S. Pat. Nos. 5,576,220 and 5,541,061 disclose high throughput methods of screening for ligand/antibody binding.

Methods for screening FAAH inhibitors for an antinociceptive effect are well known to one of ordinary skill in the art. For instance, the test compounds can be administered to the subject animals in the mouse hot-plate test and the mouse formalin test and the nociceptive reactions to thermal or chemical tissue damage measured (for example, see U.S. Pat. No. 6,326,156 which teaches methods of screening for antinociceptive activity; see also Cravatt et al. *Proc. Natl. Acad. Sci. U.S.A.* (2001) 98:9371-9376).

Two pharmacologically validated animal models of anxiety are the elevated zero maze test, and the isolation-induced ultrasonic emission test. The zero maze consists of an elevated annular platform with two open and two closed quadrants and is based on the conflict between an animal's instinct to explore its environment and its fear of open spaces, where it may be attacked by predators (see, for example, Bickerdike, M. J. et al., *Eur. J. Pharmacol.*, (994) 271, 403-411; Shepherd, J. K. et al., *Psychopharmacology*, (1994) 116, 56-64). Clinically used anxiolytic drugs, such as the benzodiazepines, increase the proportion of time spent in, and the number of entries made into, the open compartments.

A second test for an anti-anxiety compound is the ultrasonic vocalization emission model, which measures the number of stress-induced vocalizations emitted by rat pups removed from their nest (see, for example, Insel, T. R. et al., Pharmacol. Biochem. Behav., 24, 1263-1267 (1986); Miczek, K. A. et al., Psychopharmacology, 121, 38-56 (1995); Winslow, J. T. et al., Biol. Psychiatry, 15, 745-757 (1991).

The effect of the compound of the invention in the treatment of depression can be tested in the model of chronic mild stress induced anhedonia in rats. This model is based on the observation that chronic mild stress causes a gradual decrease in sensitivity to rewards, for example consumption of sucrose, and that this decrease is dose-dependently reversed by chronic treatment with antidepressants. The method has previously been described and more information with respect to the test appears from Willner, Paul, Psychopharmacology, 1997, 134, 319-329.

Another test for antidepressant activity is the forced swimming test (Nature 266, 730-732, 1977). In this test, animals are administered an agent, preferably by the intraperitoneal route or by the oral route, 30 or 60 minutes before the test. The animals are placed in a crystallizing dish filled with water and the time during which they remain immobile is clocked. The immobility time is then compared with that of the control group treated with distilled water. Imipramine 25 mg/kg. can be used as the positive control. The antidepressant compounds decrease the immobility time of the mice thus immersed.

Another test for antidepressant activity is the caudal suspension test on the mouse (Psychopharmacology, 85, 367-370, 1985). In this test, animals are preferably treated with the study compound by the intraperitoneal route or by the oral route 30 or 60 minutes before the test. The animals are then suspended by the tail and their immobility time is automatically recorded by a computer system. The immobility times are then compared with those of a control group treated with distilled water. Imipramine 25 mg/kg can be used as the positive control. Antidepressant compounds decrease the immobility time of the mice.

Animals models are available to one of ordinary skill in the art for studying anticonvulsant activity of test compounds. See for instance, U.S. Pat. No. 6,309,406 and U.S. Pat. No. 6,326,156 which describe methods for performing such tests.

Inhibition of FAAH has been reported to induce sleep in test animals (U.S. Pat. No. 6,096,784). Methods for studying sleep inducing compounds are well known to one of ordinary skill in the art. In particular, methods for testing the ability of a FAAH inhibitory compound to induce sleep or treat insomnia are disclosed in U.S. Pat. No. 6,096,784 and U.S. Pat. No. 6,271,015. Most obviously, the compounds can be administered to a test animal (e.g., rat or mouse) or a human and the subsequent time (e.g., onset, duration) spent sleeping (e.g., eyes closed, motor quiescence) can be monitored. See also WO 98/24396.

Methods for screening FAAH inhibitors which induce catalepsy are also well known to one of ordinary skill in the art. See Quistand et al. in Toxicology and Applied Pharmacology 173: 48-55 (2001). See Cravatt et al. Proc. Natl. Acad. Sci. U.S.A. 98:9371-9376 (2001).

Methods of assessing appetitive behavior are known to one of ordinary skill in the art. For instance, Maruani et al. (U.S. Pat. No. 6,344,474) teach two such assays. One method of assessing the effect on appetite behavior is to administer a FAAH inhibitor to a rat and assess its effect on the intake of a sucrose solution. This method is taught in W. C. Lynch et al., Physiol. Behav., 1993, 54, 877-880.

8. Covalent Complex Formation Between Serine-241 of FAAH and Boronic Acid Inhibitors Compounds provided by the present invention form reversible covalent complexes with the nucleophilic side chain of Ser-241 FAAH.

Thus, the present invention also provides compounds of formulae (I), (II) or (III), as described above and herein, associated with (e.g., complexed with) a serine residue of a protein:

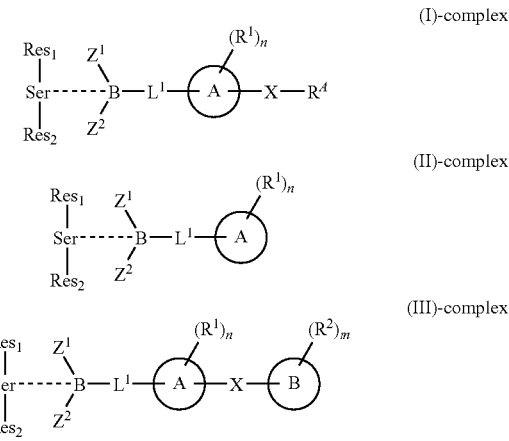

wherein $Res_1$-Ser-$Res_2$ is a protein having a length between about 400 to about 600 residues.

By "Ser" is meant a serine residue. In certain embodiments, Ser is $Ser_{241}$ of FAAH protein. In some embodiments, the protein is rat FAAH. In other embodiments, the protein is human FAAH (SEQ ID NO. 1). In certain embodiments, the active site of the protein has a Lys at 142; a Ser at 217; and a Ser at 241. In certain embodiments, the compound binds at Ser$_{241}$.

By Res$_1$ is meant the residue(s) closer to the N-terminus than Ser. By Res$_2$ is meant the residue(s) closer to the C-terminus than Ser. In certain embodiments, Res$_1$ has a serine residue that is 24 amino acids closer to the N terminus than (Ser) and a lysine residue that is 99 amino acids closer to the N terminus than (Ser).

In certain embodiments, $Z^1$ and $Z^2$ are both —OH. Thus, in certain embodiments, the compound is a boronic acid compound.

In certain embodiments, Ring A is an optionally substituted phenyl.

For example, in certain embodiments, the present invention provides compounds of formulae (III-a), as described above and herein, associated with a serine residue of a protein:

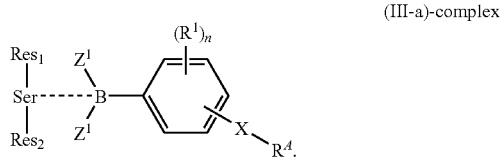

(III-a)-complex

In certain embodiments, Ring A is a substituted phenyl comprising at least one fluorine substitutent. In certain embodiments, n is 1 and $R^1$ is fluorine. In certain embodiments, $R^1$ is ortho to the boron atom.

In other embodiments, Ring B is an optionally substituted phenyl. For example, in certain embodiments, the present invention provides compounds of formulae (III-b), as described above and herein, associated with a serine residue of a protein:

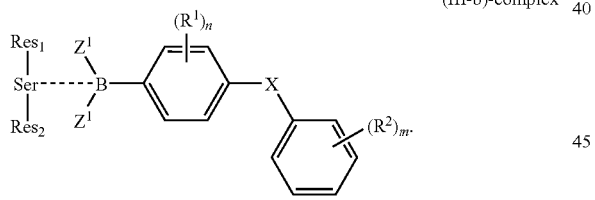

(III-b)-complex

In certain embodiments, Ring B is a substituted phenyl comprising at least one fluorine substitutent. In certain embodiments, m is 1 and $R^2$ is fluorine. In certain embodiments, $R^2$ is meta to the linker group X.

9. Methods of Synthesis

A number of methods are known in the art to synthesize the compounds of the present invention. A common method of synthesizing boronate esters is the reaction of an organometallic species with an organic borate, such as trimethyl borate. Common organometallic species include, but are not limited to, alkyl lithium and Grignard reagents. Other methods for the synthesis of boronates are employed when the boronate contains sensitive functionality that may not tolerate alkyl lithium reagents or Grignard reagents. These methods include palladium coupling reactions of aryl or akenyl halides and diboronates or dialkoxy boranes and hydroboration of alkenes or alkynes. Using these methods a diverse collection of boronates can be synthesized. Boronates can be readily transformed in to boronic acids by hydrolyzing the boronate under aqueous acidic conditions using a suitable acid. Suitable acids include, but are not limited to HCl, $H_2SO_4$, and HBr. Another method of hydrolyzing boronates is an oxidative hydrolysis employing an oxidizing agent, such as NaIO$_4$, as exemplified in Example 5. The boronic acid compounds of the present invention readily form boronic esters when exposed to alcohols. The resulting boronic esters may also be used in the methods of the present invention. Cyclic boronates are formed when certain diols (e.g., 1,2- and 1,3-diols) are used. Boronic acid compounds of the present invention readily form oligomeric anhydrides by dehydration of the boronic acid moiety to form dimers, trimers, and tetramers, and mixtures thereof. These species in the presence of water and under physiological conditions convert back to the boronic acid by hydrolysis.

EXEMPLIFICATION

The invention now being generally described, it will be more readily understood by reference to the following examples, which are included merely for purposes of illustration of certain aspects and embodiments of the present invention, and are not intended to limit the invention.

Example 1

Synthesis of 3,4'-difluorobiphenyl-4-ylboronic acid (1)

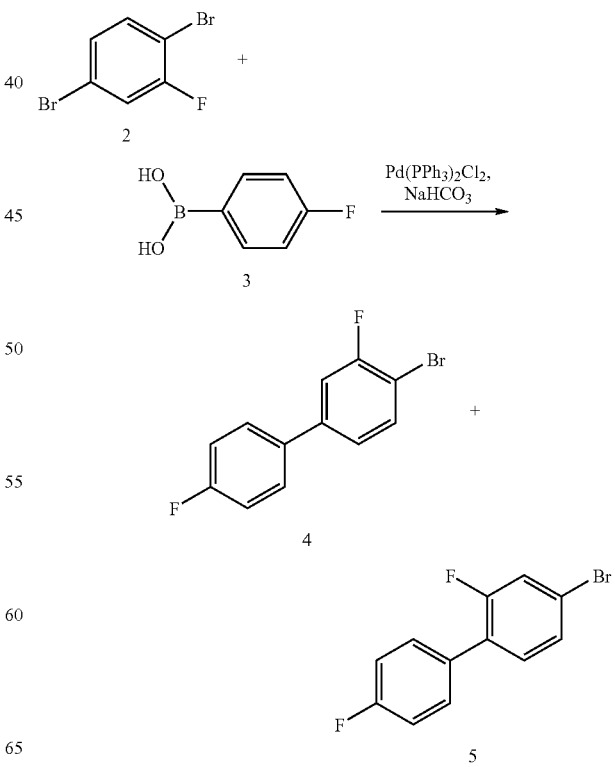

-continued

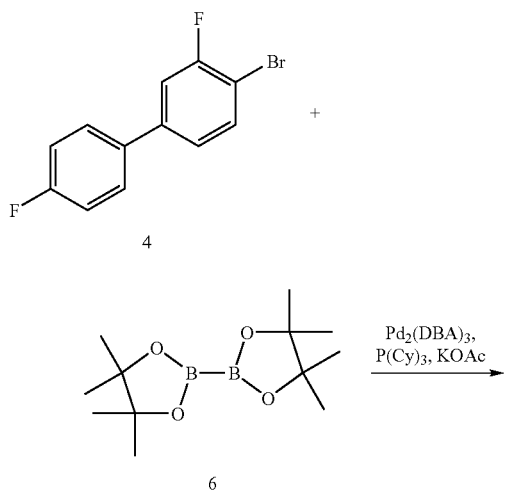

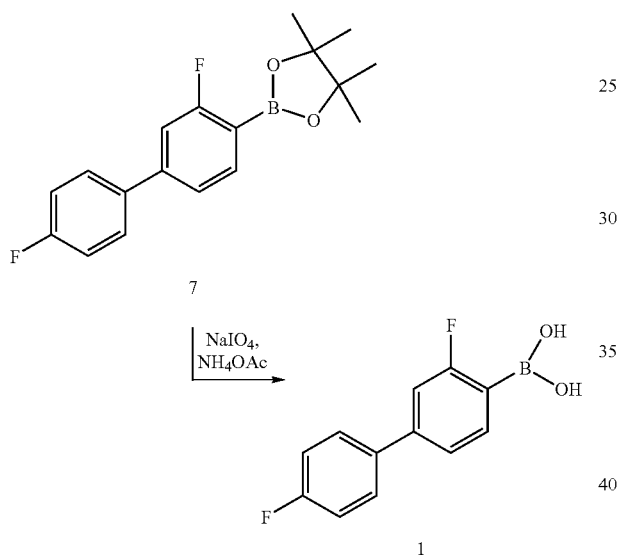

Compound (5): In an oven-dried 100 mL round bottom flask boronic acid 3 (1.00 g, 1.0 eq.) was added, followed by dibromobenzene 2 (3.60 g, 2.0 eq) and palladium reagent (150 mg) were dissolved in dioxane to give a yellow solution. Sodium bicarbonate aqueous solution (2 M, 14 mL) was added causing a beige suspension to form. The suspension was heated at 80° C. for 20 h. The reaction was evaporated to dryness and the residue partitioned between EtOAc (75 mL) and water (25 mL). The layers were separated and the organic layer washed with brine, dried over magnesium sulfate, filtered and evaporated to a yellow oil. The oil was chromatographed with hexanes to yield 1.07 g (57% yield) of 4 as a white solid and 528 mg (30% yield) of 5 as a white solid.

Compound (7): Palladium reagent (61 mg, 0.12 eq) and tricyclohexylphosphine (70 mg, 0.28 eq) were dissolved in dioxane under an Ar atmosphere and stirred for 30 min at rt. To the red solution the boron reagent 6 (246 mg, 1.1 eq), potassium acetate (130 mg, 1.5 eq) and biphenyl bromide 4 (237 mg, 1.0 eq.) were added in that order. The deep red solution was then heated at 80° C. for 72 h during which time it turned a green color. LCMS shows incomplete reaction, so new portions of Pd$_2$(dba)$_3$ and (C$_6$H$_{11}$)$_3$P were added and heating continued for another 24 h. Reaction was cooled to rt and treated with water (7 mL), extracted with EtOAc (3×35 mL). The organic layers were combined, washed with brine (25 mL), dried over magnesium sulfate, filtered and evaporated to a dark brown oil. The oil was chromatographed with 9:1 Hexanes/Ethyl Acetate to result in isolation of a white solid to yield 66 mg (27% yield) of 7 as a white solid.

Compound (1): The boronate ester 7 (66 mg, 1.0 eq), sodium periodate (130 mg, 3.0 eq) and ammonium acetate (48 mg, 3.0 eq) were dissolved in acetone/water 2:1 (12 mL/6 mL) and stirred for 48 h until LCMS indicated reaction was complete. The reaction was then evaporated to a white solid which was taken up in water and acidified with 1 N HCl. The suspension was extracted with EtOAc and the organic layer washed with brine, dried over magnesium sulfate, filtered and evaporated to a white solid which was triturated with hexanes to result in isolation of 20 mg (40% yield) of the desired product 1. MS (ESI(−)) m/e 233.01 (M−H).

Example 2

Synthesis of Compound (8)

Compound 8 may be synthesized using the same procedure described in Example 1 using compound 5 in place of 4. MS (ESI(−)) m/e 233.04 (M−H).

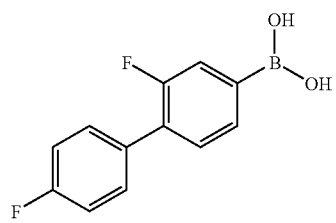

Example 3

Compound 9 was synthesized according to the procedure described in Example 1 using 3-fluorophenylboronic acid in place of 3. MS (ESI(−)) m/e 233.04 (M−H).

Example 4

Compound 10 was synthesized according to the procedure described in Example 1 using 2-fluorophenylboronic acid in place of 3. MS (ESI(−)) m/e 233.04 (M−H).

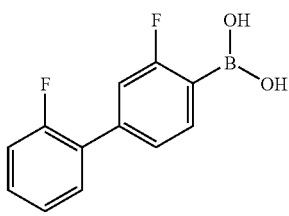

Example 5

Compound 11 was synthesized according to the procedure described in Example 1 using 4-Bromo-4'-methoxybiphenyl in place of 4. MS (ESI(−)) m/e 227.03 (M−H).

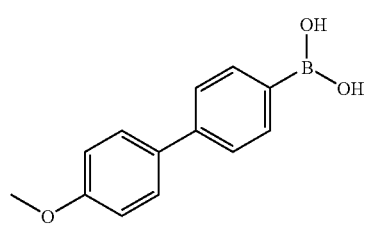

Example 6

Compound 12 was synthesized according to the procedure described in Example 1 using 4-Acetoxy-4'-bromobiphenyl in place of 4. MS (ESI(−)) m/e 256.09 (M−H).

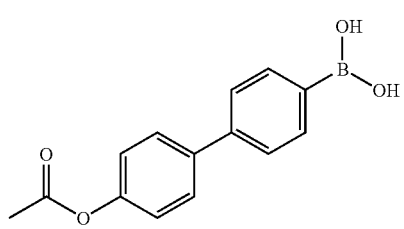

Example 7

Compound 13 was synthesized according to the procedure described in Example 1 using 4-Benzoyl-4'-bromobiphenyl in place of 4. MS (ESI(−)) m/e 301.10 (M−H).

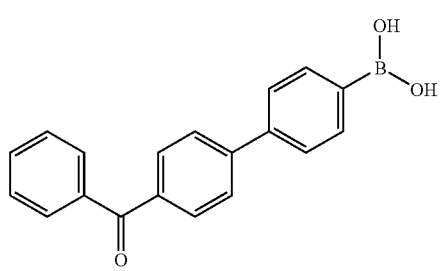

Example 8

Compound 14 was synthesized according to the procedure described in Example 1 using 4-Bromo-4'-n-propylbiphenyl in place of 4. MS (ESI(−)) m/e 239.09 (M−H).

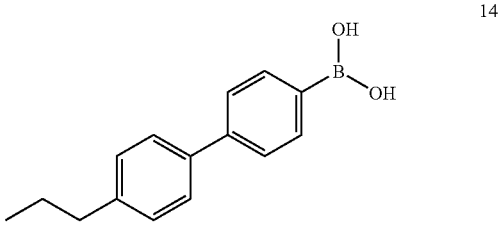

Example 9

Compound 15 was synthesized according to the procedure described in Example 1 using 4-Bromo-4'-tert-butylbiphenyl in place of 4. MS (ESI(−)) m/e 253.11 (M−H).

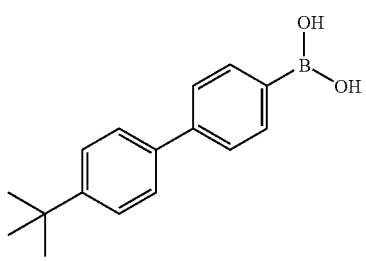

Example 10

Compound 16 was synthesized according to the procedure described in Example 1 using 4-Acetyl-4'-bromobiphenyl in place of 4. MS (ESI(−)) m/e 240.04 (M−H).

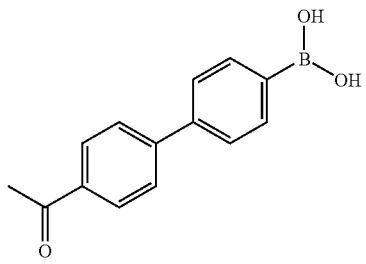

Example 11

Synthesis of 5'-(trifluoromethyl)biphenyl-3-yl)methylboronic acid (17)

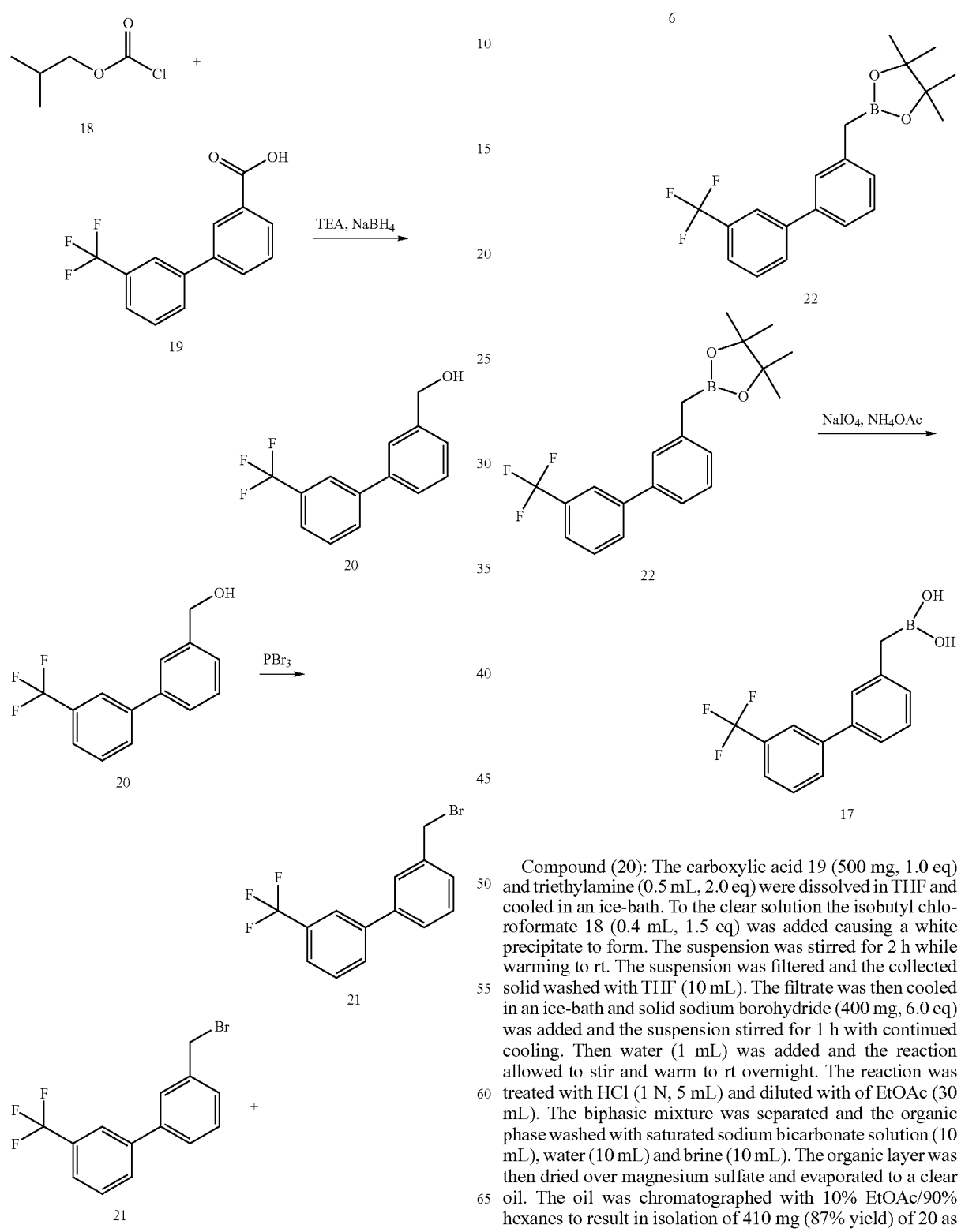

Compound (20): The carboxylic acid 19 (500 mg, 1.0 eq) and triethylamine (0.5 mL, 2.0 eq) were dissolved in THF and cooled in an ice-bath. To the clear solution the isobutyl chloroformate 18 (0.4 mL, 1.5 eq) was added causing a white precipitate to form. The suspension was stirred for 2 h while warming to rt. The suspension was filtered and the collected solid washed with THF (10 mL). The filtrate was then cooled in an ice-bath and solid sodium borohydride (400 mg, 6.0 eq) was added and the suspension stirred for 1 h with continued cooling. Then water (1 mL) was added and the reaction allowed to stir and warm to rt overnight. The reaction was treated with HCl (1 N, 5 mL) and diluted with of EtOAc (30 mL). The biphasic mixture was separated and the organic phase washed with saturated sodium bicarbonate solution (10 mL), water (10 mL) and brine (10 mL). The organic layer was then dried over magnesium sulfate and evaporated to a clear oil. The oil was chromatographed with 10% EtOAc/90% hexanes to result in isolation of 410 mg (87% yield) of 20 as a clear oil.

Compound (21): The benzyl alcohol 20 (410 mg, 1.0 eq) was dissolved in of THF (10 mL) and cooled in an ice bath. To the clear solution phosphorous tribromide (0.18 mL, 1.2 eq), dissolved in THF (5 mL) was added dropwise. The clear solution was stirred for 2.5 h with continued cooling. The reaction mixture was poured into water (20 mL) and diluted with EtOAc (20 mL). The layers were separated and the organic layer washed with brine (10 mL), dried over magnesium sulfate and evaporated to a clear oil 21. The oil was used in the next step without further purification.

Compound (22): Biphenyl bromide 21 (510 mg, 1.0 eq), boron reagent 6 (490 mg, 1.2 eq), palladium reagent (110 mg, 0.1 eq), and potassium carbonate (670 mg, 3.0 eq) were all placed in an oven-dried flask under an Ar atmosphere in dioxane. The resulting yellow suspension was then heated to 80° C. and stirred for 36 h. The now dark solution was diluted with EtOAc (50 mL) and water (25 mL). The layers were separated and the organic layer washed with brine (25 mL), dried over magnesium sulfate, filtered and evaporated to a yellow oil. The oil was chromatographed with 95:5 hexanes/ethyl acetate to yield 55 mg (9% yield) of the desired product 22.

Compound (17): The boronate ester 22 (55 mg, 1.0 eq), sodium periodate (110 mg, 3.0 eq) and ammonium acetate (40 mg, 3.0 eq) were dissolved in acetone/water 2:1 (12 mL/6 mL) and stirred for 48 h until LCMS indicated reaction was complete. The reaction was then evaporated to a white solid which was taken up in water and acidified with 1 N HCl. The suspension was extracted with EtOAc and the organic layer washed with brine, dried over magnesium sulfate, filtered and evaporated to a white solid which was triturated with hexanes to result in isolation of a white solid upon filtration to yield 8 mg (16% yield) of the desired product 17.

Example 12

Compound 23 was synthesized according to the procedure described in Example 11 using 4'-Trifluoromethyl[1,1'-biphenyl]-3-carboxylic acid in place of 3'-Trifluoromethyl[1,1'-biphenyl]-3-carboxylic acid.

Example 13

Synthesis of 4-benzamidophenylboronic acid (29)

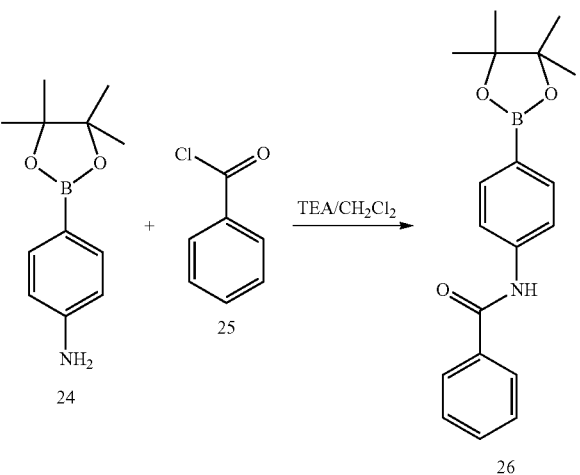

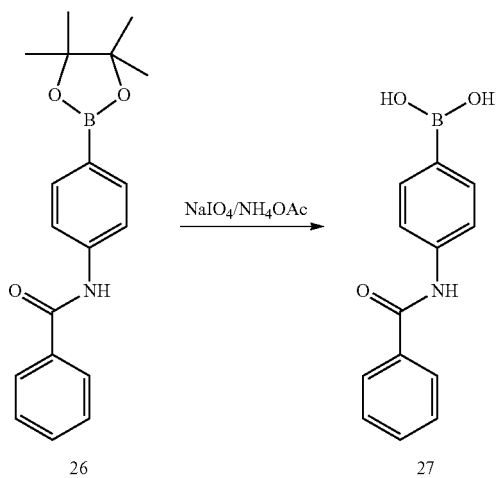

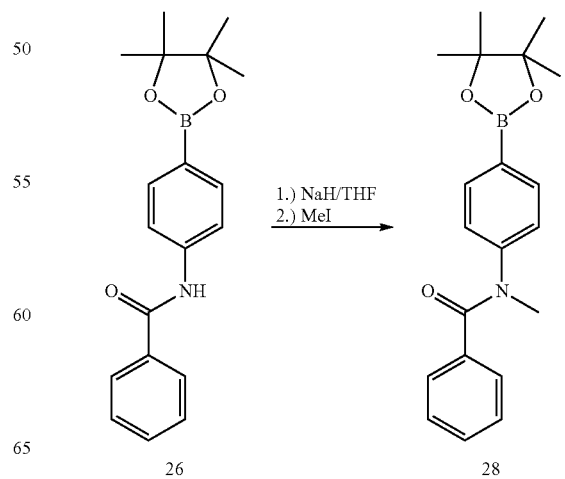

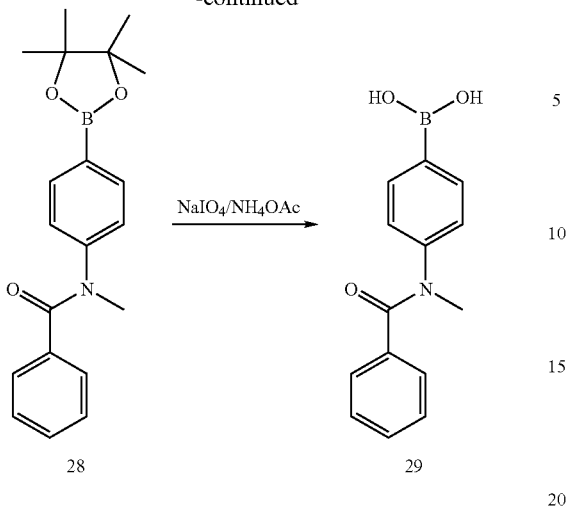

28    29

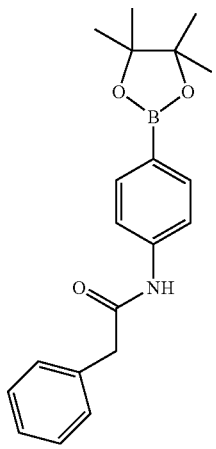

30

Example 15

Compound 31 was synthesized according to the procedure described in Example 13 Part B by replacing Compound 26 with Compound 30. MS (ESI(−)) m/e 254.05 (M−H).

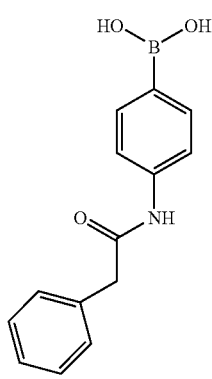

31

Example 16

Synthesis of 4-((4-fluoro-3-methylbenzyloxy)carbonyl)phenylboronic acid (35)

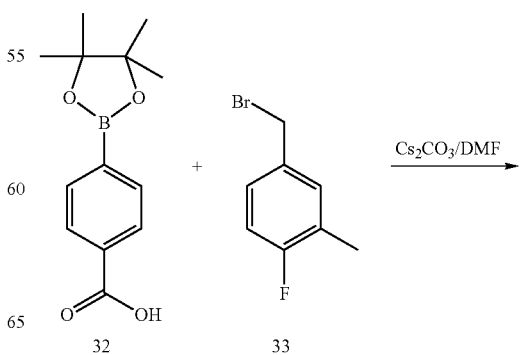

32    33

Compound (26): The boronate ester 24 (500 mg, 1.0 eq) was dissolved in DCM (10 mL). To the solution triethylamine (0.60 mL, 1.5 eq) and benzoyl chloride 25 (0.29 mL, 1.1 eq) were added and the solution stirred for 3 h at which time LCMS indicated complete reaction. The solution was then washed with water, 1 N HCl, 5% NaHCO₃, water and brine. The organic layer was dried over magnesium sulfate, filtered and evaporated to a white solid which was crystallized from ethyl acetate to give the desired product 26 as 420 mg (57% yield) of a white solid.

Compound (27): Compound 27 was synthesized as described in Example 1 Part C starting with boronate ester 26. MS (ESI(−)) m/e 240.01 (M−H).

Compound (28): The boronate ester 26 (200 mg, 1.0 eq) was dissolved in THF (5 mL) and cooled in an ice-water bath. To the cooled solution sodium hydride (30 mg, 1.2 eq) was added and stirred for 30 min with continued cooling. Then methyl iodide (132 mg, 1.5 eq) was added and the reaction stirred for 16 h. The reaction was quenched with water and diluted with EtOAc. The layers were separated and the organic layer dried over magnesium sulfate, filtered, and evaporated to a yellow oil. The oil was chromatographed on silica gel with hexanes/ethyl acetate (0-80% in 20% gradients) to result in isolation of 52 mg of 28 as a beige solid.

Compound (29): The boronate ester 26 (52 mg, 1.0 eq), sodium periodate (100 mg, 3.0 eq) and ammonium acetate (40 mg, 3.0 eq) were dissolved in acetone/water 2:1 (1 mL/0.5 mL) and stirred for 24 h at rt, until TLC indicated reaction was complete. The reaction was then evaporated to a white solid which was taken up in water and acidified with 1 N HCl. The suspension was extracted with EtOAc and the organic layer was washed with brine, dried over magnesium sulfate, filtered and evaporated to a white solid which was chromatographed (DCM/MeOH; 0%-3% in 0.5% gradients every 50 mL) to give 29 (30 mg; 20% yield) as a white solid. MS (ESI(−)) m/e 254.05 (M−H).

Example 14

Compound 30 was synthesized according to the procedure described in Example 13 Part A by replacing benzoyl chloride with 2-phenylacetyl chloride.

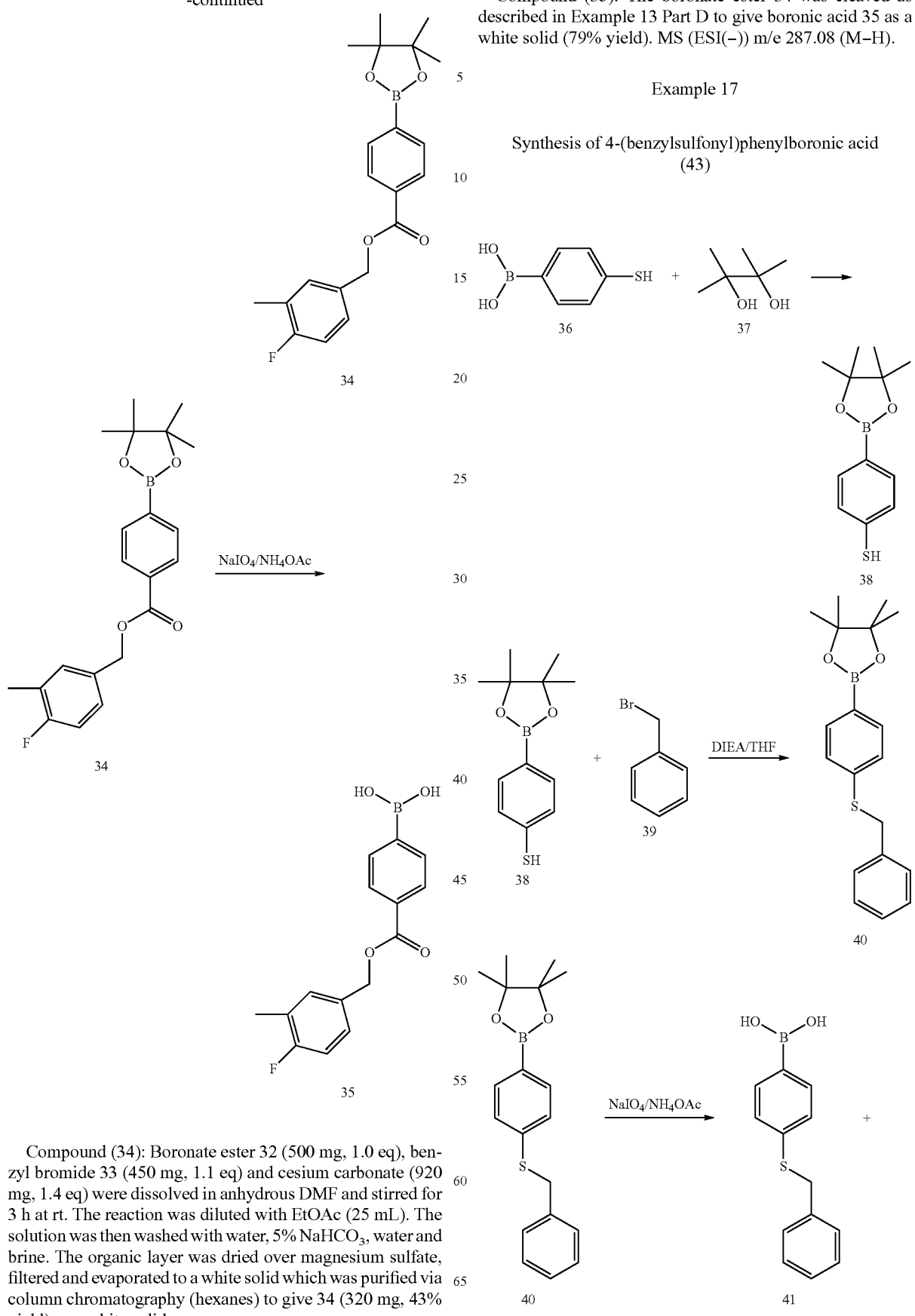

Compound (35): The boronate ester 34 was cleaved as described in Example 13 Part D to give boronic acid 35 as a white solid (79% yield). MS (ESI(−)) m/e 287.08 (M−H).

Example 17

Synthesis of 4-(benzylsulfonyl)phenylboronic acid (43)

Compound (34): Boronate ester 32 (500 mg, 1.0 eq), benzyl bromide 33 (450 mg, 1.1 eq) and cesium carbonate (920 mg, 1.4 eq) were dissolved in anhydrous DMF and stirred for 3 h at rt. The reaction was diluted with EtOAc (25 mL). The solution was then washed with water, 5% NaHCO$_3$, water and brine. The organic layer was dried over magnesium sulfate, filtered and evaporated to a white solid which was purified via column chromatography (hexanes) to give 34 (320 mg, 43% yield) as a white solid.

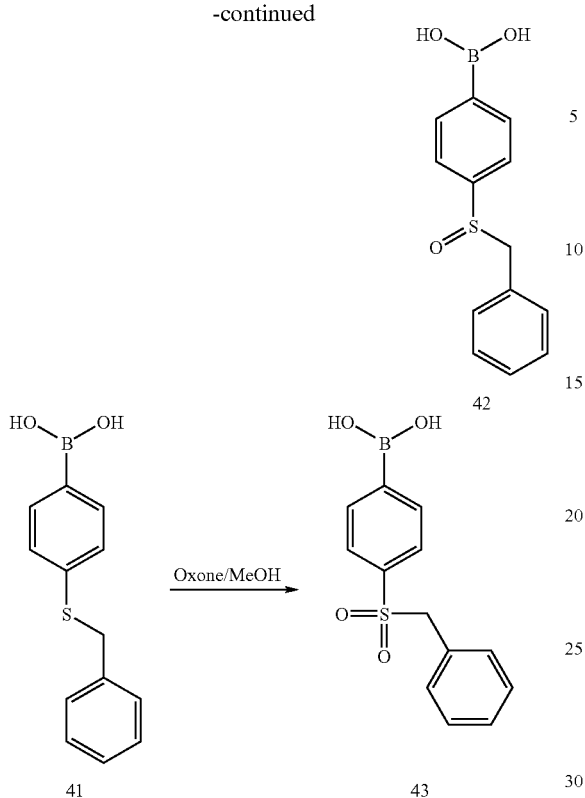

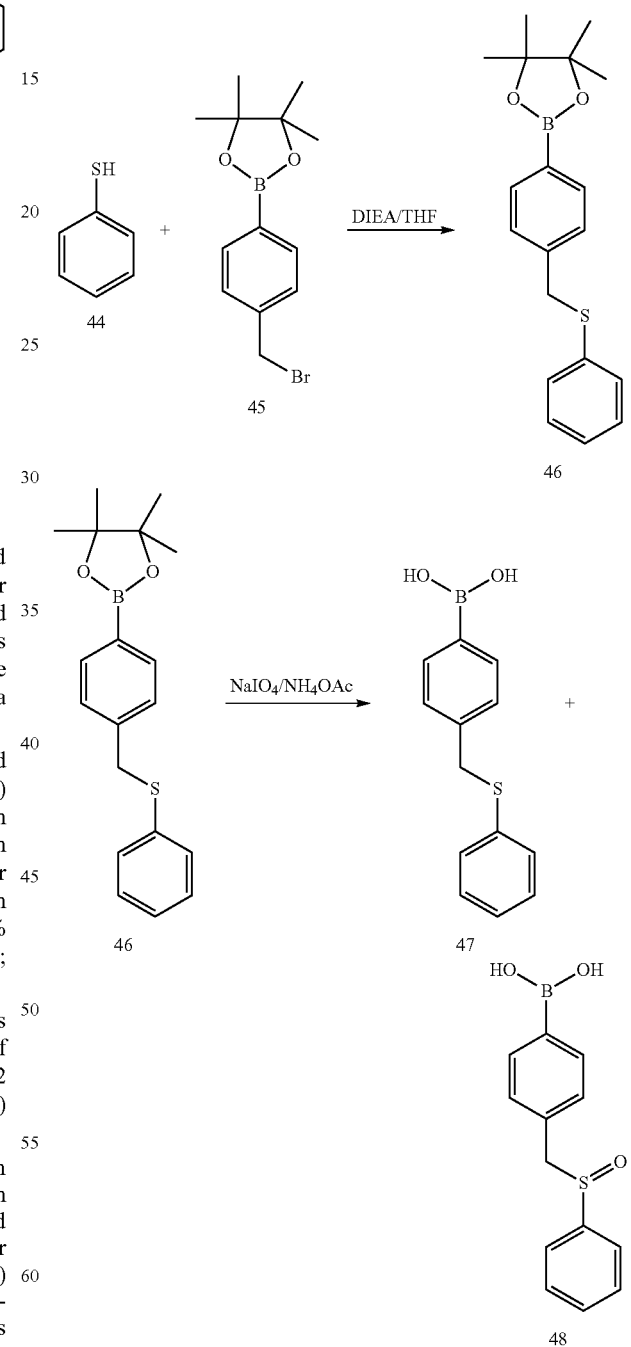

Compound (38): Boronic acid 36 (535 mg, 1.0 eq) and pinacol 37 (430 mg, 1.0 eq) were dissolved in diethyl ether (10 mL) at rt. To the solution magnesium sulfate was added and the reaction stirred overnight at rt. The reaction was filtered and the magnesium sulfate washed with ether. The filtrate was evaporated to give 38 (790 mg; 96% yield) as a beige solid.

Compound (40): Benzyl bromide 39 (0.10 mL, 1.1 eq) and Hunig's base (0.30 mL, 2.0 eq) were dissolved in THF (5 mL) to which thiol 38 (200 mg, 1.0 eq.) was added and the reaction stirred overnight at rt. The reaction was then diluted with EtOAc (50 mL), washed with water and brine, dried over magnesium sulfate and evaporated to a pale yellow oil which was chromatographed with hexanes/EtOAc (100% to 80% hexanes in 5% gradients every 100 mL) to give 40 (105 mg; 38% yield) as a clear oil.

Compound (41): The boronate ester 40 was cleaved as described in Example 13 Part D to result in isolation of boronic acids 41 (38% yield; MS (ESI(−)) m/e 243.12 (M−H)) and 42 (12% yield; MS (ESI(−)) m/e 259.10 (M−H)) as white solids.

Compound (43): Sulfide 41 (40 mg, 1 eq) was dissolved in MeOH (1 mL) and cooled in an ice water bath. To the solution of oxone (50 mg, 1 eq) dissolved in water (100 μL) was added dropwise which formed a white suspension. Then another portion of oxone (50 mg, 1 eq) dissolved in water (100 μL) was added. The suspension was stirred for 2.5 h while warming to rt. The suspension was treated with a 10% aqueous solution of $Na_2S_2O_3$ (2 mL) solution and then diluted with water (5 mL). The solution was extracted with DCM (2×10 mL) and evaporated to a white solid which was chromatographed with DCM/methanol (1% increments every 100 mL from 0% MeOH to 5% MeOH) to result in isolation of a white solid which was dissolved in acetonitrile/water and lyophilized to 12 mg (27%) of 43 as a white solid. MS (ESI(−)) m/e 275.11 (M−H).

Example 18

Synthesis of 4-(phenylthiomethyl)phenylboronic acid (47) and 4-(phenylsulfinylmethyl)phenylboronic acid (48)

Compound (46): Benzyl bromide 45 (200 mg, 1.0 eq) and Hunig's base (0.24 mL, 3.0 eq.) were dissolved in THF (5 mL) to which the thiol 44 (0.07 mL, 1.0 eq) was added and the reaction stirred overnight at rt. After about 30 min the solution became a cloudy white suspension. The reaction was diluted with EtOAc (50 mL), washed with water and brine, dried over magnesium sulfate and evaporated to a clear oil which was chromatographed with hexanes/EtOAc (100% to 80% hexanes in 5% gradients every 100 mL) to give 46 (135 mg, 61% yield) as a clear oil.

Compounds (47) and (48): The boronate ester 46 was cleaved as described in Example 13 to result in isolation of boronic acids 47 (27% yield) MS (ESI(−)) m/e 243.09 (M−H) and 48 (30% yields) MS (ESI(−)) m/e 259.11 (M−H) as white solids.

Example 19

Synthesis of 4-(methyl(phenyl)carbamoyl)phenylboronic acid (51)

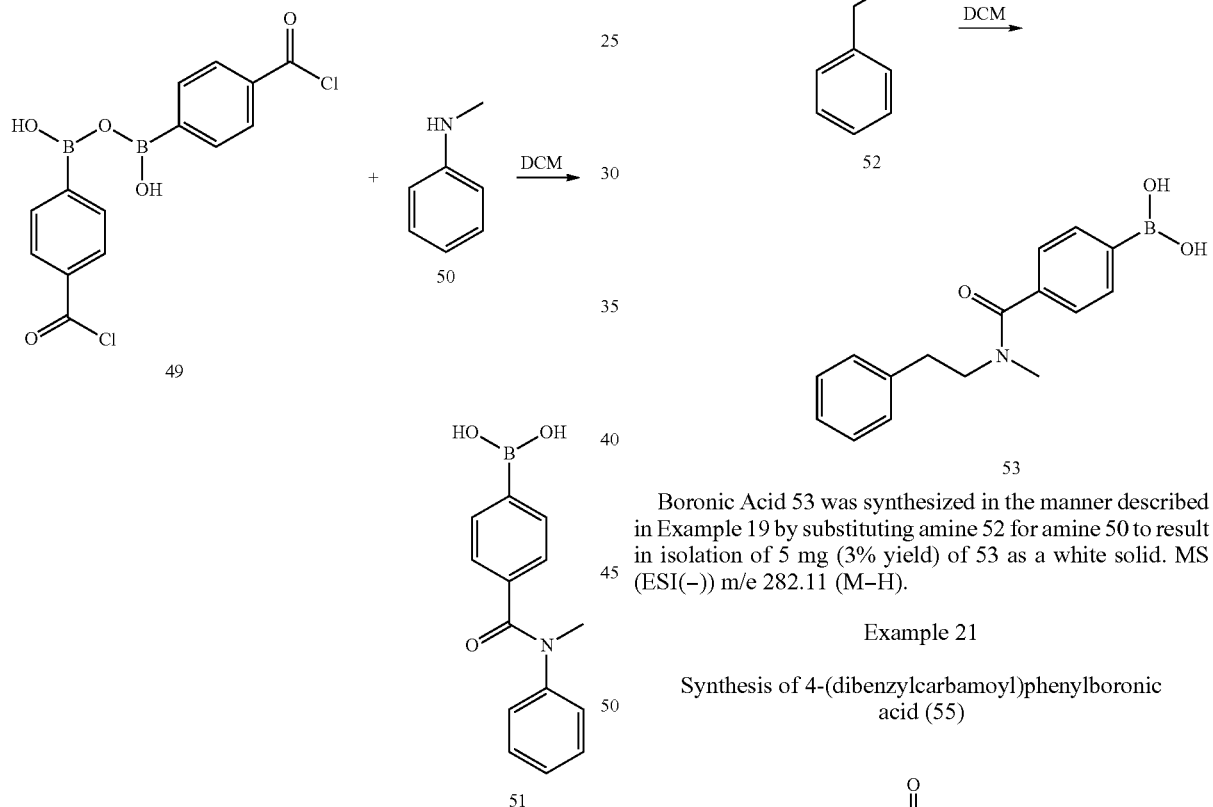

Boronic acid anhydride 49 (200 mg, 1.0 eq) and amine 50 (0.25 mL, 4.0 eq) were suspended in DCM and stirred overnight at rt. The reaction was diluted with EtOAc, and water was added and the reaction was stirred for 10 min. The layers were separated and the organic layer washed with brine, dried over magnesium sulfate, filtered and evaporated to a yellow oil. The oil was chromatographed with DCM/methanol to give a white solid which was dissolved in acetonitrile water and lyophilized to give 40 mg (28% yield) of 51 as a white solid. MS (ESI(−)) m/e 254.08 (M−H).

Example 20

Synthesis of 4-(methyl(phenethyl)carbamoyl)phenylboronic acid (53)

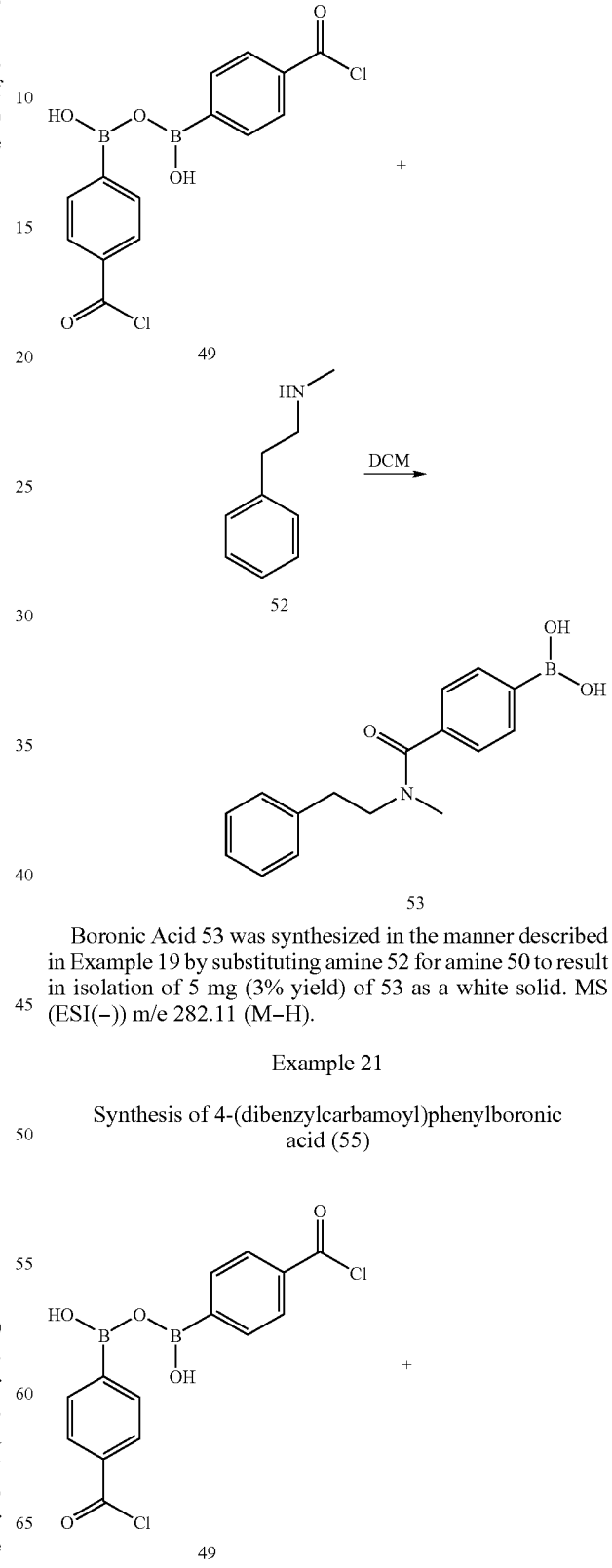

Boronic Acid 53 was synthesized in the manner described in Example 19 by substituting amine 52 for amine 50 to result in isolation of 5 mg (3% yield) of 53 as a white solid. MS (ESI(−)) m/e 282.11 (M−H).

Example 21

Synthesis of 4-(dibenzylcarbamoyl)phenylboronic acid (55)

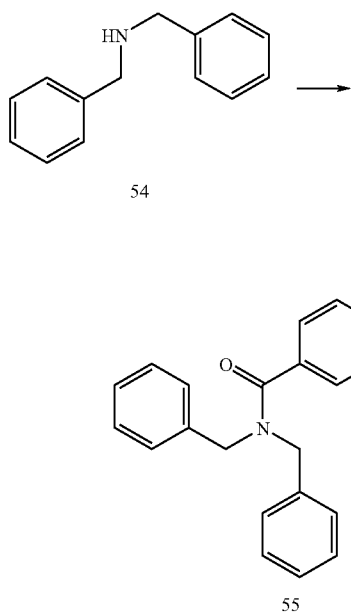

Boronic Acid 55 was synthesized in the manner described in Example 18 by substituting amine 54 for amine 50 to result in isolation of 5 mg of 55 as a white solid (100 mg, 52% yield). MS (ESI(−)) m/e 344.12 (M−H).

Example 22

Synthesis of 4-((4-chloro-3-methylphenoxy)methyl)phenylboronic acid (58)

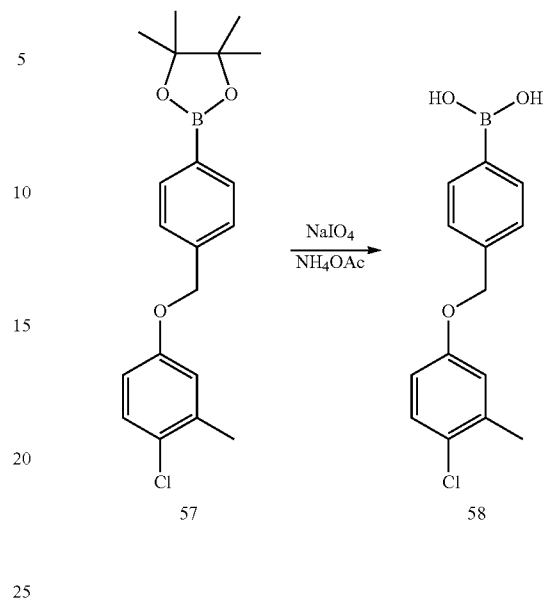

Compound (57): Phenol 56 (392 mg, 3.5 eq) was dissolved in THF (10 mL), cesium fluoride on Celite (695 mg, 3.5 eq) was added, and then boronate ester 45 (233 mg, 1.0 eq) was added. Heated for 40 h, filtered and concentrated. Ran silica column with hexanes, and then 10:1 hexanes:EtOAc, then 5:1. Isolated 158 mg (56% yield) of 57 as a beige solid.

Compound (58): The boronate ester 57 was cleaved as described in Example 13 to result in isolation of boronic acid 58 (22% yield) as a white solid. MS (ESI(−)) m/e 275.51 (M−H).

Example 23

Synthesis of 4-(phenoxymethyl)phenylboronic acid (61)

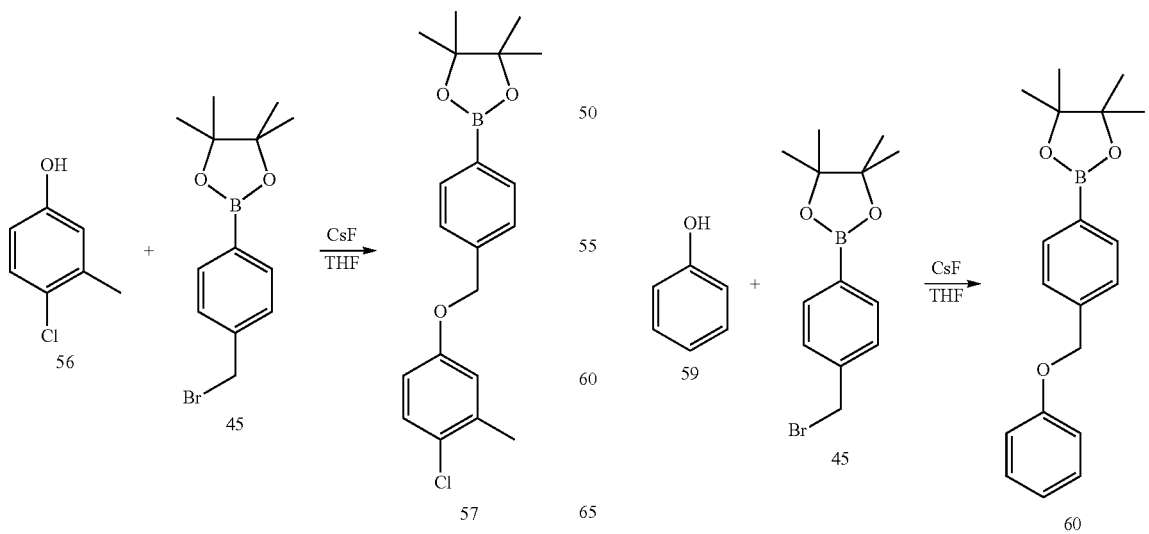

211
-continued

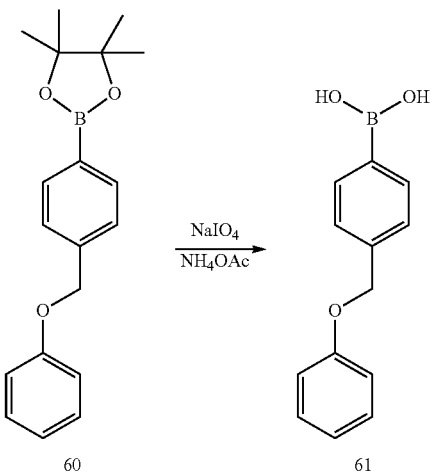

Compound (60): The boronate ester 60 was synthesized as described in Example 21 by replacing phenol 56 with phenol 59 to result in isolation of 61 mg (58% yield) of 60 as a white solid.

Compound (61): The boronate ester 60 was cleaved as described in Example 13 Part D to result in isolation of boronic acid 61 (20% yield) as a white solid. MS (ESI(−)) m/e 227.05 (M−H).

Example 24

Synthesis of 4-(3-fluoro-4-methylphenoxy)phenylboronic acid (62)

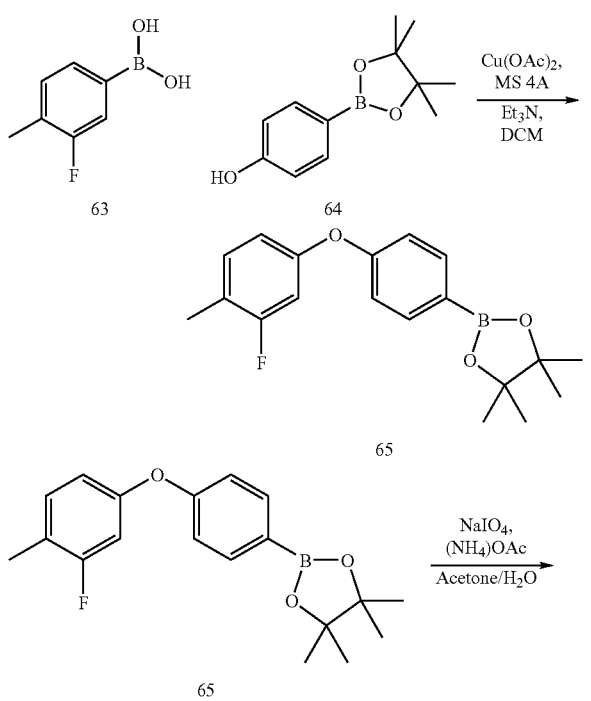

212
-continued

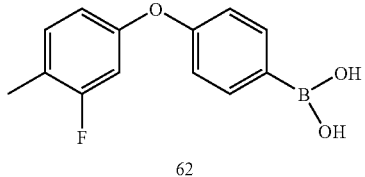

A flask is charged with phenol 64 (100 mg, 0.45 mmol, 1 eq), Cu(OAc)$_2$ (83 mg, 1 eq), arylboronic acid 63 (140 mg, 2 eq), and powered molecular sieves (300 mg). The mixture was diluted with DCM (10 mL) followed by the addition of Et$_3$N (0.32 mL, 5 eq). The reaction mixture was stirred at rt for 20 h. TLC analysis showed desired product. The reaction mixture was filtered through Celite 545, the filtrate was washed with EtOAc. The combined organic layers were concentrated and the crude product was purified by flash chromatography (5% EtOAc in hexanes then 10% EtOAc) to afford partially pure desired product 89 mg.

Boronate ester 65 (89 mg, 1 eq) was dissolved in acetone/water (10 mL, 1:1). Ammonium acetate (132 mg, 8 eq) and sodium periodate (326 mg, 8 eq) were added to the solution. The cloudy solution was stirred for 16 h. The reaction mixture was filtered through a short plug of Celite and sodium sulfate. The plug was washed with EtOAc and the combined filtrates were concentrated under reduced pressure and the crude product was purified by flash chromatography (25% EtOAc in hexanes then 50% EtOAc to 1% MeOH in DCM) to afford partially pure desired product 41 mg. Yield 78%. MS (ESI(−)) m/e 245.04 (M−H).

Example 25

Compound 66 was synthesized according to the procedure described in Example 24 using pyridine-3-boronic acid in place of boronic acid 63. MS (ESI(−)) m/e 214.09 (M−H)⁻.

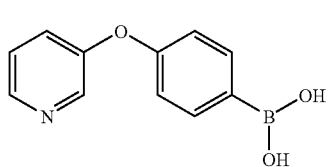

Example 26

Compound 67 was synthesized according to the procedure described in Example 24 using pyridine-4-boronic acid in place of boronic acid 63. MS (ESI(−)) m/e 214.08 (M−H)⁻.

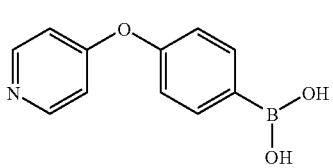

Example 27

Compound 68 was synthesized according to the procedure described in Example 24 using 3-fluorophenyl boronic acid in place of boronic acid 63. MS (ESI(−)) m/e 231.02 (M−H)⁻.

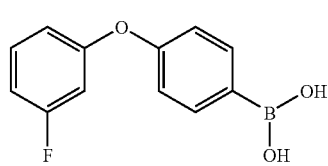

68

Example 28

Compound 69 was synthesized according to the procedure described in Example 24 using 4-fluorophenyl boronic acid in place of boronic acid 63. MS (ESI(−)) m/e 231.02 (M−H)⁻.

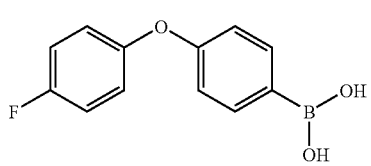

69

Example 29

Compound 70 was synthesized according to the procedure described in Example 24 using 3-methoxycarbonylphenyl boronic acid in place of boronic acid 63. MS (ESI(−)) m/e 271.05 (M−H)⁻.

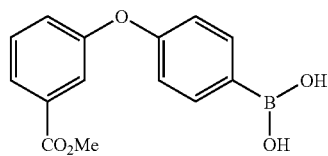

70

Example 30

Compound 71 was synthesized according to the procedure described in Example 24 using 4-methoxycarbonylphenyl boronic acid in place of boronic acid 63. MS (ESI(−)) m/e 271.05 (M−H)⁻.

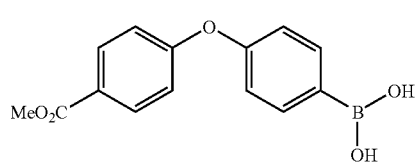

71

Example 31

Compound 72 was synthesized according to the procedure described in Example 24 using 3-methylphenyl boronic acid in place of boronic acid 63. MS (ESI(−)) m/e 227.12 (M−H)⁻.

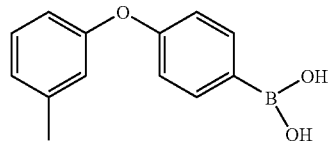

72

Example 32

Compound 73 was synthesized according to the procedure described in Example 24 using 4-methylphenyl boronic acid in place of boronic acid 63. MS (ESI(−)) m/e 227.07 (M−H)⁻.

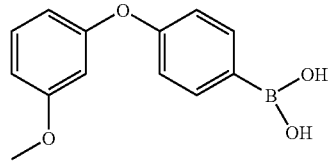

73

Example 33

Compound 74 was synthesized according to the procedure described in Example 23 using 3-methoxyphenyl boronic acid in place of boronic acid 63. MS (ESI(−)) m/e 243.03 (M−H)⁻.

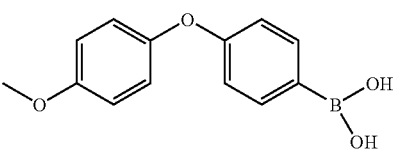

74

Example 34

Compound 75 was synthesized according to the procedure described in Example 24 using 4-methoxyphenyl boronic acid in place of boronic acid 63. MS (ESI(−)) m/e 243.05 (M−H)⁻.

75

Example 35

Compound 76 was synthesized according to the procedure described in Example 24 using 3-(N,N-dimethylamino)phenyl boronic acid in place of boronic acid 63. MS (ESI(−)) m/e 256.09 (M−H)⁻.

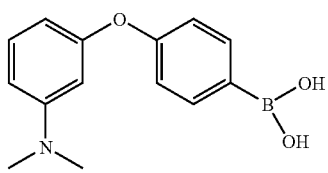

76

Example 36

Compound 77 was synthesized according to the procedure described in Example 24 using 3,4-dimethylphenyl boronic acid in place of boronic acid 63. MS (ESI(−)) m/e 241.04 (M−H)⁻.

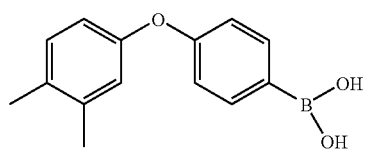

77

Example 37

Compound 78 was synthesized according to the procedure described in Example 24 using (3-chloro-4-methylphenyl) boronic acid in place of boronic acid 63. MS (ESI(−)) m/e 261.16 (M−H)⁻.

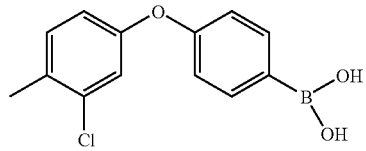

78

Example 38

Compound 79 was synthesized according to the procedure described in Example 24 using (4-methyl-3-nitrophenyl)boronic acid in place of boronic acid 63. MS (ESI(−)) m/e 272.06 (M−H)⁻.

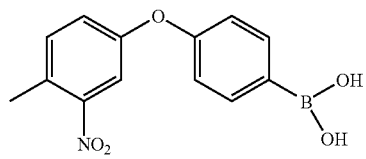

79

Example 39

Compound 80 was synthesized according to the procedure described in Example 24 using 3,4-methylenedioxybenzene boronic acid in place of boronic acid 63. MS (ESI(−)) m/e 257.03 (M−H)⁻.

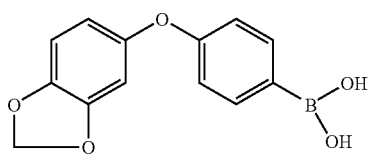

80

Example 40

Compound 81 was synthesized according to the procedure described in Example 24 using 3-fluoro-4-propyloxyphenyl boronic acid in place of boronic acid 63. MS (ESI(−)) m/e 289.32 (M−H)⁻.

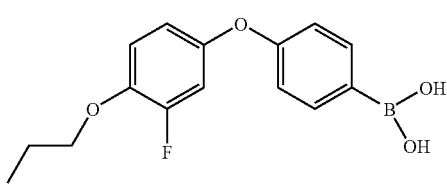

81

Example 41

Compound 82 was synthesized according to the procedure described in Example 24 using 4-butyloxy-3-fluorophenyl boronic acid in place of boronic acid 63. MS (ESI(−)) m/e 302.97 (M−H)⁻.

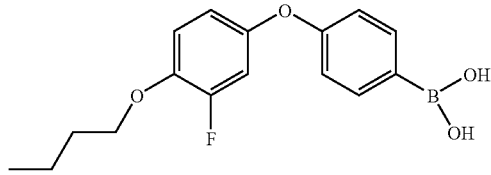

82

Example 42

Compound 83 was synthesized according to the procedure described in Example 24 using 3,4,5-trifluorophenyl boronic acid in place of boronic acid 63. MS (ESI(−)) m/e 266.99 (M−H)⁻.

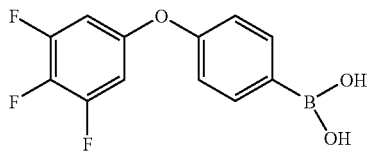

83

Example 43

Compound 84 was synthesized according to the procedure described in Example 24 using 3,4-difluorophenyl boronic acid in place of boronic acid 63. MS (ESI(−)) m/e 249.03 (M−H)⁻.

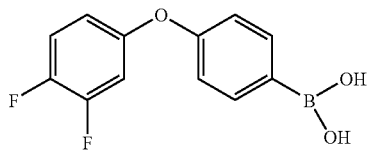

Example 44

Compound 85 was synthesized according to the procedure described in Example 24 using 3,5-difluorophenyl boronic acid in place of boronic acid 63. MS (ESI(−)) m/e 249.01 (M−H)⁻.

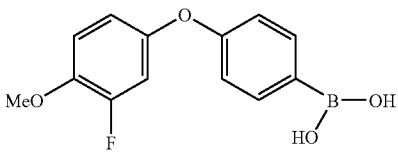

Example 48

Compound 89 was synthesized according to the procedure described in Example 24 using 4-chloro-3-(trifluoromethyl) phenyl boronic acid in place of boronic acid 63. MS (ESI(−)) m/e 314.83 (M−H)⁻.

85

Example 45

Compound 86 was synthesized according to the procedure described in Example 24 using 3,4-dichlorophenyl boronic acid in place of boronic acid 63. MS (ESI(−)) m/e 281.32 (M−H)⁻.

89

Example 49

Compound 90 was synthesized according to the procedure described in Example 24 using 3-chloro-4-(trifluoromethyl) phenyl boronic acid in place of boronic acid 63. MS (ESI(−)) m/e 315.47 (M−H)⁻.

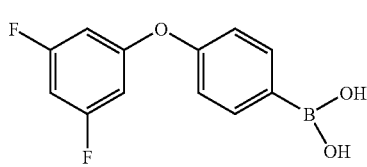

Example 46

Compound 87 was synthesized according to the procedure described in Example 24 using 3,5-dichlorophenyl boronic acid in place of boronic acid 63. MS (ESI(−)) m/e 281.32 (M−H)⁻.

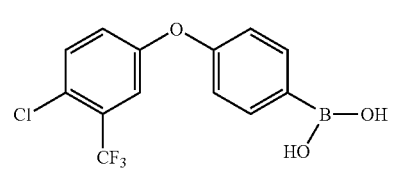

Example 50

Compound 91 was synthesized according to the procedure described in Example 24 using 4-chloro-3-methylphenyl boronic acid in place of boronic acid 63. MS (ESI(−)) m/e 261.41 (M−H)⁻.

87

Example 47

Compound 88 was synthesized according to the procedure described in Example 24 using 3-fluoro-4-methoxyphenyl boronic acid in place of boronic acid 63. MS (ESI(−)) m/e 261.03 (M−H)⁻.

91

Example 51

Compound 92 was synthesized according to the procedure described in Example 24 using 4-fluoro-3-methylphenyl boronic acid in place of boronic acid 63. MS (ESI(−)) m/e 245.45 (M−H)⁻.

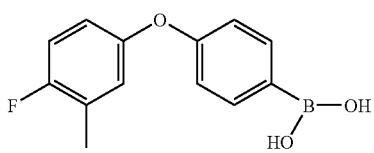

92

Example 52

Compound 93 was synthesized according to the procedure described in Example 24 using 3-chloro-4-methoxyphenyl boronic acid in place of boronic acid 63. MS (ESI(−)) m/e 277.45 (M−H)⁻.

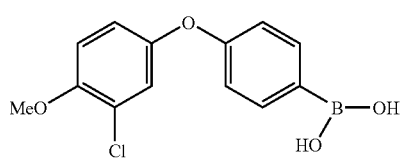

93

Example 53

Compound 94 was synthesized according to the procedure described in Example 24 using 4-ethoxy-3-fluorophenyl boronic acid in place of boronic acid 63. MS (ESI(−)) m/e 275.07 (M−H)⁻.

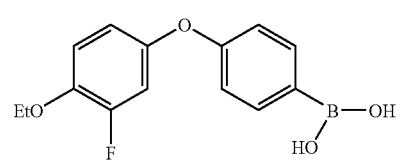

94

Example 54

Compound 95 was synthesized according to the procedure described in Example 24 using 3-isopropylphenyl boronic acid in place of boronic acid 63. MS (ESI(−)) m/e 255.07 (M−H)⁻.

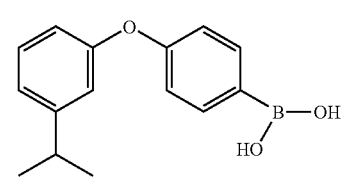

95

Example 55

Compound 96 was synthesized according to the procedure described in Example 24 using 3-isopropoxyphenyl boronic acid in place of boronic acid 63. MS (ESI(−)) m/e 271.77 (M−H)⁻.

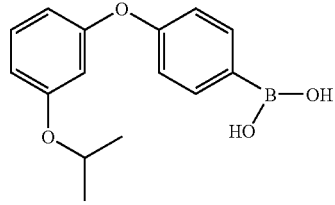

96

Example 56

Compound 97 was synthesized according to the procedure described in Example 24 using 3-trifluoromethoxyphenyl boronic acid in place of boronic acid 63. MS (ESI(−)) m/e 297.05 (M−H)⁻.

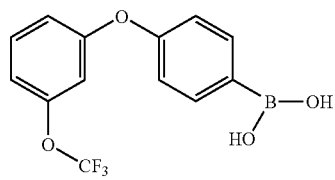

97

Example 57

Compound 98 was synthesized according to the procedure described in Example 24 using 3-butoxyphenyl boronic acid in place of boronic acid 63. MS (ESI(−)) m/e 285.11 (M−H)⁻.

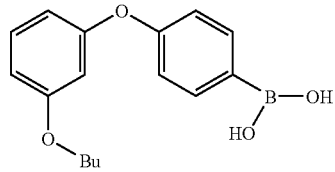

98

Example 58

Compound 99 was synthesized according to the procedure described in Example 24 using 3,4,5-trimethoxyphenyl boronic acid in place of boronic acid 63. MS (ESI(−)) m/e 302.96 (M−H)⁻.

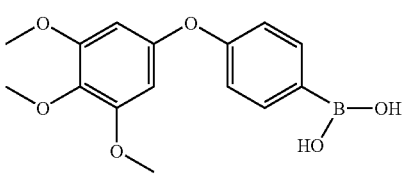

99

Example 59

Compound 100 was synthesized according to the procedure described in Example 24 using 4-methoxy-3,5-dimethylphenyl boronic acid in place of boronic acid 63. MS (ESI(−)) m/e 271.08 (M−H)⁻.

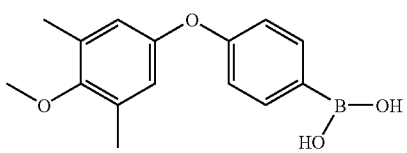

Example 60

Compound 101 was synthesized according to the procedure described in Example 24 using 3-isopropoxycarbonylphenyl boronic acid in place of boronic acid 63. MS (ESI(−)) m/e 299.11 (M−H)⁻.

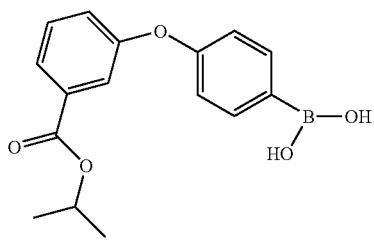

Example 61

Compound 102 was synthesized according to the procedure described in Example 24 using 3-(N,N-dimethylaminocarbonyl)phenyl boronic acid in place of boronic acid 63. MS (ESI(−)) m/e 284.66 (M−H)⁻.

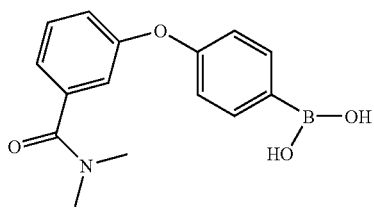

Example 62

Compound 103 was synthesized according to the procedure described in Example 24 using 4-(N,N-dimethylaminocarbonyl)phenyl boronic acid in place of boronic acid 63. MS (ESI(−)) m/e 284.32 (M−H)⁻.

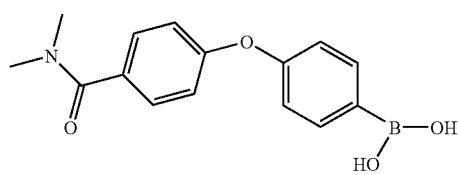

Example 63

Compound 104 was synthesized according to the procedure described in Example 24 using 3-(pyrrolidine-1-carbonyl)phenyl boronic acid in place of boronic acid 63. MS (ESI(−)) m/e 310.16 (M−H)⁻.

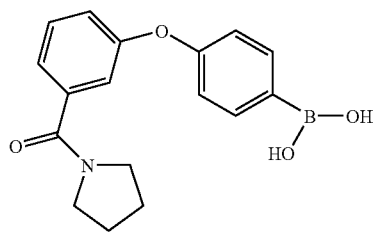

Example 64

Compound 105 was synthesized according to the procedure described in Example 24 using 3-(N-isopropylaminocarbonyl)phenyl boronic acid in place of boronic acid 63. MS (ESI(−)) m/e 298.06 (M−H)⁻.

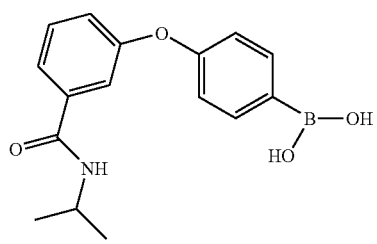

Example 65

Compound 106 was synthesized according to the procedure described in Example 24 using 3-(butylaminocarbonyl)phenyl boronic acid in place of boronic acid 63. MS (ESI(−)) m/e 312.14 (M−H)⁻.

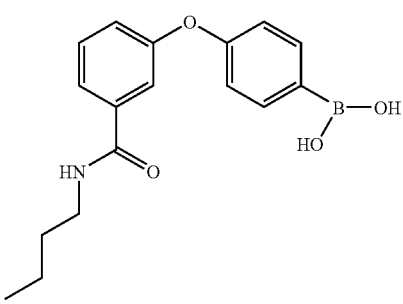

Example 66

Compound 107 was synthesized according to the procedure described in Example 24 using 3-(N-benzylaminocarbonyl)phenyl boronic acid in place of boronic acid 63. MS (ESI(−)) m/e 346.11 (M−H)⁻.

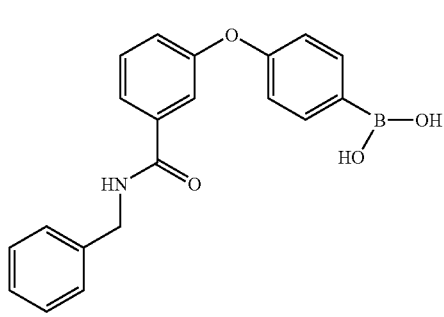

107

Example 67

Compound 108 was synthesized according to the procedure described in Example 24 using 3-(t-Boc-amino)phenyl boronic acid in place of boronic acid 63. MS (ESI(−)) m/e 327.94 (M−H)⁻.

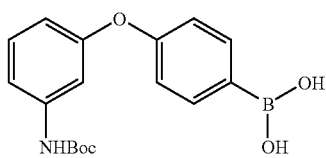

108

Example 68

Synthesis of 4-(3-aminophenoxy)phenylboronic acid (109)

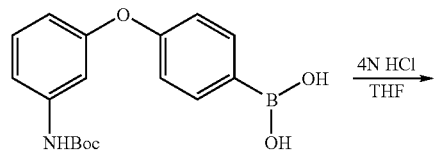

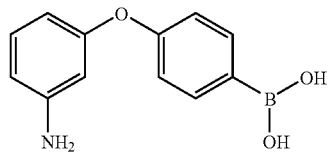

109

Boronic acid 108 (30 mg) was dissolved in dry THF (2 mL) under nitrogen. HCl (4N dioxane solution, 1 mL) was added. After 2 h, the reaction mixture was concentrated and the resulted solid was washed with EtOAc, the slurry was filtered through a short plug of cotton. The solid residue was redissolved in methanol to give 22 mg of desired product 109. MS (ESI(−)) m/e 228.09 (M−H)⁻.

Example 69

Compound 110 was synthesized according to the procedure described in Example 24 using 4-(t-Boc-amino)phenyl boronic acid in place of boronic acid 63. MS (ESI(−)) m/e 327.92 (M−H)⁻.

110

Example 70

Compound 111 was synthesized according to the procedure described in Example 68 using 110 in place of 108. MS (ESI(−)) m/e 228.03 (M−H)⁻.

111

Example 71

Compound 112 was synthesized according to the procedure described in Example 24 using 3,4-dimethoxyphenyl boronic acid in place of boronic acid 63. MS (ESI(−)) m/e 373.07 (M+H$_2$O—H)⁻.

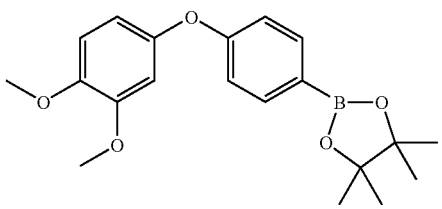

112

Example 72

Compound 113 was synthesized according to the procedure described in Example 24 using 112 in place of compound 65. MS (ESI(−)) m/e 273.09 (M−H)⁻.

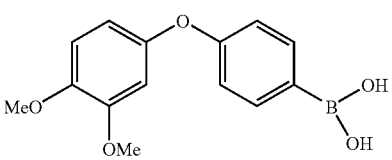

113

Example 73

Compound 114 was synthesized according to the procedure described in Example 24, using 3-fluorophenyl boronic acid in place of boronic acid 63, and 2,6-dimethyl-4-(4,4,5,5-tetramethyl-1,3,2-dioxaborolan-2-yl)phenol in place of phenol 64. MS (ESI(−)) m/e 259.02 (M−H)⁻.

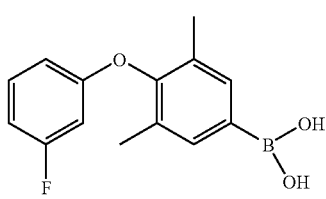

114

Example 74

Compound 115 was synthesized according to the procedure described in Example 24, using 3-fluorophenyl boronic acid in place of boronic acid 63, and 2-methoxy-4-(4,4,5,5-tetramethyl-1,3,2-dioxaborolan-2-yl)phenol in place of phenol 64. MS (ESI(−)) m/e 260.99 (M−H)−.

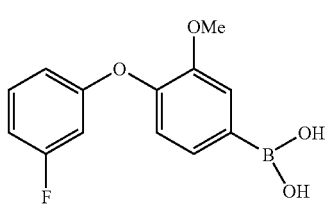

115

Example 75

Synthesis of 3-fluoro-4-(3-fluorophenoxy)phenylboronic acid (116)

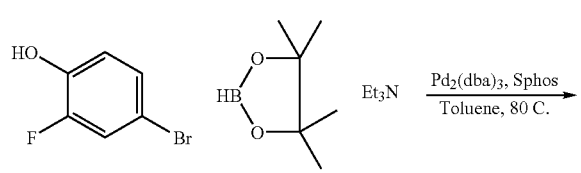

117    118

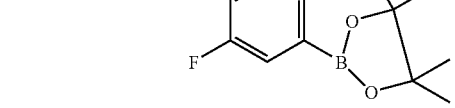

119

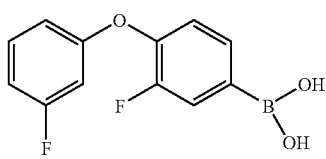

116

Compound (119): To a flask containing 2-fluoro-4-bromo phenol 117 (2 g, 10 mmol, 1 eq), borolane 118 (2 g, 1 eq), SPHOS (100 mg, 0.03 eq), and Et₃N (1 g, 1 equiv.) in toluene (10 mL) was added Pd₂(dba)₃ (0.1 g, 0.015 eq). The flask was purged with Ar and then heated at 80° C. for 5 h. The reaction was quenched with methanol, and filtered through Celite. Flash chromatography on silica gel (hexane, 10% followed with 30% EtOAc in hexane) gave desired product 119 (1.9 g).

Compound (116): Compound 116 was synthesized according to the procedure described in Example 24, using 3-fluorophenyl boronic acid in place of boronic acid 63, and phenol 119 in place of phenol 64. MS (ESI(−)) m/e 249.04 (M−H)−.

Example 76

Synthesis of 2-fluoro-4-(3-fluorophenoxy)phenylboronic acid (120)

121    118

122

120

Compound (122): Phenol 122 was synthesized according to the procedure described in Example 75 using 3-fluoro-4-Bromo phenol 122 in place of phenol 117.

Compound (120): Compound 120 was synthesized according to the procedure described in Example 24, using 3-fluorophenyl boronic acid in place of boronic acid 63, and phenol 122 in place of phenol 64. MS (ESI(−)) m/e 249.01 (M−H)−.

Example 77

Compound 123 was synthesized according to the procedure described in Example 24, using 3-trifluoromethoxyphenyl boronic acid in place of boronic acid 63, and phenol 122 in place of phenol 64. MS (ESI(−)) m/e 315.35 (M−H)−.

123

Example 78

Compound 124 was synthesized according to the procedure described in Example 24, using (4-chloro-3-methylphenyl)boronic acid in place of boronic acid 63, and phenol 122 in place of phenol 64. MS (ESI(−)) m/e 279.12 (M−H)−.

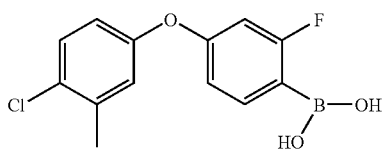

124

Example 79

Compound 125 was synthesized according to the procedure described in Example 24, using 3,4-difluorophenyl boronic acid in place of boronic acid 63, and phenol 122 in place of phenol 64. MS (ESI(−)) m/e 266.48 (M−H)⁻.

125

Example 80

Compound 126 was synthesized according to the procedure described in Example 23, using (3-chloro-4-methylphenyl)boronic acid in place of boronic acid 63, and phenol 122 in place of phenol 64. MS (ESI(−)) m/e 279.03 (M−H)⁻.

126

Example 81

Synthesis of 4-(3-methylbenzyloxy)phenylboronic acid (127)

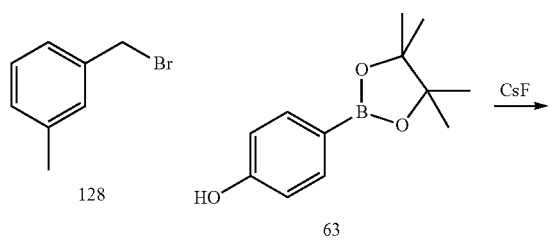

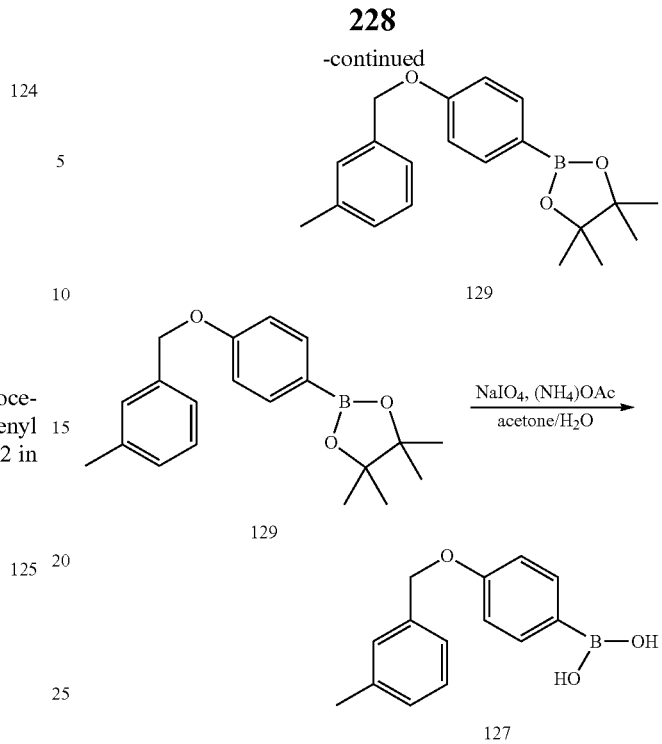

Compound (129): A tube was charged with phenol 63 (100 mg, 1 eq), CsF on Celite (180 mg, 60% by weight, 1.5 eq), acetonitrile (6 mL). To this tube 3-methylbenzyl bromide 128 (168 mg, 2 eq) was added. The reaction was stirred at rt for 20 h. TLC showed desired product. The reaction mixture was filtered, concentrated. The residue was purified by flash chromatography (5% EtOAc in hexanes then 10% EtOAc) to afford 80 mg of desired product 129.

Compound (127): Compound 127 was synthesized according to the procedure described in Example 24. MS (ESI(−)) m/e 241.03 (M−H)⁻.

Example 82

Compound 130 was synthesized according to the procedure described in Example 81 using 4-chlorobenzyl bromide in place of 3-methylbenzyl bromide 128. MS (ESI(−)) m/e 261.07 (M−H)⁻.

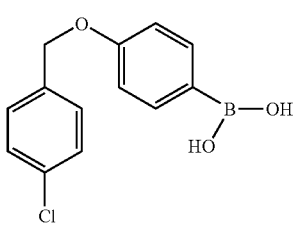

130

Example 83

Compound 131 was synthesized according to the procedure described in Example 81 using 2-fluoro-3-methylbenzyl bromide in place of 3-methylbenzyl bromide 128. MS (ESI(−)) m/e 259.04 (M−H)⁻.

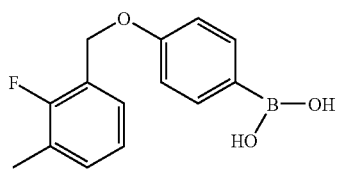

Example 84

Compound 132 was synthesized according to the procedure described in Example 81 using 4-fluoro-3-methylbenzyl bromide in place of 3-methylbenzyl bromide 128. MS (ESI(−)) m/e 259.05 (M−H)⁻.

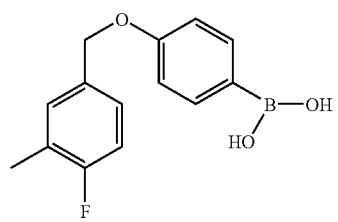

Example 85

Compound 133 was synthesized according to the procedure described in Example 81 using 2-chloro-5-fluoro-3-methylbenzyl bromide in place of 3-methylbenzyl bromide 128. MS (ESI(−)) m/e 293.91 (M−H)⁻.

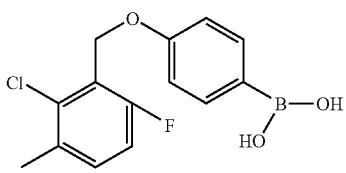

Example 86

Compound 134 was synthesized according to the procedure described in Example 81 using 4-fluoro-3-methylbenzyl bromide in place of 3-methylbenzyl bromide 128, and phenol 119 in place of phenol 64. MS (ESI(−)) m/e 277.06 (M−H)⁻.

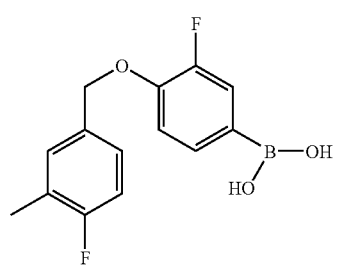

Example 87

Compound 135 was synthesized according to the procedure described in Example 81 using 4-fluoro-3-methylbenzyl bromide in place of 3-methylbenzyl bromide 128, and phenol 122 in place of phenol 64. MS (ESI(−)) m/e 277.13 (M−H)⁻.

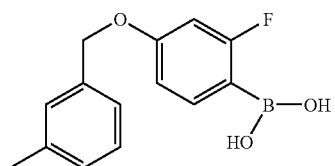

Example 88

Compound 136 was synthesized according to the procedure described in Example 80 using (1-bromoethyl)benzene in place of 3-methylbenzyl bromide 128. MS (ESI(−)) m/e 241.09 (M−H)⁻.

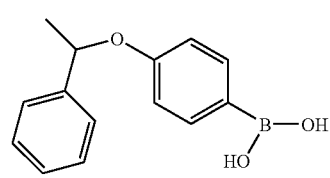

Example 89

Compound 137 was synthesized according to the procedure described in Example 80 using bromocyclohexane in place of 3-methylbenzyl bromide 128. MS (ESI(−)) m/e 219.07 (M−H)⁻.

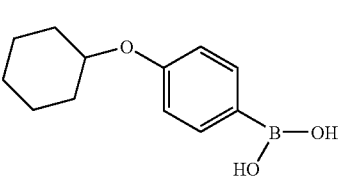

Example 90

Synthesis of 4-(2-methoxy-2-oxo-1-phenylethoxy)phenylboronic acid (138)

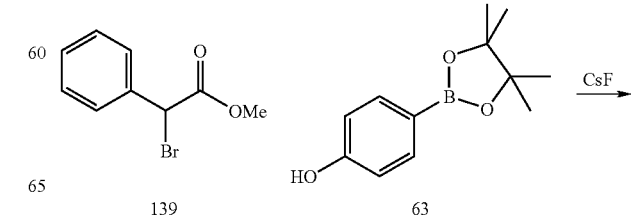

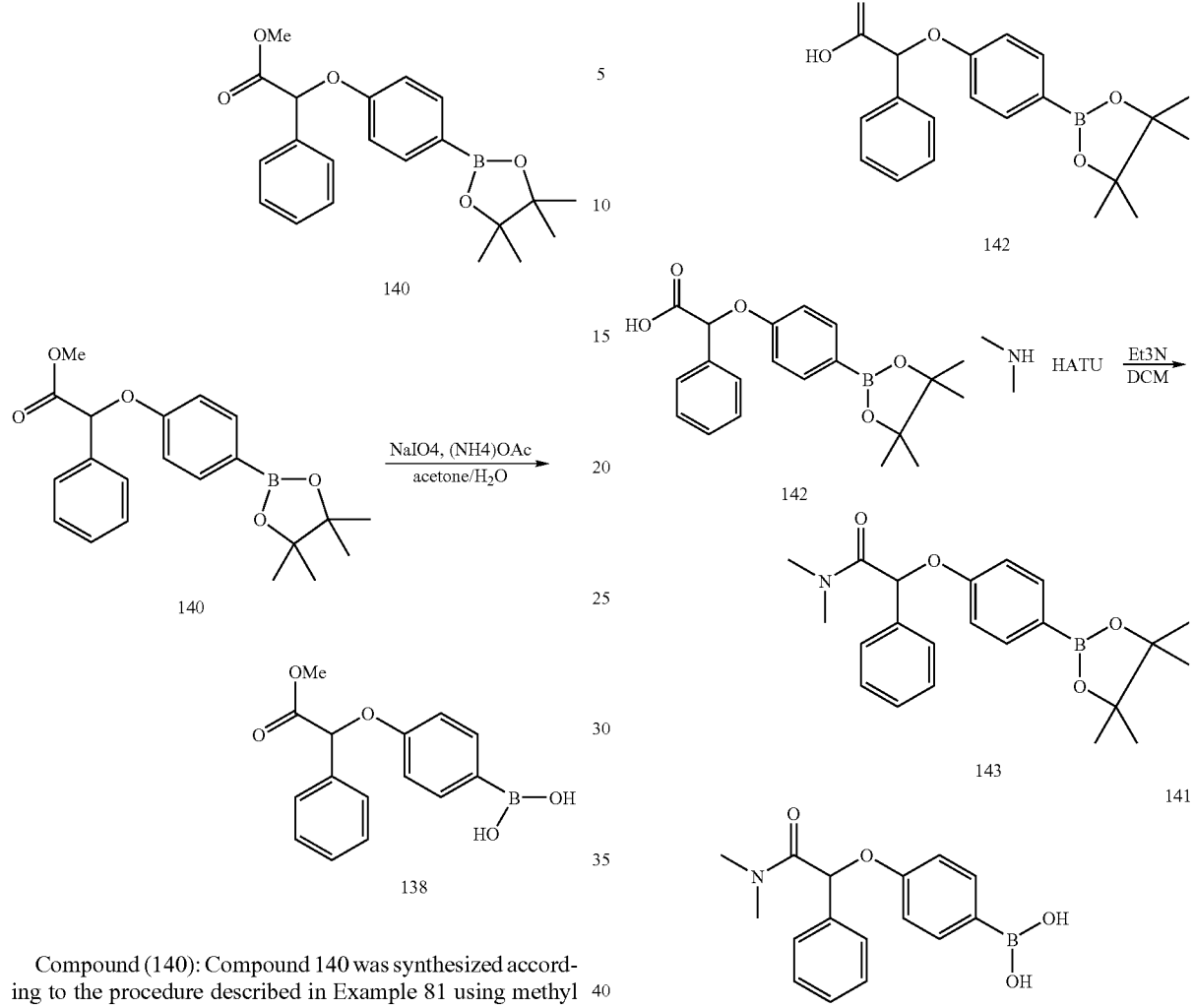

Compound (140): Compound 140 was synthesized according to the procedure described in Example 81 using methyl alpha-bromophenylacetate 139 in place of 3-methylbenzyl bromide 128

Compound (138): Compound 138 was synthesized according to the procedure described in Example 23. MS (ESI(−)) m/e 285.46M−H)⁻.

Example 91

Synthesis of 4-(2-(dimethylamino)-2-oxo-1-phenylethoxy)phenylboronic acid (141)

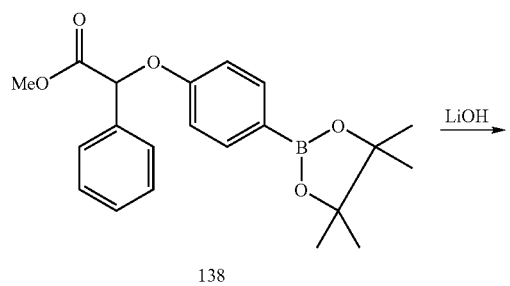

Compound (142): Compound 138 (300 mg, 1 eq) was dissolved in THF/MeOH (3:2; 2 mL). A solution of LiOH monohydrate (171 mg, 5 eq) in water (2 mL) was added. The reaction mixture was stirred at rt for 2 h. The mixture was diluted with EtOAc (150 mL), washed with dilute HCl, brine, dried with Na₂SO₄, concentrated to give 300 mg of crude product 142.

Compound (143): A flask is charged with acid 142 (60 mg, 1 eq), dimethylamine (9 mg, 1.2 eq), HATU (77 mg, 1.2 eq), and Et₃N (51 mg, 3 eq). The mixture was added with DCM (3 mL). The reaction mixture was stirred at rt for 4 h. TLC analysis showed desired product. The reaction mixture was diluted with DCM, washed with diluted HCl, then sodium bicarbonate, followed with brine. The resulting organic mixture was dried and concentrated. Flash chromatography (hexanes, 10%-25% EtOAc in Hexanes) gave 45 mg of desired product 143.

Compound (142): Compound 142 was synthesized from 143 according to the procedure described in Example 23, path B. MS (ESI(−)) m/e 297.69 (M−H)⁻.

Example 92

Compound 144 was synthesized according to the procedure described in Example 91 using butylamine in place of dimethylamine. MS (ESI(−)) m/e 326.52 (M−H)⁻.

144

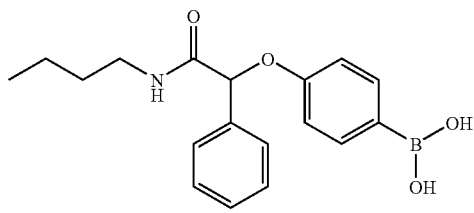

Example 93

Compound 145 was synthesized according to the procedure described in Example 91 using benzylamine in place of dimethylamine. MS (ESI(−)) m/e 360.41 (M−H)⁻.

145

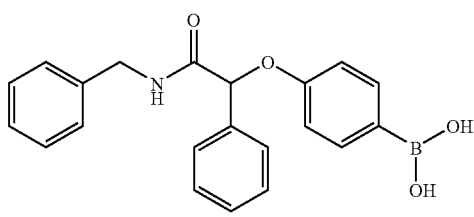

Example 94

Compound 146 was synthesized according to the procedure described in Example 91 using piperidine in place of dimethylamine. MS (ESI(−)) m/e 338.37 (M−H)⁻.

146

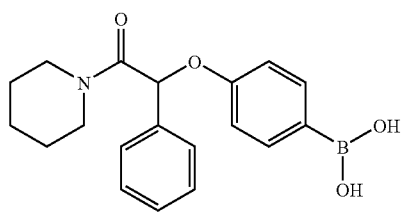

Example 95

Compound 147 was synthesized according to the procedure described in Example 91 using N,N-dimethylethylenediamine in place of dimethylamine. MS (ESI(−)) m/e 341.13 (M−H)⁻.

147

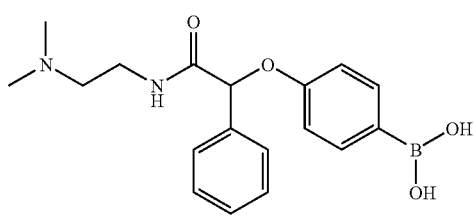

Example 96

Compound 148 was synthesized according to the procedure described in Example 91 using N'-benzyl-N,N-dimethylethylenediamine in place of dimethylamine. MS (ESI(−)) m/e 431.12 (M−H)⁻.

148

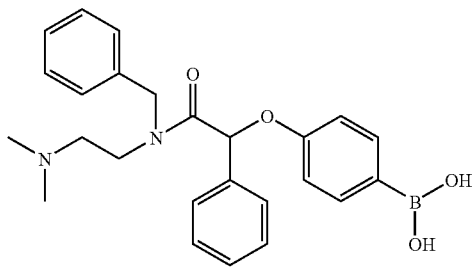

Example 97

Compound 149 was synthesized according to the procedure described in Example 1 using 3-methyl-1,4-di-bromobenzene in place of 2 and 3-fluorophenylboronic acid in place of 3. MS (ESI(−)) m/e 229.14 (M−H).

149

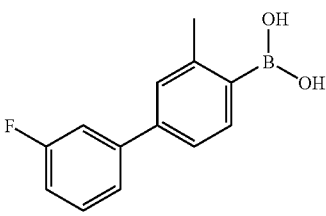

Example 98

Compound 150 was synthesized according to the procedure described in Example 1 using 4-bromo-2-methylbiphenyl MS (ESI(−)) m/e 211.03 (M−H).

150

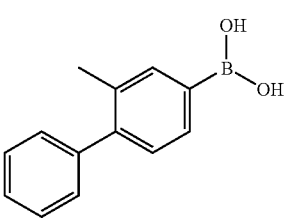

Example 99

Compound 151 was synthesized according to the procedure described in Example 1 using 3-biphenylboronic acid in place of 3. MS (ESI(−)) m/e 291.04 (M−H).

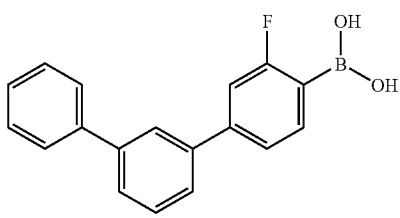

151

Example 100

Compound 152 was synthesized according to the procedure described in Example 1 using 3-Fluoro-2'chloro-4'-bromobiphenyl in place of 4. MS (ESI(−)) m/e 249.01 (M−H).

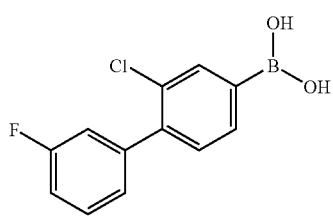

152

Example 101

Compound 153 was synthesized according to the procedure described in Example 1 using 1-naphthylboronic acid in place of 3. MS (ESI(−)) m/e 265.04 (M−H).

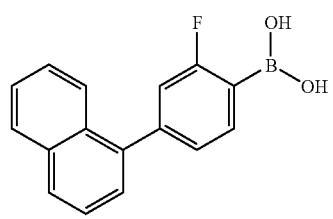

153

Example 102

Compound 154 was synthesized according to the procedure described in Example 1 using 3-pyridylboronic acid in place of 3. MS (ESI(−)) m/e 216.17 (M−H).

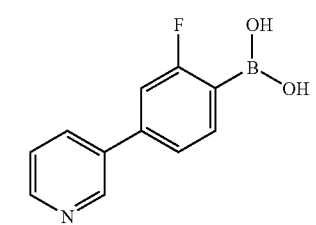

154

Example 103

Compound 155 was synthesized according to the procedure described in Example 1 using 3-fluoro-4-biphenylboronic acid in place of 3. MS (ESI(−)) m/e 309.10 (M−H).

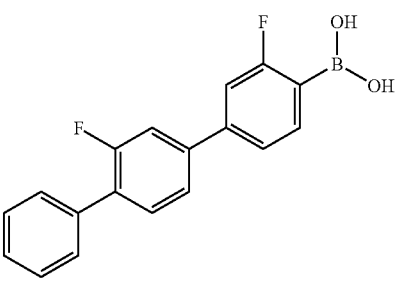

155

Example 104

Compound 156 was synthesized according to the procedure described in Example 1 using 3-N,N-dimethyaminophenylboronic acid in place of 3. MS (ESI(−)) m/e 258.08 (M−H).

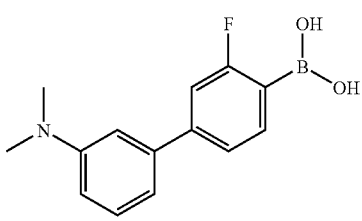

156

Example 105

Compound 157 was synthesized according to the procedure described in Example 1 using 3-Fluoro-4-methylphenylboronic acid in place of 3. MS (ESI(−)) m/e 247.08 (M−H).

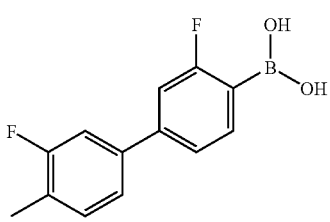

157

Example 106

Compound 158 was synthesized according to the procedure described in Example 1 using 3,4-Di-fluorophenylboronic acid in place of 3. MS (ESI(−)) m/e 251.11 (M−H).

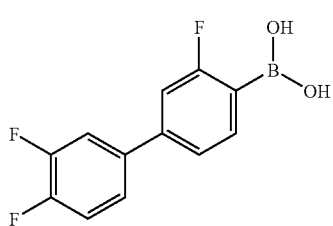

158

Example 107

Compound 159 was synthesized according to the procedure described in Example 17 using 3-fluoro-4-methylbenzyl bromide in place of 39. MS (ESI(−)) m/e 293.12 (M−H).

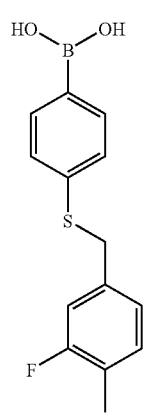

159

Example 108

Boronic Acid 160 was synthesized in the manner described in Example 19 by substituting N-phenylbenzylamine for amine 50 to result in isolation of 160 as a white solid. MS (ESI(−)) m/e 330.12 (M−H).

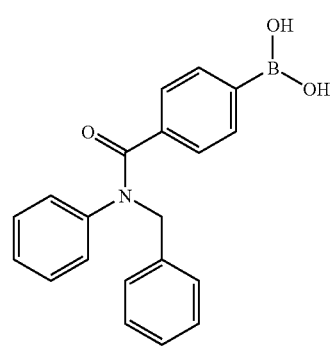

160

Example 109

Boronic Acid 161 was synthesized in the manner described in Example 19 by substituting N-methylbenzylamine for amine 50 to result in isolation of 161 as a white solid. MS (ESI(−)) m/e 268.11 (M−H).

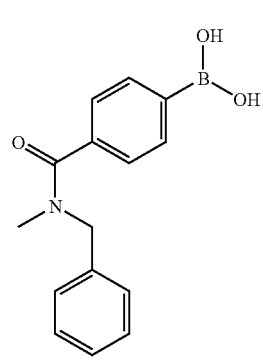

161

Example 110

Boronic Acid 162 was synthesized in the manner described in Example 19 by substituting (S)-alpha-methylbenzylamine for amine 50 to result in isolation of 162 as a white solid. MS (ESI(−)) m/e 268.06 (M−H).

162

Example 111

Boronic Acid 163 was synthesized in the manner described in Example 19 by substituting (R)-alpha-methylbenzylamine for amine 50 to result in isolation of 163 as a white solid. MS (ESI(−)) m/e 268.10 (M−H).

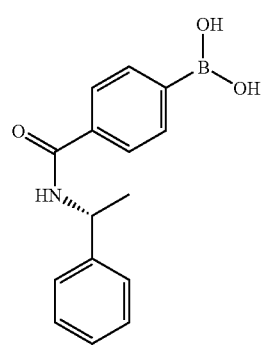

163

Example 112

Boronic Acid 164 was synthesized in the manner described in Example 19 by substituting piperidine for amine 50 to result in isolation of 164 as a white solid. MS (ESI(−)) m/e 232.09 (M−H).

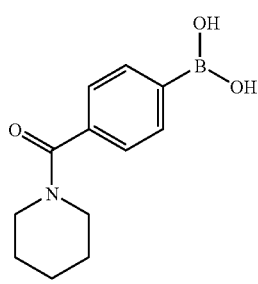

164

Example 113

Synthesis of Compound 165

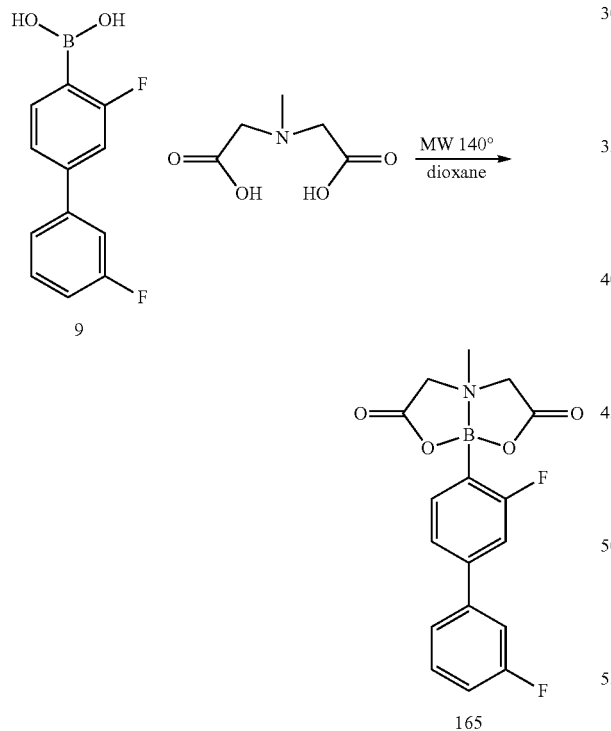

9

165

Compound 9 (50 mg, 1.0 eq.) and N-Methyliminodiacetic acid (37.8 mg, 1.2 eq.) were dissolved in 4 mL of 1,4-dioxane and placed under microwave irradiation for 40 minutes at a temperature of 140 C. After the reaction was cooled down the reaction was partitioned between 10 mL of ethyl acetate and 5 ml of water. The organic layer was separated, washed with 5 mL of brine, dried over magnesium sulfate, filtered and evaporated to a white solid which was crystallized from ethyl acetate to result in a 15 mg of 165 being isolated as a white solid. MS (ESI(−)) m/e 345.11 (M−H).

Example 114

Synthesis of 4-(benzyloxymethyl)phenylboronic acid (168)

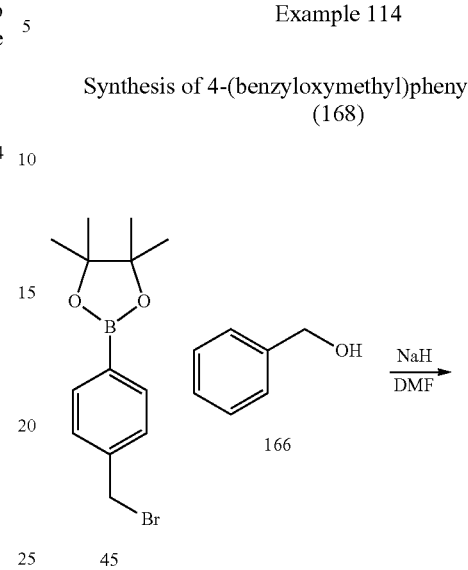

45

166

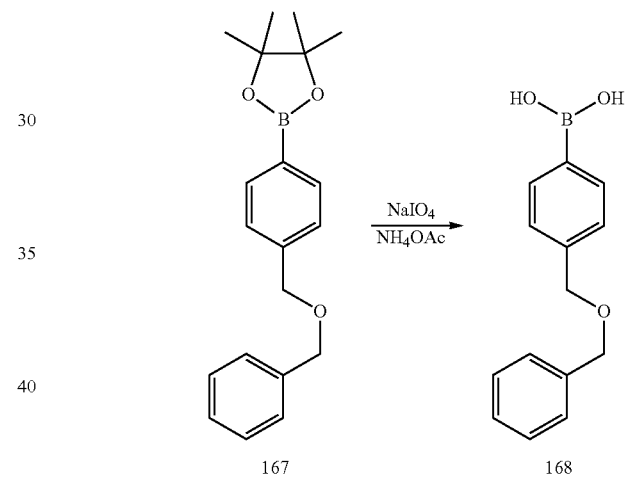

167

168

Compound (167): Boronate ester 45 (200 mg, 1.0 eq.) and alcohol 166 (146 mg, 2.0 eq.) were dissolved in 2 mL of DMF. To the solution a 60% oil dispersion of sodium hydride was added (81 mg, 3.0 eq.) and the reaction stirred for 18 hours. The reaction was diluted with 50 mL of ether, washed consecutively with water (10 mL), brine (10 mL), dried over sodium sulfate, filtered and concentrated. The residue was purified on silica gel using 4% ethyl acetate/96% hexanes to give 100 mg of a beige solid.

Compound (168): The boronate ester 167 was cleaved as described in Example 13 to result in isolation of boronic acid 168 as a beige solid. MS (ESI(−)) m/e 241.07 (M−H).

Example 115

Compound 169 was synthesized according to the procedure described in Example 114 using 1-hydroxymethylnaphthatene in place of alcohol 166. MS (ESI(−)) m/e 291.13 (M−H)⁻.

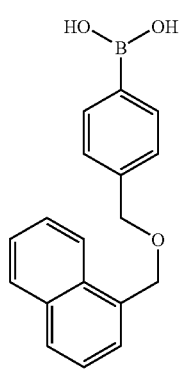

Example 116

Compound 170 was synthesized according to the procedure described in Example 114 using 1-hydroxynaphthatene in place of alcohol 166. MS (ESI(−)) m/e 277.13 (M−H).

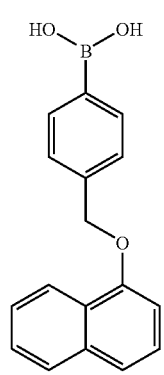

Example 117

Compound 171 was synthesized according to the procedure described in Example 114 using 2-hydroxymethylbiphenyl in place of alcohol 166. MS (ESI(−)) m/e 317.17 (M−H)⁻.

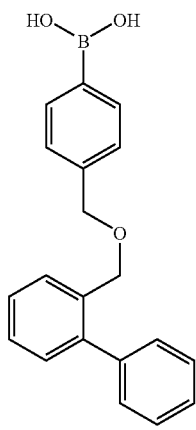

Example 118

Synthesis of 4-(benzyloxymethyl)-2-fluorophenylboronic acid (175)

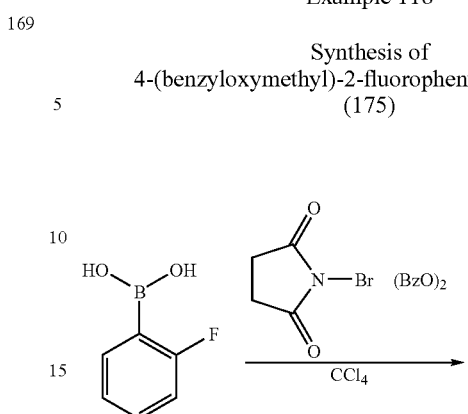

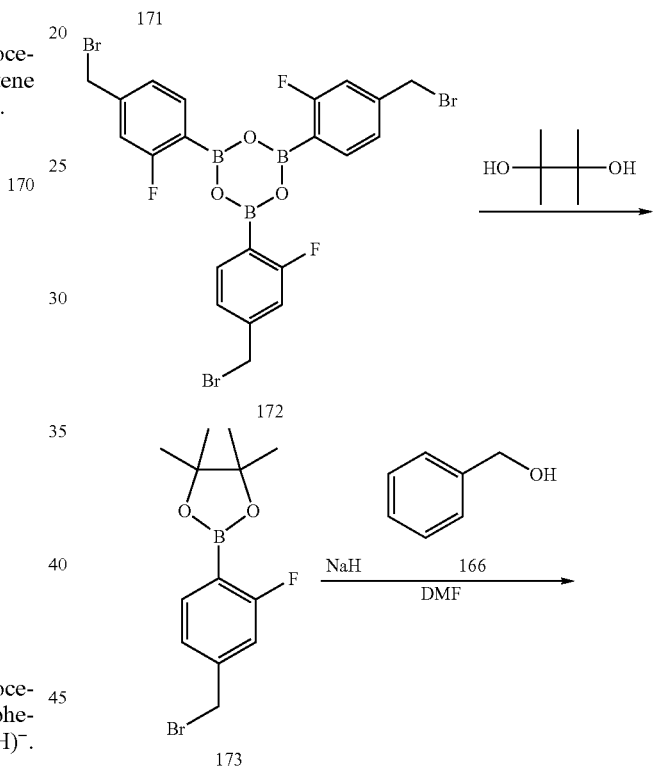

Compound (173): Boronate 171 (1.00 g, 1.0 eq.) and carbon tetrachloride (40 mL) are heated together; the solid eventually goes into solution and some water comes out on the sides of the flask. The mixture is poured through a plug of cotton wool and the filtrate treated with NBS (1.16 g, 1.0 eq.) and (BzO)$_2$ (50 mg, cat. amt.) and refluxed during 2 h. The hot reaction mixture is filtered through a fluted filter paper and the filtrate cooled in the freezer; the ppt is filtered off, washed with a little bit of hexane, and dried in vacuo. The solid is dissolved in 20 mL of ether to which pinacol (300 mg, 3.0 eq.) is added and the solution stirred for 30 minutes. The solution is dried over sodium sulfate and evaporated to yield boronate ester 173 as a waxy white solid (500 mg).

Compound (174): Boronate ester 173 (200 mg, 1.0 eq.) and alcohol 166 (146 mg, 2.0 eq.) were dissolved in 2 mL of DMF. To the solution a 60% oil dispersion of sodium hydride was added (81 mg, 3.0 eq.) and the reaction stirred for 18 hours. The reaction was diluted with 50 mL of ether, washed consecutively with water (10 mL), brine (10 mL), dried over sodium sulfate, filtered and concentrated. The residue was purified on silica gel using 4% ethyl acetate/96% hexanes to give 100 mg of a beige solid.

Compound (175): The boronate ester 174 was cleaved as described in Example 13 to result in isolation of boronic acid 175 as a beige solid. MS (ESI(−)) m/e 259.06 (M−H).

Example 119

Compound 176 was synthesized according to the procedure described in Example using 2-trifluoromethylbenzyl alcohol in place of alcohol 166. MS (ESI(−)) m/e 327.06 (M−H)$^-$.

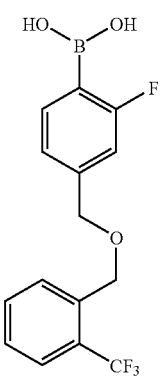

176

Example 120

Compound 177 was synthesized according to the procedure described in Example 118 using 3-trifluoromethylbenzyl alcohol in place of alcohol 166. MS (ESI(−)) m/e 327.06 (M−H).

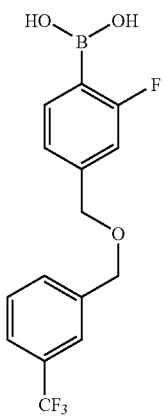

177

Example 121

Compound 178 was synthesized according to the procedure described in Example 118 using 4-trifluoromethylbenzyl alcohol in place of alcohol 166. MS (ESI(−)) m/e 327.06 (M−H)$^-$.

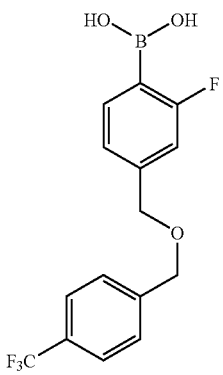

178

Example 122

Compound 179 was synthesized according to the procedure described in Example 118 using 3-chloro-4-methylphenylboronic acid in place of boronate 171. MS (ESI(−)) m/e 275.02 (M−H)$^-$.

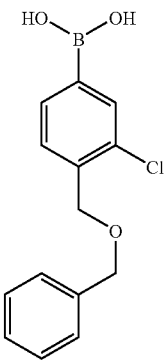

179

Example 123

Synthesis of 4-((phenylamino)methyl)phenylboronic acid (182)

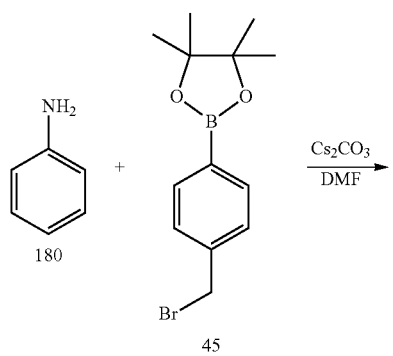

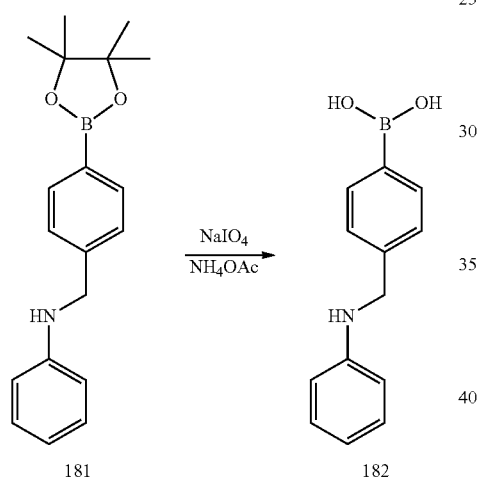

Compound (181): Amine 180 (86 mg, 1.1 eq) was dissolved in DMF (10 mL), cesium carbonate (302 mg, 1.1 eq) was added, and then boronate ester 45 (250 mg, 1.0 eq) was added. Heated for 18 h, filtered and concentrated. Ran silica column with 95:5 hexanes:EtOAc, then 9:1. Isolated 169 mg (65% yield) of 181 as a beige solid.

Compound (182): The boronate ester 181 was cleaved as described in Example 13 to result in isolation of boronic acid 182 as a white solid (43 mg, 55%). MS (ESI(–)) m/e 226.07 (M–H).

Example 124

Compound 183 was synthesized according to the procedure described in Example 123 using indole in place of amine 180. MS (ESI(–)) m/e 249.09 (M–H)⁻.

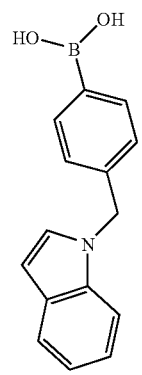

Example 125

Compound 184 was synthesized according to the procedure described in Example 123 using indoline in place of amine 180. MS (ESI(–)) m/e 251.10 (M–H)⁻.

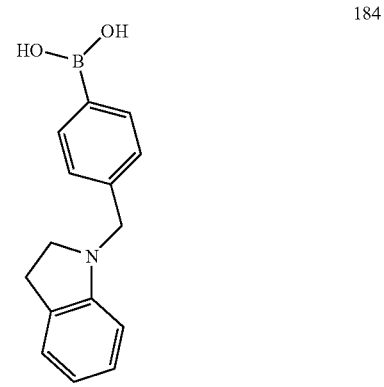

Example 126

Compound 185 was synthesized according to the procedure described in Example 123 using tetrahydroquinoline in place of amine 180. MS (ESI(–)) m/e 266.13 (M–H)⁻.

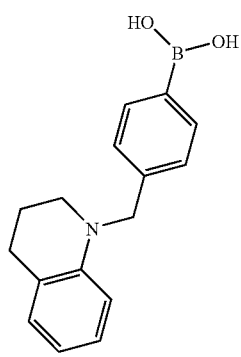

Example 127

Compound 186 was synthesized according to the procedure described in Example 123 using N-Methylaniline in place of amine 180. MS (ESI(−)) m/e 240.09 (M−H)⁻.

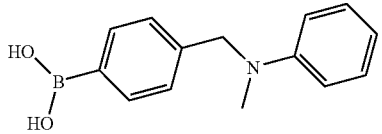

186

Example 128

Compound 187 was synthesized according to the procedure described in Example 123 using 1-naphthylamine in place of amine 180. MS (ESI(−)) m/e 276.12 (M−H)⁻.

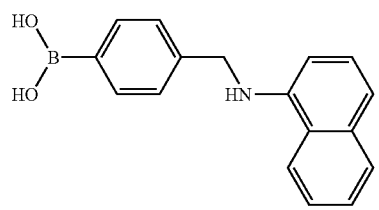

187

Example 129

Compound 188 was synthesized according to the procedure described in Example 123 substituting boronate ester 45 for 2-fluoro-substituted boronate ester, and using indoline in place of amine 180. MS (ESI(−)) m/e 270.10 (M−H)⁻.

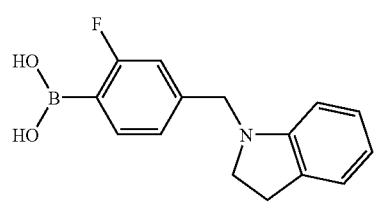

188

Example 130

Synthesis of 4-((phenylamino)methyl)phenylboronic acid (191)

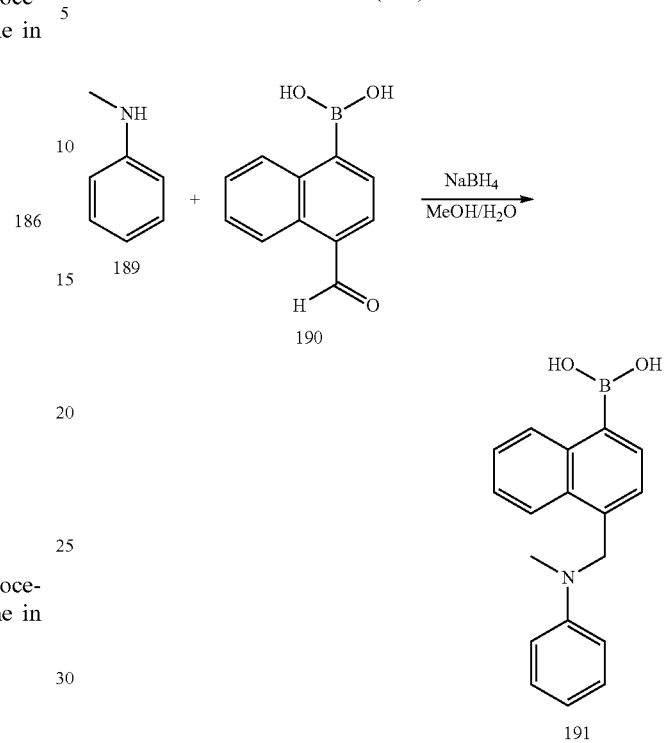

191

Boronic acid 189 (50 mg, 1.0 eq.) was dissolved in methanol (1 mL) with 1% water to which amine 190 (53.6 mg, 2.0 eq.) was added. The solution was stirred for 1 hour. Then sodium borohydride (10 mg, 1.0 eq.) was added and stirring continued for another 1 hour. The reaction was diluted with 10 mL of methylene chloride and quenched with 0.1 mL of acetic acid. The solution was directly placed on silica and eluted with 30% ethyl acetate/70% hexanes to result in isolation of 191 as a yellow solid (4 mg, 5% yield). MS (ESI(−)) m/e 290.15 (M−H).

Example 131

Compound 192 was synthesized according to the procedure described in Example 24 using 3-hydroxy phenylboronic acid in place of boronic acid 63 and 3-(4,4,5,5-tetramethyl-1,3,2-dioxaborolan-2-yl)phenol in place of phenol 64. MS (ESI(−)) m/e 214.09 (M−H)⁻.

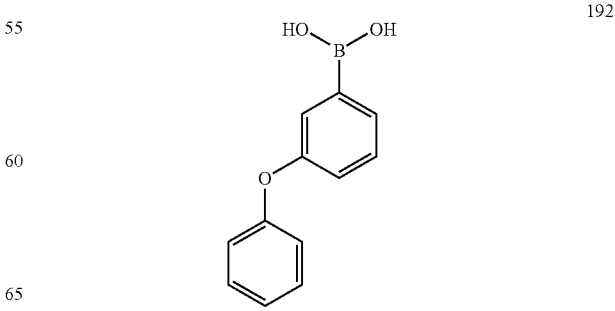

192

Example 132

Compound 193 was synthesized according to the procedure described in Example 24 using 3-N,N-dimethyl boronic acid in place of boronic acid 63, and phenol 119 in place of phenol 64. MS (ESI(−)) m/e 274.08 (M−H)⁻.

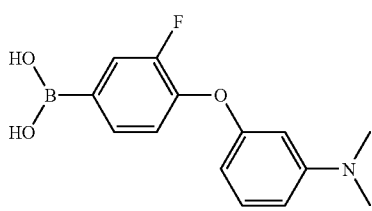

Example 133

Compound 194 was synthesized according to the procedure described in Example 24 using 3-methoxy boronic acid in place of boronic acid 63, and phenol 122 in place of phenol 64. MS (ESI(−)) m/e 261.04 (M−H)⁻.

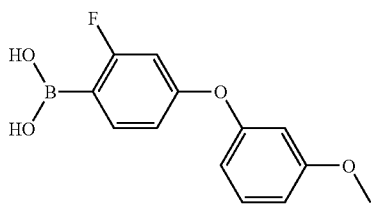

Example 134

Compound 195 was synthesized according to the procedure described in Example 24 using 3-N,N-dimethyl boronic acid in place of boronic acid 63, and phenol 122 in place of phenol 64. MS (ESI(−)) m/e 274.08 (M−H)⁻.

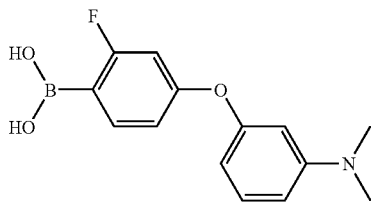

Example 135

Compound 196 was synthesized according to the procedure described in Example 24 using 3-N-methyl boronic acid in place of boronic acid 63, and phenol 122 in place of phenol 64. MS (ESI(−)) m/e 260.05 (M−H)⁻.

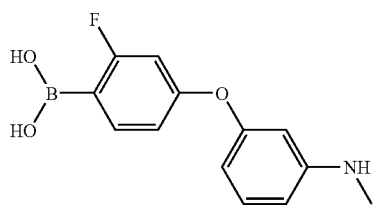

Example 136

Compound 197 was synthesized according to the procedure described in Example 24 using 3-piperidyl boronic acid in place of boronic acid 63, and phenol 122 in place of phenol 64. MS (ESI(−)) m/e 314.14 (M−H)⁻.

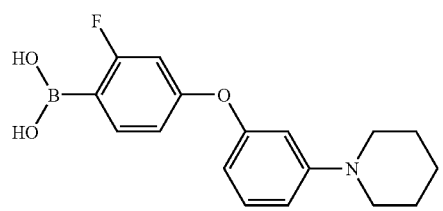

Example 137

Compound 198 was synthesized according to the procedure described in Example 24 using 3-pyrrolidinyl boronic acid in place of boronic acid 63, and phenol 122 in place of phenol 64. MS (ESI(−)) m/e 300.12 (M−H)⁻.

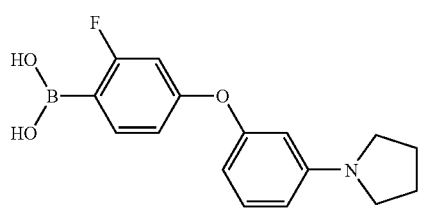

Example 138

Synthesis of 2-chloro-4-(3-fluorophenoxy)phenylboronic acid (201)

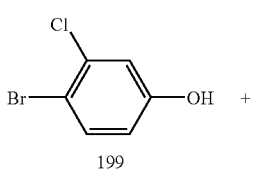

251
-continued

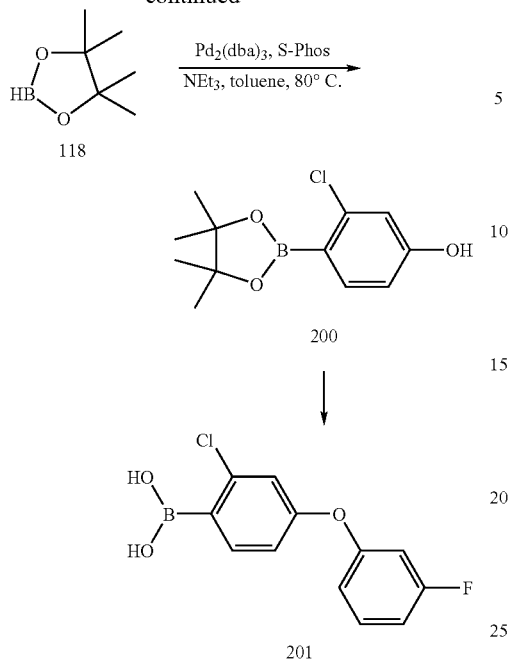

Compound (200): Phenol 200 was synthesized according to the procedure described in Example 75 using 3-chloro-4-Bromo phenol 199 in place of phenol 117.

Compound (201): Compound 201 was synthesized according to the procedure described in Example 24 using 3-fluorophenyl boronic acid in place of boronic acid 63, and phenol 200 in place of phenol 64. MS (ESI(−)) m/e 265.06 (M−H)⁻.

Example 139

Synthesis of 4-(3-fluorophenoxy)-2-methylphenylboronic acid (204)

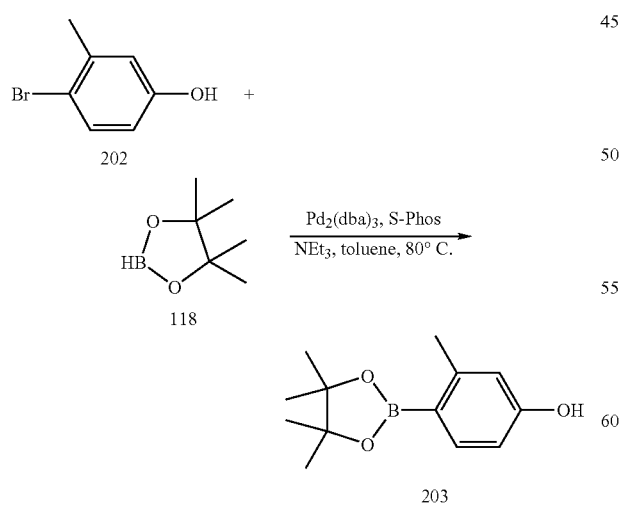

252
-continued

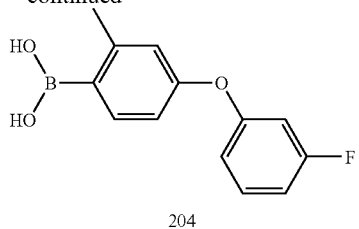

Compound (203): Phenol 203 was synthesized according to the procedure described in Example 75 using 3-chloro-4-Bromo phenol 202 in place of phenol 117.

Compound (204): Compound 204 was synthesized according to the procedure described in Example 24 using 3-fluorophenyl boronic acid in place of boronic acid 63, and phenol 204 in place of phenol 64. MS (ESI(−)) m/e 265.06 (M−H)⁻.

Example 140

Synthesis of 4-(3-fluorophenoxy)-2-methoxyphenylboronic acid (207)

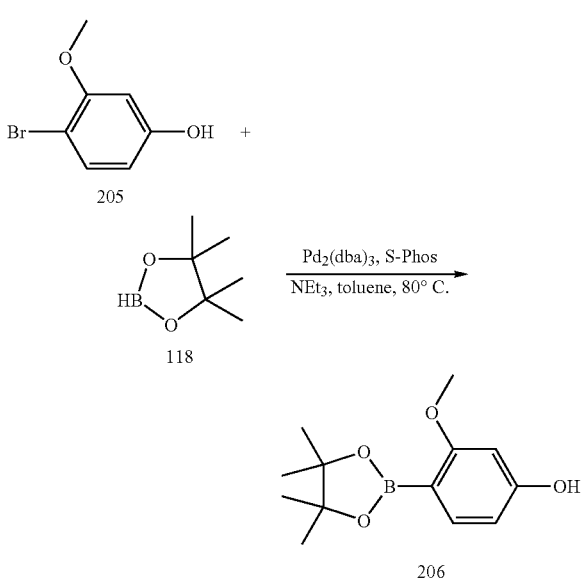

Compound (206): Phenol 206 was synthesized according to the procedure described in Example 75 using 3-methoxy-4-Bromo phenol 205 in place of phenol 117.

Compound (207): Compound 207 was synthesized according to the procedure described in Example 24 using 3-fluorophenyl boronic acid in place of boronic acid 63, and phenol 206 in place of phenol 64. MS (ESI(−)) m/e 261.04 (M−H)⁻.

Example 141

Synthesis of 2-cyano-4-(3-fluorophenoxy)phenylboronic acid (210)

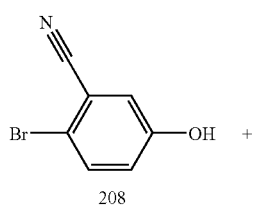
208

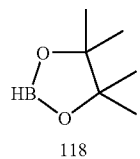
118

Pd₂(dba)₃, S-Phos
NEt₃, toluene, 80° C.

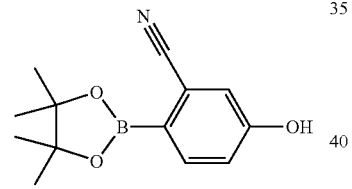
209

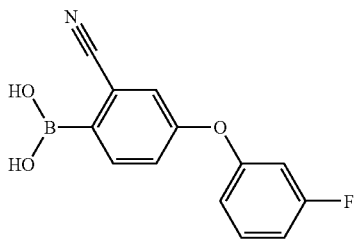
210

Compound (209): Phenol 209 was synthesized according to the procedure described in Example 75 using 3-cyano-4-Bromo phenol 208 in place of phenol 117.

Compound (210): Compound 210 was synthesized according to the procedure described in Example 24 using 3-fluorophenyl boronic acid in place of boronic acid 63, and phenol 209 in place of phenol 64. MS (ESI(−)) m/e 256.02 (M−H)⁻.

Example 142

Synthesis of 4-(3-fluorophenoxy)-2-(trifluoromethyl)phenylboronic acid (211)

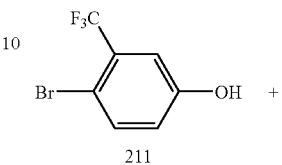
211

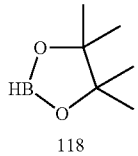
118

Pd₂(dba)₃, S-Phos
NEt₃, toluene, 80° C.

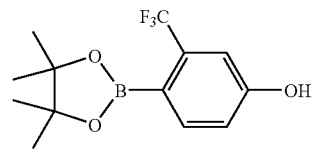
212

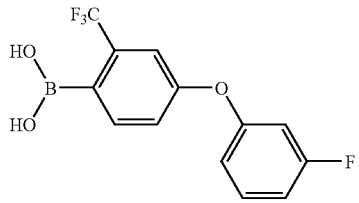
213

Compound (212): Phenol 212 was synthesized according to the procedure described in Example 75 using 3-trifluoromethyl-4-Bromo phenol 211 in place of phenol 117.

Compound (213): Compound 213 was synthesized according to the procedure described in Example 24 using 3-fluorophenyl boronic acid in place of boronic acid 63, and phenol 212 in place of phenol 64. MS (ESI(−)) m/e 299.01 (M−H)⁻.

Example 143

Synthesis of 4-(3-fluorophenoxy)-2-(methoxycarbonyl)phenylboronic acid (216)

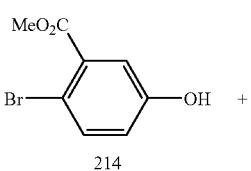
214

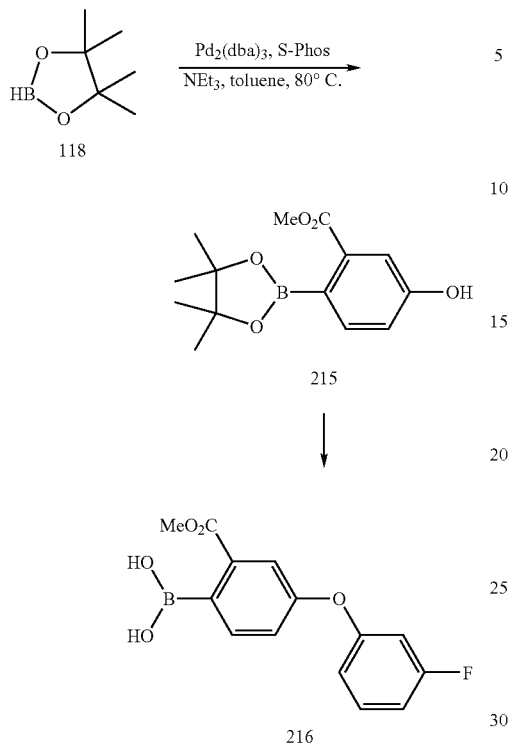

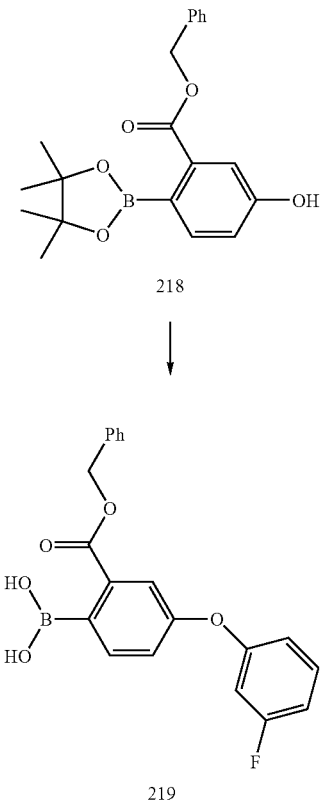

Compound (215): Phenol 215 was synthesized according to the procedure described in Example 75 using methyl-2-Bromo-5-hydroxy benzoate 214 in place of phenol 117.

Compound (216): Compound 216 was synthesized according to the procedure described in Example 24 using 3-fluorophenyl boronic acid in place of boronic acid 63, and phenol 215 in place of phenol 64. MS (ESI(−)) m/e 289.05 (M−H)⁻.

Example 144

Synthesis of 2-(benzyloxycarbonyl)-4-(3-fluorophenoxy)phenylboronic acid (219)

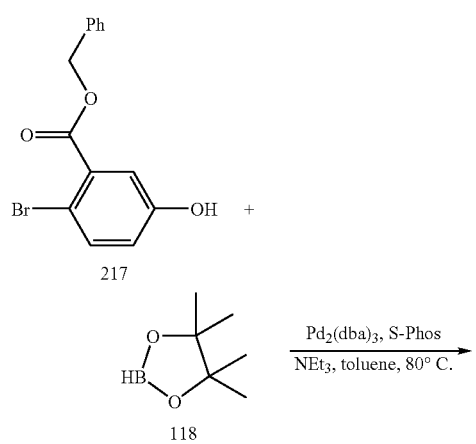

Compound (218): Phenol 218 was synthesized according to the procedure described in Example 75 using 3-chloro-4-Bromo phenol 217 in place of phenol 117.

Compound (219): Compound 219 was synthesized according to the procedure described in Example 24 using 3-fluorophenyl boronic acid in place of boronic acid 63, and phenol 218 in place of phenol 64. MS (ESI(−)) m/e 365.14 (M−H)⁻.

Example 145

Compound 220 was synthesized according to the procedure described in Example 24 using 3-N,N-dimethyl boronic acid in place of boronic acid 63, and phenol 122 in place of phenol 64. MS (ESI(−)) m/e 232.00 (M−H)⁻.

Example 146

Synthesis of 3,5-difluoro-4-(3-fluorophenoxy)phenylboronic acid (223)

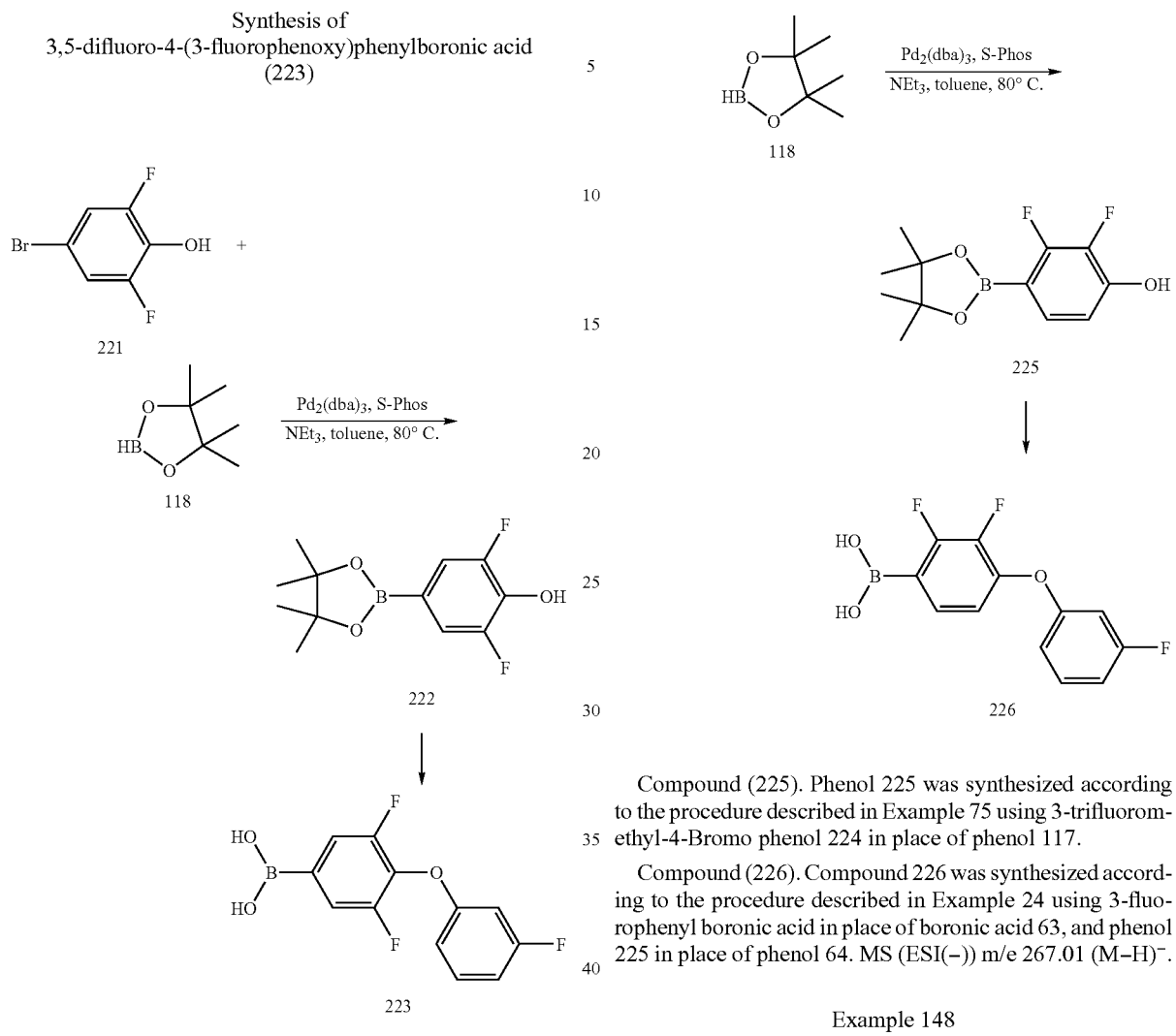

Compound (222): Phenol 222 was synthesized according to the procedure described in Example 75 using 3-trifluoromethyl-4-Bromo phenol 221 in place of phenol 117.

Compound (223). Compound 223 was synthesized according to the procedure described in Example 24 using 3-fluorophenyl boronic acid in place of boronic acid 63, and phenol 222 in place of phenol 64. MS (ESI(−)) m/e 267.01 (M−H)⁻.

Example 147

Synthesis of 2,3-difluoro-4-(3-fluorophenoxy)phenylboronic acid (226)

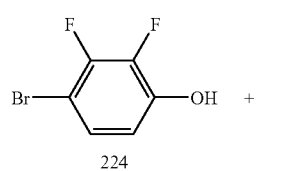

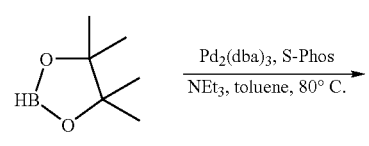

Compound (225). Phenol 225 was synthesized according to the procedure described in Example 75 using 3-trifluoromethyl-4-Bromo phenol 224 in place of phenol 117.

Compound (226). Compound 226 was synthesized according to the procedure described in Example 24 using 3-fluorophenyl boronic acid in place of boronic acid 63, and phenol 225 in place of phenol 64. MS (ESI(−)) m/e 267.01 (M−H)⁻.

Example 148

Synthesis of 2,6-difluoro-4-(3-fluorophenoxy)phenylboronic acid (229)

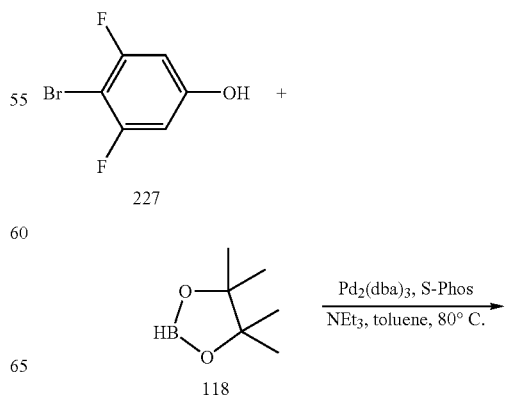

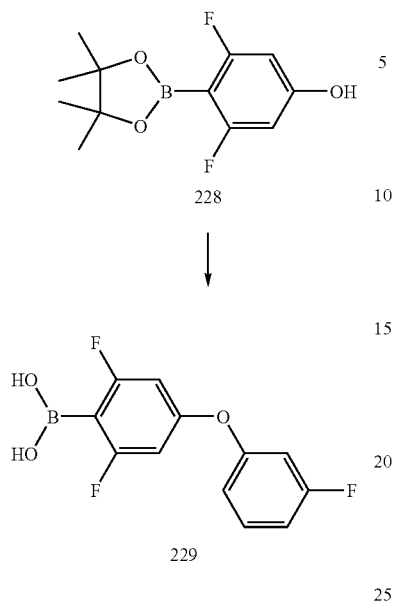

228

229

Compound (228). Phenol 228 was synthesized according to the procedure described in Example 75 using 3-trifluoromethyl-4-Bromo phenol 227 in place of phenol 117.

Compound (229). Compound 229 was synthesized according to the procedure described in Example 24 using 3-fluorophenyl boronic acid in place of boronic acid 63, and phenol 228 in place of phenol 64. MS (ESI(−)) m/e 267.01 (M−H)⁻.

Example 149

Compound 230 was synthesized according to the procedure described in Example 81 using 4-bromomethylpyridine in place of 3-methylbenzyl bromide 128, and phenol 122 in place of phenol 64. MS (ESI(−)) m/e 246.04 (M−H)⁻.

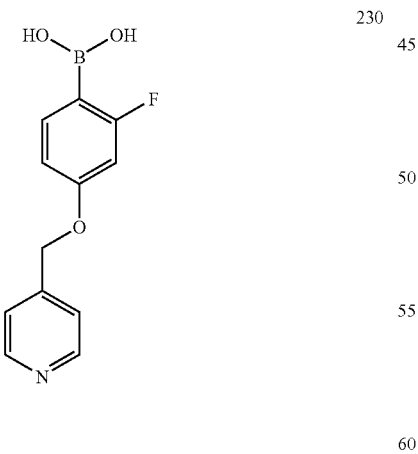

230

Example 150

Compound 231 was synthesized according to the procedure described in Example 81 using 3-Bromomethylpyridine in place of 3-methylbenzyl bromide 128, and phenol 122 in place of phenol 64. MS (ESI(−)) m/e 246.04 (M−H)⁻.

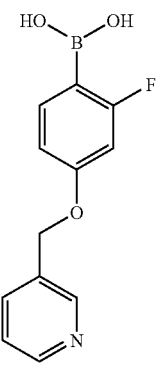

231

Example 151

Compound 232 was synthesized according to the procedure described in Example 81 using 2-Bromomethylpyridine in place of 3-methylbenzyl bromide 128, and phenol 122 in place of phenol 64. MS (ESI(−)) m/e 246.04 (M−H)⁻.

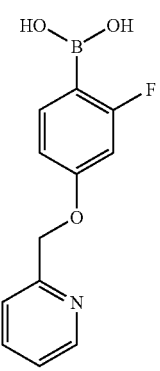

232

Example 152

Compound 233 was synthesized according to the procedure described in Example 81 using 5-Bromomethylthiazole in place of 3-methylbenzyl bromide 128, and phenol 122 in place of phenol 64. MS (ESI(−)) m/e 252.05 (M−H)⁻.

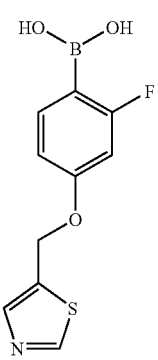

233

Example 153

Compound 234 was synthesized according to the procedure described in Example 81 using 1-Bromo2-phenylethane in place of 3-methylbenzyl bromide 128. MS (ESI(−)) m/e 241.07 (M−H)⁻.

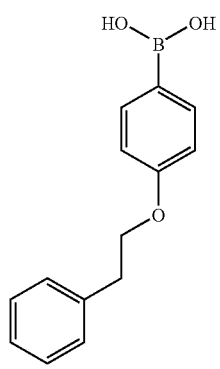

234

Example 154

Compound 235 was synthesized according to the procedure described in Example 81 using 1-Bromo2-phenylethane in place of 3-methylbenzyl bromide 128 and 3-(4,4,5,5-tetramethyl-1,3,2-dioxaborolan-2-yl)phenol in place of phenol 64. MS (ESI(−)) m/e 241.07 (M−H)⁻.

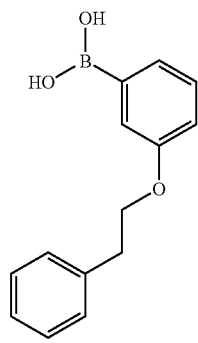

235

Example 155

Compound 236 was synthesized according to the procedure described in Example 81 using 1-Bromo-3-phenypropane in place of 3-methylbenzyl bromide 128. MS (ESI(−)) m/e 255.07 (M−H)⁻.

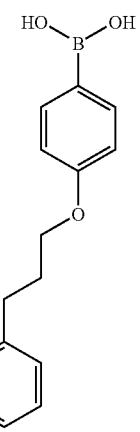

236

Example 156

Compound 237 was synthesized according to the procedure described in Example 81 using 1-Bromo-3-phenylpropane in place of 3-methylbenzyl bromide 128 and 3-(4,4,5,5-tetramethyl-1,3,2-dioxaborolan-2-yl)phenol in place of phenol 64. MS (ESI(−)) m/e 255.07 (M−H)⁻.

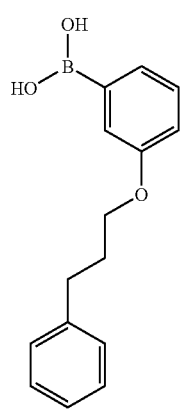

237

Example 157

Compound 238 was synthesized according to the procedure described in Example 81 using 1-Bromo-4-phenybutane in place of 3-methylbenzyl bromide 128. MS (ESI(−)) m/e 269.07 (M−H)⁻.

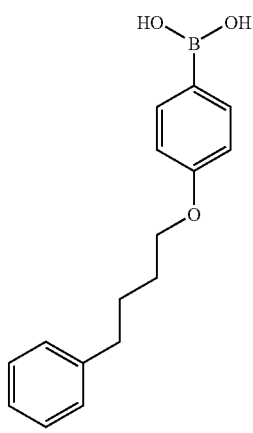

Example 158

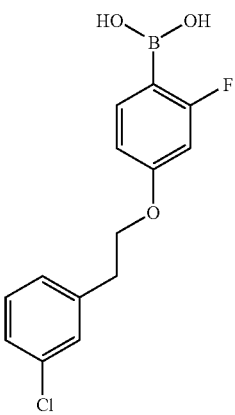

Example 160

Compound 239 was synthesized according to the procedure described in Example 81 using 1-Bromo-2-phenylethane in place of 3-methylbenzyl bromide 128, and phenol 122 in place of phenol 64. MS (ESI(−)) m/e 259.06 (M−H)⁻.

Compound 241 was synthesized according to the procedure described in Example 81 using 1-Bromo-2-(3,4-dichlorophenyl)ethane in place of 3-methylbenzyl bromide 128, and phenol 122 in place of phenol 64. MS (ESI(−)) m/e 327.08 (M−H)⁻.

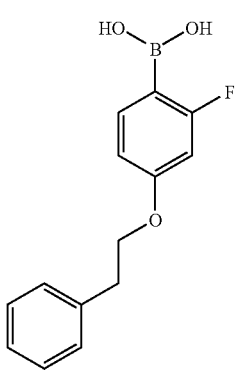

Example 159

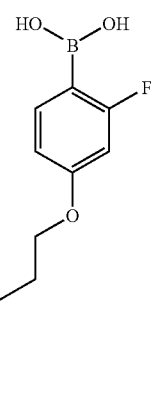

Example 161

Compound 240 was synthesized according to the procedure described in Example 81 using 1-Bromo-2-(3-chlorophenyl)ethane in place of 3-methylbenzyl bromide 128, and phenol 122 in place of phenol 64. MS (ESI(−)) m/e 293.06 (M−H)⁻.

Compound 242 was synthesized according to the procedure described in Example 81 using 1-Bromo-2-(3-trifluoromethylphenyl)ethane in place of 3-methylbenzyl bromide 128, and phenol 122 in place of phenol 64. MS (ESI(−)) m/e 327.06 (M−H)⁻.

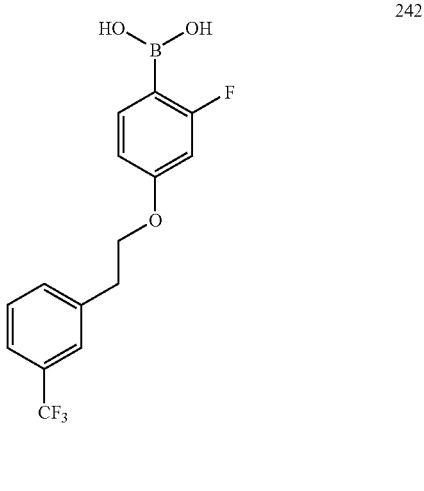

242

Example 162

Compound 243 was synthesized according to the procedure described in Example 81 using 1-Bromo-2-(4-trifluoromethylphenyl)ethane in place of 3-methylbenzyl bromide 128, and phenol 122 in place of phenol 64. MS (ESI(−)) m/e 327.06 (M−H)⁻.

243

Example 163

Compound 244 was synthesized according to the procedure described in Example 81 using 1-Bromo-2-(3-methoxylphenyl)ethane in place of 3-methylbenzyl bromide 128, and phenol 122 in place of phenol 64. MS (ESI(−)) m/e 289.09 (M−H)⁻.

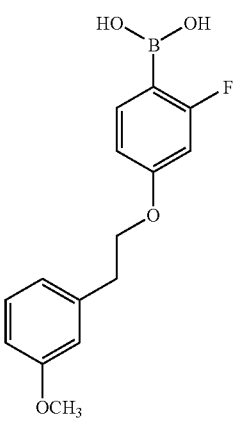

244

Example 164

Compound 245 was synthesized according to the procedure described in Example 81 using 1-Bromo-2-(4-methoxylphenyl)ethane in place of 3-methylbenzyl bromide 128, and phenol 122 in place of phenol 64. MS (ESI(−)) m/e 289.09 (M−H)⁻.

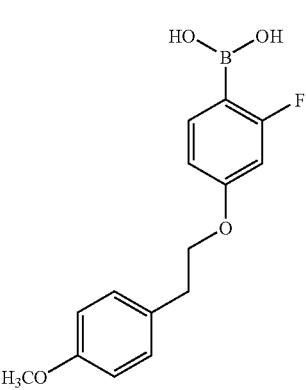

245

Example 165

Compound 246 was synthesized according to the procedure described in Example 81 using 1-Bromo2-phenylethane in place of 3-methylbenzyl bromide 128 and 2-Chloro-4-(4,4,5,5-tetramethyl-1,3,2-dioxaborolan-2-yl)phenol in place of phenol 64. MS (ESI(−)) m/e 275.02 (M−H)⁻.

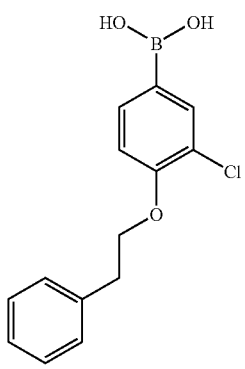

Example 166

Synthesis of (R)-4-(2,3-bis(benzyloxy)propoxy)-2-fluorophenylboronic acid (249)

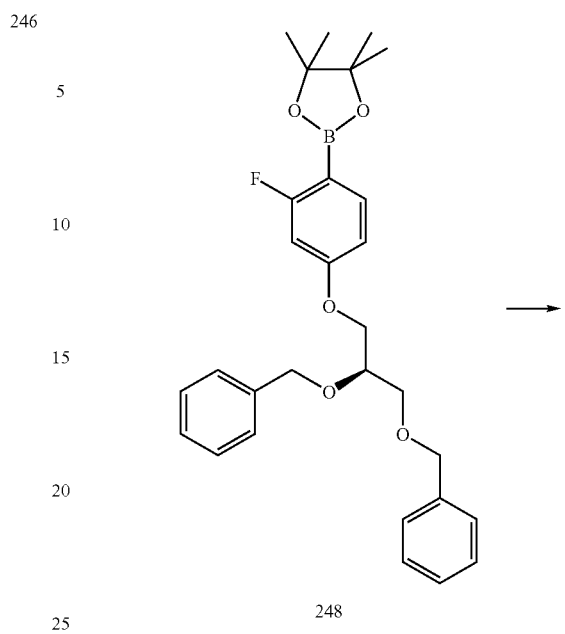

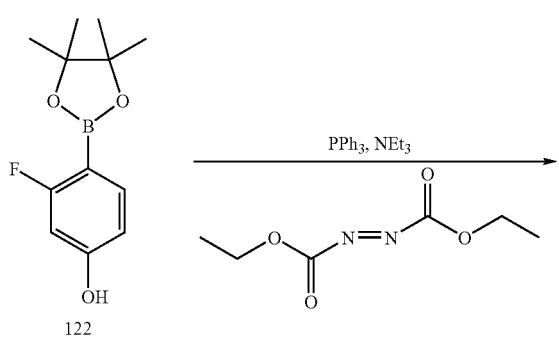

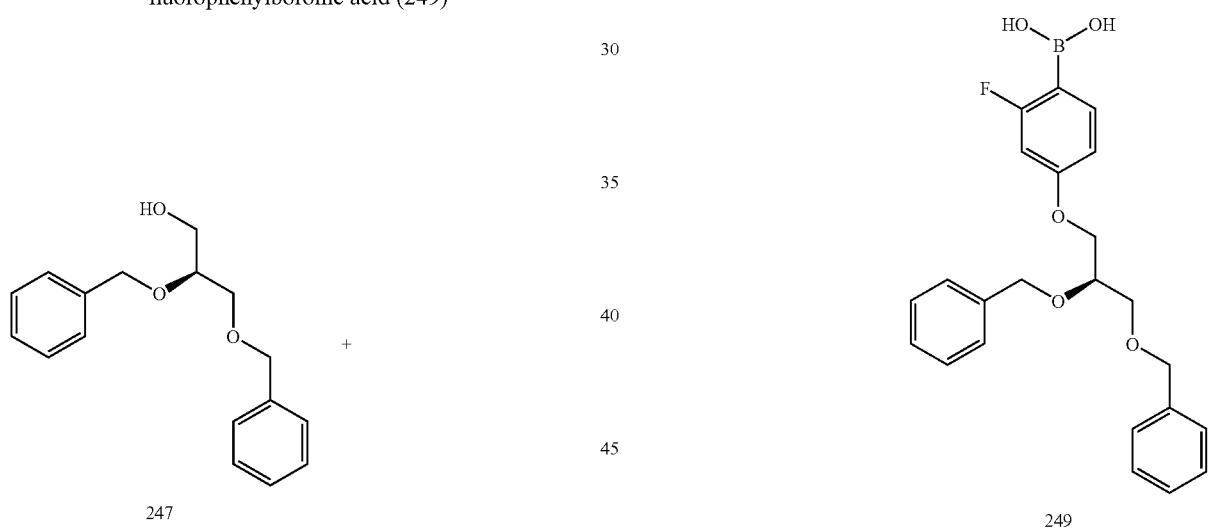

Compound (248): Phenol 122 (250 mg, 1.0 eq.), alcohol 247 (343 mg, 1.2 eq.), PPh$_3$ (551 mg, 2.0 eq.), TEA (128 mg, 1.2 eq.) were dissolved in 50 ml of andydrous THF and cooled to 0° C. under a nitrogen atmosphere. DIAD (366 mg, 2.0 eq.) was added dropwise and the reaction warmed to room temperature after addition was complete. The reaction was stirred for 18 hours and quenched with 1N HCL and extracted with EtoAc and water. The organic layer was washed with sat NaHCO$_3$ and brine, dried over Na2SO4, concentrated onto silica and chromatographed in 12-25% EtoAc/hex to produce 248 as a white solid (130 mg, yield 25%)

Compound (249): Compound 249 was synthesized according to the procedure described in Example 24. MS (ESI(−)) m/e 409.12 M−H)$^-$.

Example 167

Synthesis of (R)-4-(2-(dimethylamino)-3-phenylpropoxy)-2-fluorophenylboronic acid (254)

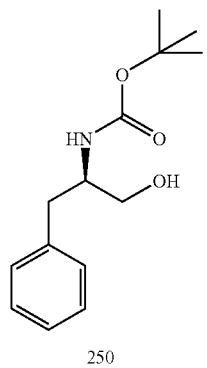

250

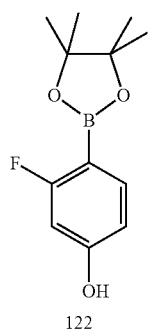

122

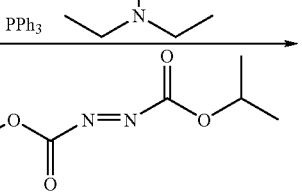

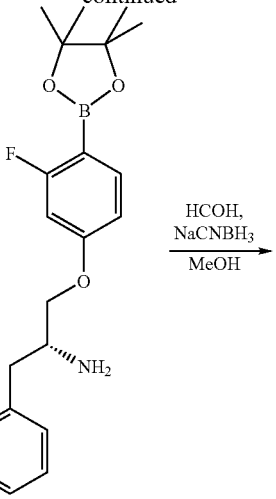

252

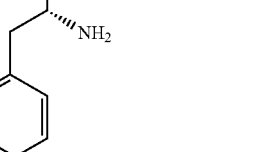

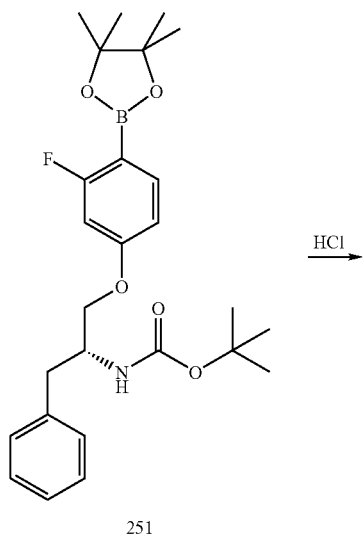

251

Compound (251): Compound 251 was synthesized as described in Example 166 except for replacing alcohol 247 with alcohol 250.

Compound (252): Compound 251 (700 mg, 10 eq.) was dissolved in 3 ml of dry THF. HCl (4.0M in dioxane, 200 mL, 10 eq.) was added. The mixture was stirred for 10 h. Hexane was added until a white precipatate came out of the solution. The white precipatate was collected through filtration to give 170 mg of Compound 252.

Compound (253): The amine 252 (18.0 mg, 10 eq.) was dissolved in 4 ml MeOH. Formaldehyde (37% sol'n in water, 0.021 mL, 6.0 eq.) was added and stirred for 15 min. Then sodium cyanoborohydride (9.0 mg, 3.0 eq.) was added and the reaction stirred for 2 h. Flash chromatography on silica gel (10-20% EtOAc in Hexanes) gave 17 mg of Compound 253.

Compound (254): Compound 254 was synthesized according to the procedure described in Example 24. MS (ESI(−)) m/e 316.12 M−H)⁻.

Example 168

Compound 255 was synthesized as described in Example 167 except for substituting the (R)-alcohol 250 with its S-isomer, MS (ESI(−)) m/e 316.12 M−H)⁻.

271

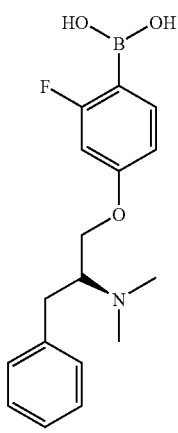

Example 169

Compound 256 was synthesized as described in Example 167 except for substituting benzaldehyde in place of formaldehyde, MS (ESI(−)) m/e 392.15 M−H)⁻.

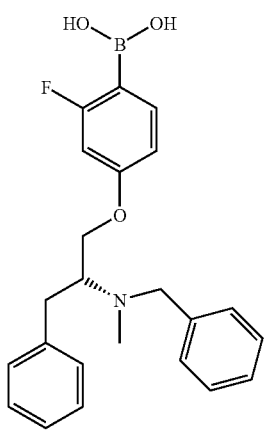

Example 170

Compound 257 was synthesized as described in Example 169 except for substituting the (R)-alcohol 250 with its S-isomer, MS (ESI(−)) m/e 392.15 M−H)⁻.

272

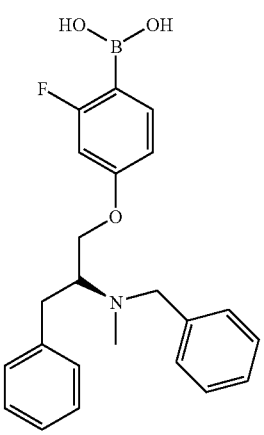

Example 171

Prodrugs

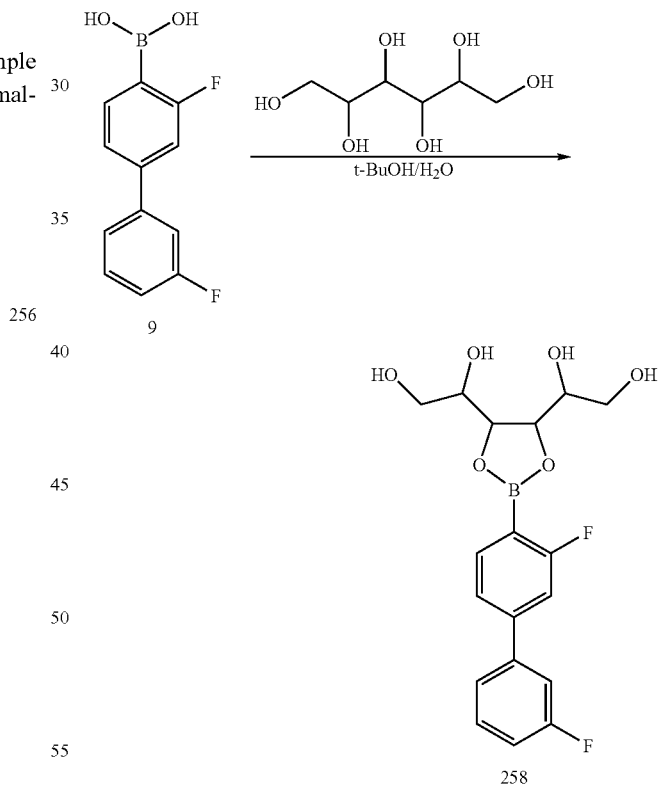

Compound (258): 300 mg (1.0 eq.) of boronic acid (9) was dissolved in 2 mL of t-butanol. To this 4.5 g (excess) of mannitol dissolved in 10 mL of water was added and the homogeneous solution stirred for 1 hour. The solution was then lyophilized and the material used without further characterization.

Other prodrugs of the any of the above compounds are encompassed by the present invention. Prodrugs of boronic acids can be in the form of the "ate" form when the boron is in its tetrahedral form. Exemplary prodrugs of compound (9) include, but are not limited to, any of the following compounds:

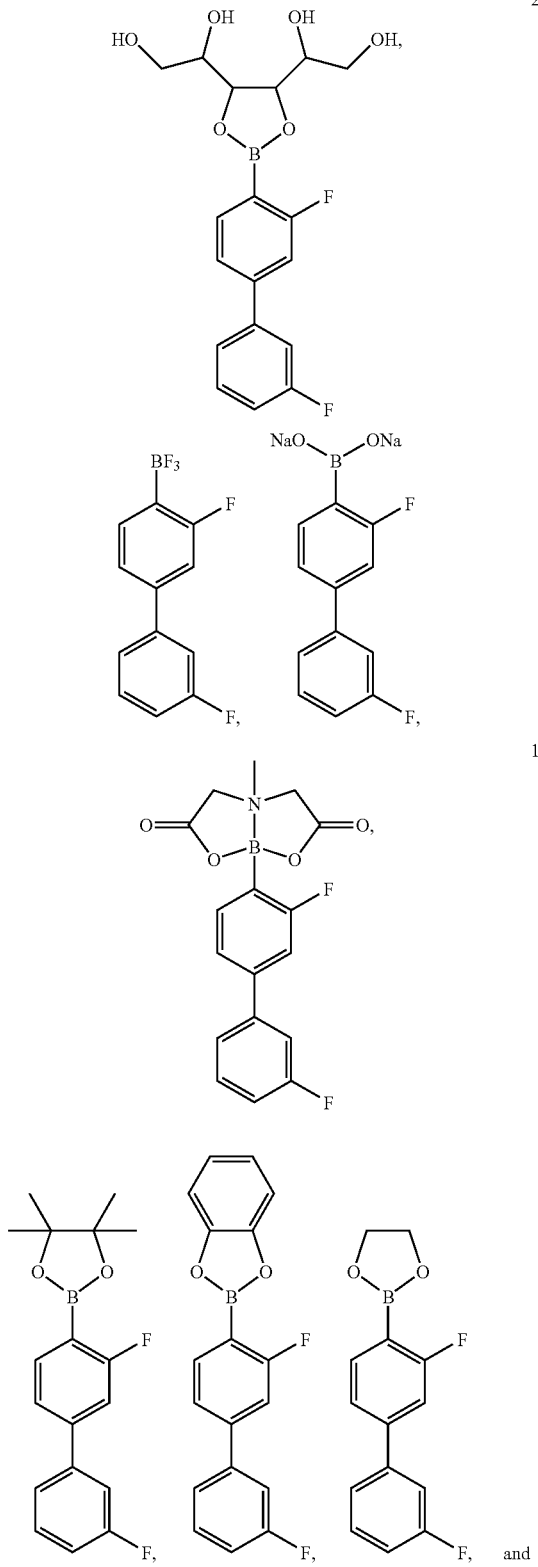

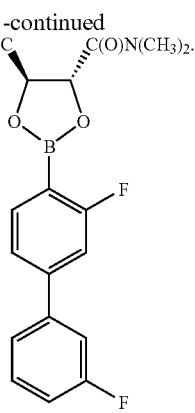

Example 172

Inhibition of Rat and Human FAAH

The following assays may be used to determine the inhibition of FAAH by the compounds of the present invention: (1) a fluorescence-based assay for fatty acid amide hydrolase compatible with high-throughput screening as described in Manjunath et al., *Analytical Biochemistry* (2005) 343:143-151; and (2) a high-throughput screening for the discovery of inhibitors of fatty acid amide hydrolase using a microsome-based fluorescent assay. Wang et al., *Biomolecular Screening* (2006) 1-9.

Rat FAAH Preparation: Five rat livers are homogenized in five fold volume with ice cold Tris (20 mM pH 8.0) and 0.32 M Sucrose solution via an Ultra Turrax T25 homogenizer. All subsequent preparation steps are carried out at 4° C. The homogenate is centrifuged at 6000 g, for 20 minutes and the pellet, containing nuclear debris and mitochondria is discarded. The supernatant is centrifuged at 40,000 g for 30 minutes. The supernatant is discarded and the pellet solubilized via a dounce homogenizer in resuspension buffer (20 mM Hepes pH 7.8, 10% v/v glycerol, 1 mM EDTA, 1% triton X-100) overnight at 4° C. to resolubilize membrane bound FAAH. The solution is centrifuged at 40,000 g for 30 minutes and the pellet discarded. The supernatant containing rat FAAH is aliquoted and flash frozen with liquid nitrogen and stored for long term usage at −80° C.

Human FAAH Preparation: COS-7 cells were split the day before, 1:5 into 150 mm×25 mm cell culture dishes (Corning Inc., Cat. No. 430599). Transient transfection takes place at 30-40% confluency according to FuGENE 6 Transfection Reagent (Roche, Cat. No. 11814 443 001) insert sheet procedure.

Transfection Procedure: The FuGENE transfection 6 reagent (45 uL) is added to 1410 uL of media (DMEM, serum free without pen/strep) in a 15 mL conical tube and incubated at room temp for 5 minutes, followed by the addition of FAAH plasmid DNA (15 ug) (OriGene Cat. No. TC119221, Genbank Accession No. NM_001441.1, 0.67 ug/uL) and a further incubation of 15 minutes at room temperature. The resulting solution is added into one dish of 30-40% confluent COS-7 cells in a drop-wise manner. The COS-7 cell dish is subsequently incubated for 48 hours. The cells are then harvested.

Harvest procedure: Media was aspirated from the dishes and the cells rinsed with 10 mL PBS. The PBS was removed and 3 mLs of PBS added to the dish. The dish was scraped to resuspend the cells, and the subsequent cell suspension collected into a 15 ml conical tube. The cells were pelleted by centrifugation at 1200 rpm for 5 minutes in a bench top centrifuge. PBS was removed and the cell pellet snap frozen in liquid nitrogen, store at −80 C.

COS-7 cells—FAAH Purification:

(1) Fractionation: Frozen cell pellets from transient transfections are thawed on ice and resuspended in: 12.5 mM Hepes pH 8.0, 100 mM NaCl, 1 mM EDTA (10 mL/0.2 g cell pellet). The pellets were dounce homogenized and then sonicated to produce cell extract. The cell extract was subsequently centrifuged at 1000 g to remove cellular debris. The pellet was discarded and the supernatant centrifuged at 13,000 g for 20 minutes. The pellet contained membrane bound FAAH. The supernatant was discarded and the pellet resolubilized.

(2) Re-solubilization: The fraction of interest, (13,000 g, membrane fraction) was re-suspended in re-suspension buffer (20 mM Hepes pH 7.8, 10% v/v Glycerol, 1 mM EDTA, 1% Triton X-100) (2.3 mL re-suspension and the sample incubated on ice for 1 hour and then centrifuged to at 13,000 g remove any particulate matter. The supernatant containing solubilized human FAAH was aliquoted and snap frozen in liquid nitrogen and stored at −80° C. until use.

(3) Characterization: Protein Concentration determined by Bradford assay.

SDS gel and Western blot to confirm presence of FAAH
FAAH activity assay
Km determination—96-well assay
Linear dependence—96-well assay
Standard compound $K_i$ determination—384-well assay Rat FAAH Biochemical Inhibition Assay; Materials and methods: Rat FAAH biochemical assays are carried out in a 96 well flat bottom black non-treated polystyrene plates (Corning Costar Catalogue #3915). FAAH reaction buffer: 50 mM Hepes (pH 7.5), 1 mM EDTA, 0.2% Triton X-100. FAAH substrate—AMC Arachidonoyl Amide (Cayman Chemicals Company, Catalogue #10005098) The reaction is read in an Envision microtiter plate reader [Excitation filter 355 nm (40 nm bandpass); Emmision filter 460 nm (25 nm bandpass)]. The raw fluorescence is plotted on the y axis and the inhibitor concentration on the x axis to give a dose response inhibition curve. The data is fitted to a single site competitive inhibition equation, fixing the Km for the rat and human enzyme to 12 uM and 9 uM respectively.

Rat FAAH Biochemical Inhibition Assay; Experimental Protocol: The principle of this assay is the hydrolysis of AMC-Arichodonoyl, a fluorescent analogue of Anandamide, which results in the formation of Arachidonic acid and AMC. The formation of AMC results in an increase in fluorescence (see, for example, Manjunath et al., *Analytical Biochemistry* (2005) 343:143-151; and Wang et al., *Biomolecular Screening* (2006) 1-9). The inhibition of product formation and hence fluorescence as a function of inhibitor concentration enables the determination of Ki for the compounds.

A 0.49 mg/ml Rat liver FAAH solution is made up in FAAH reaction buffer, and 78 ul pipetted into a 96 well plate. To this is added 2 uL of a 3 fold serially diluted inhibitor from a DMSO stock solution. The FAAH solution and inhibitor are incubated for 30 minutes at room temperature. The FAAH reaction is initiated by the addition of 80 uL of 40 uM AMC Arachidonoyl Amide in FAAH reaction buffer, yielding a final reaction FAAH rat liver preparation concentration of 0.25 mg/mL and AMC-Arachidonoyl substrate concentration of 20 uM, reaction volume 160 uL. The reaction is allowed to proceed for 4 hours at room temperature. The reaction is stopped by the addition of 80 uL 12 uM a-ketoheterocycle (Cayman Chemicals, catalogue #10435). The microtiter plate is read in the envision plate reader.

Human FAAH assay; Experimental Protocol: A 0.1 mg/mL Human FAAH solution is made up in FAAH reaction buffer, and 24 ul pipeted into a 384 well plate. To this is added 1 uL of a 3 fold serially diluted inhibitor from a DMSO stock solution. The FAAH solution and inhibitor are incubated for 30 minutes at room temperature. The FAAH reaction is initiated by the addition of 25 uL of 40 uM AMC Arachidonoyl Amide in FAAH reaction buffer, yielding a final reaction human FAAH preparation concentration of 0.05 mg/ml and AMC-Arachidonoyl substrate concentration of 20 uM, reaction volume 50 uL. The reaction is allowed to proceed for 4 hours at room temperature. The reaction is stopped by the addition of 25 uL 12 uM a-ketoheterocycle (Cayman Chemicals, catalogue #10435). The microtiter plate in read in the envision plate reader.

The raw fluorescence is plotted on the y axis and the inhibitor concentration on the x axis to give a dose response inhibition curve. The data is fitted to a single site competitive inhibition equation, fixing the Km for the rat and human enzyme to 12 uM and 9 uM respectively.

Example 173

Inhibition of FAAH in its Native Cellular Environment

Cellular FAAH inhibition assay: This assay measures the activity of FAAH in its native cellular environment. Radiolabelled anandamide, tritiated on its ethanolamine component is added to a cell suspension. Anadamide diffuses into the cell, whereby the native cellular FAAH hydrolyses anandamide into arachdonic acid and ethanolamine. The cellular reaction is quenched in a methanol/chloroform mixture. Ethanolamine partitions into the aqueous phase and is counted via a scintillation counter giving a measure of cellular FAAH activity. Inhibition studies are performed by pre-incubating the cells with serially diluted inhibitor, followed by the addition of radiolabeled anandamide.

Cell preparation: RBL-2H3 and T-47D adherent cells were cultured via the standard protocols. Cells were trypsinized and washed 3 times in RPMI buffer plus 0.1% BSA. The cells were resuspended, counted and diluted to a final cell density of $1 \times 10^6$ cells/ml. Human PBMC were isolated from whole blood and used at a final cell density of $4.5 \times 10^6$ cells/ml in RPMI plus 0.1% BSA buffer.

Anandamide substrate solution: A 10 nM $^3$H anandamide substrate solution was prepared by diluting from a 16.7 uM (1 uCi/ul) stock in RPMI buffer plus 0.1% BSA, and incubated at room temperature for 90 minutes. A substrate-inhibitor solution is made by adding serially diluted inhibitor from a DMSO stock solution to the desired concentration into the substrate solution.

Assay: A 350 uL cell suspensions was incubated with serially diluted inhibitor added from a DMSO stock and incubated for 30 minutes with constant agitation. Cells were pelleted and the supernatant removed. The cells were resuspended in 300 ul of 10 nM substrate+serially diluted inhibitor, to maintain a constant free inhibitor concentration during the time-course of the reaction. The RBL-2H3 and T-47D cells were incubated with the substrate–inhibitor for 5 minutes and PBMC for 15 minutes. The reaction was quenched by the addition of 700 uL of methanol:chloroform (1:1 v/v), which lyses the cells and inactivates FAAH. Sampled were vortexed and centrifuged to separate the aqueous and organic solutions. $^3$H ethanolamine, the polar product of anandamide hydrolysis partitions into the aqueous phase and is counted via a scintillation counter.

Data Analysis: The radioactivity in the aqueous phase is plotted with respect to inhibitor concentration to generate dose response inhibition curves, and the data fitted to determine the IC$_{50}$.

Example 174

FAAH Cell-Based Assay Protocol for Human and Rat Whole Blood

This assay measures the cellular activity of FAAH in whole blood via the hydrolysis of radiolabeled anandamide by the same methodology and principle used in the cell based assay described in Example 172. FAAH is found to be expressed in the cells of the immune system.

Substrate Solution: $^3$H Anandamide (1 uC/uL, 16.7 uM stock) is added to a final concentration of 40 nM (4x) for the human whole blood assays and 20 nM (2x) for rat whole blood assays to the RMPI buffer plus 0.1% BSA. The $^3$H anandamide stock solutions are incubated for 90 minutes at room temperature prior to use in the whole blood assay.

Human whole Blood Cellular FAAH assay: Human blood (262.5 uL) is pre-incubated with serially diluted inhibitor added from DMSO stock solution for 30 minutes. The assay is initiated by the addition of 40 nM $^3$H anandamide (87.5 uL) yielding a final assay volume of 350 ul and $^3$H anandamide substrate concentration of 10 nM. The reaction mixture is incubated for 30 minutes at room temperature, and the reaction stopped by the addition of 700 uL of methanol:chloroform (1:1 v/v). This lyses the cells and inactivates the FAAH. The solution is vortexed and $^3$H ethanolamine, the radiolabeled product of $^{3H}$ anandamide hydrolysis partitioning into the aqueous phase, and is counted via a scintillation counter.

Rat whole Blood Cellular FAAH assay: Rat blood (175 uL) is pre-incubated with serially diluted inhibitor added from DMSO stock solution for 30 minutes. The assay is initiated by the addition of 20 nM $^3$H anandamide (175 uL) yielding a final assay volume of 350 ul and $^3$H anandamide substrate concentration of 10 nM. The reaction mixture is incubated for 30 minutes at room temperature, and the reaction stopped by the addition of 700 uL of methanol:chloroform (1:1 v/v). This lyses the cells and inactivates the FAAH. The solution is vortexed and $^3$H ethanolamine, the radiolabeled product of $^3$H anandamide hydrolysis partitioning into the aqueous phase, and is counted via a scintillation counter.

Data Analysis: The radioactivity in the aqueous phase is plotted with respect to inhibitor concentration to generate dose response inhibition curves, and the data fitted to determine the IC$_{50}$.

Example 175

In Vivo Analysis of Boronic Acid and Boronic Ester Derivatives in a Pain Model

This assay may be used to evaluate the effect of the compounds of the present invention on the reflexive withdrawal of the rat from an acute noxious stimulus (hot surface).

(1) Heat plate to testing temperature (Hot plate analgesia meter; Harvard Apparatus)-takes about 10-15 min (the actual surface temperature is not reflected in the LED read out. The actual surface temperature is 10° less than the read out indicates).

| Read-out | Surface temp |
|---|---|
| 57° C. | 47° C. |
| 62° C. | 52° C. |
| 65° C. | 55° C. |

(2) Place plexi-glass cylinder on hot plate. Place rat within cylinder and start timer. When the rat either licks its hind paw or jumps, stop the timer and remove from hot plate. Record the response latency (in sec), usually 6-7 sec at 52° C. Measure baseline latencies for all rats.

(3) Inject drug or vehicle.

(4) Measure response 5, 15, 30, 60, 90, 120 min, etc. after drug injection. Cut-off time for 52° C. is 30 sec. A rat that does not respond by 30 sec. is assigned a latency of 30 sec.

(5) Clean hot plate surface in between time points with water, dry with kimwipe and wait until temperature read out has returned to 57° C.

Data may be expressed as either latency or percent maximum possible effect [% MPE=(drug latency−baseline latency)/(cut-off−baseline latency)×100].

Other temperatures may be used (e.g., 47, 55° C.). Cut-off time should be adjusted accordingly (e.g., 40 sec at 47° C.; 20 sec at 55° C.). Increased temperatures recruit myelinated afferents (Aδ-fibers) whereas lower temperatures involve unmyelinated afferents (c-fibers). Sensitivity to drug effects may be altered with different plate temperatures.

Example 176

Evidence for Covalent Complex Formation Between Serine-241 of FAAH and Boronic Acid Inhibitors Treatment of rat FAAH protein with the active site-directed irreversible inhibitor methoxy arachidonyl fluorophosphonate results in a crystal structure wherein methoxy arachidonyl phosphonate is covalently bound to the side chain of Ser-241 (Bracey et al., Science (2002) 298:1793-1796).

Based on this data, it is hypothesized that the boronic acid compounds provided by the present invention form reversible covalent complexes with the nucleophilic side chain of Ser-241. This hypothesis is consistent with the kinetic data. Molecular modeling studies of aryl boronic acid compounds provided by the present invention indicates that the aryl ring can be directed to bind either in the narrow hydrophobic channel of the enzyme near Ser241, which is confluent with the membrane portion and the acyl chain binding pocket, or alternatively bind toward the cytosolic portion.

To distinguish between these two binding modes, a mutant protein was cloned and expressed which was identical to the rat FAAH protein sequence, except at four positions in the sequence: I491V, V495M, L192F, and F194Y. These four residues line the narrow hydrophobic channel near Ser-241 in the rat x-ray structure. Starting from the published X-ray crystal structure of rat FAAH, a 3-D homology model was built of human FAAH using the program DeepView (Nicolas Guex, Manuel Peitsch, Torsten Schwede Alexandre Diemand "DeepView/Swiss-Pdbviewer" http://www.expasy.org/spdbv (1995-2001)). Based on this 3-D homology model of the human protein, mutation of these four residues to the corresponding amino acids in the human sequence was predicted to significantly influence the binding of the aryl boronic acid compounds If the aryl ring is in close proximity to these residues.

The inhibition constant ($K_i$) was measured for a panel of eleven boronic acid-containing compounds differing in their ability to inhibit rat and human FAAH. Table 4 below summarizes the statistical analysis for the panel of eleven compounds, comparing the ratio of inhibition constants for the wild-type rat and human enzymes (R/H) to ratio of inhibition constants for the mutant rat and human enzymes (M/H). The data indicates that the compounds bind at Serine-241 with the aryl ring directed toward the narrow hydrophobic channel.

TABLE 4

| R/H | M/H | |
|---|---|---|
| 11 | 11 | nObs |
| 2.99 | 1.08 | Mean |
| 3.45 | 0.48 | StDev |
| 0.02 | 0.49 | Min |
| 11.86 | 1.8 | Max |

EQUIVALENTS

Those skilled in the art will recognize, or be able to ascertain using no more than routine experimentation, many equivalents to the specific embodiments of the invention described herein. Such equivalents are intended to be encompassed by the following claims.

---

We claim:

1. A pharmaceutically acceptable composition, comprising a compound of formula III,

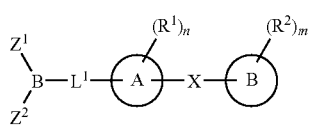

(III)

or a pharmaceutically acceptable salt thereof, and a pharmaceutically acceptable excipient;

wherein:

$Z^1$ is —OR and $Z^2$ is —OR;

each R is, independently, hydrogen or an optionally substituted $C_{1-6}$ aliphatic, $C_{6-12}$ aryl, or $C_{6-12}$ heteroaryl group;

$L^1$ is a covalent bond;

Ring A is phenyl, wherein Ring A has at least one fluorine substituent;

X is a covalent bond or a bivalent $C_{1-6}$ hydrocarbon chain, wherein one, two or three methylene units of X are optionally and independently replaced with one or more —O—;

Ring B is phenyl;

each occurrence of $R^1$ is, independently, halogen;

$R^2$ is —CN, —$NO_2$, —NC, —C(O)N(R')$_2$, —$N_3$, $N_2R$, —N(R)$_2$, or —N(R')$_2$;

each R' is hydrogen, —C(O)R, a suitable amino protecting group, or an optionally substituted $C_{1-6}$ aliphatic, $C_{6-12}$ aryl, or $C_{6-12}$ heteroaryl group;

each instance of n is, independently, 1, 2, 3 or 4; and m is 1.

2. The composition according to claim 1, wherein the group

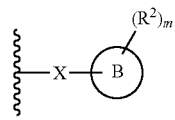

is attached to Ring A para to the boron atom.

3. The composition according to claim 1, wherein Ring A is phenyl and at least one $R^1$ group is fluoro in the ortho position relative to the boron atom.

4. The composition according to claim 1, wherein $R^2$ is —N(R')$_2$.

5. The composition according to claim 1, wherein X is a covalent bond.

6. The composition according to claim 1, wherein $R^1$ is selected from fluoro or chloro, wherein at least one $R^1$ group is fluoro.

7. The composition according to claim 1, wherein n is 1.

8. The composition according to claim 1, wherein Ring A is selected from the group consisting of:

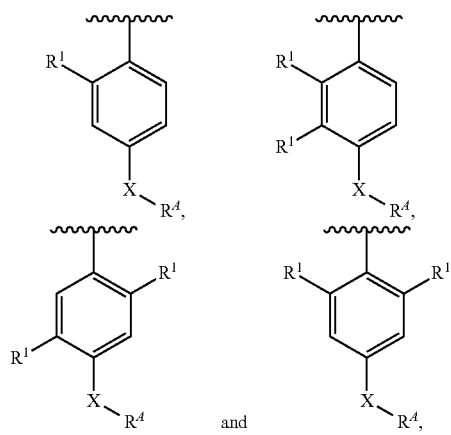

wherein $R^A$ is Ring B.

9. The composition according to claim 1, wherein Ring B is:

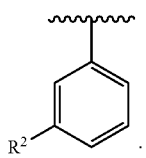

10. The composition according to claim 9, wherein $R^2$ is —N(R')$_2$.

11. The composition according to claim 1, wherein the compound of formula III is:

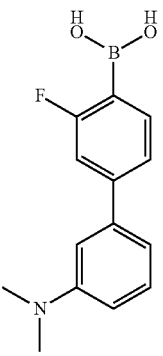

or a pharmaceutically acceptable salt thereof.

12. The composition according to claim 1, wherein the compound of formula III is selected from the group consisting of:

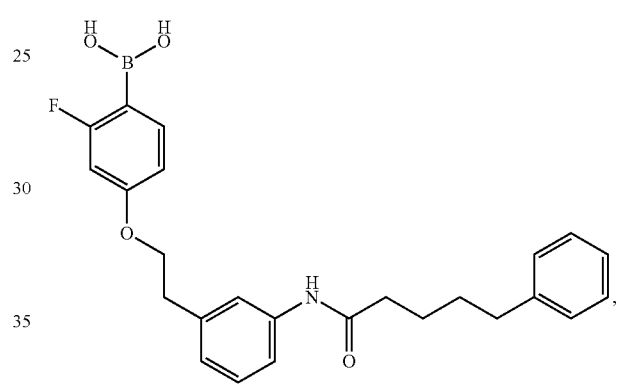

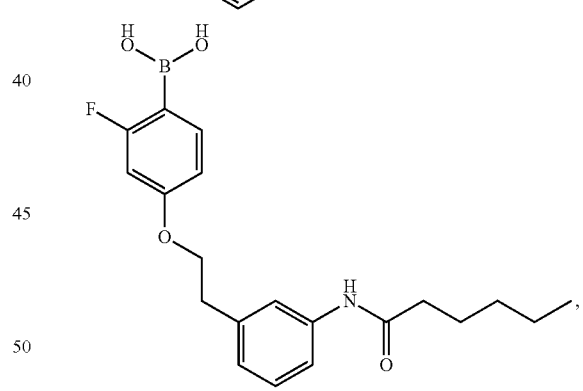

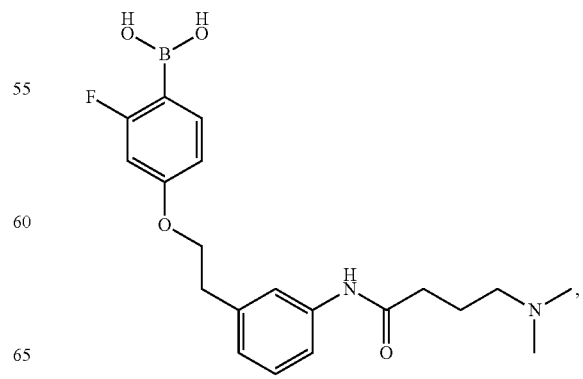

-continued
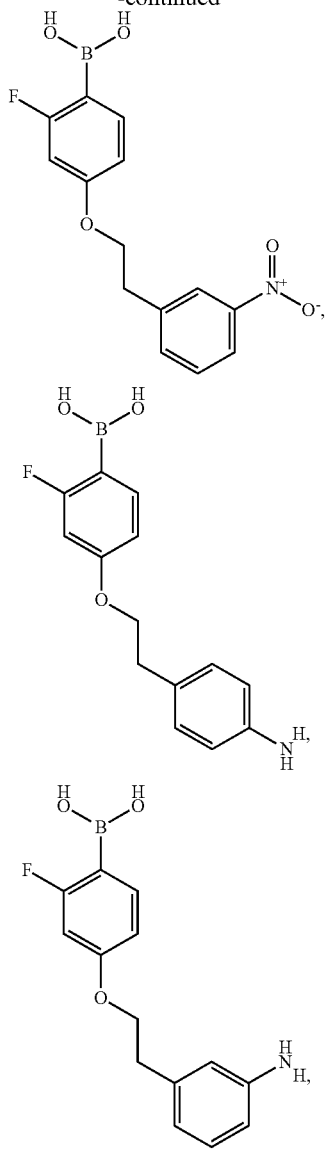
-continued
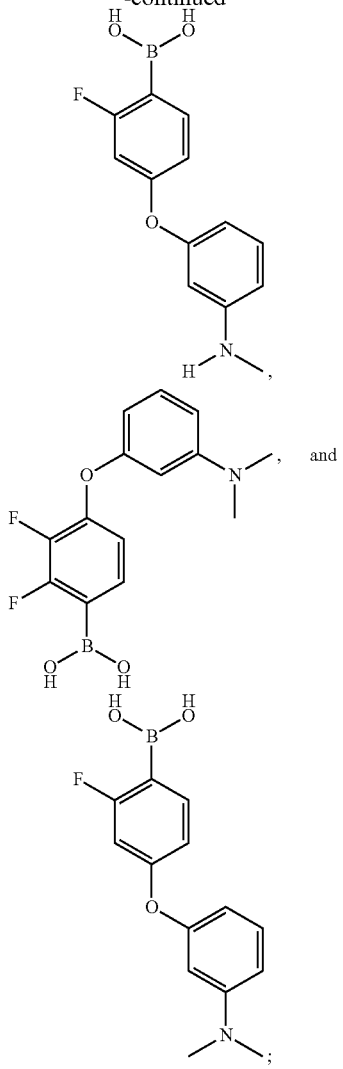
or a pharmaceutically acceptable salt thereof.
* * * * *

SEQUENCE LISTING

<160> NUMBER OF SEQ ID NOS: 1

<210> SEQ ID NO 1
<211> LENGTH: 579
<212> TYPE: PRT
<213> ORGANISM: Homo sapiens

<400> SEQUENCE: 1

```
Met Val Gln Tyr Glu Leu Trp Ala Ala Leu Pro Gly Ala Ser Gly Val
1               5                   10                  15

Ala Leu Ala Cys Cys Phe Val Ala Ala Val Ala Leu Arg Trp Ser
                20                  25                  30

Gly Arg Arg Thr Ala Arg Gly Ala Val Val Arg Ala Arg Gln Arg Gln
            35                  40                  45

Arg Ala Gly Leu Glu Asn Met Asp Arg Ala Ala Gln Arg Phe Arg Leu
        50                  55                  60

Gln Asn Pro Asp Leu Asp Ser Glu Ala Leu Leu Ala Leu Pro Leu Pro
65                  70                  75                  80

Gln Leu Val Gln Lys Leu His Ser Arg Glu Leu Ala Pro Glu Ala Val
                85                  90                  95

Leu Phe Thr Tyr Val Gly Lys Ala Trp Glu Val Asn Lys Gly Thr Asn
                100                 105                 110

Cys Val Thr Ser Tyr Leu Ala Asp Cys Glu Thr Gln Leu Ser Gln Ala
                115                 120                 125

Pro Arg Gln Gly Leu Leu Tyr Gly Val Pro Val Ser Leu Lys Glu Cys
            130                 135                 140

Phe Thr Tyr Lys Gly Gln Asp Ser Thr Leu Gly Leu Ser Leu Asn Glu
145                 150                 155                 160

Gly Val Pro Ala Glu Cys Asp Ser Val Val His Val Leu Lys Leu
                165                 170                 175

Gln Gly Ala Val Pro Phe Val His Thr Asn Val Pro Gln Ser Met Phe
                180                 185                 190

Ser Tyr Asp Cys Ser Asn Pro Leu Phe Gly Gln Thr Val Asn Pro Trp
            195                 200                 205

Lys Ser Ser Lys Ser Pro Gly Gly Ser Ser Gly Gly Glu Gly Ala Leu
                210                 215                 220

Ile Gly Ser Gly Gly Ser Pro Leu Gly Leu Gly Thr Asp Ile Gly Gly
225                 230                 235                 240

Ser Ile Arg Phe Pro Ser Ser Phe Cys Gly Ile Cys Gly Leu Lys Pro
                245                 250                 255
```

-continued

```
Thr Gly Asn Arg Leu Ser Lys Ser Gly Leu Lys Gly Cys Val Tyr Gly
            260                 265                 270

Gln Glu Ala Val Arg Leu Ser Val Gly Pro Met Ala Arg Asp Val Glu
            275                 280                 285

Ser Leu Ala Leu Cys Leu Arg Ala Leu Leu Cys Glu Asp Met Phe Arg
            290                 295                 300

Leu Asp Pro Thr Val Pro Pro Leu Pro Phe Arg Glu Glu Val Tyr Thr
305                 310                 315                 320

Ser Ser Gln Pro Leu Arg Val Gly Tyr Tyr Glu Thr Asp Asn Tyr Thr
                325                 330                 335

Met Pro Ser Pro Ala Met Arg Arg Ala Val Leu Glu Thr Lys Gln Ser
                340                 345                 350

Leu Glu Ala Ala Gly His Thr Leu Val Pro Phe Leu Pro Ser Asn Ile
            355                 360                 365

Pro His Ala Leu Glu Thr Leu Ser Thr Gly Gly Leu Phe Ser Asp Gly
    370                 375                 380

Gly His Thr Phe Leu Gln Asn Phe Lys Gly Asp Phe Val Asp Pro Cys
385                 390                 395                 400

Leu Gly Asp Leu Val Ser Ile Leu Lys Leu Pro Gln Trp Leu Lys Gly
                405                 410                 415

Leu Leu Ala Phe Leu Val Lys Pro Leu Leu Pro Arg Leu Ser Ala Phe
            420                 425                 430

Leu Ser Asn Met Lys Ser Arg Ser Ala Gly Lys Leu Trp Glu Leu Gln
            435                 440                 445

His Glu Ile Glu Val Tyr Arg Lys Thr Val Ile Ala Gln Trp Arg Ala
    450                 455                 460

Leu Asp Leu Asp Val Val Leu Thr Pro Met Leu Ala Pro Ala Leu Asp
465                 470                 475                 480

Leu Asn Ala Pro Gly Arg Ala Thr Gly Ala Val Ser Tyr Thr Met Leu
                485                 490                 495

Tyr Asn Cys Leu Asp Phe Pro Ala Gly Val Val Pro Val Thr Thr Val
                500                 505                 510

Thr Ala Glu Asp Glu Ala Gln Met Glu His Tyr Arg Gly Tyr Phe Gly
            515                 520                 525

Asp Ile Trp Asp Lys Met Leu Gln Lys Gly Met Lys Lys Ser Val Gly
    530                 535                 540

Leu Pro Val Ala Val Gln Cys Val Ala Leu Pro Trp Gln Glu Glu Leu
545                 550                 555                 560

Cys Leu Arg Phe Met Arg Glu Val Glu Arg Leu Met Thr Pro Glu Lys
                565                 570                 575

Gln Ser Ser
```